United States Patent
Hijazi et al.

(10) Patent No.: US 11,975,132 B2
(45) Date of Patent: May 7, 2024

(54) EXTRACORPOREAL DEVICE AND MATRIX FOR REMOVING FIBRINOLYTIC PROTEINS FROM BIOLOGICAL FLUIDS, METHODS AND USES THEREOF

(71) Applicant: PLAS-FREE LTD., Nazareth Illit (IL)

(72) Inventors: Abd Alrauf Hijazi, D.N. Shimshon (IL); Zeev Dvashi, Kiryat Ono (IL)

(73) Assignee: PLAS-FREE LTD, Nazareth (IL)

( * ) Notice: Subject to any disclaimer, the term of this patent is extended or adjusted under 35 U.S.C. 154(b) by 786 days.

(21) Appl. No.: 16/976,259

(22) PCT Filed: Feb. 28, 2019

(86) PCT No.: PCT/IL2019/050228
§ 371 (c)(1),
(2) Date: Aug. 27, 2020

(87) PCT Pub. No.: WO2019/167048
PCT Pub. Date: Sep. 6, 2019

(65) Prior Publication Data
US 2021/0001023 A1 Jan. 7, 2021

Related U.S. Application Data

(60) Provisional application No. 62/636,511, filed on Feb. 28, 2018.

(51) Int. Cl.
*C07C 217/06* (2006.01)
*A61K 35/16* (2015.01)
(Continued)

(52) U.S. Cl.
CPC ........... *A61M 1/3486* (2014.02); *A61K 35/16* (2013.01); *A61M 1/0281* (2013.01); *A61P 7/04* (2018.01);
(Continued)

(58) Field of Classification Search
None
See application file for complete search history.

(56) References Cited

U.S. PATENT DOCUMENTS 3,998,946 A    12/1976  Condie et al.
5,690,914 A *  11/1997  Suetsugu ............... A61Q 19/02
                                              424/59
(Continued)

FOREIGN PATENT DOCUMENTS

CN      1636594      7/2005
CN    101239075      8/2008
(Continued)

OTHER PUBLICATIONS

The Protein Man: "Which agarose (Sepharose) to choose? 2, 4 or 6%? Crosslinked?", G-Biosciences, 2014.
(Continued)

*Primary Examiner* — Sudhakar Katakam
*Assistant Examiner* — Jennifer C Sawyer
(74) *Attorney, Agent, or Firm* — BROWDY AND NEIMARK, PLLC

(57) ABSTRACT

The presently disclosed subject-matter provides specific compositions, conjugates, device, kits and systems for depleting fibrinolytic agents from biological fluids. The presently disclosed subject-matter further relates to the resulting biological fluid products that are devoid in fibrinolytic activity, therapeutic methods and uses thereof. The conjugates comprise a particle, at least one linker and at least one amino acid, derivative thereof or analog thereof being at least one of 4-(aminomethyl)-cyclo-hexane-carboxylic acid (tranexamic acid), epsilon-amino caproic acid, lysine, cyclohexanecarboxylic acid and 4-methyl-cyclohexanecarboxylic
(Continued)

acid. A plurality of different conjugates (e.g. differing in particle size or type of linker) can be used.

22 Claims, 16 Drawing Sheets

Specification includes a Sequence Listing.

(51) Int. Cl.

| | |
|---|---|
| *A61M 1/02* | (2006.01) |
| *A61M 1/34* | (2006.01) |
| *A61P 7/04* | (2006.01) |
| *A61P 7/08* | (2006.01) |
| *C07C 233/47* | (2006.01) |
| *G01N 33/86* | (2006.01) |

(52) U.S. Cl.
CPC .............. *A61P 7/08* (2018.01); *C07C 217/06* (2013.01); *C07C 233/47* (2013.01); *G01N 33/86* (2013.01); *A61M 2202/0449* (2013.01); *A61M 2205/8206* (2013.01)

(56) References Cited

U.S. PATENT DOCUMENTS

| | | | |
|---|---|---|---|
| 5,792,845 | A | 8/1998 | O'Reilly et al. |
| 5,872,222 | A | 2/1999 | Chang |
| 6,258,577 | B1 | 7/2001 | Goodrich, Jr. et al. |
| 7,125,569 | B2 | 10/2006 | Nur et al. |
| 9,138,529 | B2 | 9/2015 | Ho |
| 2003/0124703 | A1 | 1/2003 | Nur et al. |
| 2008/0154007 | A1 | 6/2008 | Mori et al. |
| 2013/0005947 | A1 | 1/2013 | Meidler et al. |
| 2013/0035663 | A1 | 2/2013 | Ho |
| 2016/0058937 | A1 | 3/2016 | Gaitas et al. |
| 2020/0238253 | A1 | 7/2020 | Yonezawa et al. |

FOREIGN PATENT DOCUMENTS

| | | | | |
|---|---|---|---|---|
| JP | H06-072895 | A | 3/1994 | |
| JP | 2006-160731 | | 6/2006 | |
| JP | 2007-131668 | | 5/2007 | |
| JP | 2013-523411 | | 6/2013 | |
| WO | 02/095019 | A1 | 11/2002 | |
| WO | WO-02095019 | A1 * | 11/2002 | ........... C07C 215/66 |
| WO | 2018/025809 | A1 | 2/2018 | |
| WO | 2018/042438 | A2 | 3/2018 | |

OTHER PUBLICATIONS

Selighson U et al. Classification, Clinical Manifestations & Evaluation of Disorders of Hemostasis. In: Williams Hematology, 8th ed, 2010, pp. 2322-2330.

Abdel-Wahab Ol et al. Effect of fresh-frozen plasma transfusion on prothrombin time and bleeding in patients with mild coagulation abnormalities. Transfusion 2006; 46:1279-1285.

Holland LL et al. Toward rational fresh frozen plasma transfusion: The effect of plasma transfusion on coagulation test results. Am J Clin Pathol 2006; 126:133-139.

Meheux CJ et al. Efficacy of Intra-articular Platelet-Rich Plasma Injections in Knee Osteoarthritis: A Systematic Review. Arthroscopy, 2016, 32, 495-505.

Pap G et al. Expression of stromelysin and urokinase type plasminogen activator protein in resection specimens and biopsies at different stages of osteoarthritis of the knee. Pathol. Res. Pract. 2000, 196: 219-226.

Bachi et al Performance of Combinatorial Peptide Libraries in Capturing the Low-Abundance Proteome, Anal. Chem. 2008, 80, 3557-3565.

Tsukamoto et al "Preparation of recombinant murine tumor necrosis factoralpha . . . " Protein Expression and Purification, 56:138-144 (2007).

Bagge et al "The Primary fibrinolysis inhibitor and trauma" Thrombosis Research Tarrytown, NY, US, 13:1131-1136 (1978).

Gregori Luisa et al Reduction of transmissible spongiform encephalopathy infectivity from human, TRANSFUSION, 46:1152-1161 (2006).

DNA acc. NT_167187.1.

* cited by examiner

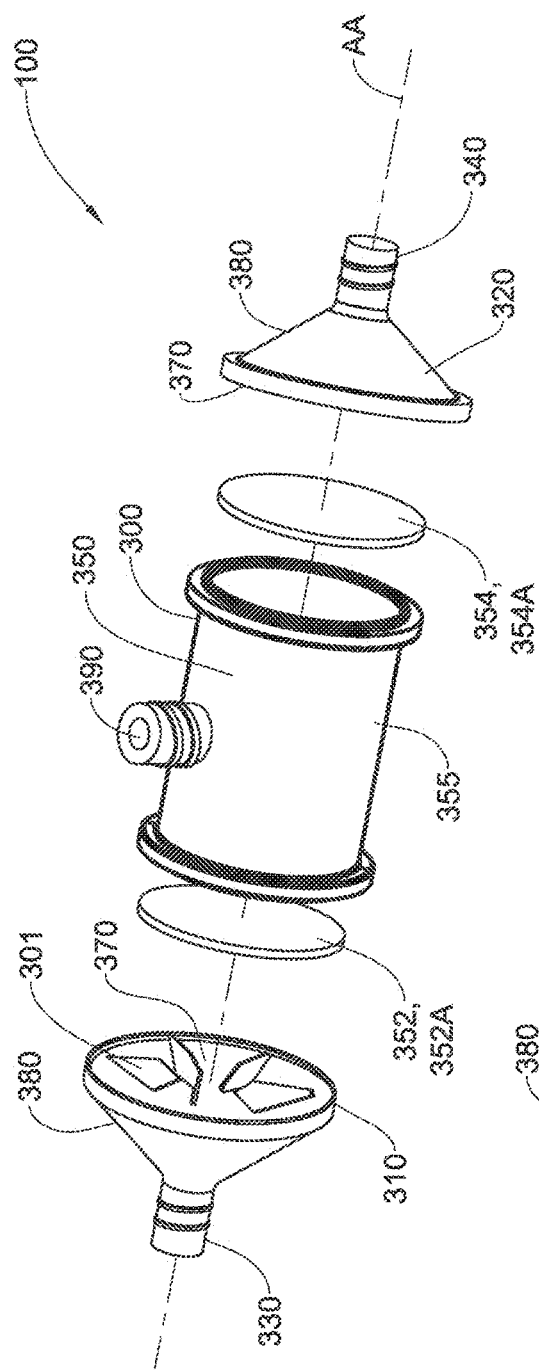
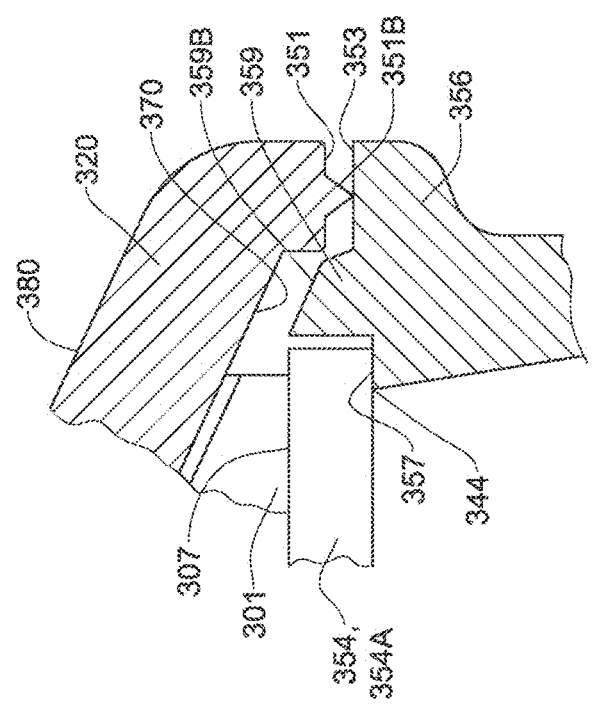
Fig. 12A
Fig. 12B

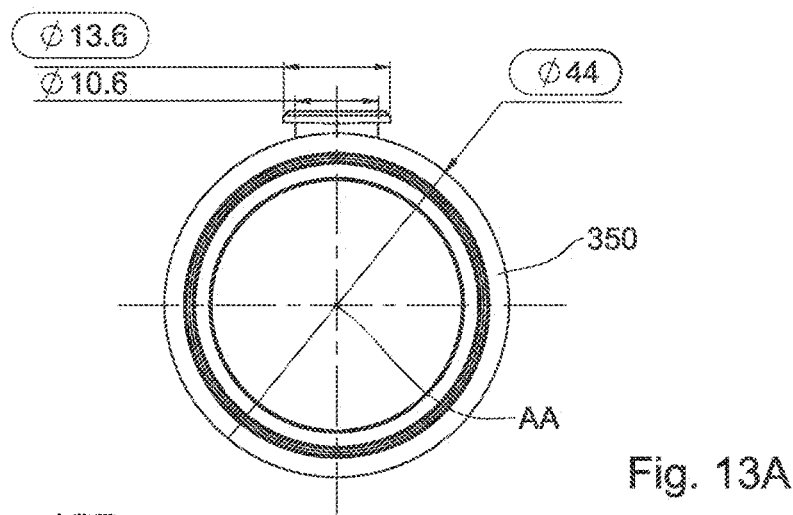
Fig. 13A
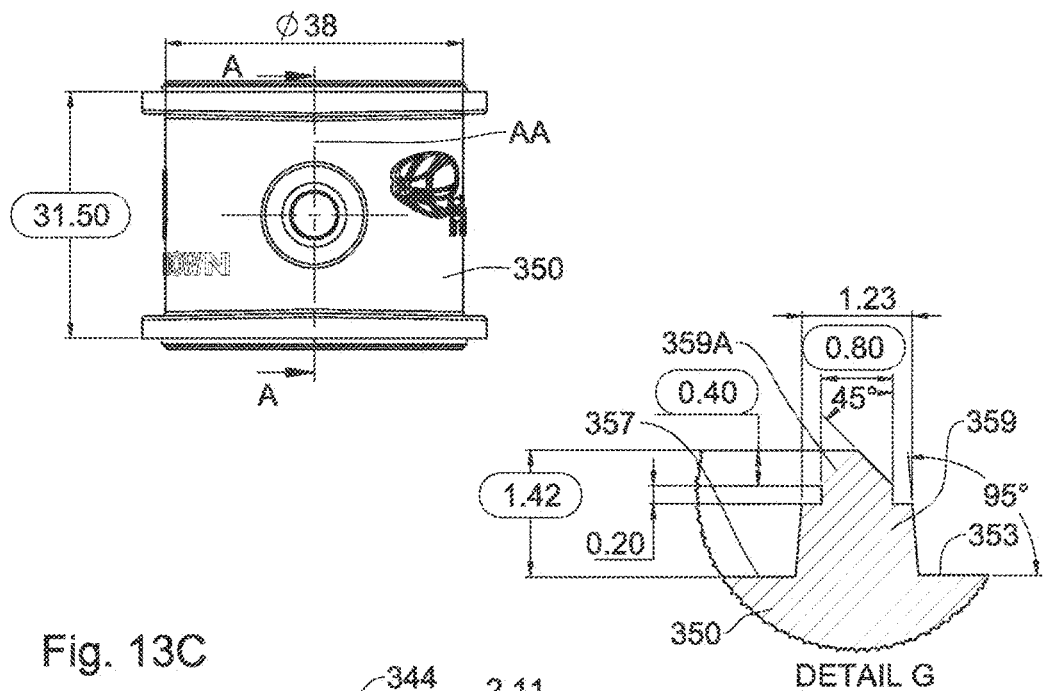
Fig. 13B
Fig. 13D
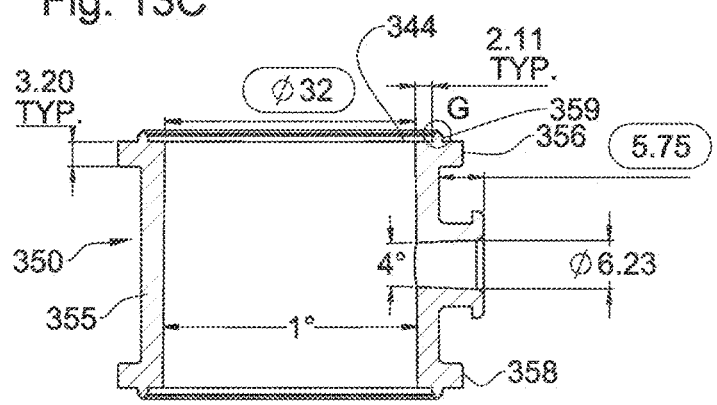
Fig. 13C
SECTION A-A

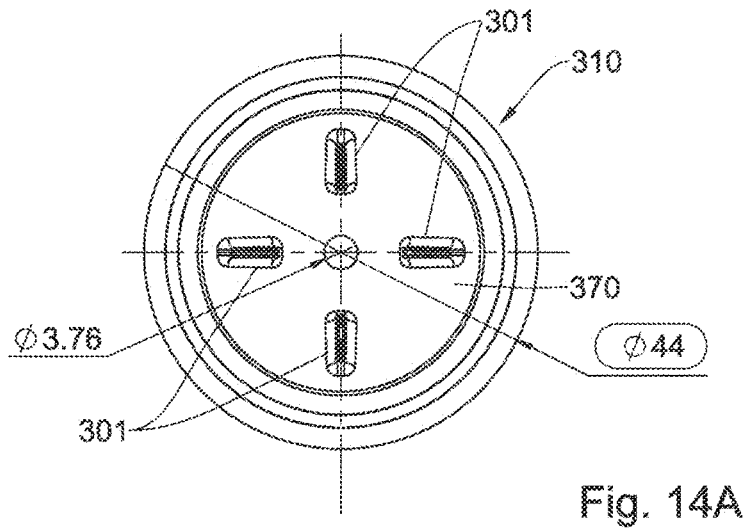
Fig. 14A
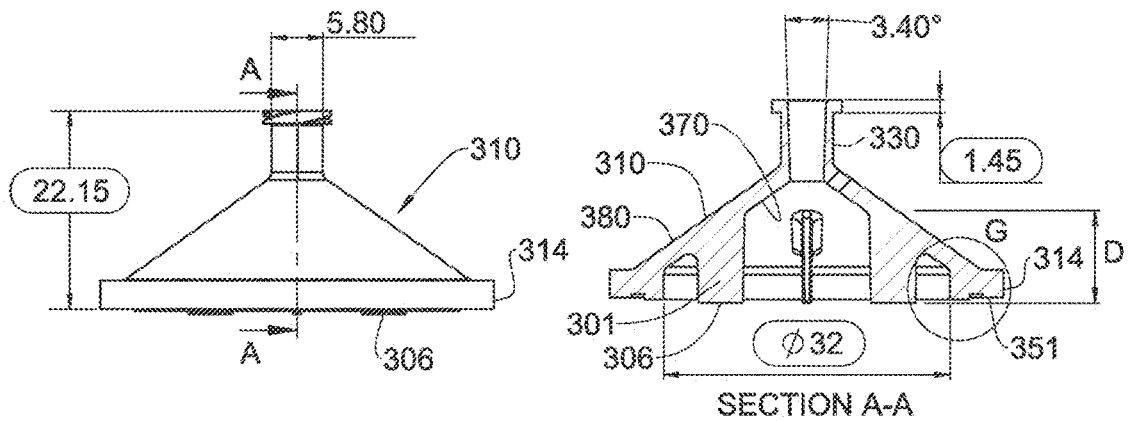
Fig. 14B
Fig. 14C
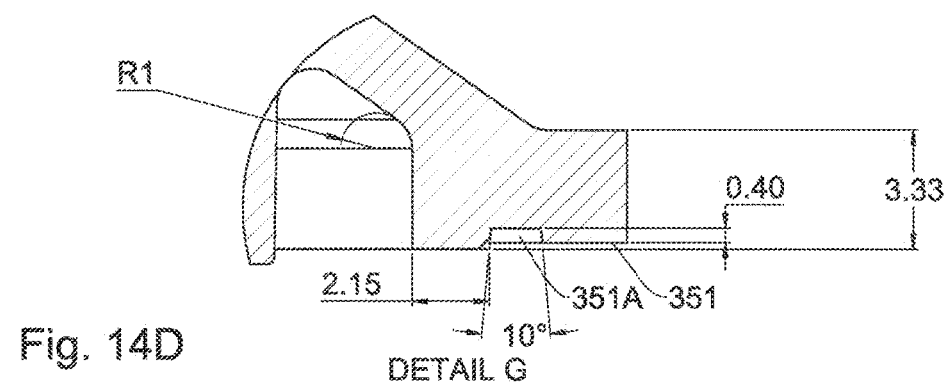
Fig. 14D

EXTRACORPOREAL DEVICE AND MATRIX FOR REMOVING FIBRINOLYTIC PROTEINS FROM BIOLOGICAL FLUIDS, METHODS AND USES THEREOF

FIELD OF THE INVENTION

The present invention pertains to the field of coagulation and transfusion medicine. More specifically, the present invention provides specific device and matrix for depleting fibrinolytic agents from biological fluids, the resulting biological fluid products that are devoid of fibrinolytic activity, methods and uses thereof.

BACKGROUND ART

References considered to be relevant as background to the presently disclosed subject matter are listed below.

Selighson U et al. Classification, Clinical Manifestations & Evaluation of Disorders of Hemostasis. Williams Hematology, 8$^{th}$ ed, 2010, pp 2322-2330.

Abdel-Wahab O I et al. Effect of fresh-frozen plasma transfusion on prothrombin and bleeding in patients with mild coagulation abnormalities. Transfusion 2006; 46: 1279-1285.

Holland L L et al. Toward rational fresh frozen plasma transfusion: The effect of plasma transfusion on coagulation test results. Am J Clin Pathol 2006; 126: 133-139.

Meheux C J et al. Efficacy of Intra-articular Platelet-Rich Plasma Injections in Knee Osteoarthritis: A Systematic Review. Arthroscopy, 2016, 32, 495-505.

Pap G et al. Expression of stromelysin and urokinase type plasminogen activator protein in resection specimens and biopsies at different stages of osteoarthritis of the knee. Pathol. Res. Pract. 2000, 196: 219-226.

U.S. Pat. No. 7,125,569.

U.S. Pat. No. 3,998,946.

Acknowledgement of the above references herein is not to be inferred as meaning that these are in any way relevant to the patentability of the presently disclosed subject matter.

BACKGROUND OF THE INVENTION

Normal hemostasis is a very delicately balanced system. When it functions as it should, the blood is maintained in a fluid state in the vasculature, yet rapidly clots when the need to seal an injury arrives. In the 1960s, two groups proposed a model for clot formation that envisaged a sequential series of steps in which activation of one clotting (coagulation) factor led to the activation of another, finally leading to a clot formation. When these coagulation factors by sequential activation cause formation of the clot, the counterpart system, called fibrinolytic system, is further activated to become a cause of dissolution (lysis) of the clot. This fibrinolytic system comprises of anti-clotting proteins (plasminogen activator, plasminogen and plasmin), which following sequential activation lead to lysis of the clot (Selighson U et al.).

The failure of hemostatic function due to coagulation factors deficiency causes impairment (or lack) in clot formation. Likewise, the result of an excessive fibrinolytic activity results in rapid and unwarranted dissolution of the formed clot. On the other hand, over stimulation of the coagulation cascade or inhibition of the fibrinolytic system would cause the formation of pathological clots. Thus, the outcome of the failure of each one of the above systems could be bleeding or increased coagulation tendency.

Replacement therapy is effective in treating bleeding disorders, however, this treatment may not be sufficient. Fresh-frozen plasma (FFP) is frequently transfused to bleeding patients or patients with prolongation of coagulation tests under the assumption that it will improve hemostasis and will correct and/or prevent bleeding. The effect of FFP on coagulation parameters such as prothrombin time (PT) and international normalized ratio (INR) was examined in a prospective audit performed at Massachusetts General Hospital (Abdel-Wahab O I et al.). The data showed that transfusion of FFP in this setting failed to correct the PT in 99% of patients and in only 15% of patients was INR corrected by at least halfway to normal. Similarly, Holland et al. reported that FFP failed to change INR over time. They hypothesized that failure of FFP to correct INR results from the dilution of the coagulation factors present in the infused FFP by recipient plasma. FFP contains all components (proteins) of the coagulation and fibrinolytic systems, thus being in theory suitable for the treatment of bleeding in patients with hereditary or acquired coagulation factor deficiencies. In addition, this product is supposed to prevent bleeding in subjects with coagulopathy before, during and after surgical procedures. However, since these plasma derived products contain in addition to coagulation factors fibrinolytic proteins, they have a potential to induce undesired lysis (dissolution) of the hemostatic clot formed during and following the replacement of coagulation factors of the product.

It therefore appears that to-date, there are limited solutions for the treatment of excessive bleeding. Over 192,000 patients die every year due to injury associated blood loss in the US (according to the National trauma institute). Massive blood loss is concomitant to trauma surgery, childbirth, Disseminated intravascular coagulation (DIC), gastrointestinal bleeding, etc. In all of these instances there is a need for an efficient plasma transfusion to stop the bleeding. However, recent studies have shown that plasma transfusion fails to halt massive bleeding while other treatments show low efficacy and increased mortality risk. Most of the treatment options are focused on coagulation enhancement, however, these treatments of massive bleeding result in insufficient outcome and in some cases death. In contrast, there are several treatments for hyperfibrinolysis that also contribute to massive bleeding. Hyperfibrinolysis occurs when fibrinolytic activity is potentially faster than fibrin formation such that clot integrity is threatened. Today, 57% of trauma patients and 60% of cirrhotic patients present hyperfibrinolysis, thus enhanced coagulation has poor outcome for these patients with no alternative treatment options. The presently disclosed subject-matter was developed to produce an innovative extracorporeal device that effectively and specifically extracts and removes plasma proteins responsible for hyperfibrinolysis. Using the medical device of the presently disclosed subject-matter, physician can improve transfused plasma and shift the hemostasis from hyperfibrinolysis to coagulation and subsequently preventing massive bleeding.

U.S. Pat. No. 3,998,946 discloses methods for treating blood plasma or related products with fumed colloidal silica to remove fibrinogen without polymerization to fibrin, plasminogen and plasmin and other compounds but retain coagulation factor II. As being devoid of fibrinogen, the resulting product cannot support clot formation and as such, cannot be used for the treatment of bleeding and hemostatic disorders.

U.S. Pat. No. 7,125,569, and its corresponding applications and patents disclose specific methods using a very particular resin for removal of only plasmin(ogen) from protein mixture/s. The resulting products were produced for the purpose of preparing plasmin(ogen) free fibrinogen for use as a biological glue. However, the resulting mixtures still contain Tissue plasminogen activator (tPA) and as such, clearly exhibit fibrinolytic activity. More specifically, the tPA present in the product activated the plasminogen in the treated area, thereby leading to cleavage of the newly formed fibrin net. Plasminogen is normally present at high concentrations in the blood (about 2 μM), therefore, any blood leakage during any surgical intervention increases the plasminogen concentration in the extra vascular area. Furthermore, in case such glue is applied on the injured blood vessels during surgical intervention, the tPA present in the biological glue may contact the plasminogen present in the blood and by that, may activate the fibrinolytic cascade. Thus, the plasminogen-free products disclosed in U.S. Pat. No. 7,125,569 may be used only for topical applications as a biological glue, and are irrelevant for systemic use in transfusion or for treating bleeding associated with fibrinolytic or thrombolytic therapy.

There is therefore need in the art for effective device and conjugates for depleting fibrinolytic proteins from mammalian body fluids, specifically, blood, plasma an any products thereof.

SUMMARY OF THE INVENTION

In accordance with a first aspect, the present disclosure provides a plurality of conjugates or a composition comprising the plurality of conjugates, each conjugate comprises a particle, at least one linker and at least one amino acid, derivative thereof or analog thereof, wherein the plurality of conjugates comprises at least two different conjugates. The amino acid or analog thereof may be at least one of 4-(aminomethyl)-cyclo-hexane-carboxylic acid (tranexamic acid), ε-amino caproic acid (also referred to herein as Aminocaproic acid) and lysine or any combinations thereof, whereas the amino acid derivative may be at least one of cyclohexanecarboxylic acid, 4-methyl-cyclohexanecarboxylic acid or any combinations thereof.

In accordance with some further aspects, the present disclosure provides a conjugate comprising at least one particle, at least one linker and at least one amino acid, derivative thereof or analog thereof. In some specific embodiments, the conjugate of the presently disclosed subject-matter may be any one of:

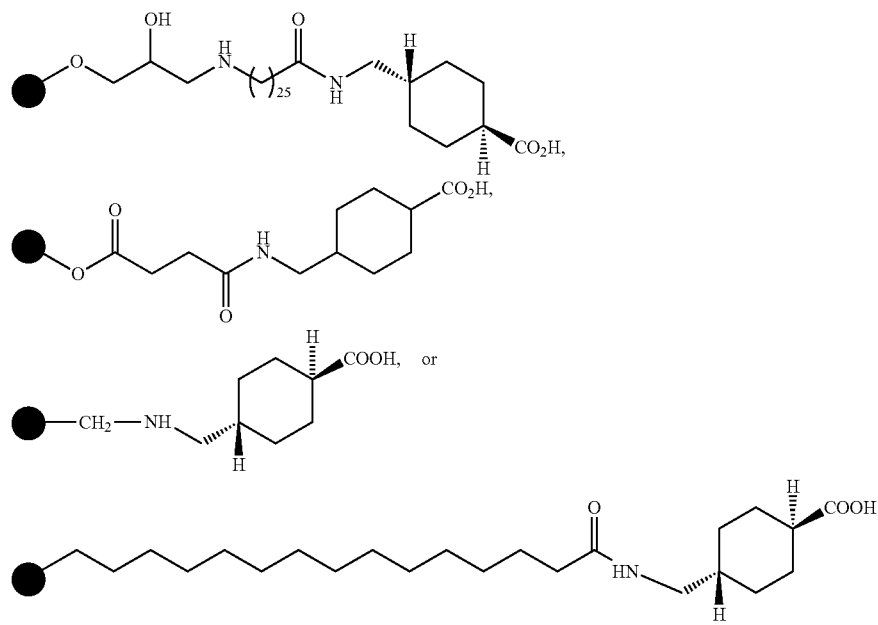

wherein

represents a particle.

In yet another aspect, the presently disclosed subject-matter provides a device for depleting at least one fibrinolytic protein from mammalian body fluid/s, comprising:
a housing having at least one fluid inlet port, and at least one fluid outlet port;
the housing including at least one chamber, said at least one chamber defining a control volume in fluid communication with the at least one fluid inlet port and the at least one fluid outlet port;
said control volume accommodating at least one of a plurality of conjugates or a composition comprising the plurality of conjugates as defined by the presently disclosed subject-matter and a conjugate as defined herein above.

According to another aspect of the presently disclosed subject matter, there is provided a device for depleting at least one fibrinolytic protein from mammalian body fluid/s, comprising:
a housing having at least one fluid inlet port, and at least one fluid outlet port;
the housing including at least one chamber, said at least one chamber defining a control volume in fluid communication with the at least one fluid inlet part and the at least one fluid outlet port;

said control volume accommodating a plurality of groups of particles, including at least a first group of first particles and a second group of second particles;

wherein said first particles are dimensionally different from said second particles;

wherein at least one of said first particles and said second particles are conjugated particles, being conjugated with amino acid, a derivative thereof or analog thereof, wherein said amino acid or analog thereof is at least one of 4-(aminomethyl)-cyclo-hexane-carboxylic acid (tranexamic acid), $\epsilon$-amino caproic acid and lysine and said amino acid derivative thereof is cyclohexanecarboxylic acid, 4-methyl-cyclohexanecarboxylic acid or any combinations thereof.

For example, said first particles and said second particles are conjugated particles, each conjugated particle being conjugated with amino acid, a derivative thereof or analog thereof, wherein each said amino acid or analog thereof is at least one of 4-(aminomethyl)-cyclo-hexane-carboxylic acid (tranexamic acid), $\epsilon$-amino caproic acid and lysine and said amino acid derivative thereof is cyclohexanecarboxylic acid, 4-methyl-cyclohexanecarboxylic acid or any combinations thereof.

Additionally, and/or alternatively, for example, said first particles and said second particles are TXA conjugated particles, specifically, cyclohexanecarboxylic acid conjugated particles, 4-methyl-cyclohexanecarboxylic acid conjugated particles or any combination thereof. Still additionally, for example, said first particles and said second particles are TXA conjugated particles.

As used herein the term conjugated particles refers to particles conjugated to an amino acid, a derivative thereof or analog thereof, via a linker.

Additionally, or alternatively, for example, said conjugated particles are defined by the plurality of conjugates or compositions defined herein above.

Additionally, or alternatively, for example, said housing comprises a longitudinal axis, and comprises a main body portion, and a pair of end caps, including an inlet end cap having said at least one fluid inlet port, and an outlet end cap having said at least one fluid outlet port.

For example, said control volume is defined by corresponding barrier members provided at opposite longitudinal ends of the main body portion.

For example, said barrier members are configured for preventing said particles from exiting said control volume.

For example, said barrier members are configured for concurrently permitting the through-flow of the mammalian body fluid/s through the control volume, or, said barrier members are configured for concurrently permitting the through-flow of the mammalian body fluid/s through the control volume, wherein in use of the device, the mammalian body fluid/s enter the control volume via the inlet end cap and the fluid inlet port, and subsequent to exiting the control volume, flow via the outlet end cap and the fluid outlet port.

Additionally, or alternatively, for example, said barrier members each comprises a plurality of openings for allowing through-flow of the mammalian body fluid/s through the openings, the openings being of a size smaller than said particles.

In further aspects, the presently disclosed subject-matter relates to a battery for use in depleting at least one fibrinolytic protein from mammalian body fluid/s, comprising a plurality of devices, wherein each device is as defined by the presently disclosed subject-matter. The devices of the plurality of devices are interconnected in a manner to provide fluid communication between the respective said control volumes of said plurality of devices.

Another aspect of the presently disclosed subject-matter relates to a kit for depleting at least one fibrinolytic protein from mammalian body fluid/s, comprising:

at least one device as defined by the presently disclosed subject-matter, a saline reservoir in selective fluid communication with said at least one inlet port;

an acceptor plasma reservoir and a wash waste reservoir, wherein said acceptor plasma reservoir and said wash waste reservoir are in selective and non-concurrent fluid communication with said at least one fluid outlet port.

In yet another aspect the presently disclosed subject-matter provides a system for depleting at least one fibrinolytic protein from mammalian body fluid/s, comprising:

at least one device as defined by the presently disclosed subject-matter, a saline reservoir and a donor reservoir, wherein said saline reservoir and said donor reservoir are in selective and non-concurrent fluid communication with said at least one fluid inlet port;

an acceptor plasma reservoir and a wash waste reservoir, wherein said acceptor plasma reservoir and said wash waste reservoir are in selective and non-concurrent fluid communication with said at least one fluid outlet port.

Thus, in yet another aspect, the presently disclosed subject-matter relates to a method for depleting at least one fibrinolytic protein from mammalian body fluids or any products thereof. More specifically, the method comprising the steps of: (i) subjecting said body fluid/s to affinity-depletion procedure specific for the at least one fibrinolytic protein/s; and (ii) recovering the at least one fibrinolytic protein-depleted body fluid obtained in step (i). It should be note that affinity-depletion procedure may comprise contacting the body fluid with an effective amount of a plurality of conjugates or of at least one composition comprising the plurality of conjugates. Alternatively, the body fluid may be applied on a device latter, kit or system comprising the plurality of conjugates or any composition thereof. In some embodiments, each conjugate comprises at least one particle, at least one linker and at least one amino acid, derivative thereof or analog thereof. In some specific embodiments, the plurality of conjugates comprises at least two different conjugates, and wherein said amino acid, derivative thereof or analog thereof is at least one of 4-(aminomethyl)-cyclo-hexane-carboxylic acid (tranexamic acid), $\epsilon$-amino caproic acid lysine, cyclohexanecarboxylic acid and 4-methyl-cyclohexanecarboxylic acid. In some further specific embodiments, the plurality of conjugates comprises at least two different conjugates, and wherein said amino acid, derivative thereof or analog thereof is at least one of 4-(aminomethyl)-cyclo-hexane-carboxylic acid (tranexamic acid), $\epsilon$-amino caproic acid and lysine.

In yet another aspect, the presently disclosed subject-matter provides a method for the treatment, prevention, prophylaxis, amelioration, inhibition of bleeding, hemostatic disorders and any bleeding or pathologic condition associated therewith in a subject in need thereof. More specifically, the method may comprise the step of administering to the treated subject a therapeutically effective amount of at least one blood and/or blood-derived product that has a reduced fibrinolytic activity. In some embodiments the product may be prepared by the method as described herein.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

Schematic representation of the chemical reaction for the preparation of Conjugate 2.

Figure 2:
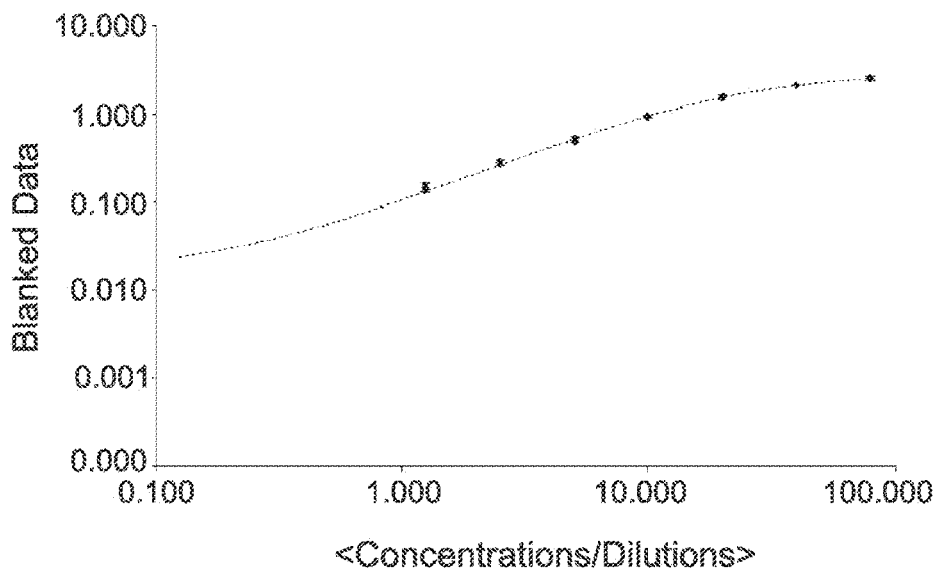

FIG. 2: Plasminogen (PLG) standard curve

Graph representing a standard curve for calculation of PLC concentration.

Figure 3:
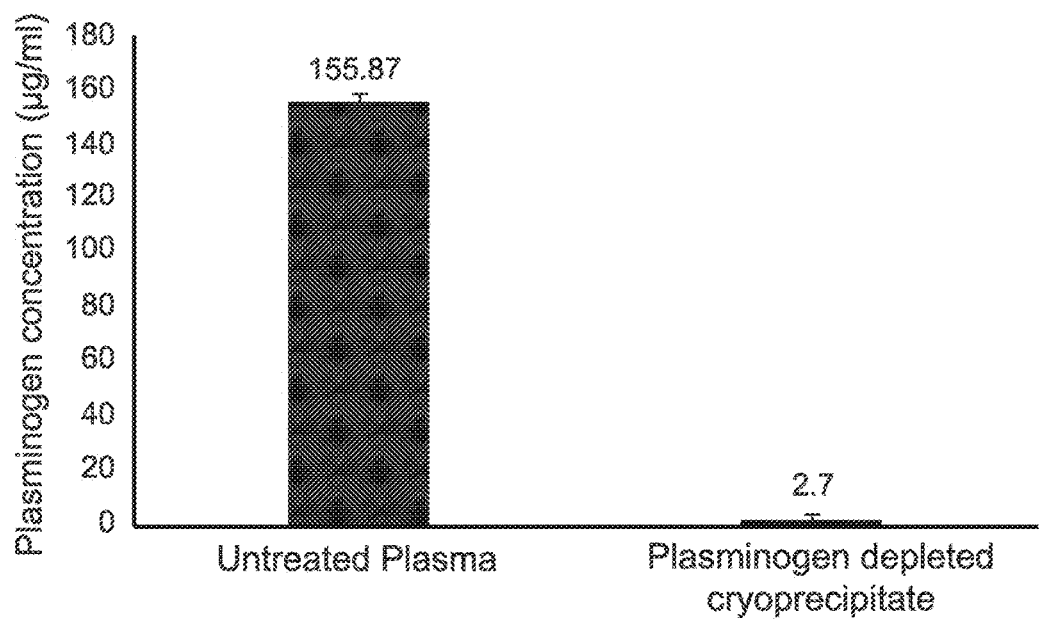

FIG. 3: Plasminogen depleted cryoprecipitate

Graph representing the concentration of plasminogen into untreated cryoprecipitate versus cryoprecipitate that was filtrated using ClearPlasma.

Figure 4:
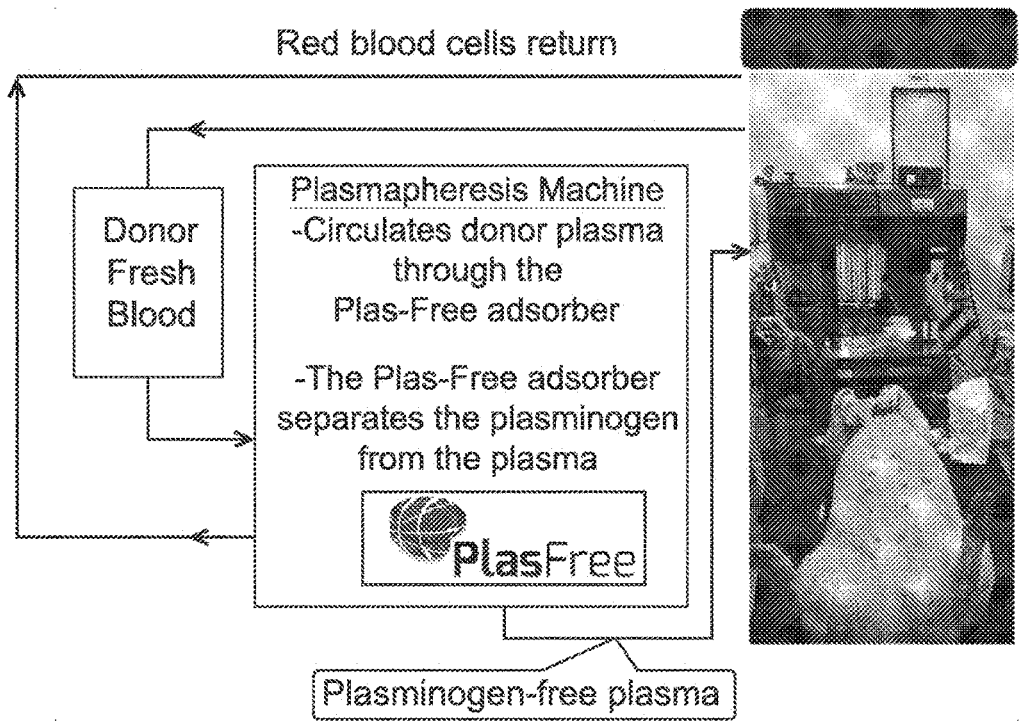

FIG. 4: Plasma filtration by ClearPlasma with conjugate 1 ("[TXA conjugated to Agarose 4% beads]")

Schematic diagram demonstrating the blood flow and separation for plasma and red blood cells. In addition, the schema demonstrates the use of ClearPlasma generating plasminogen depleted plasma having reduced tPA levels.

Figure 5:
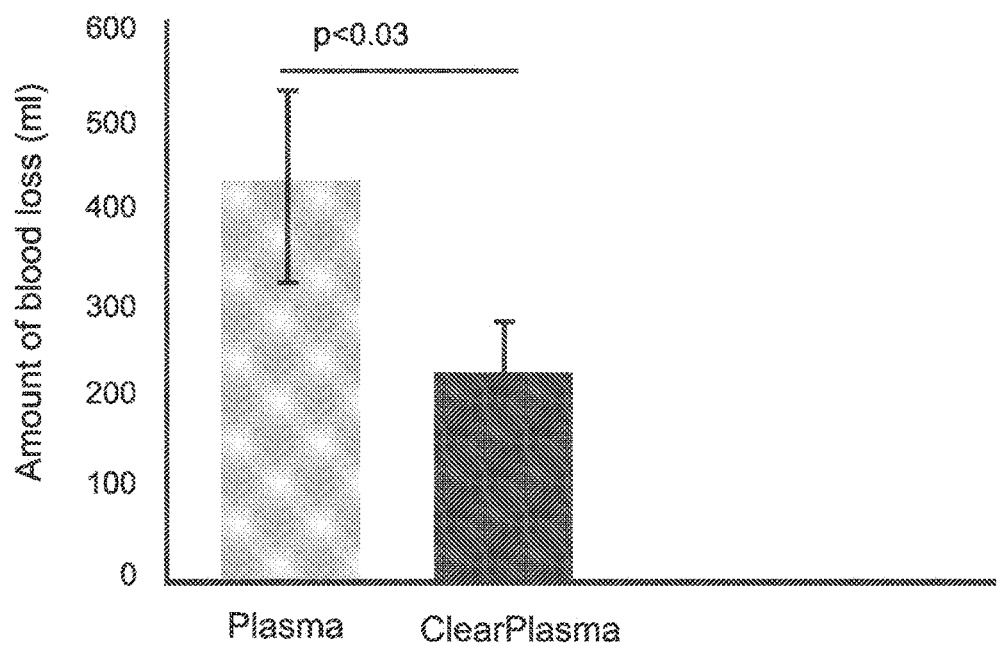

FIG. 5: The use of ClearPlasma reduces blood loss in liver injury of pigs

Histogram demonstrating the amount of blood loss as manifested during 30 min after liver laceration. Statistics were computed using student t-test (Two tailed distribution equal variance). Data is expressed as the Mean±SD. Values of $P<0.05$ were considered significant.

FIG. 6A-6L: ClearPlasma with conjugate 1 ("TXA conjugated to Agarose 4% Superflow beads") abolishes fibrinolytic activity Pigs underwent plasmapheresis, plasma was treated using ClearPlasma or untreated. Coagulation and fibrinolysis of resultant pigs' whole blood was evaluated by TEG.

Figure 6A:
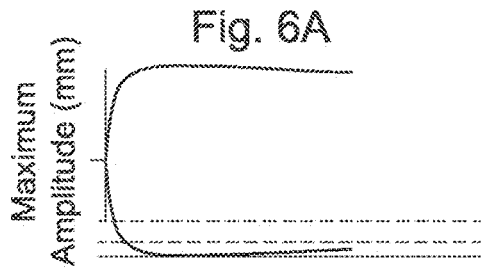
Figure 6B:

FIG. 6A: Coagulation of blood obtained from control pigs before anesthesia,

FIG. 6B: Blood from control pigs with 0.083 μM Wt-tPA before anesthesia

Figure 6C:
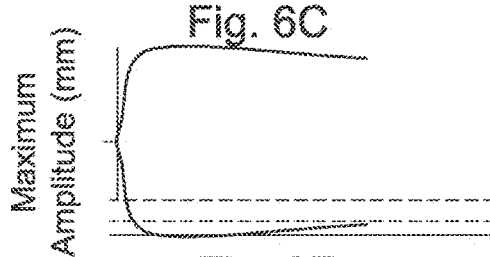

FIG. 6C: Blood of control pig after anesthesia.

Figure 6D:
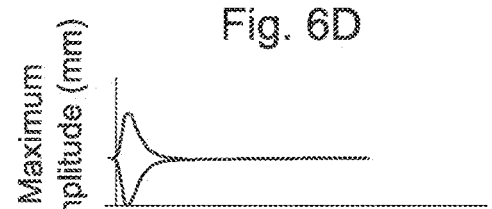

FIG. 6D: Blood of control pigs with 0.083 μM Wt-tPA after anesthesia.

Figure 6E:
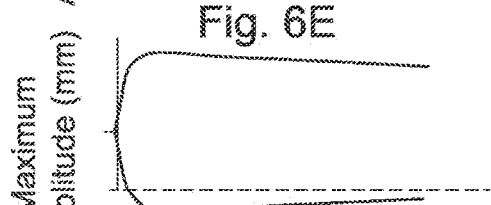

FIG. 6E: Blood of control pigs before plasmapheresis and plasminogen depletion.

Figure 6F:
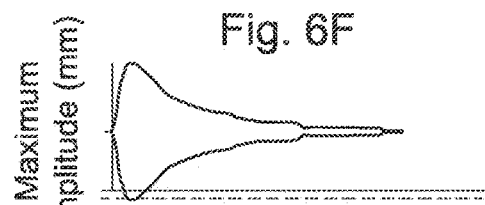

FIG. 6F: Blood of pigs before plasmapheresis and plasminogen depletion with 0.083 μM Wt-tPA.

Figure 6G:
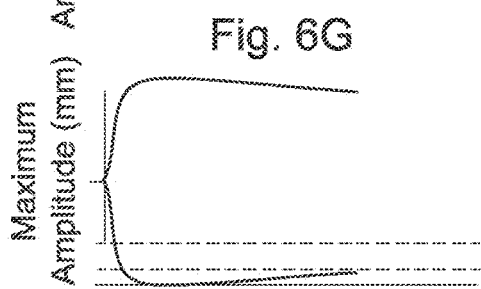

FIG. 6G: Blood of pigs before plasmapheresis.

Figure 6H:
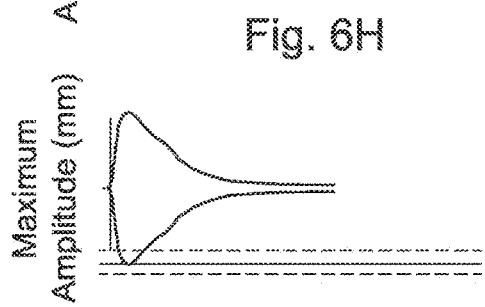

FIG. 6H: Blood of pigs before plasmapheresis with 0.083 μM Wt-tPA.

Figure 6I:
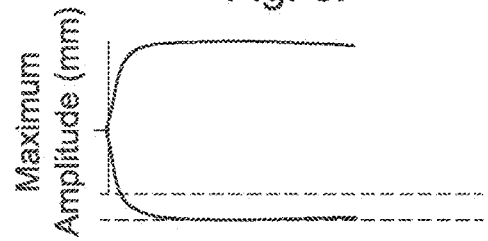

FIG. 6I: Blood of control pigs after plasmapheresis and plasminogen depletion.

Figure 6J:
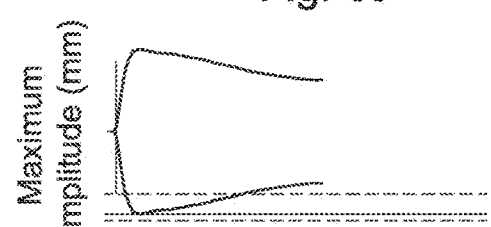
Figure 6K:
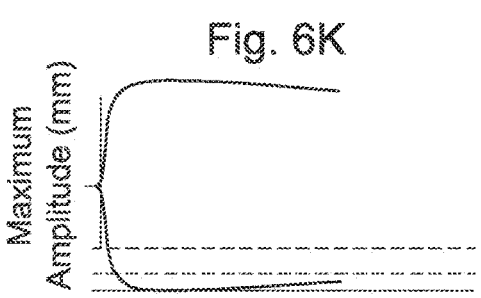

FIG. 6J: Blood of pigs after plasmapheresis and plasminogen depletion with 0.083 μM Wt-tPA FIG. 6K: Blood of pigs after plasmapheresis control.

Figure 6L:
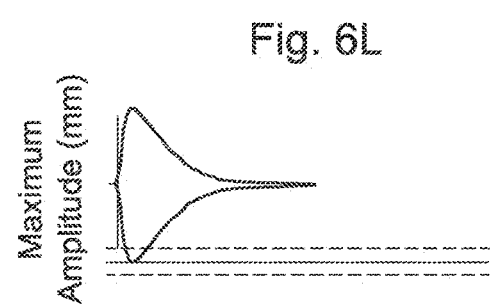

FIG. 6L: Blood of pigs after plasmapheresis with 0.083 μM Wt-tPA

FIG. 7A-7F: TEG analysis—ClearPlasma abolishes fibrinolytic activity in human plasma Coagulation and fibrinolysis of Fresh frozen plasma flow through ClearPlasma (denoted by PDP) were compared to coagulation and fibrinolysis of untreated plasma (as denoted by FFP) by thromboelastography (TEG).

Figure 7A:
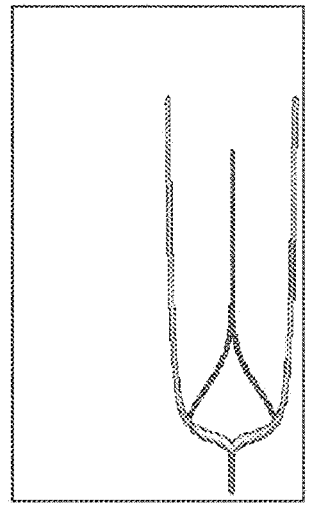

FIG. 7A: FFP demonstrates clot formation without additional treatment.

Figure 7B:
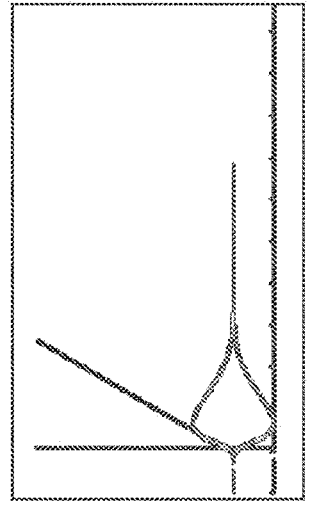

FIG. 7B: Addition of tissue plasminogen activator (tPA-1.85 nM) generates clot disassembly.

Figure 7C:
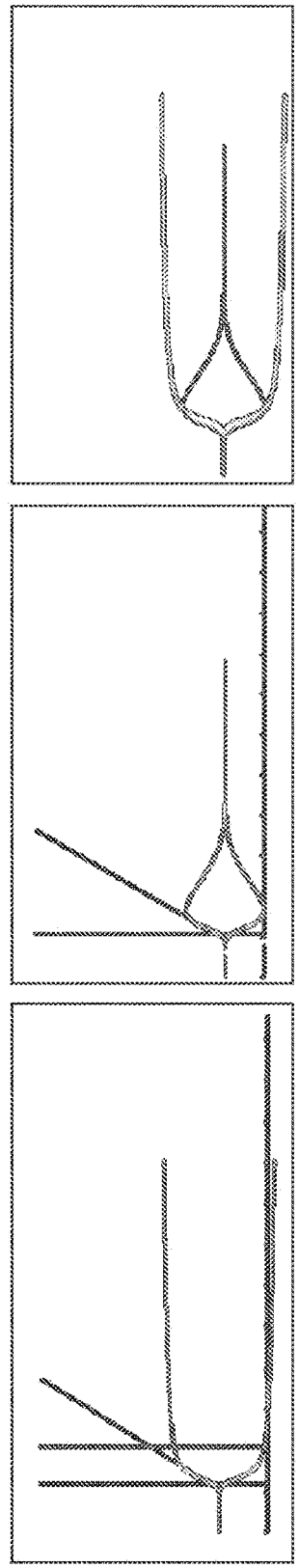

FIG. 7C: Overlay of FIGS. 7A and 7B.

Figure 7D:

FIG. 7D: Plasminogen depleted plasma (PDP) demonstrates clot formation without additional treatment.

Figure 7E:
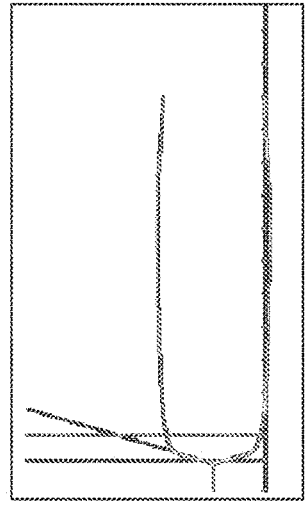

FIG. 7E: Addition of tissue plasminogen activator (tPA-1.85 nM) did not generates clot disassembly.

Figure 7F:
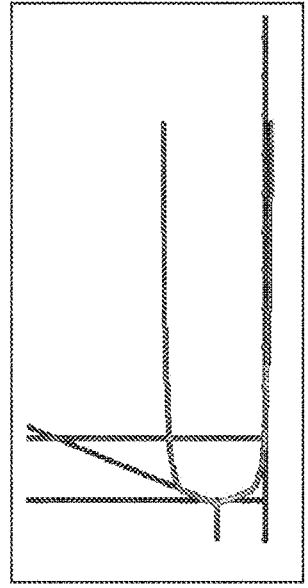

FIG. 7F: Overlay of FIGS. 7D and 7E.

The Data shows a representative experiment (from three independent experiments).

Figure 8:
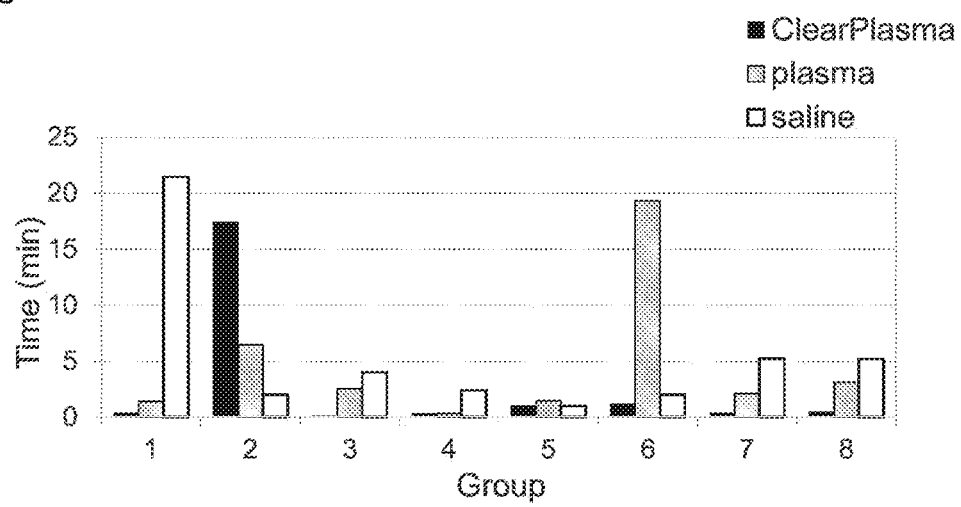

FIG. 8: Bleeding time after tail snipping in mice

Graph showing the time of bleeding of individual mouse (numbered 1 to 8) after tail snipping treated either with ClearPlasma, plasma or saline.

Figure 9:
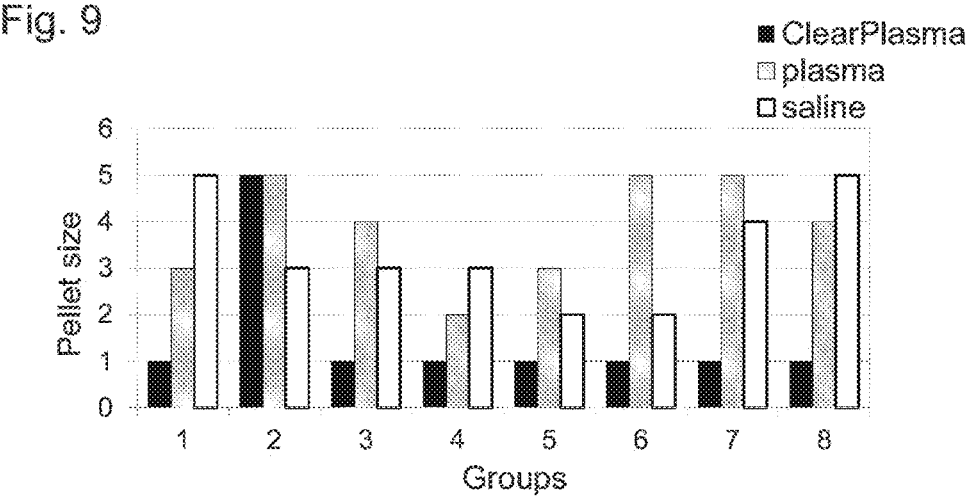

FIG. 9: Pellet size results for each mouse (at 24 hours)

Graph showing the pellet size of individual mouse (numbered 1 to 8) after tail snipping treated either with ClearPlasma, plasma or saline.

Figure 10:
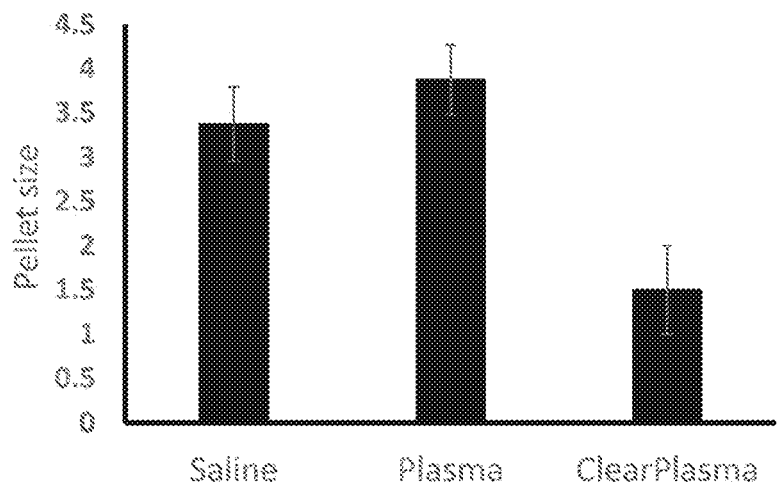

FIG. 10: Bleeding test after tail snipping in mice

Pellet size results: blood cell pellet from the bleeding test was centrifuged and the supernatant was aspirated. Pellet size was then measured using a ruler. Statistical analysis of pellet size measurement was performed using One-way ANOVA followed by posthoc LSD/SCHELF($p<0.05$ considered significant)

Figure 11A:
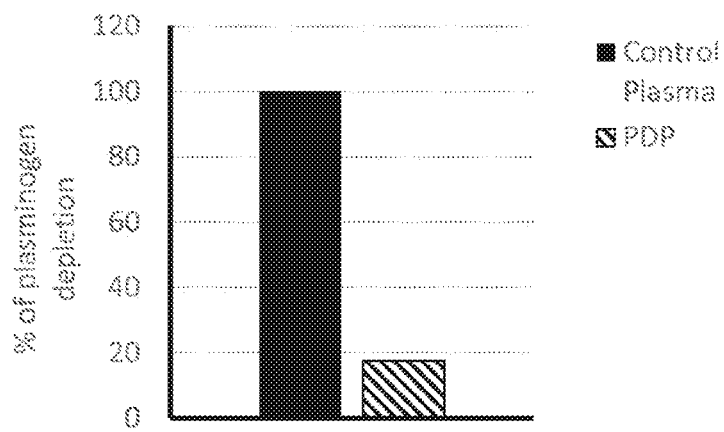
Figure 11B:
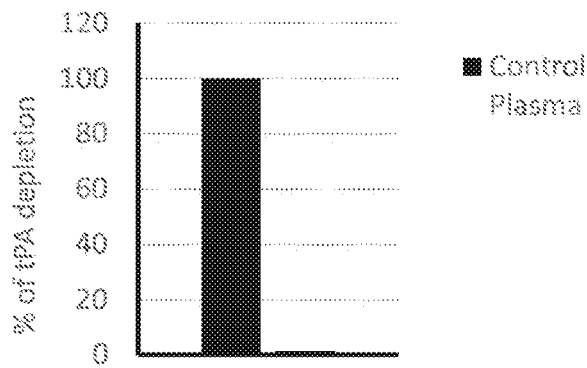

FIG. 11A-11B: ClearPlasma reduces both plasminogen and tPA protein levels in pigs Females pig underwent plasmapheresis using Haemonetics mcs+ system under anesthesia. Both procedures were similarly conducted (amount of blood filtrated, anticoagulant treated, time and amount of plasma collected).

FIG. 11A: Graph representing plasminogen depletion in samples of plasma from pigs that were filtered with ClearPlasma (as denoted by PDP) in comparison with unfiltered control plasma.

FIG. 11B: Graph representing tPA depletion in samples of plasma from pigs that were filtered with ClearPlasma (as denoted by PDP) in comparison with unfiltered control plasma. Representative results from four independent experiments.

Figure 12:
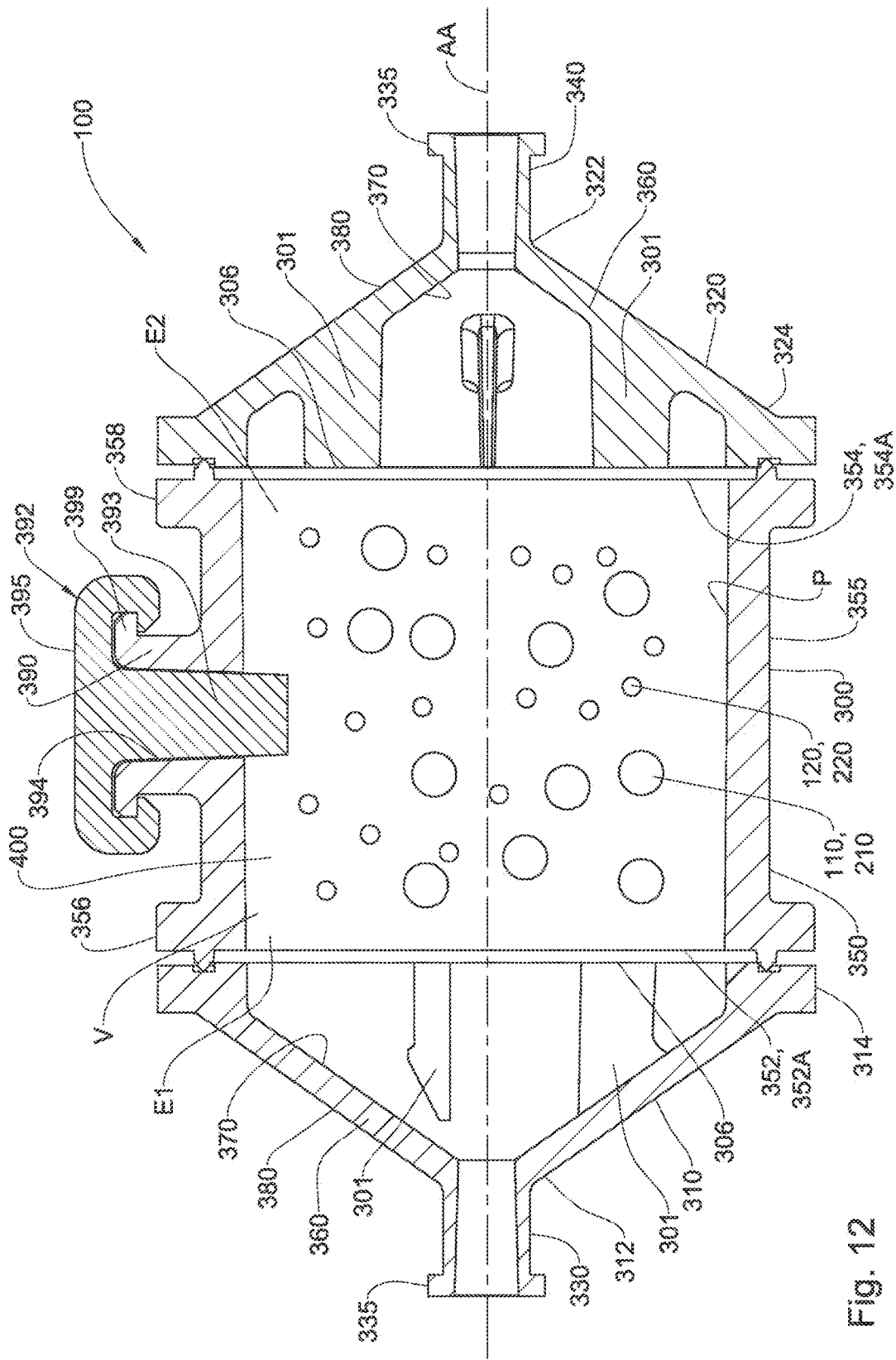

FIG. 12: The device shows in transverse cross-sectional sideview a device according to a first example of the presently disclosed subject matter.

FIG. 12A: shows in exploded isometric view the device according to an alternative variation of the example of FIG. 12.

FIG. 12B: shows in cross-sectional detail side view a portion of the device according to an alternative variation of the example of FIG. 12.

FIG. 13A-13D: The device

FIG. 13A: shows in top view a main body portion of the device according to the example of FIG. 12.

FIG. 13B: shows in side view the main body of the device according to the example of FIG. 13A.

FIG. 13C: shows in cross-sectional side view the main body portion of the device according to the example of FIG. 13B, taken along A-A.

FIG. 13D: shows in cross-sectional detail side view a portion of the device according to the example of FIG. 13C at "G".

FIG. 14A-14D: The end cap of the device

FIG. 14A: shows in top view an end cap of the device according to the example of FIG. 2.

FIG. 14B: shows in side view the end cap of the device according to the example of FIG. 14A.

FIG. 14C. shows in cross-sectional side view the end cap of the device according to the example of FIG. 14B, taken along A-A.

FIG. 14D: shows in cross-sectional detail side view a portion of the device according to the example of FIG. 14C at "G".

Figure 15:
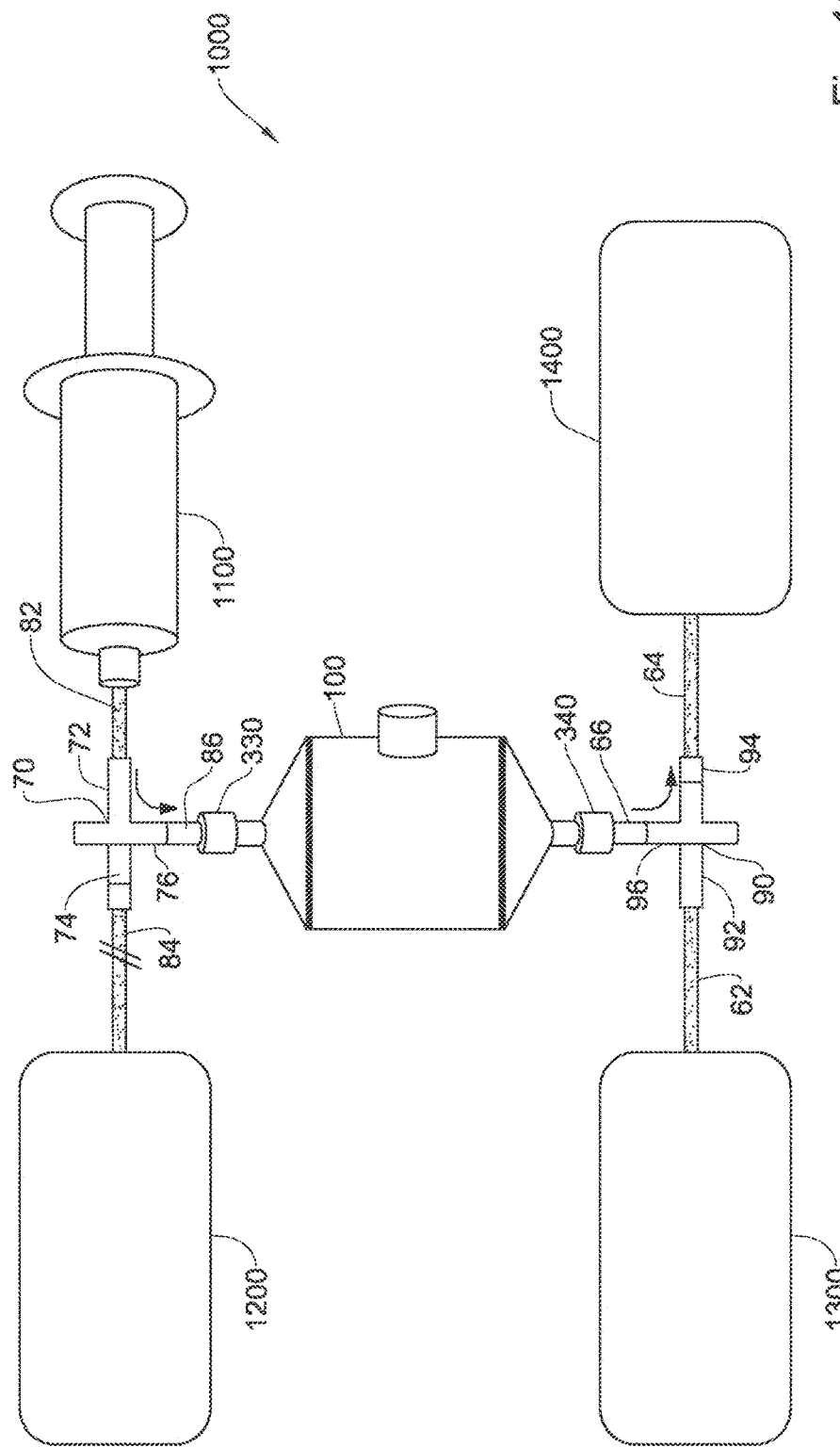

FIG. 15 The system Schematically illustrates a system according to an example of the presently disclosed subject matter, the system being in wash configuration.

Figure 16:
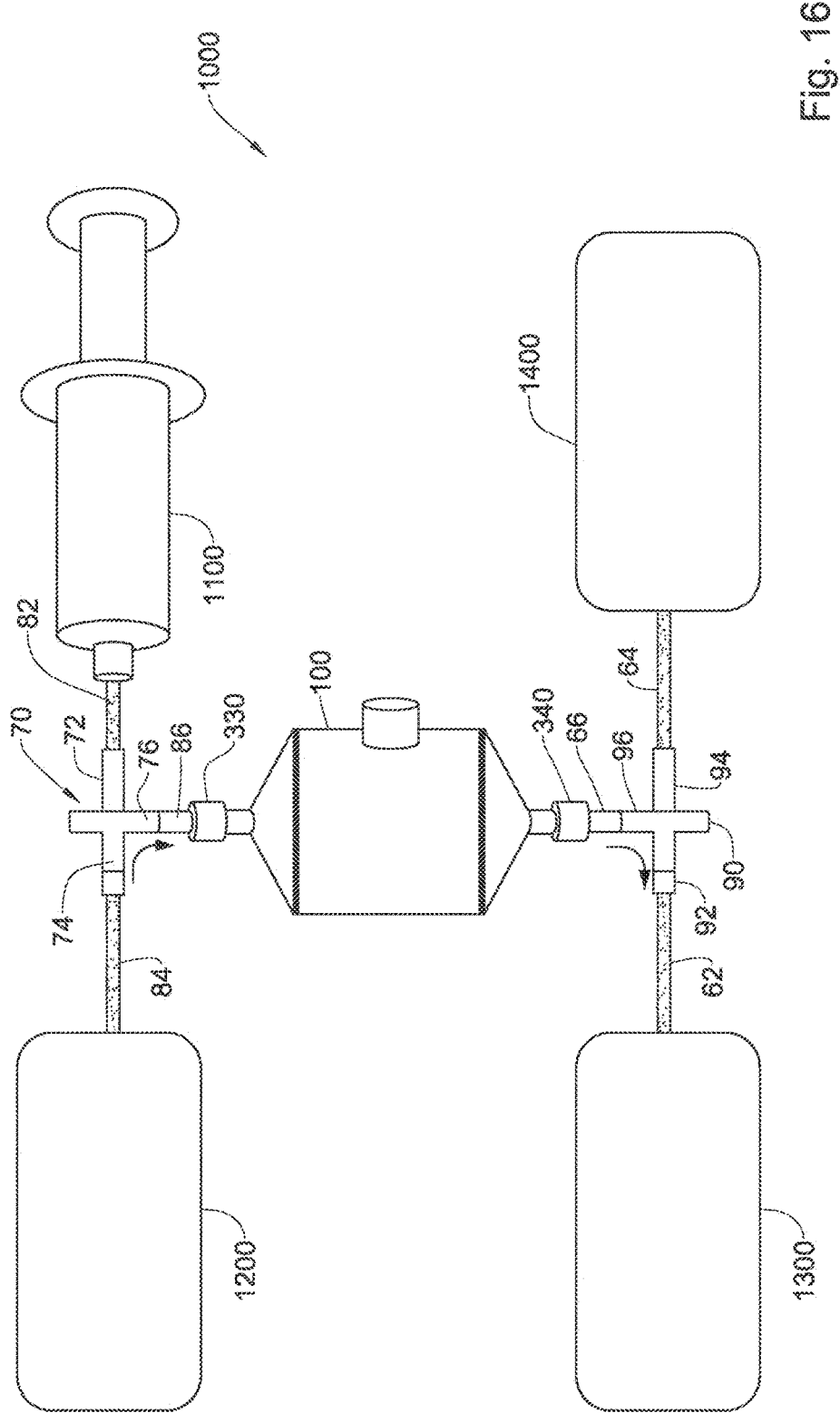

FIG. 16 The system schematically illustrates the system according to the example of FIG. 15, the system being in treatment configuration.

Figure 17:
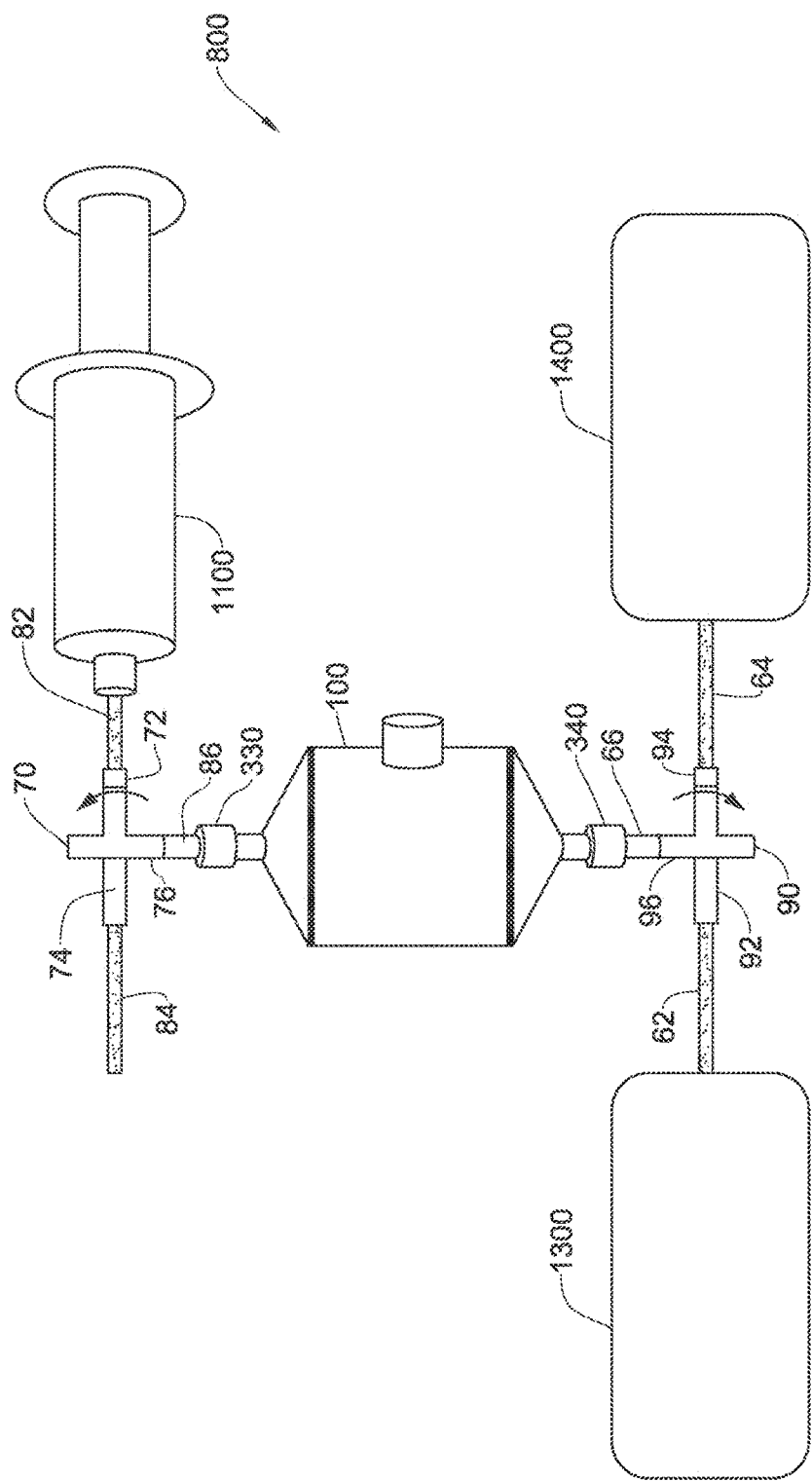

FIG. 17 The kit schematically illustrates a kit corresponding to the system according to the example of FIG. 15.

Figure 18:
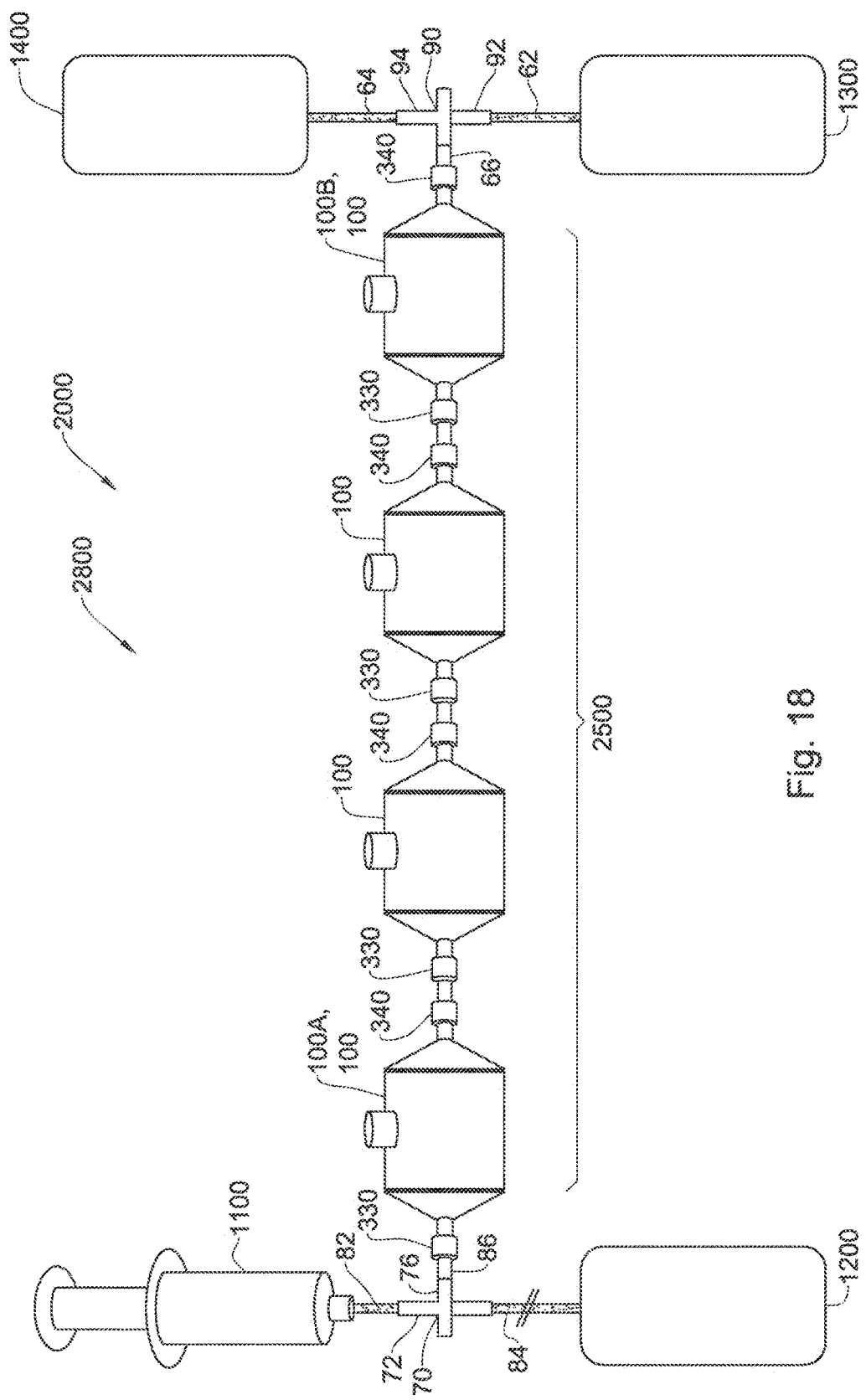

FIG. 18. The system Schematically illustrates a system according to another example of the presently disclosed subject matter, the system including a battery of devices.

Figure 19:
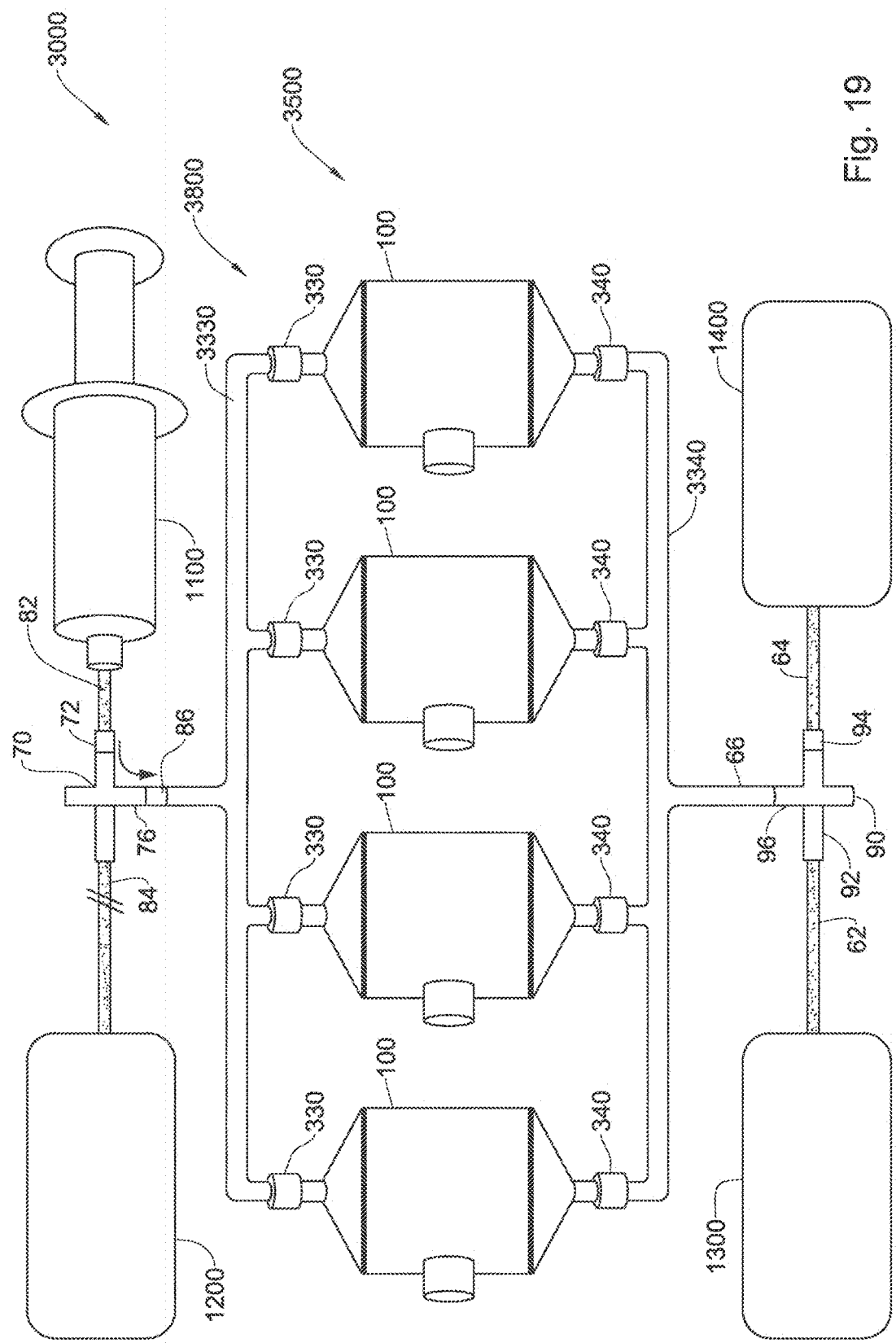

FIG. 19 The system Schematically illustrates a system according to another example of the presently disclosed subject matter, the system including a battery of devices.

DETAILED DESCRIPTION OF THE INVENTION

The present disclosure provides, in accordance to its broadest aspect, a plurality of conjugates or a composition comprising the plurality of conjugates, each conjugate is of a general Formula (I)

  (I)

wherein
X is a solid support moiety, for example a particle;
Y is a chemically reactive moiety linking moieties X and Z;
Z is a moiety comprising at least one of, an amino acid, a derivative thereof or analog thereof; and
wherein each "—" designates an interaction/association, for example a chemical bond containing optionally one or multiple intervening atoms that serve as spacers or as selectivity directing moieties.

The term amino acid as used herein refers to a compound (e.g., an organic compound) containing an amine (—NH2) and carboxyl (—COOH) groups, and encompasses any derivative thereof or any analog thereof, as detailed herein. The term "moiety" in the context of the disclosure may refer to an atom, a group of atoms and any functional fragment of a molecule which functions as recited herein. The moiety may also be in the form of a physical element such as a capsules, spheres, nanoparticles, liposomes etc. of at least one material (i.e. of a single atom or multiple atoms) which functions as recited herein.

"Amino acid analog" is a compound that has the same chemical structure (also referred to herein as structural analog) as naturally occurring amino acid, i.e., a carboxyl group and an amino group, or an R group. Examples include homoserine, norleucine, methionine sulfoxide, methionine methyl sulfonium. In yet some further embodiments, the term Amino acid analog also encompasses functional analogs, specifically, molecules performing the same biological function. A non-limiting example for such functional analog of an amino acid, for example, lysine, is tranexamic acid (TXA) that serves as a functional analog to lysine, thereby functioning as an antifibrinolytic agent by reversibly binding four to five lysine receptor sites on plasminogen.

"Amino acid derivative" as used herein, is a compound that comprises at least a fragment (part, portion) of an amino acid or any analog (structural and/or functional) thereof, for example lacking at least the amino group. In a specific example, the amino acid derivative comprises a cyclohexanecarboxylic acid fragment of an amino acid or analog thereof, i.e. lacking the amino group.

The amino acid, derivative thereof or an analog thereof may be in accordance with some embodiments, at least one of 4-(aminoethyl)-cyclo-hexane-carboxylic acid (tranexamic acid), ε-amino caproic acid, lysine, cyclohexanecarboxylic acid, 4-methyl-cyclohexanecarboxylic acid or any combinations thereof.

In accordance with a first aspect, the present disclosure provides a plurality of conjugates or a composition comprising the plurality of conjugates, each conjugate comprises a particle, at least one linker and at least one amino acid, a derivative thereof or analog thereof. In some embodiments, the plurality of conjugates comprises at least two different conjugates. Still further, in some embodiments, the amino acid, a derivative thereof or analog thereof may be at least one of 4-(aminomethyl)-cyclo-hexane-carboxylic acid (tranexamic acid), ε-amino caproic acid, lysine, cyclohexanecarboxylic acid and 4-methyl-cyclohexanecarboxylic acid or any combinations thereof. Still further, in some embodiments, the amino acid, a derivative thereof or analog thereof may be at least one of 4-(aminomethyl)-cyclo-hexane-carboxylic acid (tranexamic acid), ε-amino caproic acid and lysine, or any combinations thereof. In yet some embodiments, the amino acid, a derivative thereof or analog thereof may be tranexamic acid (TXA).

A conjugate as used herein refers to a compound constructed from several elements (components), including at least one particle, at least one linker and at least one an amino acid, a derivative thereof or an analog thereof which are all associated thereto. It should be noted that while the application refers to a "at least one particle", any solid support being applicable for the claimed plurality of conjugate is encompassed herein.

Any one of the conjugates of the presently disclosed subject-matter or any compositions thereof, may also be referred to as a composition of matter. In most general terms, a "composition of matter" similarly to a "conjugate", both used interchangeably, refers to the association of the at least one particle, the at least one linker and the at least one amino acid, derivative thereof or analog thereof, that as detailed below produces properties which may be attributed to the composition of matter (or conjugate) as a whole and not to any one of conjugate's components in their separate state.

In some embodiments, any one of the conjugates of the presently disclosed subject-matter encompasses an association of the at least one particle with the at least one chemically reactive moiety being a linker and the association of the at least one linker with the at least one amino acid, derivative thereof or an analog thereof such that the linker is positioned between the particle and the amino acid, derivative thereof or an analog thereof and hence being associated at one end (at one arm) to the particle and at another end (at a second different arm) to the amino acid, derivative thereof or an analog thereof.

As used herein, the term "association" or any linguistic variation thereof refers to the chemical or physical force which holds two entities together (e.g. the particle and the linker). Such force may be any type of chemical or physical bonding interaction known to a person skilled in the art. Non-limiting examples of such association interactions are covalent bonding, ionic bonding, coordination bonding, complexation, hydrogen bonding, van der Waals bonding, hydrophobicity-hydrophilicity interactions, etc. Thus, the association/conjugation of the linker with the at least one particle and of the linker with the amino acid may be via any chemical bonding, including covalent bonding, electrostatic interaction, acid base interaction, van der Waals interaction, etc. As appreciated, the association of the particle and the linker and the association of the linker with the amino acid, a derivative thereof or an analog thereof may be the same or may be different as further detailed below.

For example and as detailed below, for an amino acid derivative being cyclohexanecarboxylic acid or 4-methyl-cyclohexanecarboxylic acid (i.e. lacking at least the $NH_2$ group (amino group) of an amino acid analog), the linker may comprise an amino group (alone or hound to a methylene group, namely being $-NH_2-CH_2-$, "—" is a covalent bond). In an alternative example, for an amino acid or analog thereof (i.e. comprising the $NH_2$ group (amino group) of an amino acid), the linker may not comprise an amino group (alone or bound to a methylene group, namely being $-NH_2-CH_2-$, "—" is a covalent bond).

As indicated above, the plurality of conjugates may be provided by the presently disclosed subject-matter in a composition. The composition as used herein comprises a plurality of conjugates including at least two different conjugates. Different conjugates are to be understood as being different in at least one parameter. More specifically, as being different variations of conjugates in at least one parameter or property of at least one of the conjugate components, e.g. particle, linker, amino acid, a derivative thereof or an analog thereof at times in at least two of the conjugate components and at times in at least three of the conjugate components. Thus, the at least two different conjugates of the plurality of conjugates or compositions thereof, may comprise different particles and/or different linkers and/or different amino acids, a derivative thereof or an analog thereof. In other words, the conjugates referred herein as "different conjugates" comprise the conjugate components, e.g. particle, linker, amino acid such that at least one, at least two or all three components are not identical (e.g. are different).

In some embodiments the at least two different conjugates comprise different particles.

In some embodiments the at least two different conjugates comprise different linkers.

In some embodiments the at least two different conjugates comprise different amino acids, derivative thereof or analog thereof.

In some embodiments the at least two different conjugates comprise identical particles, identical linkers and different amino acids, derivative thereof or analog thereof.

In some other embodiments the at least two different conjugates comprise identical particles, different linkers and identical amino acids, derivative thereof or analog thereof.

In some other embodiments the at least two different conjugates may comprise different particles, identical linkers and identical amino acids, derivative thereof or analog thereof.

In some embodiments the at least two different conjugates comprise different particles and different linkers. In some embodiments the at least two different conjugates comprise different particles, different linkers and identical amino acids, derivative thereof or analog thereof.

In some embodiments the at least two different conjugates comprise different particles and different amino acids, derivative thereof or analog thereof. In some embodiments the at least two different conjugates comprise different particles, different amino acids, derivative thereof or analog thereof and identical linkers.

In some embodiments the at least two different conjugates comprise different linkers and different amino acids, derivative thereof or analog thereof. In some embodiments the at least two different conjugates comprise different linkers, different amino acids, derivative thereof or analog thereof and identical particles.

In some embodiments the at least two different conjugates comprise different particles, different linkers and different amino acids, derivative thereof or analog thereof.

The term different linker should be understood such that the difference may be in the linker properties such as the chemical formula of the linker.

As noted above, the plurality of conjugates or any compositions thereof as provided by the presently disclosed subject-matter may comprise at least two different conjugates, at least three different conjugates, at least four, at least five, at least six, at least seven at least eight, at least ten different conjugates, at least 11, 12, 13, 14, 15, 16, 17, 18, 19, 20, 25, 30, 40, 45, 50, 55, 60, 65, 70, 75, 80, 85, 90, 95, 100 or more different conjugates.

Still further, when referring to different conjugates, it should be understood such that the difference may be in at least one feature (characteristics, parameters) of the conjugate or any component thereof (e.g. particle, linker and amino acid), for example size, chemical composition, shape, structure, density, conductivity, solubility, material etc. For example, at least one of particles, linkers or amino acids that differ in at least one of size and/or different compositions and/or different shapes and/or different structure are considered different particles.

It was surprisingly found that a plurality of conjugates comprising at least two different conjugates or composition comprising at least two different conjugates as described herein is effective in depletion of fibrinolytic proteins such as plasminogen, plasmin and/or tPA from body fluids, specifically, blood, plasma and any blood product.

In some embodiments, the plurality of conjugates comprises particles having an average particle size of between about 10 μm or less, to about 500 μm or more. Specifically, μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 250 μm, 300 μm, 350 μm, 400 μm, 450 μm, 500 μm or more. In some specific embodiments, he plurality of conjugates comprise particles having an average particle size of at least 70 μm or less, at times at least 80 μm, at times at least 90 μm, at times at least 100 μm, at times at least 110 μm, at times at least 120 μm, at times at least 130 μm, at times at least 140 μm, at times at least 150 μm, In some embodiments, the plurality of conjugates have an average particle size of between about 90 μm to about 150 μm or more.

The term "average size" or "average diameter" or "mean size" refers to the arithmetic mean of measured diameters, wherein the diameters range ±25% of the mean. The mean size of the particles can be measured by any method known in the art.

In some embodiments, the plurality of conjugates comprise at least two different particles having different average size. It should be noted that without being bound by theory, using two or more different sizes of particles (e.g. beads) has the advantage of maximization of surface area, so the body fluid, plasma, runs mostly on the surface of the beads, with little dead space. As many there are different sizes of beads, the less free space is in the resin bed.

On the other hand, packing the resin tightly with little way for the plasma to flow means lower flow rate.

More specifically, the inventors surprisingly found that mixture of different size of particles may improve the micro fluidity and expose more plasma to the conjugate (resin) while maintaining the same flow rate. Moreover, mixing at conjugates of at least two particle size may reduce the amount of beads thereby minimizing costs of the conjugate used. In some embodiments, the conjugates of the presently disclosed subject-matter may form a resin comprising conjugate using at least two groups of particles having different size, in some particular embodiments, particles may be present at a ratio of between about 0.001:1 to about 1:10000, more specifically, between about 0.01:1 to 1:10000, between about 1:1 to 1:1000. In yet some further embodiment the ratio may be 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000. More specifically, the particles of the plurality of conjugates or compositions thereof in accordance with the presently disclosed subject-matter may be of at least two different sizes presented in some embodiments at a ratio of between about 1:1 to 1:10, specifically, 1:4. In some embodiments, the plurality of conjugates of the presently disclosed subject-matter, also referred to herein as the resin of the presently disclosed subject-matter, may comprise a mixture of different conjugates of particles having an average size of about 90 μm or less, and particles having an average size of 1.50 μm or more. In yet some further specific embodiments, the plurality of conjugates or compositions of the presently disclosed subject-matter may comprise conjugates of particles having an average size of 90 μm and particles having an average size of 150 μm at a ratio of 4:1.

The term particles as used herein refers to a portion of matter having a surface that can be attached to chemical or biological compounds, small or large molecules that may be attached through either covalent or non-covalent bonds. The particle may comprise a porous material. The particles may be "spherical" (refers generally to a substantially (nearly) round-ball geometry) or "non-spherical" for example, ("elongated" in shape and has a defined long and short axis). Non-limiting examples of particles include beads such as at least one of polysaccharide bead, glass beads, cotton bead, plastic bead, nylon bead, latex bead, magnetic bead, paramagnetic bead, super paramagnetic bead, starch bead and the like, silicon bead, PTFE bead, polystyrene bead, gallium arsenide bead, gold bead, or silver bead. In some embodiments, the particle is a bead comprising agarose beads, optionally at different degree of crosslinking at different % of material (agarose).

As such, agarose beads encompasses beads comprising agarose at varying degree of crosslinking, for example beads denoted as sepharose beads. In some embodiments, the bead comprises agarose beads. In some embodiments, the bead comprises sepharose beads. In some embodiments, the plurality of conjugates comprises a combination of particles comprising agarose beads and sepharose beads. In accordance with the present disclosure, it should be noted that particles being either agarose beads and Sepharose beads are considered as two different conjugates having different particles.

Sepharose is a tradename for a crosslinked, beaded-form of agarose, a polysaccharide polymer material extracted from seaweed. Its brand name is derived from Separation-Pharmacia-Agarose. Sepharose is a registered trademark of GE Healthcare (formerly: Pharmacia, Pharmacia LKB Biotechnology, Pharmacia Biotech, Amersham Pharmacia Biotech, and Amersham Biosciences). Various grades and chemistries of sepharose are available.

As described herein, the plurality of conjugates may comprise at least two different conjugates, optionally having particles with different properties, such as different size, different shape, different composition and different material. In some embodiments the plurality of conjugates may comprise agarose beads with an average size of about 90 μm. In some embodiments the plurality of conjugates may comprise agarose beads with an average size of about 150 μm. In some embodiments the plurality of conjugates may comprise Sepharose beads with an average size of about 90 μm. In some embodiments the plurality of conjugate may comprises sepharose beads with an average size of about 150 μm. In accordance with the present disclosure, it should be noted that particles being either sepharose beads with an average size of about 90 μm and sepharose beads with an average size of about 150 μm are considered as two different conjugates having different particles.

The particle and specifically the bead as described herein may be associated to a chemically reactive moiety, denoted herein as a linker. The linker as used herein may be any chemical entity that is composed of any assembly of atoms, including oligomeric and polymeric chains of any length, which according to some embodiments, is capable of binding on one end to the particle and on the other end the at least one amino acid, a derivative thereof or an analog thereof. Further, it was found by the inventors that the linker coverage of the particle's surface may range between about 9 to about 23 μmol beads/ml drained medium. More specifically, it should be noted that in some embodiments, drained, medium refers to herein to dry beads.

As described herein, the linker is capable of binding at one end to the particle and at a second end to the amino acid, derivative thereof or analog thereof and thus the linker has, a functional end at both sides. In other words, the linker may be a bifunctional linker. In some embodiment, the linker is a bifunctional crosslinker and the particle is a bead that binds to the bifunctional crosslinker. As used herein the term "crosslinker" refers to a reagent which contain two or more reactive ends capable of chemically attaching to specific functional groups (for example primary amines, carboxyl, sulfhydryl's, etc.) on amino acids, peptides, proteins or other molecules.

In some embodiments, the linker (or crosslinker) may be a bifunctional linker or comprise part/fragment of the bifunctional linker.

As appreciated, the linker may have different length depending on variety of experimental requirements. The length refers to the molecular span of a crosslinker, the distance between conjugated components e.g. the particle and the amino acid. In some embodiments, the crosslinker is cleavable (i.e., whether the linkage can be reversed or broken when desired, for example, EDC). In some embodiments, the crosslinker is a zero-length crosslinker. In some embodiments, the crosslinker cause direct conjugation of without becoming part of the final crosslink covalent bond. The crosslinker may be a homobifunctional crosslinker or heterobifunctional crosslinker. Homobifunctional crosslinkers are reagents that have the same type of reactive group at either end. Amine crosslinkers (namely bind amine reactive groups) may be selected for example from glutaraldehyde, bis (imidoesters) or bis (succinimidylesters) (also known as NHS esters). According to some embodiments, homobifunctional crosslinkers such as but not limited to dimethyl pimelimidate (DMP) or glutaraldehyde can bind to $NH_2$ groups (primary groups) on the magnetic bead and to NH₂ groups of the tranexamic acid. Sulfhydryl crosslinkers may be selected for example from maleimides or pyridyldithiols.

In some embodiments, the linker is a heterobifunctional crosslinker. Heterobifunctional crosslinkers are reagents that have different type of reactive group at either end for example but not limited to amine-to-sulfhydryl or amine-to-carboxyl.

Amine-to-Sulfhydryl crosslinkers may have NHS esters and maleimides at each end, or NHS esters and pyridyldithiols at each end. Examples of heterobifunctional crosslinkers that can bind amine and Sulfhydryl groups are selected from but not limited to N-Succinimidyl 3-[2-pyridyldithio]-propionate (SPDP), Succinimidyl-4-(N-maleimidomethyl)cyclohexane-1-carboxylate (SACC), or Succinimidyl-4-(p-maleimidophenyl) butyrate (SMPB).

Amine-to-carboxyl crosslinkers may have carbodiimide. Such carbodiimide crosslinker that activates carboxyl groups for spontaneous reaction with primary amines. These crosslinkers may conjugate carboxyl groups (glutamate, aspartate, C-termini) to primary amines (lysine, N-termini) and N-hydroxysuccinimide (NHS). Examples of heterobifunctional crosslinkers that can bind amine and carboxyl groups are selected from but not limited to dicyclohexyl-carbodiimide (DCC) and (1-ethyl-3-(3-dimethylaminopropyl)carbodiimide hydrochloride (EDC) 1-Ethyl-3-(3-Dimethylaminopropyl)carbodiimide, Hydrochloride (EDAC). These crosslinkers are used for the conjugation of carboxyl groups (glutamate, aspartate, C-termini) to primary amines (lysine, N-termini) and N-hydroxysuccinimide (NHS) for stable activation of carboxylates for amine-conjugation.

In some embodiments, the linker is an aromatic system. Non-limiting examples include benzoic acid or substituted benzoic acid, benzenesulfonyl chloride, benzaldehyde, chloromethyl-benzene.

In some specific embodiments, the linker used is 1-ethyl-3-(3-dimethylaminopropyl)carbodiimide hydrochloride (EDC).

As detailed herein above, for conjugates comprising amino acid derivatives, for example cyclohexanecarboxylic acid or 4-methyl-cyclohexanecarboxylic acid (i.e. lacking the NH₂ group (amino group) of an amino acid), the linker may comprise an amino group (alone or bound to a methylene group, namely being —NH₂—CH₂—, "—" is a covalent bond). Thus, it should be noted that in some embodiments, the linker described herein may comprise at least an additional amino group or an amino group bound to a methylene group. Therefore, in accordance with such embodiments, the linker end that binds to the amino acid derivatives is an amino group of the linker or a methylene group of linker. In other words, the association between one end of the linker and the amino acid derivative includes a covalent bond of the cyclohexane ring and an amino group or a methylene group. Such association may be by any known synthetic method known to one versed in the field.

In some embodiments, the bead may be associated to the linker via a spacer or coating present on the bead. As such, the bead is initially activated ("activated beads") by association to a spacer/coating and then reacted with a linker. It should be noted that at times, no linker may be further required in cases the spacer/coating binds directly to the at least one amino acid. At times, the bead does not have a functional group capable of binding to the linker, and a spacer or coating may be used.

The activated beads are obtained by pre-coating the beads with a suitable material having an active moiety enabling the binding to the beads and to the linker and/or the amino acid. In other words, the beads are pre-coated to include reactive groups enabling the covalent binding to either the linker or the amino acid.

In some embodiments the beads may be activated for example by pre-coating with any coating material. Non-limiting examples of such material include for example, amino acid, protein, epoxy, tosyl, carboxylic acid, carboxylated polyvinyl alcohol, when referring to "pre-coating" it should be understood as a preliminary step which results in coating of the beads with an active material that in turn enables covalent binding of the beads with the tranexamic acid (i.e. directly) or via at least one linker. In some embodiments, the beads are pre-coated with an amino acid, peptide or any derivative thereof. Pre-coated magnetic beads may comprise for example as active groups, a primary amine (—NH2), carboxyl (—COOH), sulfhydryl (—SH) or carbonyl (—CHO). In some embodiments, the beads are pre-coated to include a moiety that may react with primary or secondary amino groups. In some other embodiments, the magnetic beads are coated with polylysine.

As used herein term "linker" encompasses any spacer or pre-coating present on the beads.

In some embodiments, the linker comprises or is a chain of atoms, for example a linear chain. In some embodiments, the linker comprises at least 1 atom, at least 4 atoms, at times 5 atoms, at times 10 atoms, at times 20 atoms, at times 30 atoms, at times 40 atoms. In some embodiments the linker is or comprises a linear chain of 1 to 40 atoms. In some embodiments the linker is or comprises a linear chain of 1 atoms. In some embodiments the linker is a linear chain comprising 5 atoms. In some embodiments the linker is a linear chain comprising 15 atoms.

In some embodiments the linker is a linear chain comprising 31 atoms. In some embodiments, the linker is a fragment of 26-(2-Hydroxy-3-methoxy-propylamino)-hexacosanoic acid 2,5-dioxo-pyrrolidin-1-yl ester. In some embodiments, the linker is a fragment of 4-Oxo-pentanoic acid methyl ester. In some embodiments, the linker is methylene.

As described herein, for an amino acid derivative, the linker comprises at one end (the end reactive with the cyclohexane ring) an amino group or a methylene (—CH₂—) group.

As appreciated, upon association of the linker with the amino acid, derivative thereof or analog thereof, the linker is modified due to the association and in some embodiments, comprises a fragment of the linker.

The linker properties depend on the nature of the atoms within the linker. It was found that linkers comprising at least one atom having at least one lone pair of electrons, such as oxygen, nitrogen or sulfur. In some embodiments, the linker comprises at least one oxygen atom.

In some other embodiments, the association between the linker to the at least one amino acid, derivative thereof or analog thereof may be covalent bonding. In some further embodiments, the association between the linker to the at least one amino acid may via bonding of a nitrogen (N) atom of the amino acid and a carbon (C) atom of the linker. As appreciated, upon association and formation of a chemical bind, the amino group (—NH₂—) losses one hydrogen atom, to become —NH—. In some embodiments, the covalent association is via amine, imine or amide bonds. In some embodiments, the amino acid is tranexamic acid (TXA). As detailed herein, in some embodiments, the amino acid derivative is cyclohexanecarboxylic acid and the association/interaction of the cyclohexanecarboxylic acid with the linker is via the cyclohexane ring and the methylene group of the linker. As detailed in Example 1.1 below, in at least part of the plurality of conjugates, the beads may be pre-coated with 26-(2-Hydroxy-3-methoxy-propylamino)-hexacosanoic acid 2,5-dioxo-pyrrolidin-1-yl ester. Thus, agarose beads associated with 26-(2-Hydroxy-3-methoxy-propylamino)-hexacosanoic acid 2,5-dioxo-pyrolidin-1-yl ester are subjected to association with at least one amino acid or analog thereof. The linker in the conjugate is a fragment of 26-(2-Hydroxy-3-methoxy-propylamino)-hexacosanoic acid 2,5-dioxo-pyrrolidin-1-yl ester and specifically 26-(2-Hydroxy-3-methoxy-propylamino)-hexacosanal. As appreciated, due to the association between the 26-(2-Hydroxy-3-methoxy-propylamino)-hexacosanoic acid 2,5-dioxo-pyrrolidin-1-yl ester and the amino acid or analog thereof, the linker is a fragment of 26-(2-Hydroxy-3-methoxy-propylamino)-hexacosanoic acid 2,5-dioxo-pyrrolidin-1-yl ester and specifically 26-(2-Hydroxy-3-methoxy-propylamino)-hexacosanal.

As detailed in Example 1.2 below, in at least part of the plurality of conjugates, the beads may be pre-coated with an hydroxide and reacted with succinic anhydride and Pyridine, followed by reaction with N-Hydroxylsuccinamide (NHS) and EDC. Thus, agarose beads associated with 4-(2,5-Dioxo-pyrrolidin-1-yl)-4-oxo-butyric acid methyl ester are subjected to associated with at least one amino acid or an analog thereof. The linker in the conjugate is a fragment of 4-(2,5-Dioxo-pyrrolidin-1-yl)-4-oxo-butyric acid methyl ester and specifically 4-Oxo-butyric acid methyl ester.

In some embodiments, the conjugate comprises agarose beads having an average size of 90 μm. In some embodiments, the linker comprises 26-(2-Hydroxy-3-methoxy-propylamino)-hexacosanal. In some embodiments, the conjugate may have the structure (denoted herein as "conjugate 1"):

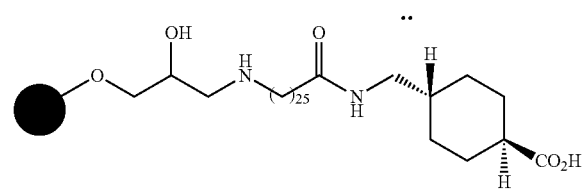

wherein

represents a particle, for example an agarose bead, specifically a 4% agarose bead having an average size of 90 μm.

In some embodiments, the amino acid is TXA, the particles are agarose beads having an average size of 90 μm and the linker comprises 26-(2-Hydroxy-3-methoxy-propylamino)-hexacosanal and the conjugate have the structure denoted herein as conjugate 1. In some embodiments wherein the amino acid derivative is cyclohexanecarboxylic acid, the particles are agarose beads having an average size of 90 μm and the linker comprises 26-(2-Hydroxy-3-methoxy-propylamino)-hexacosanoic acid methylamide and the conjugate have the structure denoted herein as conjugate 1.

In some embodiments, the conjugate of the presently disclosed subject-matter comprises sepharose beads having an average size of 150 μm. In some embodiments, the linker comprises 4-Oxo-butyric acid methyl ester. In some embodiments, the conjugate may have the structure (denoted herein as "conjugate 2"):

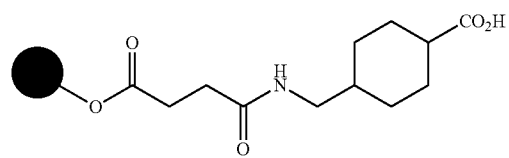 [SMILES: COC(=O)CCC(=O)NCC1CCC(C(=O)O)CC1]

wherein

represents particle, for example a sepharose bead having an average size of 150 μm.

In some embodiments, the amino acid is TXA, the particles are sepharose beads having an average size of 150 μm and the linker comprises 4-Oxo-butyric acid methyl ester and the conjugate have the structure denoted herein as conjugate 2.

In some embodiments wherein the amino acid derivative is cyclohexanecarboxylic acid, the particles are sepharose beads having an average size of 150 μm and the linker comprises N-Methyl-succinamic acid methyl ester and the conjugate have the structure denoted herein as conjugate 2. In some embodiments, the conjugate comprises agarose beads having an average size of 150 μm. In some embodiments, the linker comprises methylene. In some embodiments, the conjugate may have the structure (denoted herein as "conjugate 3"):

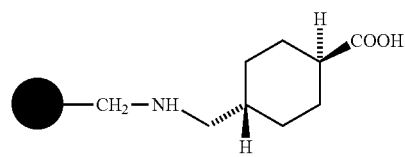

wherein

represents a particle, for example an agarose bead having an average size of 150 μm.

In some embodiments, the amino acid is TKA, the particles are agarose bead having an average size of 150 μm and the linker comprises methylene and the conjugate have the structure denoted herein as conjugate 3.

In some embodiments wherein the amino acid derivative is cyclohexanecarboxylic acid, the particles are agarose beads having an average size of 150 μm and the linker comprises dimethyl-amine and the conjugate have the structure denoted herein as conjugate 3.

In some embodiments, the conjugate comprises agarose beads. In some embodiments, the linker comprises a 15 atoms carbon chain. In some embodiments, the linker is hexadecanal. In some embodiments, the conjugate may have the structure (conjugate 4):

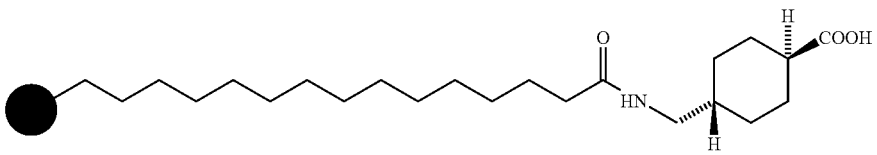

wherein

represents a particle.

In some embodiments, the conjugate comprises agarose beads. In some embodiments, the linker comprises a 15 atoms carbon chain. In some embodiments, the linker is Hexadecanoic acid methylamide. In some embodiments, the conjugate may have the structure (conjugate 4):

In accordance with some further aspects, the present disclosure provides at least one conjugate comprising at least one particle, at least one linker and at least one amino acid, derivative thereof or analog thereof. In some embodiments, the conjugate of the presently disclosed subject-matter may be any one of the following conjugates or any combinations thereof. More specifically, at least one of:

to about 500 μm or more, specifically, as defined above. More specifically, between about 90 μm to about 150 μm. In some embodiments, the conjugates of the presently disclosed subject-matter may bind at least one fibrinolytic protein, more specifically, said fibrinolytic protein may be tissue plasminogen activator (tPA) and optionally, plasminogen.

Referring to FIGS. 12 to 19, a device for treating mammalian body fluids, in particular blood plasma or whole blood, according to a first example of the presently disclosed subject matter, is generally designated with reference numeral 100, and comprises a housing 300, and a plurality of groups of particles, specifically, beads, including at least a first group 110 of first particles or beads 210 and a second group 120 of second particles or beads 220.

While the device according to this and other examples finds particular use with an blood plasma (also interchangeably used herein with "human plasma") and/or whole human blood (also interchangeably used herein with "human

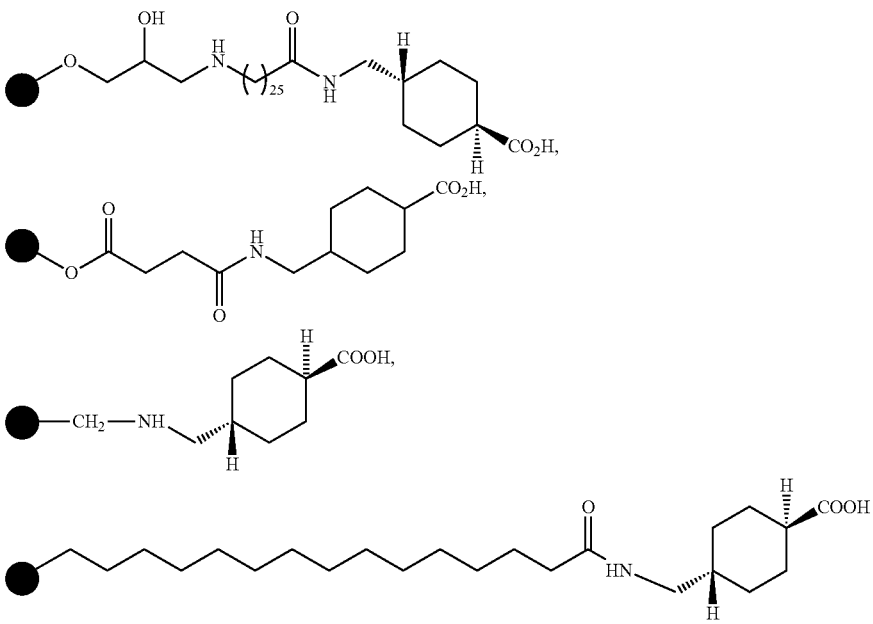

wherein

represents a particle.

In some embodiments, the particle is an agarose bead or a sepharose bead. In some other embodiments, the particle has an average particle size of between about 10 μm or less blood"), and/or any products thereof, it can also be used to treat other mammalian but non-human blood plasma or mammalian but non-human whole blood, or indeed at least some types of animal blood plasma or animal whole blood, for example including at least some types of non-mammalian blood plasma or non-mammalian whole blood.

As will become clearer herein, the device is configured for depleting at least one fibrinolytic protein (for example tPA and/or Plasminogen) from mammalian body fluids (for example human plasma and/or human whole blood and/or other mammalian plasma and/or other mammalian whole blood), as one example of treating mammalian body fluids.

The housing 300 defines a longitudinal axis AA, and comprises a main body portion 350, and a pair of end caps, including an inlet end cap 310 having a fluid inlet port 330, and outlet end cap 320 having a fluid outlet port 340. In alternative variations of this example, the housing can include more than one main body portion, and/or more than one inlet port, and/or one or more than one inlet port for each body portion, and/or more than one outlet port, and/or one or more than one outlet port for each body portion.

Each one of the inlet end cap 310 and the outlet end cap 320 has a generally frusto-conical base 360, having a respective inner frusto-conical surface 370 and a respective outer frusto-conical surface 380. In this and at least some other examples, the inner frusto-conical surfaces 370 and the outer frusto-conical surfaces 380 are highly polished. In alternative variations of this example, the inner frusto-conical surfaces 370 and/or the outer frusto-conical surfaces 380 are not polished.

For example, the fluid inlet port 330, and the fluid outlet port 340, each project away from the respective frusto-conical base 360, and can each be fitted with a suitable respective leak-free connector portion 335. For example such leak-free connector portion 335 can be in the form of Luer locks to facilitate connection of conduits (for example medical grade tubing) thereto. Alternatively, the fluid inlet port 330, and the fluid outlet port 340, can each be fitted with any other type of suitable leak-free connector portion 335 to facilitate connected of conduits (for example medical grade tubing) thereto.

In at least this example, and referring also to FIGS. 14A to 14D, each frusto-conical base 360 has a transverse cross-sectional area (orthogonal to the longitudinal axis AA) increasing from the respective small end 312, 322, to the respective large end 314, 324, thereof. In at least this example, each frusto-conical base 360 includes a plurality of web members 301, which radially and axially project inwardly from the inner surface of the respective inlet end cap 310 or outlet end cap 320. However, in at least some alternative variations of this example and in other examples, the web members can be omitted. Without being bound by theory, the web members 301 can enhance overall rigidity of the device 100, and/or can help align flow of the untreated body fluids into and out of the device 100, in particular into the chamber 400 generally along the longitudinal axis AA.

Further without being bound by theory, the web members 301 can aid in holding or otherwise maintaining the barrier members 352, 354 in place at longitudinal ends E1, E2, respectively, and more particularly for clamping the barrier members 352, 354 in the housing 300, between the respective inlet end cap 310 or outlet end cap 320 and the main body portion 350, as will become clearer below.

The web members 301 each have a free end 306 facing the respective barrier members 352, 354 in the assembled device 100. As best seen in FIGS. 14B and 14C, the free ends 306 project away from the respective inner frusto-conical surface 370 in a longitudinal direction parallel to the longitudinal axis AA past the respective large end 314, 324.

In at least this example, the fluid inlet port 330 is joined to the small end 312 of the inlet end cap 310, and the fluid outlet port 340 is joined to the small end 322 of the outlet end cap 320. In alternative variations of this example, the fluid inlet port 330 can be connected at any other suitable location to the inlet end cap 310, and/or the fluid outlet port 340 can be connected at any other suitable location to the outlet end cap 320.

In this example, and referring also to FIGS. 13A to 13D, the main body portion 350 comprises a generally cylindrical wall 355 (i.e. having a circular cross-section transverse to the longitudinal axis AA of the device), and having longitudinally opposed ends 356, 358.

In this example the housing 300, and in particular the main body portion 350 including the cylindrical wall 355 is relatively rigid. By relatively rigid is meant that the main body portion 350 maintains its shape without significant deformation (for example without deformation that is visible to the naked eye of an untrained observer) under its own weight or in operation of the device when accommodating the plurality of groups of particles as well as a flow of plasma or other fluids through the device.

In alternative variations of this example, the main body portion can be semi flexible, or fully flexible (for example in the form of a flexible bag), and/or the main body portion can have a non-cylindrical transverse cross-section, for example elliptical, polygonal, and so on.

In this and other examples, the transverse cross-section of the main body portion 350 is generally uniform along the longitudinal axis AA of the device. In alternative variations of this example, the transverse cross-section of the main body portion 350 can instead be non-uniform along the longitudinal axis AA of the device—for example the shape of the transverse cross-section can change and/or the size of the transverse cross-section can change along the longitudinal axis AA. For example the main body portion can have a frusto-conical shape, with the circular transverse cross-section of the main body portion increasing in size, or alternatively decreasing in size, along the longitudinal axis AA; for example such a frusto-conical shape can be almost cylindrical, having a half angle of about 0.5° or about 1°, for example (see FIG. 13C).

The housing 300, in particular the main body portion 350 and the inlet end cap 310 and the outlet end cap 320, can each be made from any suitable medically compatible materials. For example, such materials can include medical grade plastic, for example any one of the following: PC (Makrolon 2458), Apec®1745 polycarbonate, provided by Covestro, USA; Polypropylene; Polysulfone; Polyether ether ketone (PEEK).

In at least this example, the housing 300, in particular the main body portion 350, inlet end cap 310 and the outlet end cap 320 are transparent, i.e., made from transparent materials. However, in alternative variations of this example, the housing 300, in particular the main body portion 350 and/or the inlet end cap 310 and/or the outlet end cap 320 are non-transparent, for example, translucent or opaque, or any combination of transparent, translucent or opaque portions.

The housing 300, in particular the main body portion 350, comprises an internal chamber 400 defining a control volume V. In this example the control volume V is defined by an outer transverse periphery P thereof, defined by the inner surface of the main body portion 350, which in this example is a cylindrical inner surface, and longitudinal ends E1 and E2 at opposite longitudinal ends of the main body portion 350.

The longitudinal ends E1 and E2 of the control volume V are defined by corresponding barrier members 352, 354, respectively, provided at opposite longitudinal ends of the main body portion 350. As will become clearer herein, the barrier members 352, 354 are configured for preventing the first particles 210 and the second particles 220 from exiting the main body portion 350, in particular from exiting the control volume V, particularly via the inlet end cap 310 and the fluid inlet port 330, or via the outlet end cap and the fluid outlet port 340. The barrier members 352, 354 are also configured for concurrently permitting the through-flow of fluids, in particular liquids, more in particular blood plasma, and more in particular human plasma, through the main body portion 350, in particular through the control volume V, particularly, the mammalian body fluid/s enter the control volume V via the inlet end cap 310 and the fluid inlet port 330, and subsequent to exiting the control volume V, flow via the outlet end cap and the fluid outlet port 340.

In at least this example, the barrier members 352, 354 are similar or identical to one another, and are in the form of filter discs 352A, 354A, respectively, each having a respective upstream surface and a respective downstream surface separated by the thickness of the respective filter discs 352A, 354A. The barrier members 352, 354, in particular the filter discs 352A, 354A, comprise a plurality of pores or other openings for allowing through-flow of fluids, in particular liquids, more in particular body fluids, and more in particular human plasma or human whole blood (or alternatively, any mammalian or non-mammalian plasma or whole blood), through the pores, the pores being of a size smaller than the smaller of (a) the average size or median size of the first particles 210 or (b) the average size or median size of the second particles 220. For example, in examples where the particles of the smaller of the first particles 210 or the second particles 220 has an effective (average or median) diameter of about 90 µm (for example the larger particles having an effective (average or median) diameter of about 150 µm), the pores have an effective (average or median) diameter of less than 90 µm, for example any one of: 80 µm; 70 µm; 60 µm; 50 µm; 40 µm, or less than 40 µm. In such an example of particle diameters, the pores can have an effective (average or median) diameter within the range 45 µm to 50 µm, for example, or alternatively the pores can have an effective (average or median) diameter within any one of following ranges: 20 µm to 80 µm; 30 µm to 70 µm; 40 µm to 55 µm; 40 µm to 50 µm; 40 µm to 60 µm; 40 µm to 70 µm; 40 µm to 80 µm.

A feature of at least some examples in which the barrier members 352, 354 are in the form of filter discs 352A, 354A is that the filter discs 352A, 354A can be manufactured rapidly.

Another feature of at least some examples in of the device is that the flow through the device 100 can be controlled. For example choosing a large amount of particles (i.e. of first particles 210 and second particles 220) in the control volume V will tend to reduce the volumetric flow rate of body fluids through the device 100, while choosing to reduce the amount of particles in the control volume V will reduce the ability and efficacy of the particles to deplete the fibrinolytic proteins from the body fluids. Thus, effectively, the volumetric flow rate of the device can depend on the ratio of the amount of particles (i.e. of first particles 210 and second particles 220) in the control volume V to the volume of body fluids that can be accommodated in the control volume V when this amount of particles is accommodated in the control volume V.

In alternative variations of this and other examples, the barrier members can include, for example, filters comprising fibers or plastic substrates wherein the ligand is conjugated to the fibers or plastic substrates, in which the ligand is conjugated, or for example suitable membranes, for example one-way membranes that allow flow there though of body fluids in one direction but not in the opposite direction through the membrane.

In this and other examples, the filter discs 352A, 354A can include any one of Spectra Mesh® Woven Filters (for example including Nylon, PEEK, Polypropylene, Polyester, Stainless Steel) provided by Spectrum, USA, or MS® Nylon mesh filters, provided by Yair Technologies, Israel. In at least this example, the barrier members 352, 354, in particular the filter discs 352A, 354A, are fitted with respect to the housing 300, in particular with respect to the main body portion 350, and optionally also with respect to the inlet end cap 310 and the outlet end cap 320, such that the integrity of the control volume V is maintained. In other words, the connection between the barrier members 352, 354, in particular the filter discs 352A, 354A, and the housing 300, in particular the main body portion 350, is such as to minimize or avoid any leaks of the first particles 210 or of the second particles 220 via this connection, while maximizing the exposed area of the barrier members 352, 354, in particular the filter discs 352A, 354A with respect to the body fluids passing through the device 100. Furthermore, the barrier members 352, 354, in particular the filter discs 352A, 354A, are fitted with respect to the housing 300, in particular with respect to the main body portion 350, and optionally also with respect to the inlet end cap 310 and the outlet end cap 320, such that analog respective upstream surfaces of the two barrier members 352, 354, in particular the two filter discs 352A, 354A, are facing the upstream direction, while the respective downstream surfaces thereof are facing the downstream direction.

In at least this example, and referring in particular to FIG. 13D and FIG. 14D, each one of the ends 356, 358 of the main body portion 350 comprises a raised annular shoulder 359 radially offset from an inner edge 344 (see FIGS. 12B, 13C for example) of the respective ends 356, 358, defining a respective inner ledge 357 and outer ledge 353. Each one of the harder members 352, 354, in particular the filter discs 352A, 354A, has an external diameter greater than that of the respective inner edge 344 but smaller than the inner diameter of the respective annular shoulder 359, and thus sits on the respective inner ledge 357. The respective inlet end cap 310 and the outlet end cap 320 each have, at the respective large end 314, 324 of the frusto-conical base 360, a respective annular edge 351 that sealingly affixes the respective inlet end cap 310 and the outlet end cap 320 to ends 356, 358, respectively. For example, the respective annular edges 351 can be bonded, heat welded, ultrasonic welded or otherwise sealingly affixed to the respective outer ledges 353.

In this example, the annular shoulder 359 of each one of the respective ends 356, 358 comprises a protruding lip 359A having a generally triangular transverse cross-section, with the apex of the triangle facing away from the respective ends 356, 358, the generally triangular transverse cross-section converging towards the apex in a direction generally parallel to the longitudinal axis AA away from the main body portion 350. The respective annular edges 351 each comprise an annular recess 351A that is in registry with the protruding lip 359A when the inlet end cap 310, main body portion 350 and the outlet end cap 320 are co-aligned with respect to the longitudinal axis AA.

It is to be noted that the web members 301 have a dimension D (FIG. 14C) parallel to the longitudinal axis AA such that when the respective inlet end cap 310 or outlet end cap 320 is sealingly affixed to the main body portion 350, the respective barrier members 352, 354, in particular the filter discs 352A, 354A, are secured with respect to housing 300, being in abutting and optionally clamped relationship between the respective web members 301 and the respective inner ledge 357.

During the process of heat welding or ultrasonic welding, for example, the respective lips 359A are deformed into sealing connection with the respective annular recess 351A, thereby sealingly affixing the respective inlet end cap 310 or outlet end cap 320 to the main body portion 350.

In an alternative variation of the example of FIGS. 13A to 14D, and referring to FIG. 12B as one such example, the annular shoulder 359 of each one of the respective ends 356, 358 has a sloping surface 359B (instead of the protruding lip 359A) generally parallel to the inner frusto-conical surface 370. On the other hand, in this example the respective annular edges 351 each comprises (instead of the annular recess 351A), a protruding lip 351B that is in registry with the outer ledge 353 when the inlet end cap 310, main body portion 350 and the outlet end cap 320 are co-aligned with respect to the longitudinal axis AA. The protruding lip 351B has a generally triangular transverse cross-section, with the apex of the triangle facing towards the respective ends 356, 358, the generally triangular transverse cross-section converging towards the apex in a direction parallel to the longitudinal axis AA, i.e. towards the main body portion 350. During the process of heat welding or ultrasonic welding, the respective lips 351B are deformed into sealing connection with the respective annular outer ledge 353.

By way of non-limiting example, FIGS. 13A to 13D provide dimensional data (in mm) for various parts of the body portion 350 (with tolerance of, for example, ±0.05), according to one implementation of this example. In alternative implementations if this example, the dimensional data can be changed pro-rata, for example all annotated dimensions can be increased or decreased in the same proportion, for example can be increased by 50%, 100%, 150%, 200% and so on, or decreased by 10%, 25%, 50% and so on.

Also by way of non-limiting example, FIGS. 14A to 14D provide dimensional data (in mm) for various parts of the inlet end cap 310 (with tolerance of, for example, ±0.05), according to one implementation of this example, and similar dimensional data applies to the outlet end cap 320, mutatis mutandis. In alternative implementations if this example, the dimensional data can be changed pro-rata, for example all annotated dimensions can be increased or decreased in the same proportion, for example can be increased by 50%, 100%, 150%, 200% and so on, or decreased by 10%, 25%, 50% and so on. It is to be noted that regarding the example of FIGS. 12 and 13A to 14D, the body portion 350 has a longitudinal dimension (parallel to the longitudinal axis AA) that is about the same size as the inner diameter of the body portion 350. In alternative variations of this example, and referring for example to FIG. 12A, the longitudinal dimension can be larger than the inner diameter of the body portion 350. In yet other alternative variations of this example, the longitudinal dimension can be smaller than the inner diameter of the body portion 350.

In alternative variations of this example, the housing 300 can be formed integrally, and a transverse slot can be provided at each of the longitudinal ends E1 and E2 to enable the respective barrier members 352, 354, in particular the filter discs 352A, 354A, to be transversely inserted and sealed with respect to the housing 300.

In at least this example, the housing 300, in particular the main body portion 350, comprises a particle inlet port 390 provided on the cylindrical wall 355, and is configured for enabling the control volume V to be filled via the particle inlet port 390 with the aforesaid plurality of groups of particles, including at least the first group 110 of first particles 210 and the second group 120 of second particles 220. The particle inlet port 390 comprises a sealing cap 392, for reversibly or permanently sealing the particle inlet port 390 after control volume V is filled with the aforesaid plurality of groups of particles. For example, such a sealing cap 392 has a tapering highly-polished stem portion 393 that abuts a complementarily-tapering inner wall 394 of the particle inlet port 390, and a bead portion 395 that deformably engages an annular flange 399 provided at the mouth of the particle inlet port 390.

Alternatively the particle inlet port 390 can be reversibly or permanently sealed in another manner, after control volume V is filled with the aforesaid plurality of groups of particles. The device 100 is assembled by first placing the barrier members 352, 354, in particular the filter discs 352A, 354A, in registry with respect to the ends 356, 358 of housing 300, and then sealingly affixing the inlet end cap 310 and the outlet end cap 320 to the main body portion 350, thereby engaging the barrier members 352, 354, in particular the filter discs 352A, 354A, with respect to housing 300. The integrity of the assembly can be tested by coupling the particle inlet port 390 to a pressure source (for example set at 1 bar gauge pressure) while reversibly sealing the inlet port 330 and the outlet port 340, and checking whether there are any leaks, for example, by immersing the housing 300 in a liquid such as water for example, and any leaks can be detected by observing bubbles escaping from the housing 300. For example the housing 300 can be regarded as being sufficiently sealed if a leakage of up to one bubble every 30 seconds can be observed escaping from the housing 300.

In at least some applications of the above examples of the device 1110, the device 100 is pre-filled with the aforesaid plurality of groups of particles prior to being supplied to the end-user. In such cases a preservative can be used for the aforesaid plurality of groups of particles. For example, such a preservative can be 20% ethanol.

In other alternative applications of the above examples of the device 100, the device 100 can be filled with the aforesaid plurality of groups of particles by the end-user. In at least this example, the size of the control volume V is between 20 ml and about 35 ml.

In alternative variations of this example and in other examples the size of the control volume V can be different, for example less than 35 ml or greater than 35 ml. For example, the size of the device, and thus of the control volume V, can be scaled, for example by a linear scale factor. For example, the linear scale factor can be in any one of the following values: 2, 3, 4, 5, 10, 20, 30, 40, 50, or greater than 50. Alternatively, for example, the linear factor can be such that the control volume V is of a size "n" times greater than that of the present example, wherein n is any one of the following values: 2, 3, 4, 5, 10, 20, 30, 40, 50, 100, 150 or greater than 150; correspondingly or alternatively the control volume V can be scaled to 70 ml, 100 ml, 150 ml, 175 ml, 200 ml, 250 ml, 500 ml, 1 liter, 1.5 liter, 2 liter, 2.5 liter, 3 liter, 4 liter, 5 liter or greater than 5 liter.

In this example, the first particles 210 and/or the second particles 220 can be conjugated particles (referred to herein as "conjugate"), and each can optionally include any one of the conjugated particles, or compositions thereof that may comprise at least two or more different conjugates, as disclosed herein, for example.

In at least some alternative variations of these examples, only one group of the first group 110 and the second group 120 includes conjugated particles, while the other one of the first group 110 and the second group 120 includes non-conjugated particles. In yet other alternative variations of these examples, the first group 110 and the second group 120 both include the same conjugated particles, and thus there is effectively only a single, combined, group of conjugated particles.

In at least this example, the first particles 210 and/or the second particles 220 are conjugated particles, in which the first particles are dimensionally different from the second particles. In particular, the first conjugated particles 210 and the second conjugated particles 220 are dimensionally different from the second particles. In at least some such examples, the first conjugated particles have an average size that is different from the average size of the second particles. In yet some further embodiments, the first particles, specifically conjugates may be chemically different from the second conjugates.

Without being bound by theory, the inventors consider that including at least two groups of particles, in which the first conjugated particles have an average size that is different from the average size of the second particles, can result in providing spacings between the particles which provides an arrangement that is substantially less compact than in an analogous arrangement with all particles being the same-size or a similar size. In turn, this feature of reduced compactness provides greater exposed area for each of the particles than in analogous arrangements with same- or similar-sized particles. The greater exposed area in turn allows greater interaction between the conjugated particles and the body fluids (when such body fluids are caused to flow through the device 100), thereby increasing the effectiveness of the particles for depleting at least one fibrinolytic protein from the body fluid. Accordingly, a relative smaller global amount of first conjugated particles and second conjugated particles that are dimensionally different can be as effective as a relative larger global amount of first conjugated particles and second conjugated particles that are dimensionally similar, in terms of depleting at least one fibrinolytic protein from the body fluid, which can have economic effects.

One way of calculating how much plasminogen can be absorbed using a single group of conjugated particles is as follows:

Resin Capacity Calculation
Starting with the standard Fresh Frozen Plasma unit—
Each unit has 250 mL plasma
The concentration of Plasminogen in plasma is 160 μg/mL
Therefore, the total amount of Plasminogen in one unit of FFP is 40 mg
The molecular mass of Plasminogen is 92 kDa
1 Dalton unit is considered numerically equivalent to 1 g/mol for calculation purposes.
92000 Da is therefore 92000 g/mol or 92000 μg/μmol or 92 mg/μmol
When calculating the number of moles in the 40 mg in one FFP unit −40 mg÷92 mg/μmol=0.435 μmol
Sepharose 4 Fast Flow with the 25 atoms linker that work on 16-23 μmol beads/mL drained resin can reduce 1.317 gram of plasminogen this is 33 time fold mare than in one plasma unit.

Referring to FIGS. 15 and 16, a system for depleting at least one fibrinolytic protein from mammalian body fluid/s, generally designated with reference numeral 1000, according to an example of the presently disclosed subject matter comprises device 100, a saline reservoir 1100, a donor reservoir 1200, an acceptor plasma reservoir 1300 and a wash waste reservoir 1400.

The saline reservoir 1100 and the donor reservoir 1200 are in selective and non-concurrent fluid communication with the fluid inlet port 330 via first three-way valve 70.

The acceptor plasma reservoir 1300 and the wash waste reservoir 1400 are in selective and non-concurrent fluid communication with the fluid outlet port 340 via second three-way valve 90.

Conduits 82, 84 connect the saline reservoir 1100 and donor reservoir 1200, respectively, to respective ports 72, 74 of the first three-way valve 70, and another conduit 76 connects the third port 76 of the first three-way valve 70 to the inlet port 330 of the device 100.

Conduits 62, 64 connect the acceptor plasma reservoir 1300 and wash waste reservoir 1400, respectively, to respective ports 92, 94 of the second three-way valve 90, and another conduit 66 connects the third port 96 of the second three-way valve 90 to the outlet port 340 of the device 100.

In at least this example, the device 100 is as disclosed in the examples thereof herein, or the alternative variations of these examples. In any case, the control volume V accommodates the aforementioned plurality of groups of particles, including at least the first group of first particles and the second group of second particles.

The saline reservoir 1100 can include any suitable reservoir containing a suitable quantity of saline, this quantity typically being several times the size of the control volume V. In this example the saline reservoir 1100 is in the form of a syringe, though in alternative variations of this example the saline reservoir 1100 can take other forms, for example a non-rigid bag that can be pressed to cause the saline solution to exit the bag via conduit 82.

The donor reservoir 1200 can include a bag or other reservoir containing the mammalian body fluids to be treated by the device 100. For example, donor reservoir 1200 can contain human plasma and/or human whole blood and/or other mammalian plasma and/or other mammalian whole blood. Alternatively, donor reservoir 1200 can instead comprise a living donor, for example a human being having a blood catheter inserted into his/her blood vessels in a manner to allow blood to flow via the catheter (connected to or part of conduit 84) to the device 100 directly, or indirectly via a suitable blood products separation device that separates the plasma from the whole blood prior to delivery to the device 100.

The acceptor plasma reservoir 1300 can include a bag or other reservoir for receiving the treated mammalian body fluid, after being treated by the device 100. For example, the plasma reservoir 1300 can contain human plasma and/or human whole blood and/or other mammalian plasma and/or other mammalian whole blood that has been fully or partially depleted of least one fibrinolytic protein. Alternatively, acceptor plasma reservoir 1300 can instead comprise a living patient, for example a human being having a blood catheter inserted into his/her blood vessels in a manner to allow the treated mammalian body fluid to flow via the catheter (connected to or part of conduit 62) from the device 100.

The wash waste reservoir 1400 can include a bag or other reservoir capable of containing the saline solution after passing through the device from the saline reservoir 1100.

Referring to FIG. 17, it is to be noted that device 100, as disclosed herein, together with the saline reservoir 1100, acceptor plasma reservoir 1300 and wash waste reservoir 1400, can be provided as a kit 800. The kit 800 can further include the first three-way valve 70, as well as conduit 82 connected to the saline reservoir 1100 and to the first three-way valve 70 via port 72, and conduit 86 connected to the first three-way valve 70 and to the inlet port 330 of the device 100. The kit 800 can further include the second three-way valve 90, as well as conduits 62, 64 connected to the acceptor plasma reservoir 1300 and wash waste reservoir 1400, respectively, and to second three-way valve 90 via respective ports 92, 94, and conduit 66 connected to the third port 96 of the second three-way valve 90 and to the owlet port 340 of the device 100. The kit 800 can further include conduit 84 connected to the first three-way valve 70 via port 74, wherein another end of the conduit 84 is connectable to the donor reservoir 1200.

The system 1000 can be used as follows, for example.

The kit 800 is unpacked from its sterile packaging, and the various components can be inspected to ensure integrity of all the components.

Referring to FIG. 15, the wash configuration is set up by ensuring that the first three way valve 70 is set to provide fluid communication between the ports 72 and 76 while blocking port 74, and the second three way valve 90 is set to provide fluid communication between the ports 94 and 96 while blocking port 92. The device 100 is then primed (washed with saline) by causing saline to flow from the saline reservoir 1100 through the device 100 via the first three way valve 70 and into the wash waste reservoir 1400 via the second three way valve 90.

The donor reservoir 1200 can be connected to the kit 800 to provide system 1000. In examples where the donor reservoir is in the form of a bag or other reservoir containing the mammalian body fluids to be treated by the device 100, the donor reservoir 1200 can be fused to the conduit 84. The donor reservoir 1200 can then be hung from an IV pole, for example, or can be connected to a peristaltic pump, to enable the mammalian body fluids to be treated by the device 100, to selectively flow thereto, as will become clearer below.

In examples where the donor reservoir 1200 is a living donor, for example a human being, a blood catheter is inserted into a blood vessel of the living donor, and the catheter is connected to or is part of conduit 84.

Referring to FIG. 16, and after the wash configuration is completed and the device 100 printed with saline (using the configuration of FIG. 15), the treatment configuration is set up. The treatment configuration is set up by ensuring that the first three way valve 70 is set to provide fluid communication between the ports 74 and 76 while blocking port 72, and the second three way valve 90 is set to provide fluid communication between the ports 92 and 96 while blocking port 94. The untreated mammalian body fluids are then treated, in particular by depleting at least one fibrinolytic protein from mammalian body fluids, by causing the untreated mammalian body fluids to flow from the donor reservoir 1200 and through the device 100, via the first three way valve 70, and into the acceptor plasma reservoir 1300, via the second three way valve 90.

Referring to FIG. 18, another example of a system for depleting at least one fibrinolytic protein from mammalian body fluid/s, generally designated with reference numeral 2000, according to the presently disclosed subject matter, comprises a battery 2500 comprising a plurality of devices 100. In the illustrated example of FIG. 18, battery 2500 comprises four devices 100, and in alternative variations of this example the battery 2500 can instead comprise two, three or more than four devices 100, mutatis mutandis.

The system 2500 also comprises a saline reservoir 1100, a donor reservoir 1200, an acceptor plasma reservoir 1300 and a wash waste reservoir 1400, as well as a first three way valve 70 and a second three way valve 90, as disclosed herein for system 1000 illustrated in FIGS. 15 and 16, mutatis mutandis. In this example, battery 2500 comprises a plurality of devices 100 interconnected in a manner to provide fluid communication between the respective control volumes V of the plurality of devices 100.

In at least this example, each device 100 (of battery 2500) is as disclosed in the examples thereof herein, or the alternative variations of these examples. In any case, the control volume V of each device 100 of battery 2500 accommodates a respective said plurality of groups of particles, including at least the first group of first particles and the second group of second particles.

In at least this example, the plurality of devices 100 of battery 2500 are interconnected serially, wherein for each pair of the serially (adjacently) interconnected devices 100, the respective fluid inlet port 330 of one device 100 of the pair is connected to and in fluid communication with the respective fluid outlet port 340 of the other device 100 of the pair. The most upstream device 100 (also designated as device 100A in FIG. 18) of battery 2500 is connected to saline reservoir 1100 and to the donor reservoir 1200 via first three way valve 70, in a similar manner to the device 100 of system 1000 illustrated in FIGS. 15 and 16, mutatis mutandis. The most downstream device 100 (also designated as device 100B in FIG. 18) of battery 2500 is connected to acceptor plasma reservoir 1300 and to wash waste reservoir 1400 via the second three way valve 90, in a similar manner to the device 100 of system 1000 illustrated in FIGS. 15 and 16, mutatis mutandis.

In this example, the saline reservoir 1100 has sufficient saline to wash and prime all of the devices 100 in the battery 2500.

It is to be noted that battery 2500 of devices 100, as disclosed herein, together with the saline reservoir 1100, acceptor plasma reservoir 1300 and wash waste reservoir 1400 (and with the exclusion of the respective donor reservoir 1200), can be provided as a kit 2800. The kit 2800 can further include the first three-way valve 70, as well as conduit 82 connected to the saline reservoir 1100 and to the first three-way valve 70 via port 72, and conduit 86 connected to the first three-way valve 70 and to the inlet port 330 of the most upstream device 100A. The kit 2800 can further include the second three-way valve 90, as well as conduits 62, 64 connected to the acceptor plasma reservoir 1300 and wash waste reservoir 1400, respectively, and to second three-way valve 90 via respective ports 92, 94, and conduit 66 connected to the third port 96 of the second three-way valve 90 and to the outlet port 340 of the most downstream device 100B. The kit 2800 can further include conduit 84 connected to the first three-way valve 70 via port 74, wherein another end of the conduit 84 is connectable to the donor reservoir 1200.

System 2000 can be used in a similar manner to system 1000, in particular starting with a respective wash configuration followed by a respective treatment configuration, similar to the wash configuration and treatment configuration as disclosed herein for system 1000, mutatis mutandis.

A feature of system 2000 is that the mammalian body fluids from the donor reservoir 1200 to each device 100 successively in the battery 2500, thereby enabling a higher quality of treated mammalian body fluids to be provided, i.e., wherein the level of the least one fibrinolytic protein in the mammalian body fluid gets successively depleted further and further as the treated depleting mammalian body fluid is passed from one device 100 to the next device 100 in the battery 2500.

On the other hand it may be possible that the plurality of devices 100 in serial connection can set up a back-pressure in the system 2000 that could result in the flow rate through the system 2000 of mammalian body fluid being less than, for example, in system 1000.

Referring to FIG. 19, another example of a system for depleting at least one fibrinolytic protein from mammalian body fluid/s, generally designated with reference numeral 3000, according to the presently disclosed subject matter, comprises a battery 3500 comprising a plurality of devices 100. In the illustrated example of FIG. 19, battery 3500 comprises four devices 100, and in alternative variations of this example the battery 3500 can instead comprise two, three or more than four devices 100, mutatis mutandis.

The system 3500 also comprises a saline reservoir 1100, a donor reservoir 1200, an acceptor plasma reservoir 1300 and a wash waste reservoir 1400, as well as a first three way valve 70 and a second three way valve 90, as disclosed herein for system 1000 illustrated in FIGS. 15 and 16, mutatis mutandis. In this example, battery 3500 comprises a plurality of devices 100 interconnected in a manner to provide fluid communication between the respective control volumes V of the plurality of devices 100.

In at least this example, each device 100 (of battery 3500) is as disclosed in the examples thereof herein, or the alternative variations of these examples. In any case, the control volume V of each device 100 of battery 3500 accommodates a respective said plurality of groups of particles, including at least the first group of first particles and the second group of second particles.

In at least this example, the plurality of devices 100 of battery 3500 are interconnected in parallel, and the respective fluid inlet port 330 of the devices 100 are interconnected to and in fluid communication with one another via inlet manifold 3330. Furthermore, the respective fluid outlet port 340 of the devices 100 are interconnected to and in fluid communication with one another via outlet manifold 3340. The inlet manifold 3330 of battery 3500 is connected to saline reservoir 1100 and to the donor reservoir 1200 via first three way valve 70, in a similar to the device 100 of system 1000 illustrated in FIGS. 15 and 16, mutatis mutandis. The outlet manifold 3340 of battery 3500 is connected to acceptor plasma reservoir 1300 and to wash waste reservoir 1400 via the second three way valve 90, in a similar to the device 100 of system 1000 illustrated in FIGS. 15 and 16, mutatis mutandis.

In this example, the saline reservoir 1100 has sufficient saline to wash and prime all of the devices 100 in the battery 3500.

It is to be noted that battery 3500 of devices 100, as disclosed herein, together with the saline reservoir 1100, acceptor plasma reservoir 1300 and wash waste reservoir 1400, inlet manifold 3330 and outlet manifold 3340 (and with the exclusion of the respective donor reservoir 1200), can be provided as a kit 3800. The kit 3800 can further include the first three-way valve 70, as well as conduit 82 connected to the saline reservoir 1100 and to the first three-way valve 70 via port 72, and conduit 86 connected to the first three-way valve 70 and to the inlet manifold 3330. The kit 3800 can further include the second three-way valve 90, as well as conduits 62, 64 connected to the acceptor plasma reservoir 1300 and wash waste reservoir 1400, respectively, and to second three-way valve 90 via respective ports 92, 94, and conduit 66 connected to the third port 96 of the second three-way valve 90 and to the outlet manifold 3340. The kit 3800 can further include conduit 84 connected to the first three-way valve 70 via port 74, wherein another end of the conduit 84 is connectable to the donor reservoir 1200. System 3000 can be used in a similar manner to system 1000, in particular starting with a respective wash configuration followed by a respective treatment configuration, similar to the wash configuration and treatment configuration as disclosed herein for system 1000, mutatis mutandis.

A feature of system 3000 is that a relatively large volume flow and/or volume flow rate of mammalian body fluids from the donor reservoir 1200 can be treated by splitting the mammalian body fluids between the plurality of devices 100 in the battery 3500, and treating the mammalian body fluids simultaneously in the devices 100.

On the other hand it is possible that the plurality of devices sets up a back-pressure in the system 2000 that could result in the flow rate through the system 2000 of mammalian body fluid being less than, for example, in system 1000.

In an alternative variation of system 3000, the fluid inlet ports 330 of the plurality of devices 100 in battery 3500 can be connected directly and in fluid communication with a respective donor plasma reservoir, and/or each of the fluid outlet ports 340 can be connected directly to, and in selective fluid communication with, a respective acceptor plasma reservoir.

In another alternative variation of system 3000, each device 100 can be replaced with a battery of devices 100 in serial connection, for example corresponding to battery 2500, mutatis mutandis.

A proposed physiological cell-based model of hemostasis is initiated when activated factor VII (VIIa) binds to tissue factor bearing cells leading to further activation of factors IX and X, which in turn cut (activates) factor II (prothrombin) to form thrombin (IIa). Thrombin activates factor XI that in turn activates other factors to generate more thrombin. Thrombin then further cleaves fibrinogen to form the preliminary fibrin clot, which is then stabilized into firm hemostatic clot by the cross-linked action of factor XIII.

In response to vascular injury, the coagulation system is activated as above leading to, cross-linked fibrin deposition in tissues and blood vessels, thus compromising the flow of blood. Therefore, a further system is required that can appropriately dissolve the fibrin clot, thereby preventing further growth of the clot beyond the physiological need, and initiate clot lysis when the clot is not needed any more. This system is composed of the fibrinolytic proteins, which are then activated, converting fibrin to its soluble degradation products through the action of the serine protease, plasmin. Under physiologic conditions, fibrinolysis is precisely regulated by the measured participation of activators, inhibitors and cofactors.

Plasminogen, the main component of the fibrinolytic system, is synthesized primarily in the liver. Cleavage (activation) of plasminogen at a single Arg-Val peptide bond at position 560-561, gives rise to the active serine protease, plasmin, which in turn dissolves fibrin clot. The cleavage of plasminogen is mediated by plasminogen activators.

The main endogenous plasminogen activator is tissue plasminogen activator (tPA). Functionally, t-PA is itself a poor activator of plasminogen. However, in the presence of fibrin, the catalytic efficiency of tPA-dependent plasminogen activation increases by 500-fold. Surpassed plasmin activity also cleaves the coagulation factors and by that would prevent the formation of new clots.

The second endogenous plasminogen activator is a single chain u-PA or prourokinase. u-PA has much lower affinity for fibrin than tPA. Although uPA is an effective plasminogen activator in the presence or the absence of fibrin, its plasminogen activation activity is significantly stimulated by fibrin. u-PA is expressed by several cells including activated endothelial cells, macrophages, renal epithelial cells, and some tumor cells.

The fibrinolytic system is quite balanced by the action of activators (as detailed above) and inhibitors of fibrinolytic proteins. The main inhibitor of plasmin is $\alpha_2$ antiplasmin—a single chain glycoprotein that is synthesized primarily in the liver and circulates in plasma at relatively high concentrations (2 µM). Plasmin released into flowing blood or in the vicinity of a clot is immediately neutralized upon forming an irreversible 1:1 stoichiometric complex with $\alpha_2$ antiplasmin.

Among the inhibitors of plasminogen activators, plasminogen activator inhibitor-1 (PAI-1) is the most ubiquitous. It is released by endothelial cells, monocytes, macrophages, hepatocytes, adipocytes, and platelets. PAI-1 is the most important and rapidly acting physiologic inhibitor of both tPA and u-PA.

Plasminogen activator inhibitor 2 (PAI 2) is synthesized by human placenta. Significant levels of PAI 2 are found in human plasma primarily during pregnancy.

Finally, thrombin-activatable fibrinolysis inhibitor (TAFI) is a plasma carboxypeptidase with specificity for carboxy-terminal arginine and lysine residues that acts as a potent inhibitor of fibrinolysis.

Treatment of patients with various coagulation abnormalities is essential during spontaneous bleeding episodes, trauma and throughout surgical procedures. In most such situations blood/plasma-derived products (for example regular plasma or fresh frozen plasma—FFP) are used. These products contain coagulation factors and fibrinolytic proteins, and therefore, supposed to stop bleeding and to correct the missing or impaired coagulation abnormality by inducing formation of a hemostatic clot. In general, a lack or abnormality of any coagulation factor may end up with bleeding tendency because of an insufficient ability to make a stable hemostatic clot. Without being bound by any theory, the inventors assumed that the presence of fibrinolytic proteins is responsible for lysis of the hemostatic clot may result in dissolution of the clot and aggravation of bleeding phenomena.

Thus, once a hemostatic clot has been formed following the replacement of missing coagulation factor by blood/plasma-derived product/s available, the clot dissolution, if required, is accomplished by the fibrinolytic system. However, if dissolution of the clot is not desired and quite an opposite activity is needed, for example, to keep the hemostatic clot in situations of bleeding or to generate more blood clots, then a treatment with body fluids, specifically, blood or plasma and any derived products that consist the coagulation factors but are depleted in fibrinolytic factors may be a desirable solution.

As indicated herein, the present presently disclosed subject-matter provides conjugates, plurality of conjugates or any compositions thereof, as well as devices, kits and system for depleting fibrinolytic proteins from body fluids, specifically, blood, plasma and products thereof, and therefore provides in addition methods using these products.

Thus, in yet another aspect, the presently disclosed subject-matter relates to a method for depleting at least one fibrinolytic protein from mammalian body fluid/s or from any products thereof. More specifically, the method comprising the steps of: In a first step (i), subjecting the body fluid/s or any preparations thereof to affinity-depletion procedure specific for the at least one fibrinolytic protein/s. The Next step (ii), involves recovering the at least one fibrinolytic protein-depleted body fluid obtained in step (i).

It should be note that affinity-depletion procedure comprises contacting the body fluid with an effective amount of the plurality of conjugates according to the presently disclosed subject-matter or with at least one composition comprising the plurality of conjugates, as disclosed by the presently disclosed subject-matter. Alternatively, the affinity depletion procedure may be performed by applying the body fluid on a device, battery, kit or system comprising the conjugates of the presently disclosed subject-matter, any plurality of conjugates or any composition comprising the plurality of conjugates in accordance with the presently disclosed subject-matter.

It should be noted that in some embodiments, each conjugate comprises at least one particle, at least one linker and at least one amino acid, a derivative thereof or analog thereof. In some specific embodiments, the plurality of conjugates comprises at least two different conjugates, and wherein said amino acid, a derivative thereof or analog thereof is at least one of 4-(aminomethyl)-cyclo-hexane-carboxylic acid (tranexamic acid), ϵ-amino capsid acid, lysine, cyclohexanecarboxylic acid and 4-methyl-cyclohexanecarboxylic acid. In some further specific embodiments, the plurality of conjugates comprises at least two different conjugates, and wherein said amino acid, derivative thereof or analog thereof is at least one of 4-(aminomethyl)-cyclo-hexane-carboxylic acid (tranexamic acid), ϵ-amino caproic acid and lysine.

It should be noted that in some embodiments, the conjugated particles useful in the methods of the presently disclosed subject-matter may be as defined by the presently disclosed subject-matter herein before. In yet some further embodiments, the method of the presently disclosed subject-matter may use any of the device, battery, kits or systems provided by the presently disclosed subject-matter as defined herein before.

In some embodiments, the methods of the presently disclosed subject-matter may be applicable for depleting fibrinolytic proteins from body fluid that may be at least one of whole blood, plasma or blood-derived product comprising at least one coagulation factor.

In some specific embodiments, such blood-derived product may be at least one of whole blood, plasma, fresh frozen plasma (FFP), platelet rich plasma (PRP) and cryoprecipitate.

It should be understood that in some embodiments, the method of the presently disclosed subject matter may be performed ex vivo or in vitro. More specifically, in body fluids that are no longer part of the human body.

Blood transfusion is still the most essential factor in saving a life. In modern blood banking therapy blood components rather than whole blood is transfused.

Blood-component therapy refers to separation of blood into components to allow transfusion of only specific desired component to the patient, thus, avoiding the use of unnecessary component. By using blood components several patients can be treated with the blood from one donor.

The term "Fresh frozen plasma" (FFP) as used herein relates to the main blood component, that is the acellular liquid fraction of human blood that has been frozen and preserved after a blood donation and will be used for transfusion. Following donation, one unit of human blood is centrifuged, the cell content of the blood is separated, and the remained plasma is frozen at −18 C (0 F) or colder within eight hours of collection.

FFP contains all components (factors/proteins) of the coagulation, fibrinolytic and complement systems. Well-defined indications exist for the use of FFP in single or multiple coagulation deficiencies, as well as in existing or anticipated hemorrhage as occur in trauma or surgery.

"Cryoprecipitate" as used herein, relates to precipitated proteins of plasma obtained from a single unit of fresh plasma by rapid freezing within 6-8 hrs of collection (as done for FFP) and rapid thawing at 4° C. Cryoprecipitate is rich in Factor VIII, factor XIII, von Willebrand factor and fibrinogen. Thus, this component is suitable for treatment or prevention of bleeding in hereditary or acquired conditions associated with lack or impairment of the above mentioned coagulation proteins.

"Platelet rich plasma" (PRP) blood component is prepared from one unit of fresh (donated) blood by centrifugation or aphaeresis procedure.

Beside to being prepared from a standard unit of whole blood, blood components can be obtained by aphaeresis procedure. Aphaeresis is done using a pheresis apparatus/machine, which is a semi-automated blood-separator instrument. In this procedure if plasma is planned to be used for a donation, the donor's anticoagulated whole blood is passed through an apparatus in which the blood is separated into red cells, plasma, and a leukocyte/platelet fractions, which are then returned to the subject. Only the separated plasma is not returned to the subject but is further used for donation.

Several semi-automated blood-cell-separator instruments are available for collection of platelets, granulocytes, blood stem cells, mononuclear cells, and plasma. All of these instruments use centrifugation to separate the blood components. Some apheresis procedures involve two venipunctures with continuous flow of blood from the donor through the blood cell separator; others can be accomplished with a single venipuncture and intermittent blood withdrawal and return.

In yet some further specific embodiments, the method of the presently disclosed subject-matter may be used for depletion of fibrinolytic protein that may be at least one of plasminogen and tissue plasminogen activator (tPA).

More specifically, Plasminogen, (also known as PLG, Enzyme entry EC:3.4.21.7), as used herein, is the main component of the fibrinolytic system and is synthesized primarily in the liver. Two major glycoforms of plasminogen are present in humans—type I plasminogen that contains two glycosylation moieties (N-linked to N289 and O-linked to T346), whereas type II plasminogen contains only a single O-linked sugar (O-linked to T346). Type II plasminogen is preferentially recruited to the cell surface over the type I glycoform. Conversely, type I plasminogen appears more readily recruited to blood clots. In circulation, plasminogen adopts a closed, activation resistant conformation. Upon binding to clots, or to the cell surface, plasminogen adopts an open form that can be converted into active plasmin by a variety of enzymes, including tissue plasminogen activator (tPA), urokinase plasminogen activator (uPA), kallikrein, and factor XII (Hageman factor). More specifically, the cleavage (activation) of plasminogen at a single Arg-Val peptide bond at position 560-561, gives rise to the active serine protease, plasmin, which in turn dissolves fibrin clot.

Full length plasminogen comprises seven domains. In addition to a C-terminal chymotrypsin-like serine protease domain, plasminogen contains an N-terminal Pan Apple domain (PAp) together with five Kringle domains (KR1-5). The Pan-Apple domain contains important determinants for maintaining plasminogen in the closed form, and the kringle domains are responsible for binding to lysine residues present in receptors and substrates.

In some embodiments, the plasminogen referred to by the presently disclosed subject-matter may be the human plasminogen. In such embodiments, the plasminogen gene (GenBank: AY192161.1 mapped to chr6q26) spans about 52.5 kb of DNA and contains 19 exons (OMIM num173350). It should be noted that in some embodiments, plasminogen as used herein, refers to the human plasminogen that comprise the amino acid sequence encoded by the nucleic acid sequence comprising the sequence as denoted by SEQ ID NO. 1. In some further embodiments, the human plasminogen may comprise an amino acid sequence encoded by a nucleic acid sequence comprising a sequence having at least about 70%, 75%, 80%, 85%, 90%, 91%, 92%, 93%, 94%, 95%, 96%, 97%, 98%, 99% or 100% homology with the sequence as denoted by SEQ ID NO. 1. In yet some further embodiments, such human plasminogen molecule may comprise the amino acid sequence as denoted by SEQ ID NO. 2. In yet some other embodiments, such human plasminogen molecule may comprise an amino acid sequence having at least about 70%, 75%, 80%, 85%, 90%, 91%, 92%, 93%, 94%, 95%, 96%, 97%, 98%, 99% or 100% homology with the sequence as denoted by SEQ ID NO. 2.

A "plasminogen-deficient body fluid" or "plasminogen-free body fluid" as used herein is meant that the products of the presently disclosed subject-matter (that according to some embodiments, have been prepared by treating body fluid such as blood, plasma or blood products with fibrinolytic proteins binding agent, specifically, plasminogen-binding agents), display a reduced, decreased, attenuated, amount of plasminogen in about 100% to 50%, as compared to untreated blood or blood product. More specifically, at least about 50%, 55%, 60%, 65%, 70%, 75%, 80%, 85%, 90%, 95%, 96%, 97%, 98%, 99% or 100%, of plasminogen normally present in body fluid, specifically, blood or blood products is removed from the products of the presently disclosed subject-matter, specifically when compared to untreated blood or blood products. In other words, the product of the presently disclosed subject-matter may comprise plasminogen in an amount of about 0.01% to about 50% of the amount of the plasminogen in other products or untreated blood or blood products, Specifically, about 0.01% or less, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 60%, 70% or less of the amount of plasminogen as compared to untreated blood or blood products.

Plasminogen, when activated to form the active plasmin enzyme, display proteolytic activity, specifically, cleavage or breakdown of proteins smaller polypeptides or amino acids. In this connection, the body fluid treated by the methods of the presently disclosed subject-matter is devoid of plasminogen or plasmin proteolytic activity. In some specific embodiments, the proteolytic activity of plasmin and plasminogen involves the cleavage of fibrin, thereby dissolving fibrin clots. It should be appreciated that the term "devoid of plasmin and plasminogen activity" is meant that the body fluid treated by the method of the presently disclosed subject-matter completely lacks or at least displays "reduced", "decreased" "moderated", "inhibited" or "attenuation" proteolytic activity of plasmin and plasminogen by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9% or 100%, as compared to the proteolytic activity of active plasmin or plasminogen in a body fluid such as blood, plasma or blood product, specifically, untreated blood or blood product.

Still further, in some embodiments the body fluid treated by the methods of the presently disclosed subject-matter is devoid of tPA. The depletion of tPA using the methods, conjugates and device of the presently disclosed subject-matter has been clearly demonstrated by FIG. 9.

It should be appreciated that the term tPA used herein for the tissue plasminogen activator (also known as PLAT; enzyme entry EC 3.4.21.68,) relates to a secreted serine protease that converts and activates the proenzyme plasminogen to a potent fibrinolytic enzyme plasmin. tPA is synthesized in vascular endothelial cells as a single polypeptide chain that undergoes proteolytic cleavage by plasmin or trypsin at a centrally located arginine-isoleucine bond, resulting in a 2-chain disulfide-linked form composed of the N-terminally derived heavy chain and the C-terminal light chain. The tPA gene (DNA acc. NT_167187.1 mapped to chr. 8p11.21) contains 14 exons encoding the heavy chain domain including two kringle regions (K1 and K2) and regions homologous to growth factors and the light chain domain comprising the serine protease catalytic site. Alternative splicing of the tPA gene results in multiple transcript variants encoding different isoforms taking part in multiple biological processes, apart from fibrinolysis, such as cell migration and tissue remodeling. Increased tPA activity causes hyperfibrinolysis manifested as excessive bleeding; decreased tPA activity leads to hypofibrinolysis which can result in thrombosis or embolism. tPA linked phenotypes include familial hyperfibrinolysis (due to increased tPA release) and familial thrombophilia (due to decreased tPA release (OMIM num. 612348). It should be noted that in some embodiments, tPA, as used herein refers to the human tPA that comprise the amino acid sequence encoded by the nucleic acid sequence comprising the sequence as denoted by SEQ ID NO. 3. In some further embodiments, the human tPA may comprise an amino acid sequence encoded by a nucleic acid sequence comprising a sequence having at least about 70%, 75%, 80%, 85%, 90%, 91%, 92%, 93%, 94%, 95%, 96%, 97%, 98%, 99% or 100% homology with the sequence as denoted by SEQ ID NO. 3. In yet some further embodiments, such human tPA molecule may comprise the amino acid sequence as denoted by SEQ ID NO. 4. In yet some other embodiments, the human tPA may comprise an amino acid sequence having at least about 70%, 75%, 80%, 85%, 90%, 91%, 92%, 93%, 94%, 95%, 96%, 97%, 98%, 99% or 100% homology with the sequence as denoted by SEQ ID NO. 4.

A "tPA-deficient body fluid" or "tPA-free body fluid" as used herein is meant that the body fluid treated by the methods of the presently disclosed subject-matter (that according to some embodiments, have been prepared by treating body fluid such as blood, plasma or blood products with the conjugates of the presently disclosed subject-matter), display a reduced, decreased, attenuated, amount of tPA normally present in about 100% to 50%, as compared to untreated blood or blood product. More specifically, at least about 50%, 55%, 60%, 65%, 70%, 75%, 80%, 85%, 90%, 95%, 96%, 97%, 98%, 99% or 100%, of tPA is removed from the body fluid, specifically when compared to untreated blood, plasma or blood products. In other words, the body fluid treated by the methods of the presently disclosed subject-matter may comprise tPA in an amount of about 0.01% to about 50% of the amount of tPA in other products or in untreated blood or blood products. Specifically, about 0.01% or less, 0.05%, 0.1%, 0.5%, 1%, 2%, 3%, 4%, 5%, 6%, 7%, 8%, 9%, 10%, 15%, 20%, 25%, 30%, 35%, 40%, 45%, 50% or less, even 60% or 70% of the amount of tPA as compared to untreated body fluid, such as blood, plasma or blood products.

In yet some further embodiments, the body fluids or specifically, blood, plasma or blood derive product prepared by the methods of the presently disclosed subject-matter may be devoid of plasminogen and tPA, and as such, devoid of any fibrinolytic activity as specified above. In yet some further embodiments, the body fluid or product prepared by the methods of the presently disclosed subject-matter may be also devoid of any other fibrinolytic agent, e.g., urokinase (uPA). Still further, it should be understood that in some embodiments, additional anti fibrinolytic agents may be added to the body fluid product prepared by the methods of the presently disclosed subject-matter.

In some optional embodiments, the method may further comprise the step of measuring the amount of plasminogen in the fibrinolytic protein-depleted body fluid recovered in step (ii), by determining at least one of clotting time and time for total clot lysis in said fibrinolytic protein-depleted body fluid.

In some embodiments, the method of the presently disclosed subject-matter may be used in the preparation of at least one blood and/or blood-derived product that has a reduced fibrinolytic activity.

Fibrinolytic activity, as used herein refers to the ability of some proteolytic enzymes in the blood and blood-derived products to dissolve the fibrin and blood clots. The major proteolytic enzyme cleaving fibrin is plasmin. Plasmin is formed via activation of plasminogen by tPA and/or uPA. When plasmin breaks down fibrin, fibrin degradation products (FDPs) are formed. FDPs compete with thrombin, and thus slow down clot formation by preventing the conversion of fibrinogen to fibrin. This effect can be seen in the thrombin clotting time (TCT) test, which is prolonged in a person that has active fibrinolysis. FDPs, and a specific FDP, the D-dimer, can be measured using antibody-antigen technology. This is more specific than the TCT, and confirms that fibrinolysis has occurred. It is therefore used to indicate deep-vein thrombosis, pulmonary embolism, DIC and efficacy of treatment in acute myocardial infarction. Alternatively, a more rapid detection of fibrinolytic activity, especially hyperfibrinolysis, is possible with thromboelastometry (TEM) in whole blood, even in patients on heparin. In this assay, increased fibrinolysis is assessed by comparing the TEM profile in the absence or presence of the fibrinolysis inhibitor aprotinin. Still further, testing of overall fibrinolysis can be measured by a euglobulin lysis time (ELT) assay. The ELT measures fibrinolysis by clotting the euglobulin fraction (primarily the important fibrinolytic factors fibrinogen, PAI-1, tPA, alpha 2-antiplasmin, and plasminogen) from plasma and then observing the time required for clot dissolution. A shortened lysis time indicates a hyperfibrinolytic state and bleeding risk.

As indicated above, the body fluid, blood, plasma or blood products treated by the methods of the presently disclosed subject-matter display reduced, or decreased fibrinolytic activity. It should be appreciated that the terms "reduced", "decreased" "moderated", "inhibited" or "attenuation" as referred to herein, relate to the retardation, restraining, decrease or reduction of a process, specifically, fibrinolytic activity, by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%, or even 100% as compared to body fluids such as blood, plasma or blood products that comprise tPA and or plasminogen, to blood or blood products that were not treated with the conjugates of the presently disclosed subject-matter, to normal blood or blood products or to commercially available blood products. In other words, these products display no fibrinolytic activity, or at the most, minimal and reduced fibrinolytic activity, specifically, about 0.1% or less, 0.05%, 0.1%, 0.5%, 1%, 2%, 3%, 4%, 5%, 6%, 7%, 8%, 9%, 10%, 15%, 20%, 25%, 30%, 35%, 40%, 45%, 50% or less of the fibrinolytic activity as compared to the fibrinolytic activity of an untreated blood or blood product. In some embodiments, the body fluid, blood, plasma or blood products treated by the methods, conjugates, compositions, as well as the device, battery, kits or systems provided by the presently disclosed subject-matter, that display reduced or no fibrinolytic activity as defined above, may be used for any therapeutic applications disclosed by the presently disclosed subject-matter, as discussed herein after.

In yet some other specific embodiments, the method of the presently disclosed subject-matter may be used in vivo/ex vivo for depleting at least one fibrinolytic protein body fluid/s of and/or in a subject in need thereof.

Thus, in another aspect thereof, the presently disclosed subject-matter provides a method for depleting at least one fibrinolytic protein from body fluid/s of a subject in need thereof by an extracorporeal procedure. More specifically, the method comprising the steps of:

In a first step (i), transferring body fluids of said subject into an extracorporeal apparatus. In some embodiments, the device, battery, kits or systems provided by the presently disclosed subject-matter may be considered as such extracorporeal apparatus.

The second step (ii) involves subjecting the body fluid to affinity depletion procedure specific for at least one fibrinolytic protein/s. It should be noted that such depletion may be performed before, during or after blood is being transferred into and out-off said apparatus. In such way, an extracorporeal body fluid of the subject is obtained. This extracorporeal body fluid is depleted in at least one fibrinolytic protein.

The next step (iii) involves returning, or re-introducing the body fluid that is depleted in at least one fibrinolytic proteins, obtained in step (ii) to the subject.

It should be noted that the affinity-depletion procedure comprises contacting, specifically, ex vivo, the body fluid of the subject with an effective amount of a plurality of conjugates or any compositions thereof. Still further, the conjugates of the presently disclosed subject-matter or any compositions thereof may be comprised within said extracorporeal apparatus, or within a device, battery, kit or system connected to such extracorporeal apparatus, as defined by the presently disclosed subject-matter. As noted above, each conjugate discussed herein, may comprise in some embodiments, at least one particle, at least one linker and at least one amino acid, a derivative thereof or analog thereof. In yet some further embodiments, the plurality of conjugates comprises at least two different conjugates. In some further embodiments, the amino acid, a derivative thereof or analog thereof may be at least one of 4-(aminomethyl)-cyclohexane-carboxylic acid (tranexamic acid), ϵ-amino caproic acid, lysine, cyclohexanecarboxylic acid and 4-methyl-cyclohexanecarboxylic acid. In yet some further embodiments, the amino acid, derivative thereof or analog thereof is at least one of 4-(aminomethyl)-cyclo-hexane-carboxylic acid (tranexamic acid), ϵ-amino caproic acid and lysine. In yet some embodiments, the amino acid, a derivative thereof or analog thereof may be tranexamic acid (TXA).

In some embodiments, the extracorporeal apparatus is a cardiopulmonary bypass machine (CPB), and wherein the extracorporeal apparatus is a plasmapheresis machine.

The term "extracorporeal" refers to a medical procedure which is performed outside the body. For example, such extracorporeal procedure may relate to a circulatory procedure i.e. a procedure in which blood is taken from a patient's circulation to have a process applied to it before it is returned to the circulation. All of the apparatus carrying the blood outside the body is termed the extracorporeal circuit. Such circulatory procedures include for example but are not limited to Apheresis, Autotransfusion, Hemodialysis, Hemofiltration, Plasmapheresis, Extracorporeal carbon dioxide removal, Extracorporeal cardiopulmonary resuscitation, Extracorporeal membrane oxygenation (ECMO) and Cardiopulmonary bypass during open heart surgery.

Cardiopulmonary bypass (CPB) is a technique that temporarily takes over the function of the heart and lungs during surgery, maintaining the circulation of blood and the oxygen content of the patient's body. The CPB pump itself is often referred to as a heart-lung machine or "the pump". Cardiopulmonary bypass pumps are operated by perfusionists. CPB is a form of extracorporeal circulation. Extracorporeal membrane oxygenation is generally used for longer-term treatment.

An apheresis machine is a device which receives blood removed from a patient or donor's body and separates it into its various components: plasma, platelets, white blood cells and red blood cells.

It should be noted that in some embodiments, the conjugated particles useful in the methods of the presently disclosed subject-matter may be as defined by the presently disclosed subject-matter. In yet some further embodiments, the method of the presently disclosed subject-matter may use the device, battery, kit or system as defined herein before.

In some embodiments, the methods of the presently disclosed subject-matter may be applicable for depleting at least one fibrinolytic protein from body fluid that may be at least one of whole blood, plasma or blood-derived product comprising at least one coagulation factor.

In some specific embodiments, such blood-derived product may be at least one of whole blood, plasma, fresh frozen plasma (FFP), platelet rich plasma (PRP) and cryoprecipitate.

In yet some further specific embodiments, the method of the presently disclosed subject-matter may be used for depletion of fibrinolytic protein that may be at least one of plasminogen and tPA.

In some specific embodiments, the methods of the presently disclosed subject-matter may be used for depletion of tPA. In yet some further embodiments, the methods of the presently disclosed subject-matter may be used for depletion of plasminogen. Still further, in certain embodiments, the methods of the presently disclosed subject-matter may be used for depletion of plasminogen and tPA.

In yet some further embodiment, the method may further comprise the step of recovering at least one of plasminogen and tPA from the conjugates of the presently disclosed subject-matter, the plurality of conjugates or any compositions thereof, or specifically, the TXA conjugated particles. It should be appreciated that the depleted fibrinolytic proteins removed from the body fluids by the methods of the presently disclosed subject-matter, may be used for other purposes. In some specific embodiments, recovering plasminogen and/or tPA from the apparatus or conjugate of the presently disclosed subject-matter may be performed by applying on said apparatus, an effective amount of the conjugates, compositions thereof or specifically, TXA, derivative thereof or any analogs thereof on the compositions, conjugates or specifically, TXA conjugated particles bound to said plasminogen and/or tPA. In yet some further embodiments, the recovered plasminogen may be used for treating said subject in cases where fibrinolysis is required.

Still further, it should be understood that the present disclosure further provides an extracorporeal apparatus for use in a method for depleting at least one fibrinolytic protein from body fluid/s of a subject in need thereof by an extracorporeal procedure. More specifically, the method comprising the steps of: In a first step (i), transferring body fluids of said subject into. In some embodiments, the device, battery, kits or systems provided by the presently disclosed subject-matter may be considered as such extracorporeal apparatus. The second step (ii) involves subjecting the body fluid to affinity depletion procedure specific for at least one fibrinolytic protein/s. It should be noted that such depletion may be performed before, during or after blood is being transferred into and out-off said apparatus. In such way, an extracorporeal body fluid of the subject is obtained. This extracorporeal body fluid is depleted in at least one fibrinolytic protein. The next step (iii) involves returning, or re-introducing the body fluid that is depleted in at least one fibrinolytic proteins, obtained in step (ii) to the subject.

In yet another aspect, the presently disclosed subject-matter provides a method for the treatment, prevention, prophylaxis, amelioration, inhibition of bleeding, hemostatic disorders and any bleeding or pathologic condition associated therewith in a subject in need thereof. More specifically, the method may comprise the step of administering to the treated subject a therapeutically effective amount of at least one blood and/or blood-derived product that has a reduced fibrinolytic activity. In some embodiments the product may be prepared by the method as described herein.

In some embodiments, the method of the presently disclosed subject-matter may be applicable for hemostatic disorder that may be hereditary or acquired bleeding disorder.

Hemostatic disorders are bleeding disorders classified as either hereditary or acquired. Acquired bleeding disorders are disorders where bleeding is induced by an external (acquired) cause such as trauma, surgery or fibrinolytic, treatment, as will be discussed herein after.

Bleeding disorders caused by inherited deficiencies of one or more coagulation factors are rare disorders distributed worldwide. Homozygotes or compound heterozygotes for the mutant genes responsible for these defects exhibit bleeding manifestations that are of variable severity and usually related to the extent of the decreased activity of the particular coagulation factor.

In yet further embodiments the methods of the presently disclosed subject-matter are applicable for the treatment, prophylaxis, amelioration, inhibition or delaying the bleeding associated with hereditary hemostatic disorder and undefined bleeding tendency.

"Hereditary hemostatic disorder" as used herein relates to a hereditary deficiency in at least one coagulation factor. More specifically, numerous mutations have been identified in genes encoding coagulation factors I, II, V, VII, X and XI, that lead to deficiency of at least one of said factors or to impaired activity thereof. Homozygotes for these mutations exhibit bleeding tendency either spontaneously or following trauma/surgery. Heterozygotes for the various deficiencies rarely display a bleeding tendency.

Undefined tendency to bleed, as used herein, relates to a condition of bleeding tendency while a precise diagnosis of this condition cannot be established.

Some patients referred for an evaluation of mild bleeding symptoms have an undiagnosed bleeding tendency that may not have been recognized until challenging event that induce bleeding such as surgery or childbirth occur. Clinical variability with regard to bleeding manifestations is common among such individuals, suggesting that environmental and other genetic factors may ameliorate bleeding risks. Although mild bleeding problems may not become evident until exposure to significant hemostatic challenges (such as surgery, dental extractions, major trauma, menarche or childbirth), the predictive risk of bleeding following surgery has not been established for these individuals. Gender has an influence on the manifestations of bleeding. Females are more commonly referred for evaluation because of troublesome bleeding with menses and/or childbirth. In addition, bleeding that persists or becomes problematic 24 hours or longer after dental extractions raises the possibility of a bleeding disorder. Failure to establish a diagnosis in a patient with mild mucocutaneous bleeding is a common problem in practice.

Normal laboratory tests are a hallmark for diagnosis of the undefined bleeding tendency. Failure to establish the diagnosis can be problematic for patient who needs to undergo surgery or childbirth.

For mild bleeding symptoms of patients with undefined bleeding disorders, fibrinolytic inhibitor therapy with ε-aminocaproic acid or tranexamic acid may be used for dental and oral surgeries and it may reduce bleeding with other operative procedures. However, in case severe bleeding develops for example during surgery or childbirth, blood or blood-derived components are required.

In more specific embodiments, the hereditary hemostatic disorder may be a disorder resulting from at least one of deficiency in at least one coagulation factor and undefined tendency to bleeding.

In yet some further embodiments, the deficiency in at least one coagulation factor may be deficiency in at least one of factor XI, factor X, factor V, factor VII, factor II (prothrombin) and factor I (fibrinogen). Thus, in some embodiments, the methods described by the presently disclosed subject-matter may be applicable for any form of bleeding that accompanies hereditary hemostatic disorders caused by a deficiency in at least one of factor XI, factor X, factor V, factor VII, factor II (prothrombin) and factor I (fibrinogen) as disclosed herein.

In yet some further embodiments, the methods of the presently disclosed subject-matter may be applicable for treating disorders characterized by hereditary deficiencies of the coagulation factors I, II, V, VII, X and XI that include at least one of or any bleeding tendency associated therewith. Hereditary deficiencies of the coagulation factors I, II, V, VII, X and XI are autosomal recessive bleeding disorders that have been described in most populations. Their relative frequency varies among populations partly as a result of high frequencies of specific mutant genes in inbred populations. Several population surveys indicate that common among these bleeding disorders are factors XI and VII deficiency, less common disorders are factors V and X deficiency and afibrinogenemia, and the rarest disorders are factor II (prothrombin) and factor XIII deficiency. The severity of bleeding manifestations in affected patients who are homozygotes or compound heterozygotes for a mutant gene is variable and usually related to the extent of the deficiency. Some patients have only mild bruising or display excessive bleeding only following trauma. Other patients, usually with less than 1 percent of normal factor VII, XIII, or X activity, can exhibit intracranial hemorrhages and hemarthroses similar to patients with severe hemophiliac.

In some specific embodiments, the method of the presently disclosed subject-matter may be applicable for treating, preventing, reducing attenuating or inhibiting bleeding associated with hereditary factor XI deficiency, or any acquired bleeding or hemostatic condition in patients suffering from factor IX deficiency.

Hereditary factor XI deficiency is transmitted as autosomal recessive trait. The disorder is exhibited in homozygotes or compound heterozygotes as a mild to moderate bleeding tendency that is mainly injury related. Affected subjects have been described in most populations but in Jews, particularly of Ashkenazi origin, the disorder is common.

Factor XI deficiency as a result of a dysfunctional protein is rare and the majority of the patients have a decreased factor XI protein level. Altogether, above 150 mutations have been reported in non-Jewish and Jewish patients of various origins most of them being missense mutations.

Most bleeding manifestations in homozygotes and compound heterozygotes are injury related. Excessive bleeding can occur at the time of injury or begin several hours or days following trauma. The bleeding tendency varies depending upon the hemostatic challenge and the variable sites of injury. Surgical procedures involving tissues with high fibrinolytic activity (urinary tract, tonsils, nose, tooth sockets) frequently are associated with excessive bleeding in patients with severe factor XI deficiency, irrespective of the genotype. Site-related bleeding tendency now can be understood in light of the demonstrated function of factor XI in preventing clot lysis. Factor XI deficiency by itself is associated with increased fibrinolysis, therefore, the additional bleeding risk of surgery at sites rich in fibrinolysis in these patients may increase the bleeding tendency even further.

Current treatment of bleeding patients with factor XI deficiency is based on FFP. Patients with severe factor XI deficiency who must undergo a surgical procedure should be carefully evaluated and meticulously prepared for the operation. Use of an anti-fibrinolytic agent should be considered in patients undergoing operation at a site with high local fibrinolytic activity. Therefore, in some embodiments, the tPA and/or plasminogen-deficient FFP provided by the presently disclosed subject-matter may be particularly relevant for treating patients with Factor XI deficiency. More specifically, a subject suffering from any of the conditions discussed above.

In other embodiments, the method of the presently disclosed subject-matter may be applicable for treating, preventing, reducing attenuating, inhibiting bleeding associated with hereditary factor VII deficiency, or any acquired bleeding or hemostatic condition in patients suffering from factor VII deficiency.

Hereditary deficiency of factor VII is a rare autosomal recessive disorder that has been observed in most populations. A presumptive diagnosis can be easily made because factor VII deficiency is the only coagulation disorder that produces a prolonged clotting time test prothrombin time (PT). Most mutations causing factor VII deficiency have been missense mutations.

Bleeding manifestations occur in homozygotes and in compound heterozygotes for factor VII deficiency. Patients who have factor VII activity less than 1 percent of normal, frequently present a severe bleeding manifestations such as hemarthrosis leading to severe arthropathy and life-threatening intracerebral hemorrhage.

Patients with slightly higher levels of factor VII (factor VII activity of 5 percent of normal or more) have a much milder disease, characterized by epistaxis, gingival bleeding, menorrhagia, and easy bruising. Some surgical procedures such as dental extractions, tonsillectomy, and procedures involving the urogenital tracts frequently are accompanied by bleeding when no prior therapy is instituted prior to the procedure. In contrast, surgical procedures such as laparotomy, herniorrhaphy, appendectomy, and hysterectomy have been uneventful. This apparent discrepancy can be explained by different extents of local fibrinolysis exhibited by the respective traumatized tissues.

Replacement therapy by FFP is essential in patients who present with severe hemorrhage, such as hemarthrosis or intracerebral bleeding. When surgery is required, the site of surgery should be considered, as dental extractions, tonsillectomy, nose surgery, and urologic interventions are likely to be associated with bleeding because of local fibrinolysis. Therefore, in some embodiments, the tPA and plasminogen-deficient FFP provided by the presently disclosed subject-matter may be particularly relevant for treating patients with Factor VII deficiency, specifically, any of the conditions discussed above.

In yet further embodiments, the method of the presently disclosed subject-matter may be applicable for treating, preventing, reducing attenuating, inhibiting bleeding associated with hereditary factor X deficiency, or any acquired bleeding or hemostatic condition in patients suffering from factor X deficiency.

Hereditary factor X deficiency, a moderate to severe bleeding tendency, is an autosomal recessive disorder. The currently described 95 mutations that cause factor X deficiency include large deletions, small frameshift deletions, nonsense mutation, and missense mutations. The clinical manifestations of factor X deficiency are related to the functional levels of factor X. Individuals with severe factor X deficiency and functional factor X levels less than 1 percent of normal bleed spontaneously and following trauma. Bleeding occurs primarily into joints and soft tissues, however, bleeding from mucous membranes such as Menorrhagia may be especially problematic in women. More unusual bleedings are intracerebral hemorrhage, intramural intestinal bleeding (which can produce symptoms like those of an acute abdomen), urinary tract bleeding, and soft tissue bleeding with development of hemorrhagic pseudocysts or pseudotumors. In individuals with mild deficiencies of factor X bleeding is less common, usually occurring only after trauma or during or after surgery. Fresh-frozen plasma is used to treat patients with factor X deficiency. Therefore, in some embodiments, the tPA and/or plasminogen-deficient FFP (or any other blood products) provided by the presently disclosed subject-matter may be particularly relevant for treating patients with Factor X deficiency, specifically, patients suffering from any of the conditions discussed above.

In yet some other embodiments, the presently disclosed subject-matter may be applicable for treating, preventing, reducing attenuating, and inhibiting bleeding associated with hereditary factor V deficiency, or any acquired bleeding or hemostatic condition in patients suffering from factor V deficiency.

Hereditary factor V deficiency is among the less common inherited bleeding disorders and manifests in homozygotes or compound heterozygotes as a moderate bleeding tendency. Factor V deficiency is inherited as an autosomal recessive trait. Heterozygotes, whose plasma factor V activity ranges between 25 and 60 percent of normal, usually are asymptomatic, Assays of factor V protein indicate that most homozygotes and compound heterozygotes have a true deficiency rather than a dysfunctional protein. Above 80 total distinct mutations have been identified, of which one quarter are missense, Homozygous or compound heterozygous patients whose factor V level ranges from less than 1 to 10 percent of normal exhibit a lifelong bleeding tendency. Common manifestations include ecchymoses, epistaxis, gingival bleeding, hemorrhage following minor lacerations, and menorrhagia. Postpartum hemorrhage occurs in more than 50 percent of pregnancies in patients with severe factor V deficiency. Bleeding from other sites is less common.

Trauma, dental extractions, and surgery confer a high risk of excessive bleeding. In case a severe spontaneous bleeding occurs, or surgery is performed, fresh-frozen plasma replacement should be given. When planning plasma replacement therapy it is important to consider surgical procedures at sites having high local fibrinolytic activity such as the urogenital tract, oral cavity, and nose, since surgery at these sites will result in excessive bleeding and postpartum hemorrhage is common. Therefore, in some embodiments, the tPA and plasminogen-deficient products provided by the presently disclosed subject-matter may be particularly relevant for treating patients with Factor V deficiency, specifically, any of the conditions discussed above.

In certain embodiments, the methods of the presently disclosed subject-matter may be particularly applicable for treating, preventing, reducing attenuating, inhibiting bleeding associated with hereditary factor II deficiency, or any acquired bleeding or hemostatic condition in patients suffering from factor II deficiency.

Inherited factor II (prothrombin) deficiency is one of the rarest coagulation factor deficiencies. It presents in two forms: type I, true deficiency (hypoprothrombinemia), and type II, in which dysfunctional prothrombin is produced (dysprothrombinemia). These autosomal recessive disorders are genetically heterogeneous, and characterized by a mild to moderate bleeding tendency.

Abnormalities of prothrombin are inherited in an autosomal recessive manner. Among individuals with type I deficiency, heterozygotes exhibit prothrombin levels that are approximately 50 percent of normal, whereas homozygotes display levels that typically are less than 10 percent of normal. Above fifty mutations that cause prothrombin deficiency have been identified, most of which are missense mutations.

Inherited types I and II deficiencies are characterized by mild to moderate mucocutaneous and soft-tissue bleeding that usually correlates with the degree of functional prothrombin deficiency. With prothrombin levels of approximately 1 percent of normal, bleeding may occur spontaneously or following trauma. Surgical bleeding may be significant. Menorrhagia, epistaxis, gingival bleeding, easy bruising, and subcutaneous hematomas may occur.

Replacement therapy in patients with inherited prothrombin deficiency consists of administration of FFP. Therefore, in some embodiments, the tPA and plasminogen-deficient FFP provided by the presently disclosed subject-matter may be particularly relevant for treating patients with Factor II deficiency, specifically, any of the conditions discussed above.

In yet some other embodiments, the presently disclosed subject-matter may be applicable for treating, preventing, reducing attenuating, inhibiting bleeding associated with hereditary fibrinogen deficiency or any acquired bleeding or hemostatic condition in patients suffering from hereditary fibrinogen deficiency.

"Fibrinogen (factor I) deficiency" as used herein relates to hereditary fibrinogen abnormalities comprises the afibrinogenemia (complete absence of the fibrinogen), dysfibrinogenemia and hypodysfibrinogenemia, inherited disorders of fibrinogen are rare and can be subdivided into type I and type II disorders. Type I disorders (afibrinogenemia and hypofibrinogenemia) affect the quantity of fibrinogen in circulation. Type II disorders (dysfibrinogenemia and hypodysfibrinogenemia) affect the quality of circulating fibrinogen. Afibrinogenemia, the most severe form of fibrinogen deficiency, is characterized by autosomal recessive inheritance and the complete absence of fibrinogen in plasma.

Dysfibrinogenemia is defined by the presence of normal levels of functionally abnormal plasma fibrinogen. Hypodysfibrinogenemia is defined by low levels of a dysfunctional protein. These are heterogeneous disorders caused by many different mutations in the three fibrinogen coding genes. Dysfibrinogenemias and hypodysfibrinogenemias are autosomal dominant disorders. Most affected patients are heterozygous for missense mutations in the coding region of one of the three fibrinogen genes. Because the secreted fibrinogen hexamer contains two copies of each of the three fibrinogen chains, and the resulting fibrin network contains multiple copies of the molecule, heterozygosity for one mutant allele is sufficient to impair the structure and function of the fibrin clot.

Bleeding because of afibrinogenemia usually manifests in the neonatal period, with 85 percent of cases presenting umbilical cord bleeding, but a later age of onset is not unusual. Bleeding may occur in the skin, gastrointestinal tract, genitourinary tract, or the central nervous system with intracranial hemorrhage being the major cause of death. There is an intriguing susceptibility of spontaneous rupture of the spleen in afibrinogenemic patients. Menstruating women may experience menometrorrhagia. In addition, first trimester abortion is usual in afibrinogenemic women. These patients may also have antepartum and postpartum hemorrhage. Hemoperitoneum after rupture of the corpus luteum has also been observed.

Replacement therapy with fibrinogen containing commercial products is the only option for treatment of patients with inherited fibrinogen deficiency. Therefore, in some embodiments, the methods the presently disclosed subject-matter may be particularly relevant for treating patients with fibrinogen deficiency, specifically, any of the conditions discussed above. Particularly, in some embodiments where the fibrinolytic protein-depleted body fluid prepared by the conjugates and methods of the presently disclosed subject-matter is supplemented with fibrinogen.

In contrast to the commercial preparations of blood-derived products used for the treatment of hereditary coagulation factor deficiencies, fibrinolytic protein-depleted body fluid prepared by the conjugates, compositions and methods of the presently disclosed subject-matter have a substantial advantage, because in addition to providing the missing factor (pro-coagulant quality) the removal of t-PA and plasminogen from the products renders them antifibrinolytic qualities that are essential for preventing further clot lysis in case of bleeding.

In some embodiments, the methods of the presently disclosed subject-matter may be applicable for treating acquired hemostatic disorders. The acquired hemostatic disorder may be at least one of surgery-induced bleeding, trauma-induced bleeding, acute gastrointestinal bleeding, bleeding associated with burns, hemorrhagic stroke, lung injury associated with emphysema and chronic obstructive pulmonary disease (COPD), bleeding associated with childbirth, disseminated intravascular coagulation (DIC), and bleeding resulting from fibrinolytic or thrombolytic therapy. In some specific embodiments, the method of the presently disclosed subject-matter may be applicable for treating, preventing, reducing, attenuating, and inhibiting bleeding associated with surgical procedures, specifically, minor or major surgical procedures.

Surgical procedures are a great challenge to the hemostatic system, especially when surgery is performed at places (e.g., tissues, organs) rich in fibrinolytic proteins. Even patients with no or mild to moderate bleeding disorders can bleed excessively following surgery. In addition to the extent of the surgical trauma, the magnitude of the fibrinolytic activity at the surgical site must be considered.

It should be understood that in cases the surgical procedures are elective, expected or not urgent (e.g., cesarean surgery, or any other major surgery that allow sufficient time for pre-operative preparations), the products of the presently disclosed subject-matter may be used for pre-operative treatment to facilitate prevention or reduction of excessive bleeding during the surgical intervention. Thus, in some embodiments, the presently disclosed subject-matter may provide a preventive method particularly useful for patients having hereditary disorders, patients suffering from hyperfibrinolysis and/or patients that are expected to be operated.

In some further specific embodiments, the method of the presently disclosed subject-matter is suitable for treating trauma-induced bleeding (traumatic bleeding).

Traumatic bleeding can be caused by any type of injury, for example any injury caused by, work and car accidents, combats or falls. There are different types of traumatic wounds which may cause bleeding. In general, trauma causes damage to a blood vessels that in turn causes blood to flow externally outside the body or internally into body organs such as brain, lung, liver, kidney, spleen or into body cavities, such as thorax and abdomen.

Beside the physical measures to stop the bleeding, blood and blood-derived components are usually administered in order to initiate blood clotting, which will eventually result in a cessation of bleeding.

The tPA and/or plasminogen deficient blood and bloodderived products of the presently disclosed subject-matter display an advantage over the commercial blood-derived products, because they provide an additional antifibrinolytic quality, which will prevent dissolution of a formed clot that might be essential for rapid cessation of bleeding.

In some specific embodiments the fibrinolytic proteindepleted body fluid prepared by the conjugates and methods of the presently disclosed subject-matter may be suitable for treatment of acute or chronic gastrointestinal bleeding.

"Gastrointestinal (GI) bleeding", also known as gastrointestinal hemorrhage, as used herein, relates to all forms of bleeding in the gastrointestinal tract, from the mouth to the rectum. "Acute gastrointestinal bleeding" means that there is a significant blood loss over a short time causing acute blood loss and hemorrhagic shock. Symptoms may include vomiting (hemathemesis) either red blood or black blood (due to digested blood also called "coffee ground"), bloody stool, or black stool (digested blood called melena). In contrast, chronic gastrointestinal bleeding is bleeding of small amounts of blood over a long time. In this case the symptoms are of iron-deficiency anemia. GI bleeding is typically divided into two main types: upper gastrointestinal bleeding and lower gastrointestinal bleeding. Causes of upper GI bleeds include: peptic ulcer disease, esophageal varices, that may occur in some embodiments, due to liver cirrhosis and cancer, among others. Causes of lower GI bleeds include: hemorrhoids, cancer, and inflammatory bowel disease among others. Endoscopy of the lower and upper gastrointestinal track may locate the area of bleeding. Medical imaging may be useful in cases that are not clear.

Acute upper GI bleed is more common than lower GI bleed. An upper GI bleed occurs in 50 to 150 per 100,000 adults per year. A lower GI bleed is estimated to occur in 20 to 30 per 100,000 per year. It results in about 300,000 hospital admissions a year in the United States. Risk of death from a GI bleed is between 5% and 30%. Risk of bleeding is more common in males and increases with age.

The most common source of upper gastrointestinal bleeding is peptic ulcer. Esophageal inflammation and erosive disease are the next most common causes. In those with liver cirrhosis, 50-60% of bleeding is due to esophageal varices. Approximately half of those with peptic ulcers have an *H. pylori* infection. Other causes include gastric or duodenal ulcers, Mallory-Weiss tears, cancer, and angiodysplasia. A number of medications are found to cause upper GI bleeds: NSAIDs, COX-2 inhibitors, SSRIs, corticosteroids, and anticoagulants.

Lower gastrointestinal bleeding is typically from the colon, rectum or anus. Common causes of lower gastrointestinal bleeding include hemorrhoids, cancer, angiodysplasia, ulcerative colitis, Crohn's disease, and aortoenteric fistula.

The initial focus of the treatment of acute gastrointestinal bleeding is on resuscitation, beginning with airway management and fluid resuscitation using intravenous fluids and blood.

Colonoscopy is useful for the diagnosis and treatment of lower GI bleeding. A number of techniques may be employed including: clipping, cauterizing, and sclerotherapy. Surgery, while rarely used to treat upper GI bleeds, is still commonly used to manage lower GI bleeds by cutting out the part of the intestines that is causing the problem. Angiographic embolization may be used for both upper and lower GI bleeds.

Still further, the plasminogen and/or tPA depleted-blood products prepared by the methods of the presently disclosed subject-matter, using the conjugates and apparatus of the presently disclosed subject-matter may be used for treating Hemorrhagic stroke.

"Hemorrhagic stroke" as used herein, relates to bleeding occurring directly into the brain parenchyma. The usual mechanism is thought to be leakage from small intracerebral arteries damaged by chronic hypertension. Patients with intracerebral bleeds are more likely than those with ischemic stroke to have headache, altered mental status, seizures, nausea and vomiting, and/or marked hypertension. Even so, none of these findings reliably distinguishes between hemorrhagic and ischemic stroke. Specific symptoms may stem from focal neurologic deficits. The type of deficit depends on the area of brain involved. If the dominant (usually the left) hemisphere is involved, a syndrome consisting of the following may result: right hemiparesis, right hemisensory loss, left gaze preference, right visual field cut and aphasia. If the nondominant (usually the right) hemisphere is involved, a syndrome consisting of the following may result: left hemiparesis, left hemisensory loss, right gaze preference and left visual field cut.

Brain imaging is a crucial step in the evaluation of suspected hemorrhagic stroke and must be obtained on an emergent basis. Brain imaging aids diagnosing hemorrhage, and it may identify complications such as intraventricular hemorrhage, brain edema, or hydrocephalus. Either noncontract computed tomography (NCCT) scanning or magnetic resonance imaging (MRI) is the modality of choice.

In case the treatment with blood products is indicated for hemorrhagic stroke, blood, FFP and platelets obtained from a blood bank are used. Taking into account the prothromhoyic and antifibrinolytic quality of the fibrinolytic protein-depleted body fluid prepared by the conjugates and methods of the presently disclosed subject-matter, it seems that they are more appropriate cessation of bleeding in a patient suffering from hemorrhagic stroke than the conventional blood products.

In some specific embodiments, the methods of the presently disclosed subject-matter may be suitable for treating lung injury associated with emphysema and COPD. In more specific embodiments, the method of the presently disclosed subject-matter may comprise the step of administering to the treated subject a therapeutically effective amount of fibrinolytic protein-depleted body fluid prepared by the conjugates and methods of the presently disclosed subject-matter, due to its enrichment in alpha-1 antitrypsin, makes its use more appropriate for the treatment of a subject with emphysema and COPD. In these diseases leukocyte proteases break down the elasticity of the lungs resulting in lung fuller and consequent development of lung emphysema and chronic obstructive pulmonary disease (COPD). Therefore, alpha-1 antitrypsin within the fibrinolytic protein-depleted body fluid prepared by the conjugates and methods of the presently disclosed subject-matter may inhibit the activity of leukocyte proteases and by this means restore the elasticity if the lung tissue.

Emphysema is a form of chronic (long-term) lung disease. People with emphysema have difficulty breathing from a limitation in blowing air out. There are multiple causes of emphysema, but smoking is by far the most common.

Emphysema is one of the main types of chronic obstructive pulmonary disease (COPD). It's called "obstructive" because people with emphysema exhale as if something were obstructing the flow of air. The other form of COPD is chronic bronchitis, which can also be caused by smoking.

Emphysema results when the delicate linings of the air sacs in the lungs become damaged beyond repair. Most commonly, the toxins in cigarette smoke create the damage. The lung changes of emphysema evolve slowly over years as the fragile tissues between air sacs are destroyed and air pockets in the lungs develop. Air becomes trapped in these spaces of damaged lung tissue. The lungs slowly enlarge, and breathing requires more effort.

This problem of emphysema is called airflow limitation. During lung function testing, it takes someone with emphysema far longer to empty their lungs than it does a person without emphysema.

Besides smoking, the other major known cause of emphysema is alpha-1 antitrypsin deficiency. However, this is a minor cause compared to smoking. Alpha-1 antitrypsin is a natural protein circulating in human blood. Its main function is to keep white blood cells from damaging normal tissues. Thus, treatment of a subject with emphysema with fibrinolytic protein-depleted body fluid prepared by the conjugates and methods of the presently disclosed subject-matter enriched in alpha-1 antitrypsin may inhibit the activity of proteases and thereby restore the elasticity to the lung tissue.

Chronic obstructive pulmonary disease (COPD) is a type of obstructive lung disease characterized by long term poor airflow. The main symptoms include shortness of breath and cough with sputum production. COPD typically worsens over time. Eventually walking upstairs or carrying things will be difficult. Chronic bronchitis and emphysema are older terms used for different types of COPD. The term "chronic bronchitis" is still used to define a productive cough that is present for at least three months each year for two years.

COPD is a type of obstructive lung disease in which chronic incompletely reversible poor airflow (airflow limitation) and inability to breathe out fully (air trapping) exist. The poor airflow is the result of breakdown of lung tissue (known as emphysema) and small airways disease (known as obstructive bronchiolitis). The relative contributions of these two factors vary between people. Severe destruction of small airways can lead to the formation of large air pockets known as bullae that replace lung tissue. This form of disease is called bullous emphysema.

Tobacco smoking is the most common cause of COPD, with a number of other factors such as air pollution and genetics playing a smaller role. In the developing world, one of the common sources of air pollution is poorly vented heating and cooking fires. Long-term exposure to these irritants causes an inflammatory response in the lungs resulting in narrowing of the small airways and breakdown of lung tissue. The diagnosis is based on poor airflow as measured by lung function tests. In contrast to asthma, the airflow reduction does not improve much with the use of a bronchodilator.

The most common symptoms of COPD are sputum production, shortness of breath, and a productive cough. These symptoms are present for a prolonged period of time and typically worsen over time. It is unclear if different types of COPD exist. While previously divided into emphysema and chronic bronchitis, emphysema is only a description of lung changes rather than a disease itself, and chronic bronchitis is simply a descriptor of symptoms that may or may not occur with COPD.

Advanced COPD leads to high pressure on the lung arteries, which strains the right ventricle of the heart and right hear failure. This situation is referred to as cor pulmonale, and leads to symptoms of leg swelling and bulging neck veins. COPD is more common than any other lung disease as a cause of cor pulmonale. Cor pulmonale has become less common since the use of supplemental oxygen.

Consequently, the fibrinolytic protein-depleted body fluid prepared by the conjugates and methods of the presently disclosed subject-matter may be beneficial as a complementary treatment of COPD, since its enrichment in alpha-1 antiplasmin may inhibit leukocyte's proteases and thereby repair the elastic quality to the damaged lung tissue.

Still further, the plasminogen and/or tPA depleted-blood products prepared by the methods of the presently disclosed subject-matter, using the conjugates and apparatus of the presently disclosed subject-matter may be used for treating burns and any bleeding associated therewith. The term "burn" as used herein refers to an injury to tissues involving damage to the skin and possibly tissues underlying the skin. Burns may be caused by the contact with heat, flame, chemicals, electricity, or radiation.

Burns are primarily caused by accidents, and can be classified into heat burns, electrical burns, chemical burns, radiation burns according to the cause. The severity of a burn is divided into first-, second-, third- and fourth-degree burns according to the burned width and depth, the contact time with the temperature of objects causing burns, and skin conditions. In second or higher degree burns, scar may be left behind and treatment in hospital is required.

First-degree burns cause skin redness and itching pain. They cause damage to the epidermis, the outermost layer of the skin layer, and swelling accompanied by pain and redness. The symptoms disappear in a few days, but superficial exfoliation and pigmentation may be left behind. After recovery, cicatrix (scar) does not remain. Sunburn is the most common example of first-degree burn.

Second-degree burns affect the epidermis and dermis, and cause redness, pain, swelling, and blisters in 24 hours after accidents. Second-degree burns may affect the sweat glands or pores. Severe burning sensation and pain occurs. Rupture of blisters leaves eroded areas and releases the secretion in large amounts. When the burned area is about 15 percent or more of the body surface area, special attention should be given. Second-degree burns are cured in a few weeks, but in many cases, pigmentation or depigmentation is left behind. When secondary infections occur, partial symptoms become severer and it takes longer to heal.

Third-degree burns affect the epidermis, dermis, and even subcutaneous fat, and the skin becomes darker or lighter in color, and blood vessels immediately beneath the skin surface are coagulated. Burned regions may be benumbed, but patients feel extremely severe pain and there is the death of skin tissue and structure, requiring a lot of time to treat, with scars left behind. In 2 weeks after accidents, scabs peel away and reveal ulcerated surface. Large quantities of fluids are secreted and bleeding is likely to occur, but third-degree burns are healed when new tissues gradually form, leading to regeneration of epidermis, with cicatrix left behind. When deep skin necrosis develops, or when secondary infections occur, healing is delayed and uneven cicatrix surface is created, resulting in keloid formation or deformation or movement disorders. When the burned area is 10 percent or more of the body surface area, special attention is required.

Fourth-degree burns involve carbonized and darkened tissues of burned regions, and extend through the skin layer to injure fatty layer, ligaments, fasciae, muscles, and even bone tissues. Fourth-degree burns primarily include high voltage electrical burns, and in some cases, deep dermal 2-3 degree burns may develop to fourth-degree burns when viral infection occurs. When the burned area ranges 20 percent or more, responses may occur all over the body; hypotension, shock, acute kidney dysfunction may occur due to excessive loss of body fluids, and wound infection or pneumonia, sepsis, and multiple organ dysfunction syndrome may occur later.

At temperatures greater than 44° C. (111° F.), proteins begin losing their three-dimensional shape and start breaking down. This results in cell and tissue damage. Many of the direct health effects of a burn are secondary to disruption in the normal functioning of the skin. They include disruption of the skin's sensation, ability to prevent water loss through evaporation, and ability to control body temperature. Disruption of cell membranes causes cells to lose potassium to the spaces outside the cell and to take up water and sodium.

In large burns (over 30% of the total body surface area), there is a significant inflammatory response. This results in increased leakage of fluid from the capillaries, and subsequent tissue edema. This causes overall blood volume loss, with the remaining blood suffering significant plasma loss, making the blood more concentrated. Poor blood flow to organs such as the kidneys and gastrointestinal tract may result in renal failure and stomach ulcers.

In yet some further embodiments, the surgery-induced bleeding may be bleeding induced by a minor or major surgery. Major surgery is defined as any surgical procedure that involves anesthesia or respiratory assistance. In case of bleeding during major surgery the treatment includes replacement of missing or non-functional coagulation factors by commercial FP, FFP or cryoprecipitate.

In contrast to major surgery that, as detailed above herein, relates to any surgical procedure that involves anesthesia or respiratory assistance, minor surgery is a medical procedure involving an incision with instruments, performed to repair damage or arrest disease in a living body. Since minor surgery includes an incision or cutting, which is an act of penetrating or opening with a sharp edge of any part of a human body, in a subject with bleeding tendency this procedure may induce significant bleeding.

It should be noted that in some embodiments, the methods of the presently disclosed subject-matter may be applicable for minor surgery that may include any dental treatment or procedure. The term "dental treatment" refers to any treatment aiming at prevention and/or curing of diseases, disorders and conditions of the soft and hard tissues of the jaw (mandible), the oral cavity, maxillofacial area and the adjacent and associated structures of the human body. Such treatments relate obviously to the dentistry, orthodontics, periodontics oral medicine and oral surgery, but may relate also to other branches of the dentistry and medicinal practice which may be involved in the health of the oral cavity in general.

Still further, the major surgery may be an open heart surgery or a liver transplantation surgery.

Major surgery is defined as any surgical procedure that involves anesthesia or respiratory assistance. In case of bleeding during major surgery the treatment includes replacement of missing or non-functional coagulation factors by commercial FP, FFP or cryoprecipitate. However, this may not be sufficient since the presence of tPA and plasminogen within the above products can mediate the fibrinolytic activity at the site of injury of surgery and thereby promote the dissolution of clot formed to stop or prevent the bleeding. Therefore, administration of the t-PA and plasminogen-deficient products of the presently disclosed subject-matter that display significantly reduced fibrinolytic activity, is a better and more efficient therapeutic option that the commercial products, since in addition to supplementation of coagulation factors by the products of the presently disclosed subject-matter their antifibrinolytic activity (as demonstrated by the Examples), may decrease or prevent bleeding contributed by the clot lysis induced by fibrinolytic proteins that are present in commercial products.

In particular embodiments the methods of the presently disclosed subject-matter are applicable for open heart surgery. Some surgical procedures can be anticipated to cause severe bleeding, such as open heart surgery. In these operations extracorporeal circulation (cardiopulmonary bypass—CPB) is used.

Cardiovascular (open heart) surgery is surgery on the heart or great vessels performed by cardiac surgeons. Frequently, it is done to treat complications of ischemic heart disease (for example, coronary artery bypass grafting), correct congenital heart disease, or treat valvular heart disease from various causes including endocarditis, rheumatic heart disease and atherosclerosis. It also includes heart transplantation.

During open-heart surgery, the heart is temporarily stopped. Patients undergoing an open-heart surgery are placed on cardiopulmonary bypass, meaning a machine which pumps their blood and oxygen for them. A machine will never function the same as a normal heart and lungs, therefore, similar to many surgical procedures, the time on this machine is kept to a minimum. This artificial method provides a bypass, to overcome temporarily a patient's needs with regard to the function of the heart and lungs.

The bleeding phenomena that occur in these operations are due to the anticoagulation used during the surgery, which, deliberately induces coagulation deficiency. In addition, platelet dysfunction that stems from the passing of the blood through an extracorporeal circulation contributes to the tendency to bleed.

It should be realized that the methods of the presently disclosed subject-matter may be particularly applicable for subjects undergoing open heart surgery by CPB. The products, compositions and methods of the presently disclosed subject-matter may impart dual beneficial effect to these patients as follows:

1. During the open heart surgery, blood will flow through a tube added to the heart-lung machine (CPB machine), while the tube is coated with tranexamic acid to deplete t-PA and/or plasminogen from the blood (as detailed in Experimental Procedures). The pump will direct the blood flow from the CPB machine to the patient. While flowing through this tube, the blood depleted in t-PA and plasminogen is returned to patient's circulation.

By this way the returned blood is poor in fibrinolytic activity and enriched in antifibrinolytic activity, thereby providing protection from bleeding tendency.

2. In case bleeding occurs due to the above mentioned reasons, the patient may then be treated to stop bleeding with fibrinolytic protein-depleted body fluid prepared by the conjugates and methods of the presently disclosed subject-matter, which are expected to be more potent in cessation of bleeding due to their antifibrinolytic qualities.

In further embodiments the methods of the presently disclosed subject-matter are suitable for implementation in treatment of bleeding associated with liver transplantation surgery.

The liver plays a central role in hemostasis and thrombosis. Liver parenchymal cells are the site of synthesis of most coagulation factors, the physiologic inhibitors of coagulation, and essential components of the fibrinolytic system. The liver also regulates hemostasis and fibrinolysis by clearing activated coagulation factors and enzyme inhibitor complexes from the circulation. Therefore, when liver dysfunction occurs in patients with liver disease, a complicated hemostatic derangement ensues, which can lead to bleeding.

During the first stage of liver transplantation, the removal of the diseased liver, (the anhepatic stage), significant hemostatic changes can occur. Because activated clotting factors are not removed from the circulation, their consumption can develop together with consumption of platelets and secondary hyperfibrinolysis. Moreover, primary hyperfibrinolysis also occurs as a result of defective clearance of tPA. The most severe hemostatic changes during liver transplantation occur after reperfusion of the donor liver. Platelets are trapped in the graft, giving rise to an aggravation of thrombocytopenia and causing damage to the graft by induction of endothelial cell apoptosis. Release of tissue factor and tPA from the reperfused graft further causes fibrinolysis. Thus, hyperfibrinolysis is thought to contribute significantly to impaired hemostasis during the anhepatic and reperfusion phases. Moreover, the graft releases heparin-like substances that can inhibit coagulation. In addition, other factors such as hypothermia, metabolic acidosis, and hemodilution adversely affect hemostasis during this phase. Liver transplantation is a lengthy procedure with extensive surgical wound surfaces including potential transaction of collateral veins. Improved surgical techniques and anesthesiologic care have led to a remarkable reduction of blood loss during liver transplantation. When uncontrolled bleeding occurs, packed red cells, platelets, and fresh-frozen plasma can be transfused. Use of synthetic antifibrinolytic agents, such as tranexamic acid (a lysine analogue) and aprotinin (a serine protease inhibitor) is a common practice.

Thus it should be appreciated that the products of the presently disclosed subject-matter, conjugates, compositions, and methods described by the presently disclosed subject-matter, owing to their antifibrinolytic qualities may be particularly applicable for cessation of bleeding associated with hyperfibrinolytic state induced by liver transplantation surgery.

It should be appreciated that the methods of the presently disclosed subject-matter may be applicable for any surgery involving any organ or tissue transplantation, for example, liver, kidney, lung, heart, pancreas, skin, blood vessels and the like.

In yet some further embodiments, the methods of the presently disclosed subject-matter may be applicable for acquired hemostatic disorder that may be bleeding resulting from fibrinolytic or thrombolytic therapy.

Fibrinolytic/thrombolytic therapy is mostly administered in patients with acute myocardial infarction (acute coronary artery thrombosis) or in patients with acute stroke (acute cerebral arterial thrombosis). The goal of fibrinolytic/thrombolytic therapy is rapid restoration of blood flow in an occluded vessel achieved by accelerating fibrinolytic proteolysis of the thrombus. fibrinolytic therapy typically results in fibrinolytic state because plasminogen activation is not limited to the thrombus. These effects are complex and include a reduction in fibrinogen level, increase in fibrinogen degradation products, and decreases in coagulation factors. The complication of fibrinolytic therapy is bleeding. Bleeding complications are more frequent with fibrinolytic than with anticoagulant therapy and require rapid diagnosis and management. Two problems contribute to excess bleeding. First, the fibrinolytic effect is not limited to the site of thrombosis but is usually systemic. Therefore, any hemostatic plugs needed to prevent bleeding at sites of vascular injury caused either by catheters needed for treatment or within pathological lesions in the brain, gastrointestinal tract, or elsewhere are also susceptible to dissolution. The most serious complication is intracranial hemorrhage which occurs in approximately 1% of patients and is associated with a high mortality and serious disability in survivors. The most common bleeding complications are related to invasive vascular procedures such as placement of arterial and venous catheters. Some bleeding at these sites is frequent and should not be a reason for interrupting therapy if it can be managed with local pressure or other simple measures. The problem can be minimized by limiting venous and arterial punctures and by early institution of local measures. Major bleeding may also result from preexisting lesions such as gastrointestinal ulcers or genitourinary lesions.

Treatment of bleeding complications following fibrinolysis/thrombolysis involves measures directed to the local site as well as correction of the systemic hypercoagulable state includes replacement therapy to correct the hemostatic defect caused by systemic plasminemia. Fibrinogen replacement is often needed and can be accomplished by administration of cryoprecipitate, and fresh-frozen plasma can be used to replace other hemostatic proteins.

It should be noted that fibrinolytic/thrombolytic therapy, involves the use of anti-coagulants or anti-coagulating agents. As used herein, the term "anticoagulant agent" is intended to mean any agent which interferes with the clotting of blood. Some anticoagulants, such as the coumarin derivatives bishydroxycoumarin (Dicumarol) and warfarin (Coumadin) inhibit synthesis of prothrombin, a clot-forming substance, and other clotting factors. Anticoagulants can include but are not limited to compounds acting as beta2 Adrenoreceptor Antagonists, Neuropeptide V2 Antagonists, prostacyclin analogs, thromboxane synthase inhibitors, calcium agonists, coumarin derivatives, elastase inhibitors, Non-steroidal anti-inflammatories thrombin inhibitors, lipoxygenase inhibitors, Factor Vila inhibitors, Factor Xa inhibitors, phosphodiesterase III inhibitors, Heparins, and fibrinogen glucoprotein IIb/IIIa. Antagonists.

Coumarins are vitamin K antagonists. A prominent member of this class is warfarin (Coumadin). These anticoagulants are used to treat patients with deep-vein thrombosis (DVT), pulmonary embolism (PE) and to prevent emboli in patients with atrial fibrillation (AF), and mechanical prosthetic heart valves. Other examples are acenocoumarol, phenprocoumon, atromentin, and phenindione.

Heparin is a biological substance, usually made from pig intestines. It works by activating antithrombin III, which blocks thrombin from clotting blood. Low molecular weight heparin, a more highly processed product, is useful as it does not require monitoring of the APTT coagulation parameter and has fewer side effects as for example Enoxaparin (Clexane).

Fondaparinux is a synthetic sugar composed of the five sugars (pentasaccharide) in heparin that bind to antithrombin and is an inhibitor of factor Xa. It is a smaller molecule than low molecular weight heparin. Another example is Idraparinux sodium which has a similar chemical structure and method of action as fondaparinux.

Drugs such as rivaroxaban, apixaban and edoxaban work by inhibiting factor Xa directly (unlike the heparins and fondaparinux, which work via antithrombin activation).

Further examples include but are not limited to betrixaban from Portola Pharmaceuticals, darexaban (YMI150) from Astellas, and more recently letaxaban (TAK-442) from Takeda and eribaxaban (PD0348292) from Pfizer.

Another type of anticoagulant is the direct thrombin inhibitor. Current members of this class include but are not limited to the bivalent drugs hirudin, lepirudin, and bivalirudin; and the monovalent drugs argatroban and dabigatran.

The antithrombin protein itself is used as a protein therapeutic anticoagulant agent that can be purified from human plasma or produced recombinantly (for example, Atryn, which is produced in the milk of genetically modified goats).

As indicated above, anti-coagulants administration for example, heparin, is the standard antithrombotic therapy indicated for acute venous thrombosis, for prophylaxis of thrombosis in the post-surgical (especially orthopedic) and immobile patient, and for flushing of intravenous lines to maintain patency. However, due to their potency, heparin and LMWH suffer drawbacks. Uncontrolled bleeding as a result of the simple stresses of motion and accompanying contacts with physical objects or at surgical sites is the major complication. In addition, approximately 5% (range up to 30%) of patients treated with heparin, and about 2% of patients receiving unfractionated heparin (UFH), develop immune-mediated thrombocytopenia (HIT) which may be complicated by either bleeding (as a consequence of decreased platelet count) or by arterial and venous thrombosis due to intravascular platelet clumping. The products and methods of the presently disclosed subject-matter may prevent such undesired effects of these anti-coagulating agents.

More specifically, Disseminated intravascular coagulation (DIC) is a pathological process characterized by the widespread activation of the clotting cascade that results in the formation of blood clots in the small blood vessels throughout the body. This leads to compromised tissue blood flow and can ultimately lead to multiple organ damage. In addition, as the coagulation process consumes clotting factors and platelets, normal clotting is disrupted and severe bleeding can occur from various sites.

In yet some further embodiments, the presently disclosed subject-matter provides methods applicable for treating, prevention, prophylaxis amelioration, inhibition of any bleeding associated with childbirth or pregnancies, for example, postpartum hemorrhage (PPR). Postpartum bleeding or postpartum hemorrhage (PPH) is often defined as the loss of more than 500 ml or 1,000 ml of blood within the first 24 hours following childbirth. Signs and symptoms may initially include: an increased heart rate, feeling faint upon standing, and an increased breath rate. The condition can occur up to six weeks following delivery. The most common cause is poor contraction of the uterus following childbirth, the fact that not all of the placenta was delivered, a tear of the uterus, or poor blood clotting.

Causes of postpartum hemorrhage are uterine atony, retained placenta, and coagulopathy, commonly referred to as the "four Ts":

Tone: uterine atony is the inability of the uterus to contract and may lead to continuous bleeding. Retained placental tissue and infection may contribute to uterine atony. Uterine atony is the most common cause of postpartum hemorrhage.

Trauma: Injury to the birth canal which includes the uterus, cervix, vagina and the perineum which can happen even if the delivery is monitored properly. The bleeding is substantial as all these organs become more vascular during pregnancy.

Tissue: retention of tissue from the placenta or fetus may lead to bleeding.

Thrombin: a bleeding disorder occurs when there is a failure of clotting, such as with diseases known as coagulopathies.

It should be appreciated that in some embodiments, the tPA and/or plasminogen free product of the presently disclosed subject-matter and any methods using the same, may be applicable for the treatment and prevention of PPH as discussed above.

In yet some further embodiments, the method of the presently disclosed subject-matter may be also applicable for treating GPS. Goodpasture syndrome (GPS) is a rare autoimmune disease in which antibodies attack the basement membrane in lungs and kidneys, leading to bleeding from the lungs and kidney failure. The depletion of fibrinolytic proteins such as tPA and/or plasminogen using the conjugates and methods of the presently disclosed subject-matter, from a body fluid such as blood products that are regularly used for treating said patients may improve treatment.

In yet some further embodiments, the methods of the presently disclosed subject-matter may be applicable for treating bleeding caused by vessel rupture.

In some specific embodiments, intra-articular injection of plasma or platelet-rich plasma is used for treating patients with knee osteoarthritis (OA). It has been shown that PRP injection to the knee, results in significant clinical improvements (Meheux C J et al.). On the other hand, expression of plasminogen activators (PA) of rokinase type that degrade a variety of extracellular matrix components such as collagens and aggrecan core protein is considered to be of special importance in the development of OA (Pap G et al.). Expression of stromelysin and urokinase type plasminogen activator protein in resection specimens and biopsies at different stages of osteoarthritis of the knee (Pap G. et al.). Therefore, injection of fibrinolytic protein-depleted body fluid prepared by the conjugates and methods of the presently disclosed subject-matter, would prevent deleterious effect and improve the outcome.

Still further, surgical procedures can be anticipated to cause severe bleeding in patients with hereditary hemostatic disorders. These patients can bleed excessively during or following surgery. it should be appreciated that regarding patients with hereditary hemostatic disorders, in addition to the extent of the surgical trauma, the magnitude of the fibrinolytic activity at the surgical site must be considered. Thus, surgical procedures at sites that are rich in fibrinolytic activity such as oral, nasal pharyngeal cavities, as well as urogenital system, particularly a prostatic bed, may end up with excessive bleeding in patients with hereditary hemostatic disorders. Therefore, in some embodiments, the methods of the presently disclosed subject-matter may be specifically applicable for such bleeding as well.

As noted above, the methods of the presently disclosed subject-matter involve the administration or re-introduction of a body fluid or product thereof having reduced or no fibrinolytic activity, that results from the methods discussed herein before, using the conjugates of the presently disclosed subject-matter or any compositions, device, battery, kits or systems disclosed by the presently disclosed subject-matter.

In some particular embodiments, administration may be performed using an extracorporeal apparatus. In yet some further embodiments, the fibrinolytic activity free product may be administered to the subject using any device, battery, kits or systems as discussed herein.

It should be appreciated that in some embodiments, the product having reduced fibrinolytic activity as discussed above, may be prepared from body fluids obtained from an allogeneic subject. In yet some further embodiments, especially in case of elective procedures (e.g., planned surgery), the subject may be treated by a body fluid product of an autologous source.

Autologous" blood donation as used herein is a concept where transfusion individuals can donate blood for their own use if the need for blood can be anticipated and a donation plan developed. Most commonly this situation occurs with elective surgery. Autologous blood for transfusion can be obtained by preoperative donation. The term "allogeneic blood" as used herein relates to blood collected from an unrelated donor of the same species. More specifically, in some embodiments, where the blood or blood products of the presently disclosed subject-matter is obtained from at least one human subject or more, allogeneic source is meant that the resulting product may be used for other human individual/s.

As indicated above, the presently disclosed subject-matter provide methods for the treatment of bleeding, hemostatic disorders and any condition associate therewith. As used herein, "disease", "disorder", "condition" and the like, as they relate to a subject's health, are used interchangeably and have meanings ascribed to each and all of such terms.

It is understood that the interchangeably used terms "associated" and "related", when referring to pathologies herein, mean diseases, disorders, conditions, or any pathologies which at least one of: share causalities, co-exist at a higher than coincidental frequency, or where at least one disease, disorder, condition or pathology causes a second disease, disorder, condition or pathology.

As noted above, the presently disclosed subject-matter provides methods for treating disorders as specified above. The term "treatment" as used herein refers to the administering of a therapeutic amount of the composition of the presently disclosed subject-matter which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above. The treatment may be undertaken when a hemostatic condition initially develops, or may be a continuous administration, for example by administration more than once per day, every 1 day to 7 days, every 7 day to 15 days, every 15 day to 30 days, every month to two months, every two months to 6 months, or even more, to achieve the above-listed therapeutic effects.

The term "prophylaxis" refers to prevention or reduction the risk of occurrence of the biological or medical event, specifically, the occurrence or re occurrence of disorders associated with bleeding, that is sought to be prevented in a tissue, a system, an animal or a human being, by a researcher, veterinarian, medical doctor or other clinician, and the term "prophylactically effective amount" is intended to mean that amount of a pharmaceutical composition that will achieve this goal. Thus, in particular embodiments, the methods of the presently disclosed subject-matter are particularly effective in the prophylaxis, i.e., prevention of conditions associated with bleeding disorders. Thus, subjects administered with said compositions are less likely to experience symptoms associated with said bleeding disorders that are also less likely to re-occur in subject who has already experienced them in the past.

The term "amelioration" as referred to herein, relates to a decrease in the symptoms, and improvement in a subject's condition brought about by the compositions and methods according to the presently disclosed subject-matter, wherein said improvement may be manifested in the forms of inhibition of pathologic processes associated with the bleeding disorders described herein, a significant reduction in their magnitude, or an improvement in a diseased subject physiological state.

The term "inhibit" and all variations of this term is intended to encompass the restriction or prohibition of the progress and exacerbation of pathologic symptoms or a pathologic process progress, said pathologic process symptoms or process are associated with.

The term "eliminate" relates to the substantial eradication or removal of the pathologic symptoms and possibly pathologic etiology, optionally, according to the methods of the presently disclosed subject-matter described below.

The terms "delay", "delaying the onset", "retard" and all variations thereof are intended to encompass the slowing of the progress and/or exacerbation of a disorder associated with protein misfolding or protein aggregation, specifically, bleeding disorders and their symptoms slowing their progress, further exacerbation or development, so as to appear later than in the absence of the treatment according to the presently disclosed subject-matter.

As noted above, treatment or prevention include the prevention or postponement of development of the disease, prevention or postponement of development of symptoms and/or a reduction in the severity of such symptoms that will or are expected to develop. These further include ameliorating existing symptoms, preventing—additional symptoms and ameliorating or preventing the underlying metabolic causes of symptoms. It should be appreciated that the terms "inhibition", "moderation", "reduction" or "attenuation" as referred to herein, relate to the retardation, restraining or reduction of a process, specifically, a bleeding disorder by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99 or about 99% to 99.9%.

Single or multiple administrations on a daily, weekly or monthly schedule can be carried out with dose levels and pattern being selected by the treating physician. More specific embodiments relate to the use of typically 2-3 doses per week.

The presently disclosed subject-matter relates to the treatment of subjects, or patients, in need thereof. By "patient" or "subject in need" it is meant any organism who may be infected by the above-mentioned pathogens, and to whom the preventive and prophylactic products, kit/s and methods herein described is desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal.

By "mammalian subject" is meant any mammal for which the proposed therapy is desired, including human, equine, canine, and feline subjects, most specifically humans. It should be noted that specifically in cases of non-human subjects, the method of the presently disclosed subject-matter may be performed using administration via injection (intra venous (IV), intra-arterial (IA), intramuscular (IM) or sub cutan (SC)), drinking water, feed, spraying, oral lavage and directly into the digestive tract of subjects in need thereof.

It should be appreciated that the presently disclosed subject-matter provides in further aspects thereof, any body-fluid product that display decreased fibrinolytic activity and has been prepared by any of the methods of the presently disclosed subject-matter. Thus, the presently disclosed subject-matter encompasses in some embodiments thereof any mammalian body fluid product that lacks or has reduced amount of at least one fibrinolytic protein, specifically, at least one of tPA and/or plasminogen. In some embodiments the product produced by the methods of the presently disclosed subject-matter lack tPA. in yet some further embodiments the product produced by the methods of the presently disclosed subject-matter lack tPA and plasminogen. As indicated above, such product produced by the method of the presently disclosed subject-matter may be any body-fluid subjected to any of the procedures, conjugates, compositions devices and systems described herein, specifically, mammalian blood, plasma or any blood product.

In yet a further aspect, the presently disclosed subject-matter provides a therapeutically effective amount of at least one blood and/or blood-derived product that has a reduced fibrinolytic activity for use in a method for the treatment, prevention, prophylaxis, amelioration, inhibition of bleeding, hemostatic disorders and any bleeding or pathologic condition associated therewith in a subject in need thereof. It should be understood that such body fluid product is prepared by the methods of the presently disclosed subject-matter. In yet some further embodiments, such body fluid product may be prepared by any of the conjugates of the presently disclosed subject-matter, any compositions thereof or any device, battery, kits or systems comprising the plurality of conjugates of the presently disclosed subject-matter as defined herein.

In yet some further embodiments, the blood and/or blood-derived product used by the presently disclosed subject-matter may be specifically applicable for the treatment of any hemostatic disorder, specifically, hereditary or acquired bleeding disorder, as defined by the presently disclosed subject-matter as disclosed hereinbefore.

It should be understood that any of the conjugates described by the presently disclosed subject-matter, any compositions thereof and any device, battery, kits or systems described by the presently disclosed subject-matter in connection with other aspects of the presently disclosed subject-matter may be applicable for this aspect as well. Still further, it must be appreciated that the presently disclosed subject matter further encompasses any of the blood and/or blood-derived product disclosed herein for use by any of the therapeutic methods or any other methods described herein, for any of the conditions or disorders disclosed herein before.

All scientific and technical terms used herein have meanings commonly used in the art unless otherwise specified. The definitions provided herein are to facilitate understanding of certain terms used frequently herein and are not meant to limit the scope of the present disclosure.

All definitions, as defined and used herein, should be understood to control over dictionary definitions, definitions in documents incorporated by reference, and/or ordinary meanings of the defined terms.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%. The indefinite articles "a" and "an," as used herein in the specification and in the claims, unless clearly indicated to the contrary, should be understood to mean "at least one." it must be noted that, as used in this specification and the appended claims, the singular forms "a", and "the" include plural referents unless the content clearly dictates otherwise.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or exactly one of "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Throughout this specification and the Examples and claims which follow, unless the context requires otherwise, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures. More specifically, the terms "comprises", "comprising", "includes", "including", "having" and their conjugates mean "including but not limited to". The term "consisting of means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

It should be noted that various embodiments of this presently disclosed subject-matter may be presented in a range format. It should be understood that the description in range format is merely for convenience and brevity and should not be construed as an inflexible limitation on the scope of the presently disclosed subject-matter. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the presently disclosed subject-matter, which are, for clarity, described in the context of separate embodiments, may also be provided in combination in a single embodiment. Conversely, various features of the presently disclosed subject-matter, which are, for brevity, described in the context of a single embodiment, may also be provided separately or in any suitable sub combination or as suitable in any other described embodiment of the presently disclosed subject-matter. Certain features described in the context of various embodiments are not to be considered essential features of those embodiments, unless the embodiment is inoperative without those elements.

Various embodiments and aspects of the presently disclosed subject-matter as delineated herein above and as claimed in the claims section below find experimental support in the following examples.

Disclosed and described, it is to be understood that this presently disclosed subject-matter is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the presently disclosed subject-matter will be limited only by the appended claims and equivalents thereof.

The following examples are representative of techniques employed by the inventors in carrying out aspects of the presently disclosed subject-matter. It should be appreciated that while these techniques are exemplary of preferred embodiments for the practice of the presently disclosed subject-matter, those of skill in the art, in light of the present disclosure, will recognize that numerous modifications can be made without departing from the spirit and intended scope of the presently disclosed subject-matter.

EXAMPLES

Experimental Procedures
Reagents:
Sepharose 4B200 (Sigma Aldrich)
Human plasma—Plasma of healthy donors was obtained from MDA Blood
And/or Human Cryoprecipitate—Cryoprecipitate was obtained from Hadassah Blood Bank
Methods
Beads recovery (method #1)
1. The beads were washed 3 times with 100 mM lysine PH=9.0 and 1M NaCl at 0 g 2 minutes, at RT.
2. The beads were washed 3 times with 3M NaCl at 300×g for 2 minutes, at room temperature (RT).
3. The beads were washed 3 times X3 with H2O at 300×g for 2 minutes, at RT.
4. The beads were washed 3 times with 0.5M of NaOH at 300×g for 2 minutes, at RT, in the third wash incubate the beads with NaOH for 30 minutes.
5. The beads were washed 3 times with $H_2O$ at 300×g for 2 minutes, at RT.
6. The beads were washed 3 times with 0.5M sodium citrate at 300×g for 2 minutes, at RT
7. The beads were washed 3 times at 300×g for 2 minutes, at RT with: a—10 mM sodium citrate PH=6.8. b—120 mM NaCl. c—120 mM Glycine. 8. The beads were washed 3 times with H2O at 300×g for 2 minutes, RToC.
9. The beads were washed 3 times with 20% Ethanol+1M NaCl*. After a third wash, 20% Ethanol+1M NaCl was added to obtain 70% slurry, re-suspended by gently inverting and stored at 4° C.

Beads Recovery with Peristalic Pump (Method #2)
1—The filter was connected to Peristaltic pump.
2—150 ml of each solution was flow through the filter for 15 min:
a—100 mM lysine PH=9.0 and 1M NaCl.
b—3M NaCl
c—$H_2O$
d—0.5M NaOH (incubate the filter with NaOH for 30 min).
e—H2O.
f—0.5M sodium citrate.
g—10 mM sodium citrate PH=6.8.
120 mM NaCl.
120 mM Glycine.
h—H2O.
i—20% Ethanol+1M NaCl.
All the buffers were sterilized, with an autoclave except NaOH PLG Detection
PLG detection in Example 7 was performed using the KIT: ab196262 PLG human simple step ELISA KIT.

TABLE 1

| Plate preparation (1:$10^5$ plasma dilution): | | | |
|---|---|---|---|
| A (serial standard dilution- ng/μl) | B (serial standard dilution- ng/μl) | C Conjugate 1 | D Conjugate 6 |
| 4  1.875 | → | ↓ | ↓ |
| 5  3.75 | → | Plasma 69B | 1:10 |
| 6  7.5 | → | ↓ | ↓ |
| 7  15 | → | | Untreated plasma 69B |
| 8  30 | → | ↓ | ↓ |

Reagent Preparation:
All reagents to room temperature prior to use.
Preparation of reagents for use (for 36 wells):
1× wash buffer PT (36 mL): 3.6 mL of 10× wash buffer PT+32.4 mL of deionized water.
Antibody cocktail (1.8 mL): 180 μL of 10× Capture Antibody+180 μL of 10× Detector Antibody+1440 μL of Antibody Diluent CPI.
Sample Preparation:
Plasma was diluted at $10^5$× into sample diluent NS in serial dilutions:
1:100 plasma=10 μL plasma+990 μl sample diluent NS
1:$10^5$ plasma=1 μL plasma+999 μl sample diluent NS
Standard Preparation:
1—Stock standard solution (120 ng/mL): Reconstitution of the PLG protein standard sample by adding 200 μL water by pipette. Holding at room temperature for 10 minutes and mix gently.
2—Labeling eight 1.5 mL tubes, standards 1-8.
To tube 1, 225 μL were added of Sample diluent NS.
To tube 2-8, 150 μL were added of Sample diluent NS.
75 μL were added of stock standard solution to tube 1.
150 μL of standards were added to the next tube (tube 2 to 7)
Standard #8 contains no protein and is the blank control.
Assay Procedure:
Removing excess microplate strips from the plate frame, returning them to the foil pouch containing the desiccant pack, resealing and return to 4° C. storage.
1—50 μL of all sample or standard were added to appropriate wells.
2—50 μL of the Antibody Cocktail were added to each well.
3—The plate were sealed and incubated for 1 hour at room temperature on a plate shaker set to 400 rpm.
4—Each well was washed with 3×350 μL 1× Wash Buffer PT (washing by aspirating or decanting from wells then dispensing 350 μL 1× Wash Buffer PT into each well)
5—100 μL of TMB Substrate were added to each well and incubate for 10 minutes in the dark on a plate shaker set to 400 rpm.
6—100 μL of Stop Solution were added to each well. The plate was shaken on a plate shaker for 1 minute to mix.
7—The OD absorbance was read at 450 nm.

Thromboelastography (TEG)
TEG instrument TEG 5000 machine (60) (Haemonetics, Braintree, MA) (valid up to 2019 Oct. 31)
Disposable cups and pins [HAE-07-052]
Reagents for TEG:
1. WT-tPA 1 mg/ml (Acytilyse 50 mg,) [Acytilyse 50 mg, Boehringer Ingelheim; 1 vial of 2,333 mg powder contains 50 mg active Alteplase (WT-tPA)].

2. Calcium chloride 0.2M [Haemonetics, cat #7003 lot #: 150597BA]
3. Fresh frozen human citrated plasma.
4. FVII Valin (1 mg/ml stock) DPD-V304-037 Bulk B.
5. Level I control [Haemonetics, cat #8001, lot #: HMO3199 expiry: 2018 October]
6. Level II control [Haemonetics, cat #8002, lot #: HMO3178 expiry: 2018 October]
7. PBS×10, Biological industries lot #: 1626505
8. TEG Hemostasis system Diluent water lot #: 0110-1404

The assay was performed according to the "Clot lysis monitored by thromboelastography (TEG)" Protocol. Before using the TEG, calibration was done by using level I and level II controls, each control was tested in both channels (as described in the protocol). The WT-tPA reagent was diluted 1:90 in PBS×1 5 µl Wt-tPA (16.66 µM)+595 µl PBS*1=working concentration 0.185 µM (final concentration in samples is 1.85 nM).

External Bleeding Model (Tail Snipping in Mice)

Animals and Conditions:

Species/Strain: Mice, c57black

Gender/Number/Age: Male, 24, 8 weeks.

Source: Harlan Laboratories, Israel.

Body weight: Body weight was 20-25 g at study initiation. The minimum and maximum weights of the group were within a range of ±10% of group mean weight.

Acclimation period: 7 days.

Identification: Permanent marker (up to 24 h experiment) and cage cards.

Animal handling was carried out according to the National Institute of Health (NIH) and the Association for Assessment and Accreditation of Laboratory Animal Care (AAALAC). Animals were housed in polysulfone (PSU) cages (4-6 mice/cage), with stainless steel top grill having facilities for pellet food and drinking water in clear polycarbonate bottle; bedding: steam sterilized clean paddy husk were used. Bedding material was changed along with the cage at least twice a week.

Diet: Animals were fed a commercial rodent diet ad libitum. Animals had free access to autoclaved drinking water obtained from the municipality supply.

Contaminants: None of the expected contaminants in the food and water supplies has the potential to influence the outcome of this study.

Environment conditions: Animals are housed under standard laboratory conditions with adequate fresh air supply. Animal were kept in a climate-controlled environment. Temperatures range was between 20-24° C. and RH is between 30-70% with 12 hours light and 12 hours dark cycle.

Veterinary care: Animals were inspected on arrival in order to fit the study. Since this was a 24 hours experiment, there was no need for veterinary follow-up after initiation of the study.

Ethical committee: This study was performed after approval by "The Israel Board for Animal Experiments" and in compliance with "The Israel Animal Welfare Act".

Responsibilities:

1. The Facility Manager, oversees all aspects of animal health and husbandry, and was assisted by all the animal program personnel.
2. The Study Director ensured that all the research and technical staff were adequately trained. The staff is experienced in implementing the required procedures.

Establishment of the Test Model

Animals were anesthetized with a mixture of ketamine and xylazine (100 and 10 mg/kg, respectively) inline to their weight. Animals were treated with the different treatments by intravenous injections of: 200 µL of saline, 200 µL of plasma and 200 µL of plasminogen-depleted plasma. Following this, animals were placed in prone position. A distal of 7 mm segment of the tail was amputated with a scalpel. The tail was immediately immersed in a 50 mL Falcon tube containing isotonic saline pre-warmed in a water bath to 37° C. The position of the tail was vertical with the tip positioned about 2 cm below the body horizon. Each animal was monitored for 60 minutes even if bleeding ceased, to detect any re-bleeding. Bleeding time was determined using a stop clock. If bleeding on/off cycles occurred, the sum of bleeding times within the 60 minute period was recorded. The experiment was terminated, at the end of 60 minutes to avoid lethality during the experiment as required by the local animal ethics committee. Body weight, including the tail tip, was recorded again, and the volume of blood loss during the experimental period was estimated from the reduction in body weight. Pelleted blood was estimated after centrifugation of tubes. At the end of the experiment, animals were sacrificed by anesthesia overdose.

The selected rodent species is the c57black healthy young adult animals of commonly used laboratory strains. This mouse model is an initial step providing early information about the efficacy of plasminogen depleted plasma to treat excessive bleeding.

A total of 24 mice in 3 groups was utilized. Each group included 8 animals. The control group received only saline, the second group received untreated plasma and the third group received Plasminogen-depleted plasma (PDP). The animals were divided into groups randomly. One animal from each group received either plasma or control treatment which was applied intravenously as a single 200 µL dose. The total number of animals is based on previous studies demonstrating that this is the minimum number of animals per group that produces significant information regarding the amount of blood lost by the animals. Treatment was administered by intravenous injection.

Plasminogen Depletion Cryoprecipitate Using Clear Plasma:

1—ClearPlasma assembly:
Fill filter with resin.
Lock the filling inlet
Set the flow regulator to OFF.
Attach the clamps to the extension tube (with the flow regulator).
Close the clamp
Attach the Extension tube to the filter
Attach the clamp to the Collection bag
Close the clamp.
Attach the collection bag with filter.

1 Fill ClearPlasma with 18 ml Resin: TXA conjugated TXA and/or cyclohexanecarboxylic acid (90-100 µm superflow resin—Conjugate 1.
2 Wash the resin with 60 ml water.
3 Wash the resin with 60 ml saline.
4 Connect the Cryoprecipitate, bag to ClearPlasma
5 Flow 16 ml of Cryoprecipitate through the filters in 22 min.

6 Supernatant to new tube—Cryoprecipitate depleted plasminogen,

2—PLG detection.

E-80PMG—Human Plasminogel ELISA Kit, Lot #10—(ICL, Inc.)

The usage instructions are from Kit package insert. (1)

TABLE 2

| | Plate preparation: | | | |
|---|---|---|---|---|
| | 1 | 2 | 3 | 4 |
| A | BLK | BLK | | |
| B | 6.25 ng/ml | 6.25 ng/ml | | |
| C | 12.5 ng/ml | 12.5 ng/ml | | |
| D | 25 ng/ml | 25 ng/ml | | |
| E | 50 ng/m | 50 ng/m | | |
| F | 100 ng/ml | 100 ng/ml | | |
| G | 200 ng/m | 200 ng/ml | Untreated | Untreated |
| H | Untreated | Untreated | PDP filter | PDP filter |

Dilution of Samples:

Prepare a 1/5,000 dilution of sample in serial dilutions:

1:100 Cryoprecipitate (1:100=5 μL Cryoprecipitate (1:100+495 μl 1×diluent).

1:5000 Cryoprecipitate (1:50=10 μL of diluted Cryoprecipitate (1:100)+490 μl 1×diluent). Mix thoroughly at each stage.

Assay Procedure:

1 Bring all reagents to room temperature before use.

2 Pipette 100 μL of sample (in duplicate) into pre designated wells.

3 incubate the micro titer plate at room temperature for 60 minutes. Keep plate covered and level during incubation.

4 Following incubation, aspirate the contents of the wells.

5 Completely fill wells with wash buffer, invert the plate then pour/shake out the contents in a waste container. Follow this by sharply striking the wells on absorbent paper to remove residual buffer. Repeat 3 times for a total of four washes.

6 Pipette 100 μL of appropriately diluted Enzyme Antibody Conjugate to each well. Incubate at room temperature for 60 minutes. Keep plate covered in the dark and level during incubation.

7 Wash and blot the wells as described in Steps 5/6.

8 Pipette 100 μL of TMB Substrate Solution into each well.

9 Incubate in the dark at room temperature for precisely 10 minutes.

10 after ten minutes, add 100 μL of Stop Solution to each well.

11 Determine the absorbance (450 nm) of the contents of each well.

Example 1

Synthesis of Resins

Example 1.1—Synthesis of Conjugate 1

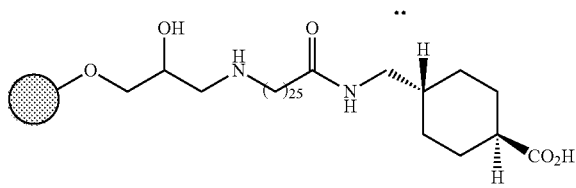

Resin Production and Filter Packing Scale Up

This process was performed according to the NHS-activated Sepharose Fast Flow (GE Healthcare cat. #17-0906-02) product instructions.

The process started with a new clean batch of naïve beads received from the manufacturer along with proper documentation.

The resin volume used for this protocol was 112 mL drained resin (8×14 mL) in 8×50 mL tube (originally 70% resin slurry; 14 mL drained resin per tube). This protocol yield a batch of three full ClearPlasma filters. Preparations, coupling and post-coupling washes were done as clean as possible. The endotoxin wash and packing stages were done in a clean environment.

Labware Used 0.2 μm filters (e.g. Steritop), 3×1 L bottle (1 mM HCl; 0.1M Tris-HCL pH 8.5; 0.1M Acetate buffer, 0.5M NaCl, pH 4.5), 2×0.5 L bottle (coupling buffer; 4M Urea), 4×1 L bottle (70% EtOH, 50 mM Tris-HCl pH 7.5, 50 mM Tris-HCl, 0.1NaCl, pH 7.5 in pyrogen-free water, 20% EtOH), Organic waste container, Autoclaved spatulas, beakers, measuring cylinders, Clean plastic pipettes, Tube roller/rotator, 50 mL catheter tip syringes, sterile ClearPlasma filter casings.

Reagents Used

Sodium Bicarbonate ($NaHCO_3$), Sodium Carbonate ($Na_2CO_3$), Sodium Chloride, Tranexamic acid, 37% HCl, NaOH, Tris-HCl, Acetic acid, Sodium acetate, Ethanol, Urea, Ddw (double distilled water), Pyrogen-free water.

Solutions

All final buffers and solutions were filtered through 0.2 μm filter before use.

Coupling buffer—100 mL 0.2M $NaHCO_3$, 0.5M NaCl, pH 8.3. An amount of 1.68 g sodium bicarbonate was weighted and dissolved in 70 mL ddw. The pH was adjusted to 8.3 with (1M NaOH or 1M HCl). An amount of 2.92 g sodium chloride was weighted and dissolved in the sodium bicarbonate solution. The volume was adjusted to 100 mL with DDW.

Ligand solution—85 mL 25 mM (1 eq) or 50 mM (2 eq) or 125 mM (5 eq) or 250 mM (10 eq) Tranexamic acid in coupling buffer, pH adjusted to 6-9. The desired amount of tranexamic acid was dissolved in 85 mL 0.2M $NaHCO_3$, 0.5M NaCl, pH 8.3, the pH was adjusted to desired level. The solution was filtered through 0.2μ.

Resin primary wash—1.5 L 1 mM HCl. Into a 50 mL tube an amount of 44 mL DDW was added. 1 mL HCL was added (~37%, 12M), making 0.25M HCl. Into a 2 L bottle 1400 mL DDW was added. 6 mL 0.25M HCl was added. The volume was adjusted to 1500 mL. The solution was filtered through 0.2μ.

Resin blocking—250 mL 0.3M Tris-HCl, pH 8.5. An amount of 11.82 g Tris-HCl was dissolved in 200 mL DDW. The pH was adjusted to 8.5 with 1M NaOH or 1M HCl. The volume was adjusted to 250 mL with ddw. The solution was filtered through 0.2μ.

Basic wash—1.5 L 0.1M Tris-HCl, pH 8.5. An amount of 23.64 g Tris-HCl was dissolved in 1300 mL DDW. The pH was adjusted to 8.5 with 1M NaOH or 1M HCl. The volume was adjusted to 1500 mL with ddw. The solution was filtered through 0.2μ.

Resin acidic wash—1.5 L 0.1M Acetate buffer, 0.5M NaCl, pH 4.5. An amount of 12.3 g sodium acetate was dissolved in 1300 mL DDW. The pH was adjusted to 4.5 with 1M NaOH or 0.1M acetic acid (1.15 mL glacial acetic acid in total 200 mL with ddw). An amount of 43.83 g sodium chloride and dissolved. The volume was adjusted to 1500 mL. The solution was filtered 0.2μ.

Endotoxin wash (EW) 1—600 mL 70% EtOH. Mix together 420 mL high grade Ethanol with 180 mL DDW.

EW2—600 mL 50 mM Tris-HCl pH 7.5. An amount of 3.63 g Tris-HCl was dissolved in 500 mL DDW. The pH was adjusted to 7.5 with 1M HCl. The volume was adjusted to 600 mL with DDW.

EW3—300 mL 4M Urea in pyrogen-free water. An amount of 72 g urea was dissolved in 200 mL DDW for irrigation. The volume was adjusted to 300 mL with water for irrigation.

EW4—600 mL 50 mM Tris-HCl, 0.1NaCl, pH 7.5 in pyrogen-free water. An amount of 3.63 g Tris-HCl was dissolved in 500 mL DDW for irrigation. The pH was adjusted to 7.5 with 1M HCl. An amount of 3.51 g sodium chloride was dissolved in the buffer. The volume was adjusted to 600 mL with water for irrigation.

Endotoxin Free Storage (EFS)—550 mL 20% EtOH in pyrogen-free water. A volume of 110 mL high grade Ethanol was mixed together with 440 mL water for irrigation.

1M HCl—pH adjustment. 4.17 mL 37% hydrochloric acid was diluted to 50 mL with DDW.

1M NaOH—pH adjustment. 2 g NaOH was diluted in 50 mL DDW.

For pH adjustments of endotoxin-free solutions, solutions made with water for irrigation were used.

Preparations

The resin was Re-suspended (NHS-activated Sepharose beads 70% slurry in 100% Isopropanol) and transferred 8×14 mL into 8×50 mL PP tubes.

The tubes were Spin-down at 400 g for 3 min.

The storage solvent was aspirated.

The tubes were Filled to 45 mL with HCl and the resin was re-suspended.

The tubes were Spin-down at 400 g for 3 min and aspirated.

The wash was repeated four more times (five washes in total).

Coupling 7 mL resin was added to each tube.

The pH was adjusted to 7.5-8 (if needed).

The tubes were Gently and continuously rotated for 2-4 hours (room temp.)/overnight (4° C.).

The resin was Spin down, aspirated and blocked with 25 mL (each tube) 0.1M Tris-HCl, pH 8.5 for 2-4 hours in rotation.

Washing

The resin was Spin down and aspirated.

30 mL 0.1M Tris-HCl pH 8-9 was added and re-suspended, spin down and aspirated.

30 mL 0.1M Acetate buffer, 0.5M NaCl, pH 4-5 was added re-suspended, spin down and aspirate.

These washes (tris to acetate) were repeated 5 times.

When the process:

Continued in another time—the wash step (add, spin down, aspirate) was performed twice in 30 mL 20% EtOH, store as 50% slurry in 20% EtOH.

Continued directly to the Endotoxin wash –30 mL 70% EtOH (EW1) was added.

Endotoxin Wash

If the resin was stored in 20% EtOH it was Spin down, aspirated and 30 mL 70% EtOH (EW1) was added.

The resin was incubated in 70% EtOH for 30 mm (rolling).

The resin was washed and 30 mL 50 mM Tris-HCl pH 7.5 (EW2) was added.

The resin was washed and 30 mL 50 mM Tris-HCl pH 7.5 was added, the resin was incubated for 30 min (rolling).

The resin was washed and 15 mL 4M Urea (EW3) was added.

The resin was washed and 15 mL 4M Urea was added, the resin was incubated for 30 min (rolling).

The resin was washed and 30 mL 50 mM Tris-HCl, 0.1M NaCl, pH 7.5 (EW4) was added.

The resin was washed and 30 mL 50 mM Tris-HCl, 0.1M NaCl, pH 7.5 was added, the resin was incubated for 30 min (rolling).

The resin was washed and 30 mL 20% EtOH (EFS) was added.

The wash was repeated.

The resin was Stored in as 70% slurry in 20% EtOH (EFS) until packing.

Packing all the resin from the tubes was pooled to one container.

If the beads were settled, the container was rotated gently to make a homogenous suspension.

a sterile 50 mL catheter tip syringe was filled with the suspension.

the casing was Gently filled with the suspension. If top-up is needed, the same method as above was used.

When approaching the fill of the filter, the outlet luer lock cover was opened to allow any excess storage solution volume out of the filter. The outlet was closed after the resin compartment is full.

The packed product was stored according to product specifications.

Example 1.2—Synthesis of Conjugate 2

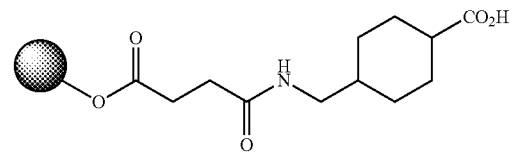 [SMILES: COC(=O)CCC(=O)NCC1CCC(C(=O)O)CC1]

Figure 1:
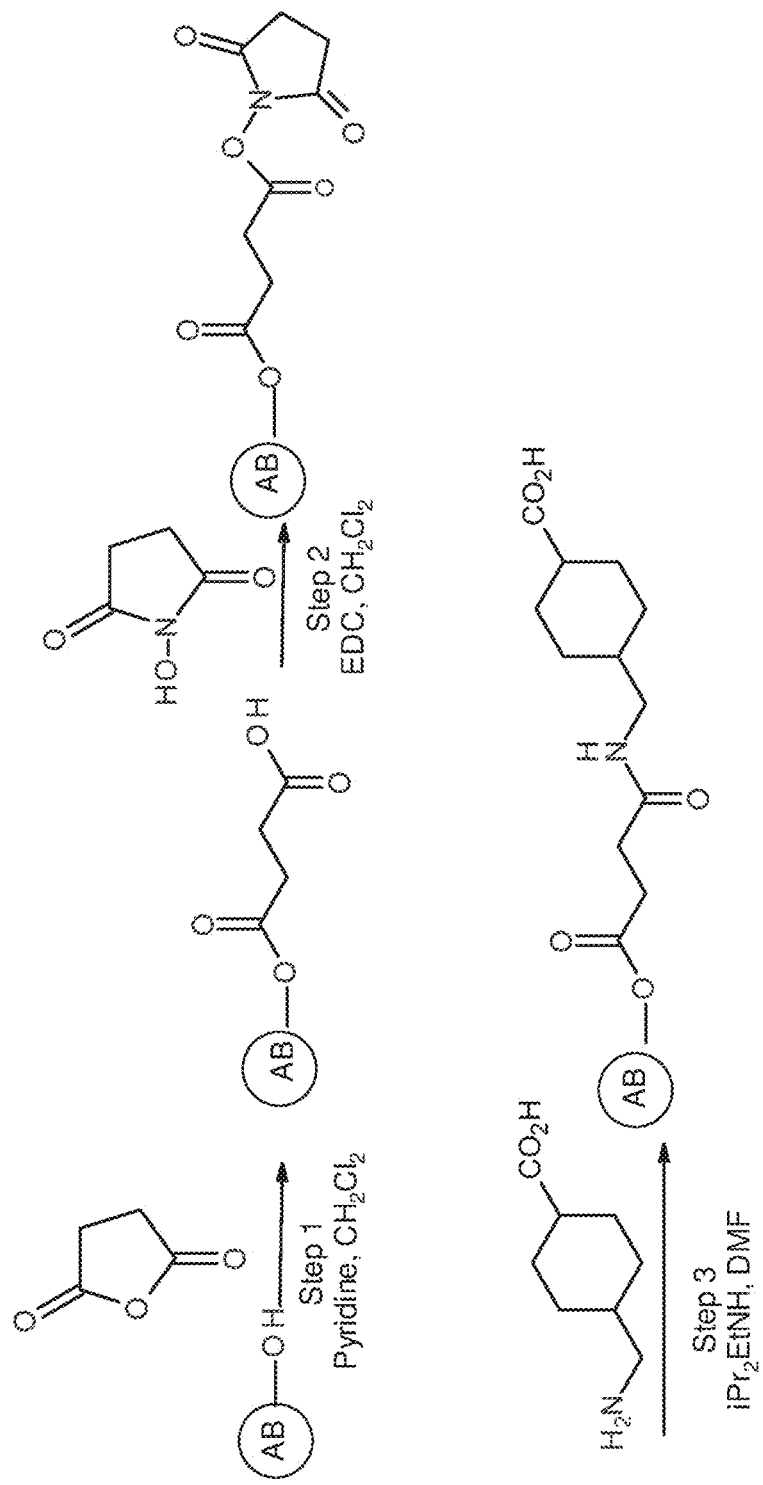
FIG. 1: Conjugate 2

The reaction for the preparation of conjugate 2 is schematically represented in FIG. 1.

More specifically, the following procedure was employed:
1. An amount of 4.2 ml of Sepharose 4B200 (Sigma Aldrich) was washed with acetone through filter glass funnel using a shaker. It was considered that the Sepharose contain 1 ml of reactive functional group and thus that 4.2 ml contain 4.2 mmol.

2. Succinic anhydride (0.42, 4 mmol) were added to the slurry of beads in $CH_2Cl_2$ (3 ml) followed by the addition of Pyridine (0.339 ml). The mixture was shacked overnight.
3. The beads were filets and washed with acetone.
4. The beads were suspended in $CH_2Cl_2$ and N-Hydroxylsuccinamide NHS (0.483 g) were added followed by the addition of EDC (0.8 g). The mixture was shaken overnight and then filtered.
5. The product was suspended in DMF (3 ml), N,N-Diisopropylethyl amine (0.54 g) and 4-(AMINOMETHYL)-CYCLOHEXANECARBOXYLIC ACID (0.66 g) were added. The mixture was shaken overnight. The product was washed with acetone and delivered for further tests.

Example 1.3—Synthesis of Conjugate 3 ("TXA-Glyoxal Agarose Resin")

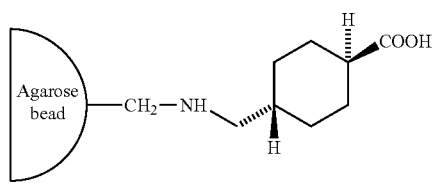

Procedure
1. Wash the Glyoxal Agarose Beads with distilled water using a glass filter.
2. Prepare the ligand solution and test the activity and/or absorbance at 280 nm.
3. Add 1 ml Glyoxal Agarose Beads to 9 ml TXA solution in a buffer at pH 10.05
4. Stir gently and check pH frequently. Withdraw aliquots of suspension and assay for activity or absorbance at 280 nm.
5. Continue gentle stirring for several hours or until the activity measurements remain constant, which indicates complete immobilization. Avoid magnetic stirring. Note: A longer immobilization time favors a strong biomolecule/bead reaction and stability, but may result in unfavorable distortions.
6. When the activity/absorbance is constant, add 10 mg solid sodium borohydride to the suspension and stir for 30 minutes at room temperature in an open container to allow hydrogen to escape. Do not perform this step near an open flame. Run near an extractor fan if possible.
7. Wash the suspension with 25 mM phosphate buffer pH 7.0 using a vacuum filter to eliminate the excess borohydride. Subsequently, wash the suspension thoroughly with distilled water, and filter to dryness.
8. The ligand-coupled Glyoxal Agarose Beads should be stored at 4-10° C. in a preservative containing 20% Ethanol in Water.

Example 1.4—Synthesis of Conjugate 4 ("TXA-ECH agarose resin")

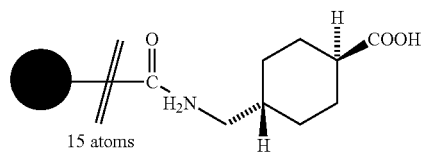

Conjugation of Tranexamic acid (TXA) to ECH-agarose beads (G-Biosciences, #786-1223)
1. Prepare ligand solution—50 mM TXA in ddw, pH adjusted to 5.2 with HCl.
2. Wash 2 mL resin in 10 mL ddw. Spin down by centrifugation 3 min*500 g.
3. Wash resin in 160 mL 0.5M NaCl.
4. Add 4 mL ligand solution to drained resin.
5. Add EDC (coupling agent) to give 100 mM in the final reaction.
6. Rotate for 1 hr, adjust pH to 5.0 with HCl. Continue rotation overnight.
7. Spin-down resin and decant.
8. Wash resin in three cycles of alternating solutions:
   a. 0.1M Acetate, 0.5M NaCl, pH 4.0
   b. 0.1M Tris-HCl, 0.5M NaCl, pH 8.0
9. Wash twice in ddw.
10. Wash once and then store in 20% EtOH at 2-8° C.

Example 1.5—Synthesis of Conjugate 5

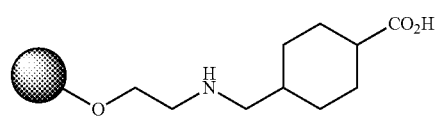

Reactant—SodiumCyano Borohydride
Agarose beads—

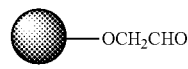

In the first stage, the Schieff base is prepared, which is then reduced with sodium cyanoborhydride ($NaCNBH_3$) or preferably sodium borohydride ($NaBH_4$) to give the final material. The double bond in the Schieff base is characteristic by IR absorbance between 1590-1690 cm-1. The Carbonyl in the aldehyde is its starting material characteristic by IR absorbance between 2700-2900 cm-1, In the final material, the tannzamic acid is also needed.

More specifically, the following procedure was employed:
1. The Glyoxal Agarose Beads was washed with distilled water using a glass filter.
2. The ligand solution was prepared and the activity and/or absorbance at 280 nm were tested.
3. An amount of 1 ml Glyoxal Agarose Beads was added to 9 ml ligand solution in a buffer at pH 10.05. If the ligand was not stable at room temperature, the following steps were run in a cold room.
4. Gentle stirring was performed the pH was checked frequently. The aliquots of suspension were withdrawn and assays for activity or absorbance at 280 nm were performed.
5. Gentle stirring was maintained for several hours or until the activity measurements remain constant, which indicates complete immobilization. Magnetic stirring was avoided.

Note: A longer immobilization time favors a strong biomolecule/bead reaction and stability, but may result in unfavorable distortions.
6. When the activity/absorbance was constant, 10 mg solid sodium borohydride was added to the suspension and stirred for 30 minutes at room temperature in an open container to allow hydrogen to escape. This step was not performed near an open flame but rather near an extractor fan if possible.

7. The suspension was washed with 25 mM phosphate buffer pH 7.0 using a vacuum filter to eliminate the excess borohydride. Subsequently, the suspension was washed thoroughly with distilled water, and filtered to dryness.
8. The ligand-coupled Glyoxal Agarose Beads were stored at 4-10° C. in a preservative containing 20% Ethanol in Water.

Example 1.6—Synthesis of Conjugate 6
TXA-Sepharose Resin

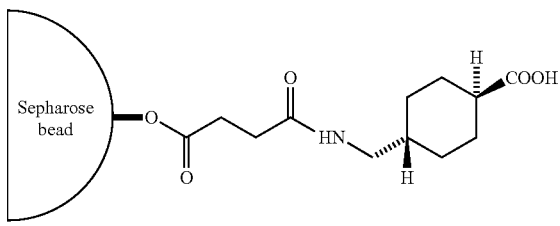

1. An amount of 4.2 ml of Sepharose beads was washed with acetone through filter glass funnel using a shaker. 1
2. Succinic anhydride (0.42, 4 mmol) were added to the slurry of beads in CH2Cl2 (3 ml) followed by the addition of Pyridine (0.339 ml). The mixture was shacked overnight.
3. The beads were filets and washed with acetone.
4. The beads were suspended in CH2Cl2 and N-Hydroxylsuccinamide NHS (0.483 g) were added followed by the addition of EDC (0.8 g). The mixture was shaken overnight and then filtered.
5. The product was suspended in DMF (3 ml), N,N-Diisopropylethyl amine (0.54 g) and 4-(AMINOMETHYL)-CYCLOHEXANECARBOXYLIC ACID (0.66 g) were added. The mixture was shaken overnight.

The final beads were washed twice with acetone, additionally washed in ethanol 70%, centrifuged and suspended in 20% ethanol.

Example 2

Evaluation of the Activity of Newly Synthesized TXA Conjugated ECH-Agarose Beads, Sterogene Superflaw and Glyoxal Agarose Beads—Conjugate 1

Materials:

Plasma: Plasma of healthy donors were obtained from MDA Blood Bank. The plasma used is Rh negative, as well as negative to different viral antigens (e.g., HBV, HCV, HTLV, HIV).

Beads:
1. TXA conjugated Glyoxal Agarose Beads synthesized according to the procedure described in Example 1 (Preparation of Conjugate 1)
2. TXA conjugated ECH-agarose beads (new beads), Daren laboratories.
3. Sterogene Superflow sterogene beads).

Instruments:
Shaker: KRS-3016 (MRC)
ELISA reader: 800TS (BioTek).

The experiment were conducted in non-sterile environment.

Solutions Preparation:
Binding buffer (30 ml):
Sodium citrate (1.0 mM)—0.3 ml
NaCl (120 mM; preparation date: 25 Sep. 2017)—1.2 ml
DDW=28.5 ml Plasminogen Depletion
1. The beads were stored already in 20% Ethanol and 70% resin. An amount of 1 ml of beads was transferred to 15 ml tubes.
2. The tubes was filled with water and
3. The tubes were Centrifuged at 300×g for 2 minutes, RTC.
4. The supernatant was removed.
5. These steps were repeated 3 times
6. The beads are suspended with binding buffer*:
   a—10 mM Sodium citrate PH=7.16
   b—120 mM Sodium chloride.
7. A Centrifuge step was performed as in section 3.
8. The supernatant was removed.
9. These steps were repeated 2 times
10. An amount of 1 ml of 74E plasma was added to the beads.
11. The mixture was thoroughly mixed by gently inverting and incubated 2 h at room temperature (if shaken in plate shaker—80 rpm).
12. A Centrifuge step was performed as in section 3 and the supernatant was transferred to a new tube containing Plasma depleted plasminogen.
13. Plasma depletion was tested using ELISA assay.
14. The rest of the plasma (containing un-depleted and depleted) was incubated in −20° C.

PLG Detection

The Kit Ab108893 Human plasminogen ELISA Kit (Abacam®) was used according to the Manufacturer's instructions.

The Plates were prepared as follows (1:20,000 plasma dilution) in Table 3:

TABLE 3

| Preparation of plates | | |
|---|---|---|
| | 1 | 2 |
| A | Blank | Un-depleted 47E plasma |
| B | ↓ | ↓ |
| C | Conjugate 1 | |
| D | ↓ | |
| E | Conjugate 3 | |
| F | ↓ | |
| G | TXA conjugated ECH agarose beads Conjugate 3 | |
| H | ↓ | |

Reagent Preparation

All reagents were equilibrate to room temperature (18-25° C.) prior to use. Fresh reagents were prepared immediately prior to use.

1—1× Diluent M: Dilution of 1.5 ml of 10× Diluent M Concentrate 1:10 with 15 ml of reagent grade water. Mixing gently and thoroughly.
2—1× Wash Buffer: Dilution of 2 ml of 20× Wash Buffer, Concentration 1:20 with 38 ml of reagent grade water. Mixing gently and thoroughly.
3—1× Biotinylated Plasminogen Detector Antibody: First spin the 50× Biotinylated Plasminogen Antibody vial to collect the contents at the bottom. Adding 12 μl of 50× stock Biotinylated Plasminogen Antibody to the 588 μl of 1× Diluent M. Mixing gently and thoroughly.
4—1× SP Conjugate: Spilling down the 100× Streptavidin-Peroxidase Conjugate (SP Conjugate) briefly and dilute the 6 μl of the conjugate 1:100 with 594 μl of 1× Diluent M.

Standard Preparation:
1—standard were equilibrate to room temperature.
2—Seven tubes were labeled #2-8
3—Adding 120 μL of 1× Diluent M to tube #2-8.
4—Preparing Standard #2, adding 120 μL of the Standard #1 into tube #2 and mixing gently.
5—Preparing Standard #3, adding 120 μL of the Standard #2 into tube #3 and mixing gently.
6—Using the table below as a guide, preparing subsequent serial dilutions.
7—1× Diluent M serves as the zero standard, 0 ng/mL (tube #8).

Sample Preparation
Samples are diluted 1:20,000 with 1× Diluent M in serial dilutions:
a—1:100 plasma=5 μL of plasma+495 μl 1× diluent M.
b—1:20,000 plasma=5 μL of diluted plasma+995 μL 1× diluent M.

The following procedures were employed:
1—All reagents, working standards and samples were prepared as instructed. The assay is performed at room temperature (18-25° C.).
2—Excess microplate strips were removed from the plate frame and returned immediately to the foil pouch with desiccant inside. The pouch was resealed securely to minimize exposure to water vapor and stored in a vacuum desiccator.
3—An amount of 50 μL of Plasminogen Standard or sample was added per well. Wells were covered with a sealing tape and incubate for one hour. The timer was started after the last sample addition.
4—Washing steps were performed five times with 200 μL of 1× Wash Buffer manually. The plate was inverted each time and the contents were decanted (tapping i4 times on absorbent paper towel to completely remove the liquid)
5—An amount of 50 μL of 1× Biotinylated Plasminogen Antibody was added to each well and incubated for one hour.
6—The microplate was washed as described above.
7—An amount of 50 μL of 1× SP Conjugate was added to each well and incubated for 30 minutes. Microplate reader was turn on and the program set up in advance.
8—The microplate was washed as described above.
9—An amount of 50 μL of Chromogen Substrate was added per well and incubated for about 12 minutes or till the optimal blue color density develops (gently tapping the plate to ensure thorough mixing and breaking the bubbles in the well with pipette tip)
10—An amount of 50 μL of Stop Solution was added to each well. The color changed from blue to yellow.
11—The absorbance was read on a microplate reader at a wavelength of 450 nm immediately. The following results were observed:

PLG Concentration:
Standard curve results* are summarized in Table 4 and illustrated in FIG. 3:

TABLE 4

| | OD of Standard at 450 nm | | | |
|---|---|---|---|---|
| Sample | O.D | Blanked Data | Mean O.D | Concentration |
| STD1 | 0.071 | 0.001 | 0 | 0 |
| | 0.07 | −0.001 | | |
| STD2 | 0.227 | 0.157 | 0.1455 | 1.25 |
| | 0.204 | 0.134 | | |
| STD3 | 0.366 | 0.296 | 0.2805 | 2.5 |
| | 0.335 | 0.265 | | |
| STD4 | 0.607 | 0.537 | 0.5105 | 5 |
| | 0.554 | 0.484 | | |
| STD5 | 1.031 | 0.961 | 0.934 | 10 |
| | 0.977 | 0.907 | | |
| STD6 | 1.664 | 1.594 | 1.533 | 20 |
| | 1.542 | 1.472 | | |
| STD7 | 2.173 | 2.103 | 2.0995 | 40 |
| | 2.167 | 2.096 | | |
| STD8 | 2.481 | 2.411 | 2.5075 | 80 |
| | 2.674 | 2.604 | | |

The formula illustrated in Table 5 was obtained. Accordingly, the concentrations and percentage of depletion of the samples were calculated and are presented in Table 6.

TABLE 5

| Formula obtained from standard curve | | | | | | |
|---|---|---|---|---|---|---|
| Curve Name | Curve Formula | A | B | C | D | R2 |
| Std. Curve | $Y = (A - D)/(1 + (X/C)^B) + D$ | 0.0158 | 1.17 | 19.6 | 3 | 1 |

TABLE 6

| PLG concentrations in samples | | | | | |
|---|---|---|---|---|---|
| Sample | O.D. | Blanked Data | Mean O.D. | Concentration (μg/ml) | % depletion |
| Blank | 0.062 | −0.002 | 0 | 0 | |
| | 0.066 | 0.002 | | | |
| Conjugate 1 | 0.148 | 0.084 | 0.0825 | 14.1 | 92.4% |
| | 0.145 | 0.081 | | | |
| Conjugate 2 | 0.164 | 0.1 | 0.0975 | 17.14 | 90.8% |
| | 0.159 | 0.095 | | | |
| Conjugate 4 | 0.662 | 0.598 | 0.594 | 114.22 | 38.75% |
| | 0.654 | 0.59 | | | |
| Un-depleted 47E plasma | 0.952 | 0.888 | 0.9 | 186.5 | |
| | 0.985 | 0.921 | | | |

It appears that the concentration of PLG in un-depleted plasma is slightly higher than the normal range of plasminogen concentration in human plasma (153.1-174.9 μg/ml, according to the Kit instruction manual). Plasminogen levels depleted in more than 92% after incubation with TXA Superflow recovered beads, more than 90% of depletion after incubation with YA2-2 beads and 38% after incubation with TXA conjugated ECH agarose beads. While once recovered TXA Superflow beads and Y2-2 beads (TXA conjugated Glyoxal Agarose Beads) showed high efficiency in removing Plasminogen from plasma, TXA conjugated ECH agarose beads showed low efficiency.

Example 3

Evaluation of the Activity of New Conjugated GE Beads, Sterogene Super-Flow Beads Materials:
Plasma: Plasma of healthy donors were obtained from MDA Blood Bank (see Appendix 0.1)
Beads:
1—Conjugate 1 ("TXA conjugated GE beads")—pH 6.5, 7.5, 8.5. For synthesis protocol see Example 1.
2—"Sterogene recovered TXA Superflow beads" [conjugate-6]]
method #1: The beads have been used for pig experiment and recovered. Instruments:
1—Shaker: KRS-3016 (MRC)
2—ELISA reader: 800TS (BioTek).
The experiment conducted in non-sterile environment.
Plasminogen Depletion.
1. a. Sterogene TXA superflow beads were already in 20% Ethanol and 70% resin. An amount of 1 ml of beads was transferred to 15 ml tubes.
b. 1 ml of each reaction of TXA conjugated GE beads already in 20% Ethanol and 70% resin.
2. The tubes was filled with water.
3. Centrifuge at 300×g for 2 minutes, RT.
4. The supernatant was removed.
5. Repeat X3
6. The beads were suspended with binding buffer*:
a—10 mM Sodium citrate PH=7.16
b—120 mM Sodium chloride.
7. Centrifuge as section 3.
8. the supernatant was removed.
9. Repeat X2
10. 1 ml of 27K plasma was added to the beads.
11. The tubes were thoroughly mixed by gently inverting and incubated 2 h at room temperature (to shake in plate shaker—80 rpm).
12. Centrifuge as section 3 and the supernatant was transferred to new tube—Plasma depleted plasminogen
13. Plasma depletion was tested using ELISA assay.
14. The rest of the plasma (un-depleted and depleted) was incubated in −20° C.

PLG Detection

The Kit Ab108893 Human plasminogen ELISA Kit (Abacam®) was used according to the Manufacturer's instructions.

The Plates were prepared as follows (1:20,000 plasma dilution):

TABLE 7

| plate preparation | | |
|---|---|---|
| | 1 | 2 |
| A | Blank | Conjugate 1 beads (method #1) |
| B | ↓ | ↓ |

TABLE 7-continued

| plate preparation | | |
|---|---|---|
| | 1 | 2 |
| C | Reaction 1, PH = 6.5 | Conjugate 1 beads (method #2) |
| D | ↓ | ↓ |
| E | Reaction 1, PH = 7.5 | Un-depleted 27K |
| F | ↓ | ↓ |
| G | Reaction 1, PH = 8.5 | |
| H | ↓ | |

Reagent Preparation:
All reagents are equilibrated to room temperature (18-25° C.) prior to use. Fresh reagents immediately prior to use.
1× Diluent M: 2 ml of 10× Diluent M Concentrate were diluted 1:10 with 18 ml of reagent grade water. Mixing gently and thoroughly.
1× Wash Buffer: 4 ml of 20× Wash Buffer Concentrate were diluted 1:20 with 76 ml of reagent grade water. Mixing gently and thoroughly.
1× Biotinylated Plasminogen Detector Antibody: 50× Biotinylated Plasminogen Antibody vial were spin to collect the contents at the bottom. Add 18 μl of 50× stock Biotinylated Plasminogen Antibody to the 882 μl of 1× Diluent M. Mix gently and thoroughly.
1× SP Conjugate: 100× Streptavidin-Peroxidase Conjugate (SP Conjugate) were spin-down briefly and 9 μl of the conjugate were diluted 1:100 with 891 μl of 1× Diluent M.

Standard were prepared as detailed in Example 2. Standard curve results are summarized Table 4 and illustrated in FIG. 2. The formula illustrated in Table 5 was obtained.

Sample Preparation:
Samples were diluted 1:20,000 with 1× Diluent M in serial dilutions:
a—1:100 plasma=5 μL of plasma+495 μl 1× diluent M.
b—1:20,000 plasma=5 μL of diluted plasma+995 μL 1× diluent M.

Assay Procedure:
12—All reagents, working standards and samples were prepared as instructed. Reagents were equilibrated to room temperature before use. The assay was performed at room temperature (18-25° C.).
13—Excess microplate strips was removed from the plate frame and was returned immediately to the foil pouch with desiccant inside. The pouch was resealed securely to minimize exposure to water vapor and stored in a vacuum desiccator.
14—50 μL of Plasminogen Standard or sample were added per well. Wells were covered with a sealing tape and incubated for one hour. Timer was started after the last sample addition.
15—Washing five times with 200 μL of 1× Wash Buffer manually. The plate was inverted each time and the contents were decanted (taping it 4 times on absorbent paper towel to completely remove the liquid).
16—50 μL of 1× Biotinylated Plasminogen Antibody were added to each well and incubated for one hour.
17—Washing of microplate as described above.
18—50 μL of 1× SP Conjugate were added to each well and incubate for 30 minutes. The microplate reader was turn on and the program set up in advance.
19—Washing of microplate as described above.

20—50 μL of Chromogen Substrate were added per well and incubated or about 12 minutes or till the optimal blue color density developed (gently tapping plate to ensure thorough mixing and breaking the bubbles in the well with pipette tip).

21—50 μL of Stop Solution were added to each well. The color changed from blue to yellow.

22—The absorbance was read on a microplate reader at a wavelength of 450 nm immediately.

PLG Concentration:

The concentrations and percentage of depletion of the samples were calculated according to the formula detailed in Table 5 and are presented in Table 8.

TABLE 8

PLG concentrations in samples

| Sample | O.D | Blanked Data | Mean O.D | Concentration (μg/ml) | % depletion |
|---|---|---|---|---|---|
| Blank | 0.081 | −0.002 | 0 | 0 | |
|  | 0.084 | 0.002 | | | |
| Reaction 1, PH = 6.5 | 0.472 | 0.389 | 0.389 | 76.5 | 63.73% |
|  | 0.472 | 0.389 | | | |
| Reaction 2, PH = 7.5 | 0.486 | 0.403 | 0.408 | 80.12 | 62.02% |
|  | 0.495 | 0.412 | | | |
| Reaction 3, PH = 8.5 | 0.573 | 0.49 | 0.477 | 73.86 | 54% |
|  | 0.56 | 0.464 | | | |
| Conjugate 1 | 0.15 | 0.067 | 0.0615 | 13.58 | 93.56% |
|  | 0.138 | 0.056 | | | |
| Un-depleted 27K plasma | 1.059 | 0.976 | 0.98 | 210.96 | |
|  | 1.067 | 0.984 | | | |

It appears that the concentration of PLG in un-depleted plasma is slightly higher than the normal range of plasminogen concentration in human plasma. About 24% of Plasminogen depleted after plasma incubation with TXA Superflow beads recovered using method #1 and more than 93% after incubation with beads recovered using method #2. Therefore, the beads with 24% of depletion should be recovered again and those with 93% can be used again in pig experiment. While TXA conjugated GE beads synthesized in PH=6.5 or PH=7.5 showed more than 60% of PLG depletion, those which synthesized in PH=8.5 showed 54% of depletion. This experiment demonstrates that the reaction is more efficient in PH=6.5. Future experiments are conducted overnight or with different ligand concentration in the reaction.

Example 4

Plasma Filtration with ClearPlasma
TXA superflow, conjugate 1
Filter Preparation:
1—25 ml of resin was packed in the filter.
2—100 ml of 70% Ethanol flowed through the filter and incubated for 30 minutes.
3—washed twice with 70% Ethanol.
4—washed three times with 20% Ethanol
5—stored in 4° C.
Resin Activation:
The resin was washed three times with DDW and two times with binding buffer) 10 mM sodium citrate+1.20 mM sodium chloride).
Plasma Filtration:
Human plasma bag was connected to the filter and the entire volume (200 ml) was flowed through the filter into the receiving bag for 1 hour.

The results are presented in Table 9 below.

TABLE 9 percent of depletion in sample

| Sample | OD | Blanked OD | Mean OD | Concentration (μg/ml) | % depletion |
|---|---|---|---|---|---|
| Depleted plasma | 0.293 | 0.19 | 0.185 | 29.22 | 81.56% |
|  | 0.282 | 0.179 | | | |
| untreated plasma | 0.868 | 0.889 | 0.78 | 158.52 | |
|  | 0.765 | 0.796 | | | |

As shown Table 9, filtration of the plasma resulted in effective depletion of plasminogen.

ClearPlasma™ device TXA conjugate beads and/or cyclohexanecarboxylic acid agarose beads=Conjugate 1.

Materials:
Plasma: Plasma from healthy donors was obtained from Magen David Adom (MDA) Blood Bank
ClearPlasma™ device: the cartridge was filled with conjugated cyclohexanecarboxylic=conjugate 2 acid agarose beads using 3 ml Pasteur pipettes; the resin was washed with 150 ml of saline and stored at 2-8° C.
Instruments: ELISA reader: 800TS (BioTek)

An amount of 250 ml of plasma was connected to the device using luer lock and flowed through the device with a speed of 2 drops/second for about 30 min. The depleted plasma was collected in sterile caps. Samples form the untreated plasma and depleted plasma were taken to analysis and the rest were frozen in −20° C. Plasminogen concentration was determined using E-80PMG—Human Plasminogen ELISA Kit, Lot #9 (ICL, Inc.).

TABLE 10 percent of depletion in sample

| Sample | Concentration (μg/ml) | Depletion % |
|---|---|---|
| Untreated plasma (control) | 172.646 | 96% |
| Plasminogen depleted plasma | 7.07 | |

It appears that more than 96% of PLG as removed from plasma after filtration with the above described ClearPlasma™ device.

Example 5

Evaluation of Clear Plasma Efficacy in Depleting Plasminogen Levels from Cryoprecipitate by Using ClearPlasma Cryoprecipitate is an important plasma derivative used to treat bleeding in general and massive bleeding in particular. Therefore, the capacity of ClearPlasma device to deplete plasminogen from cryoprecipitate was evaluated.

Materials:
a. ClearPlasma: Plastic filter (Pentracor Inc.), TXA conjugate Superflow resin (Sterogene; Lot: 1608:88), Extension line with flow regulator (Qosina; Lot: 159299), Blood collection bag (Fresenius; Lot: FA17H30126).
b. Equipments:
i. Shaker: Cat no. KRS-3016; S/N: SH30000003; Manufacturer: MRC.
ii. ELISA reader: Cat no. 800TS; S/N: 1709201B; Manufacturer: BioTek iii. Centrifuge: Cat no. Z383K; S/N: 31030005; Manufacturer: HERMLE.a.
c. Cryoprecipitate: Cryoprecipitate was obtained from Hadassah Blood Bank (Cryoprecipitate details in appendix 0.1). (Y 2002 18 170007 O Rh positive)

The experiment was conducted according to the description in the Experimental procedures. The data show that a single pass of a cryoprecipitate unit (29 ml) through ClearPlasma decreased the concentration of plasminogen in the cryoprecipitate from 155.87 to 2.7 µg/ml i.e. about 98% (see FIG. 3) without any effect of the coagulation factors. ClearPlasma device is thus suitable for use to deplete plasminogen from cryoprecipitate. Depleting plasminogen from cryoprecipitate provides a new product with increased capability to treat bleeding conditions.

Example 6

Evaluation of the Concentration a Live Plasminogen In-Vivo.

Briefly, fresh Blood was taken from healthy voluntaries. 50 µl of tPA (6 µM) or normal saline (NS) were added to 1.8 ml of fresh blood and clotting time was determined using Hemochron 401 apparatus. In parallel experiments 50 µl of tPA (6 µM) or NS were added to 1.8 ml plasminogen free plasma.

To evaluate the effect of the conjugate of the presently disclosed subject-matter, two parameters were evaluated. The clotting time, and time for total clot lysis.

Clotting Time

The clotting time was inversely related to the concentration of active plasminogen.

In control blood, the clotting time was 113±27 seconds (n=7), where in blood treated with tPA it was 255±41 seconds (n=8). In plasminogen depleted blood the clotting time in absence of tPA was 110±16 (n=6) where in presence of tPA it was 118±18 (n=7).

Time for Total Clot Lysis.

The presence of blood clot was determined by simple observation and by re-inserting the tube with blood clot in the machine.

The clot disappeared from the control blood treated with tPA after 14±5.2 min (n=6). In contrast in control blood treated with NS, the blood clot was intact at 2 hours after the complete clot formation.

In plasminogen-depleted blood with or without tPA, the clot was intact at 2 hours after the complete clot formation. These results clearly demonstrate the effectivity of the conjugate of the presently disclosed subject-matter.

Example 7

Assessment of the Efficacy of Plasmapheresis in a Swine Model of Liver Lacerations This study aimed to investigate the use of ClearPlasma™ and the benefit of plasma with reduced plasminogen as compared to normal plasma. The study was performed at Biotechfarm Ltd. (Israel).

Objective

The objective was to assess the efficacy of administration of PDP on blood loss in a Swine Liver Lacerations model.

Study Endpoints

Blood loss measured 30 min after 4 cm liver lacerations and evaluated according to the grading scheme presented below.

TABLE 11

Bleeding grading scheme in swine liver lacerations model

| Category | Minimal bleeding | Moderated bleeding | Massive bleeding |
| --- | --- | --- | --- |
| Amount of blood lose | 0-100 ml | 100-300 ml | X > 300 ml |

Study Duration
Eight to nine hours per pig
Study Design
Fourteen female domestic pigs were allocated to 4 groups (control, regular plasma, ClearPlasma™ and TXA)
The groups were treated as follows:
Control Group 1:
1. Induction of general anesthesia.
2. Plasma collection for duration of 90 minutes.
3. Induction of liver lacerations 30 minutes after termination of plasma collection.
4. Closure of abdominal wall and skin 30 minutes post induction of liver lacerations.
Control Group 2:
1. Induction of general anesthesia.
2. Induction of liver lacerations 30 minutes after termination of plasma collection.
3. Closure of abdominal wall and skin 30 minutes post induction of liver lacerations.
Control Group 3:
1. Induction of general anesthesia.
2. Treatment with TXA.
3. Induction of liver lacerations 30 minutes after termination of plasma collection.
4. Closure of abdominal wall and skin 30 minutes post induction of liver lacerations.
Test Group:
1. Induction of general anesthesia.
2. Plasma collection—filtration with ClearPlasma™ Test Device group) for duration of 90 minutes.
3. Induction of liver lacerations 30 minutes after termination of plasma collection.
4. Closure of abdominal wall and skin 30 minutes post induction of liver lacerations

TABLE 12

Animal allocation (swine liver laceration study)

| Experiment # | Animal # | Treatment |
| --- | --- | --- |
| 1 | 143 | Regular plasma |
|   | 144 | PDP |
| 2 | 145 | Regular plasma |
|   | 146 | PDP |
|   | 147 | TXA |
| 3 | 152 | PDP |
|   | 153 | TXA |
|   | 156 | Regular plasma |
| 4 | 155 | PDP |
|   | 157 | Regular plasma |
| 5 | 169 | Regular plasma |
|   | 170 | TXA |
|   | 172 | PDP |
|   | 173 | Control |

Regular plasma = fresh frozen plasma (FFP); PDP (plasminogen-depleted plasma) = FFP with plasminogen removed by ClearPlasma ™; TXA = tranexamic acid Study Procedures
1. Buprenorphine was administered prior to induction of anesthesia.
2. Anesthesia—The animals were sedated with Ketamine, Xylazine & Atropine, then intubated with endotracheal tube; anesthesia was maintained with Isoflurane in oxygen.

3. A catheter was placed in an accessible ear vein for vascular access.
4. A central vein cannula (CVC) was introduced into each jugular vein for plasma collection application.
5. Plasma was collected for a period of 90 minutes. After that, plasma transfusion with ClearPlasma™ or without was performed.
6. Thirty minutes post plasma collection, liver lacerations model was induced as follows:
   The pigs were placed in a supine position.
   Clipping of the ventral area and scrubbing was performed.
   A midline incision was made.
   The right liver lobe was exposed and exteriorized to allow sufficient working field, then rinsed with physiological saline.
   Grid pattern of lacerations was made, 4 cm (length), 1 cm apart and 0.5 cm in depth (the liver piece was weighted).
7. Blood loss was measured by determining the difference in the weights of dry sponges and bloodstained sponges after model induction. The weight difference was expressed as blood loss in grams.
8. Time to hemostasis (TTH) was measured, when applicable.
9. Thirty minutes post induction of lacerations, the abdominal wall and skin were closed.

Monitoring of Physiological Parameters

Prior to plasma collection application (baseline), immediately following collection application, just prior to induction of liver lacerations, during bleeding and immediately after the skin closure:
esophageal temperature,
mean arterial pressure,
heart rate,
oxygen saturation,
activated clotting time,
blood sample for CBC,
hematology, biochemistry and coagulation parameters, including prothrombin time (PT) and a partial thromboplastin time (PTT).

Prior to plasma collection application (baseline), 30 minutes post induction of liver laceration (just prior to closure) and at the end of the study (5 hours post closure):
detailed clinical signs: following recovery from anesthesia.

Prior to plasmapheresis application:
body weight.

Supportive Care

Animals were placed on skin-warming blankets during recovery.

Euthanasia

Animals were euthanized 5 hours post closure. Note: Two animals with continuous bleeding 60 minutes post induction of liver lacerations (i.e., just prior to closure) were euthanized on humane grounds.

Clinical Observation Methods

Behavioral attributes including, but not limited to, the following:
1. Elimination of blood, urine & feces, discolored urine (if applicable), diarrhea, absence of feces (constipation).
2. Signs of illness or injury, lethargy, vomiting, excessive salivation, abnormal posture, pain, lameness, discomfort, unwillingness or inability to move.
3. Neurological severity score (NSS)
4. Additional assessments were performed whenever warranted based on clinical observations.

Equipment

Haemonetics MCS®+, syringes, needles and glassware surgery equipment's, blood pressure monitor, oxygen monitors. All diluents and solutions for washing and rinsing of devices or parenteral injection assemblies were treated in a manner that will assure that they are sterile, pyrogen-free and protected from contamination.

Results

In all experiments pigs underwent plasma collection using the Haemonetics MCS®+ system. Whole blood was collected, centrifuged, red blood cells were returned immediately to the pig and up to 700 ml of plasma was collected and filtrated using ClearPlasma™ (for test group) or not filtrated (for control groups) as described in FIG. 4. Pigs were under anesthesia, and blood from the vein was collected and introduced into the plasmapheresis system. Then red blood cells were returned to the animal and, in the test group animals, plasma was filtered by ClearPlasma™ and returned to the animal. The detailed results obtained from each pig are detailed in Table 13.

TABLE 13

Detailed parameters of the swine liver laceration experiment.

| Exp# | Pig # (♀) | Body We. (kg) | Trea. | Anticoag. citrate dextrose sol. form. (ml) | Bl. Coll. (ml) | Plasma coll. (ml) | Dura. of blee. (min) | Amou. of blee. (g/ml) | Si. of liv. cut (g) |
|---|---|---|---|---|---|---|---|---|---|
| 1 | 143 | 38.8 | Regular plasma | 189 | 2186 | 613 | 30 | 406 | 12 |
|   | 144 | 39.1 | PDP | 185 | 2431 | 684 | 23 | 150 | 20 |
| 2 | 145 | 41.7 | Regular plasma | 195 | 2205 | 312 | 30 | 436 | 22 |
|   | 146 | 40.6 | PDP | 195 | 2238 | 700 | 30 | 180 | 20 |
|   | 147 | 40.2 | TXA (1 g boost and maintenance of 35 mg/hour) | 0 | 0 | 0 | 12 | 138 | 18 |
| 3 | 152 | 39.4 | PDP | 203 | 2577 | 702 | 30 | 430 | 26 |
|   | 153 | 37.4 | TXA (1 gr boost and maintenance of 35 mg/hour) | 0 | 0 | 0 | 21 | 206 | 28 |
|   | 156 | 36 | Regular Plasma | 202 | 1300 | 350 | 30 | 530 | 32 |
| 4 | 155 | 35.4 | PDP | 157 | 2093 | 750 | 18 | 226 | 20 |
|   | 157 | 37.6 | Regular Plasma | 167 | 2581 | 700 | 28.5 | 498 | 22 |

TABLE 13-continued

Detailed parameters of the swine liver laceration experiment.

| Exp# | Pig # (♀) | Body We. (kg) | Trea. | Anticoag. citrate dextrose sol. form. (ml) | Bl. Coll. (ml) | Plasma coll. (ml) | Dura. of blee. (min) | Amou. of blee. (g/ml) | Si. of liv. cut (g) |
|---|---|---|---|---|---|---|---|---|---|
| 5 | 169 | 40 | Regular Plasma | 201 | 1976 | 415 | 18 | 226 | 26 |
|   | 170 | 40 | TXA (1 gr boost and maintenance of 35 mg/hour) | 0 | 0 | 0 | 23 | 158 | 18 |
|   | 172 | 40 | PDP | 202 | 2500 | 650 | 15 | 108 | 24 |
|   | 173 | 40 | Control (untreated) | 0 | 0 | 0 | 22 | 146 | 26 |

Abbreviations: trea. (treatment), amou. (amount), bleed. (bleeding), Bl. (blood), Hi (high), liv. (liver), gr. (gram), exp. (experiment), We. (weight), anticoag. (anticoagulant), sol. (solution, form (formula), coll. (collect), dura. (duration), si. (size).
Regular plasma = fresh frozen plasma (FFP); PDP (plasminogen-depleted plasma) = FFP with plasminogen removed by ClearPlasma ™;
TXA = tranexamic acid Experiment 1: Plasma from pig 144 was filtered using ClearPlasma™ and returned to pig 144. Plasma from pig 143 was transfused to pig 143 after mock filtration. Then a 4 cm liver cut was preformed, and the amount of blood and time of bleeding were recorded. This experiment has shown that the depletion of plasminogen levels reduces the amount of bleeding. Even though the size of the liver cut was smaller in the control pig, the bleeding was higher than in the pig that received PDP. In addition, the clinical evaluation was improved and the pulse of the control pig was higher and unstable as competed to the pig that received PDP.

Experiment 2: The effect of PDP as compared to regular plasma and TXA. Three pigs were tested as follows: pig 145 was treated with regular plasma, pig 146 was treated with plasminogen depleted plasma and pig 147 was treated with tranexamic acid (TXA). The results demonstrate that PDP reduces the amount of bleeding as compared to regular plasma. In addition, there was minor difference in the amount of bleeding between TXA as compared to regular plasma.

Experiment 3: The effect of PDP as compared to regular plasma and to TXA. The results demonstrate that PDP reduces the amount of bleeding as compared to regular plasma.

Experiment 4: The effect of PDP as compared to regular plasma and to TXA. The results demonstrate that PDP reduces the amount of bleeding as compared to regular plasma.

Experiment 5: Reduced bleeding after liver cut in a pig administrated with PDP. Pigs were anesthetized and plasma was collected as described in the material and method section. Pigs were treated with regular plasma, PDP, with TXA 16 mg/kg or untreated. Then 4 cm liver cut was done using scalpel as described in the material and method section. The results demonstrate that PDP reduce the amount of bleeding as compared to regular plasma.

FIG. 5 demonstrates the amount of blood loss as manifested during 30 min after liver laceration. As can be seen in FIG. 5, the use of ClearPlasma™ reduces the amount of bleeding in more than ~50% in comparison with pigs that received regular plasma.

To validate the reduction in the activity of fibrinolytic proteins such as Plasminogen and tPA, Thromboelastography (TEG) was performed (see FIG. 6A-6L). (TEG) is a method of testing the efficiency of blood coagulation. Pigs were numbered: #169—control, #172—plasmapheresis and plasminogen. depletion; #173—only plasmapheresis. As can be seen in FIG. 6J, only in pig #172, there was no fibrinolytic response after tPA administration. This result demonstrates the significant reduction in fibrinolytic proteins such as plasminogen and tPA.

In conclusion, in all experiments the use of ClearPlasma™ significantly improved the clinical outcome and reduced the amount of blood the pigs lost as compared with pigs that received regular plasma transfusion.

Example 8

Safety Assessment of Administration of Plasminogen Depleted Plasma on Blood Loss in Animals Treated with Clexane in a Swine Liver Lacerations Model The study was performed at Biotechfarm Ltd. (Israel).

Objectives

Safety assessment of administration of plasminogen depleted plasma on blood loss in a swine liver lacerations model. To examine the effect of plasminogen depletion in animals treated with anticoagulants. To provide that there are no risks of development of thromboembolic complications in patients with blood thinner therapy (Clexane).

Study Endpoints

Blood loss was measured 30 min after 4 CM liver lacerations.

Study Design

The study compared plasma with reduced fibrinolytic protein and normal plasma in animals treated with Clexane to verify that the treatment with PDP does not lead to the development of deep vein thrombosis (DVT).

Species & gender: Domestic ♀ pigs. 40-50 kg at study initiation

Number of groups: 4 (3 Control Group & 1 Test Device Group)

Groups size: n=5 (♀) for the Control Group; n=5(♀) for the Test Device Group

Total number of animals: 20

Constitution of groups & dosing:

Control Group 1: 1. Control untreated: Induction of general anesthesia 2. Plasma collection for duration of 90 minutes. 3. Induction of liver lacerations 30 minutes after termination of plasma collection 4. Closure of abdominal wall and skin 30 minutes post induction of liver lacerations.

Control Group 2: 1. 4000 Units of Clexane: Pigs were injected with 4000 Units of Clexane 10 hour prior surgery. 2 induction of general anesthesia 3. Induction of liver lacerations 30 minutes after termination of plasma collection 4. Closure of abdominal wall and skin 30 minutes post induction of liver lacerations.

Control Group 3: 1. Fresh plasma and 4000 Units of Clexane: Pigs were injected with 4000 Units of Clexane 10 hour prior surgery. 2. Induction of general anesthesia 3. Treatment with TXA 4. Induction of liver lacerations 30 minutes after termination of plasma collection 5. Closure of abdominal wall and skin 30 minutes post induction of liver lacerations.

Test Group: 1. Plasminogen depleted plasma and 4000 Units of Clexane: Pigs were injected with 4000 Units of Clexane 10 hour prior surgery. 2 induction of general anesthesia 3. Plasma collection—filtration with Clear-Plasma™ (Test Device group) for duration of 90 minutes. 4. Induction of liver lacerations 30 minutes after termination of plasma collection. 5. Closure of abdominal wall and skin 30 minutes post induction of liver lacerations Study Procedures Clexane® Syringes 4,000 IU (40 mg)/0.4 ml solution for injection in pre-filled syringes was injected intravenously (IV) to the pigs 10 hours before the treatment with PDP or regular plasma. Analgesia: Buprenorphine; anesthesia: animals were sedated with Ketamine, Xylazine & Atropine, then intubated with endotracheal tube and anesthesia was maintained by Isoflurane in oxygen.

A catheter was placed for vascular access in an accessible ear vein. A central vein cannula (CVC) was introduced into each jugular vein for plasma collection application.

Plasma collected during a period of 90 minutes. The plasma was transfused after the treatment with Clear-Plasma™ or without.

Thirty minutes post application of plasma collection, liver lacerations was induced as follows:

The pigs were placed in a supine position,
Clipping of the ventral area and scrubbing,
A midline incision was made,
The right liver lobe was exposed and exteriorized to allow sufficient working field and rinsed with physiological saline,
Grid pattern of lacerations was made, 4 cm (length), 1 cm apart and 0.5 cm in depth, the liver piece was weight,
Blood loss was measured by determining the difference in the weights of dry sponges and blood-stained sponges after model induction. The weight difference is expressed as blood loss in grams.
Time to hemostasis (TTH) was measured if applicable.
Thirty minutes post induction of lacerations, the abdomen was closed and then the skin.
Monitoring of Physiological Parameters:
Prior to plasma collection application:
Baseline, immediate following collection application, just prior to induction of liver lacerations, during bleeding and immediately post closure of skin.

Esophageal temperature, mean arterial pressure, heart rate, oxygen saturation, activated clotting time blood sample for CBC.

Hematology, biochemistry and coagulation parameters including Prothrombin time (PT) and a partial thromboplastin time (PTT): prior to plasma collection application=baseline, 30 minutes post induction of liver Lacerations (just prior to closure) and at the end of the study, 5 hours post closure.

Detailed clinical signs: following recovery from anesthesia.

Body weight: once, prior to plasmapheresis application.

Supportive care: Buprenorphine was administered prior to induction of anesthesia. Animals were placed on skin-warming blankets during recovery.

Terminal Investigations: Animals were euthanized 5 hours post closure. Note: Any animal with continuous bleeding, over 60 minutes, post induction of liver lacerations (i.e., just prior to closure) were euthanized on humane grounds Study Period: 8-9 hours per pig Clinical Observation Methods: behavioral attributes including, but not limited to, the following:
1. Elimination of blood, urine & feces, discolored urine (if applicable), diarrhea, absence of feces (constipation),
2. Signs of illness or injury, lethargy, vomiting, excessive salivation, abnormal posture, pain, lameness, discomfort, unwillingness or inability to move. 3. Neurological severity score (NSS) 4. Additional assessments were performed whenever warranted based on clinical observations.

Apparatus: Haemonetics MCS®+, Syringes, needles and glassware Surgery equipment's, blood pressure monitor, oxygen monitors. All diluents and solutions for washing and rinsing of devices or parenteral injection assemblies were treated in a manner that assured that they are sterile and pyrogen-free. Assure that all test solutions are protected from contamination.

In all experiments pigs underwent plasma collection using Haemonetics MCS®+ system. Whole blood was collected, centrifugated, red blood cells were returned immediately to the pig and up to 700 ml of plasma was collected and filtrated or not using ClearPlasma™ as described in FIG. 5. Pigs were under anesthesia, and blood from the vein was collected and introduce into the plasmapheresis system. Following this, red blood cells were return to the animal and plasma was filtered by ClearPlasma™ and finally returned to the animal.

Results:

TABLE 14

Results from the safety assessment in pigs #38 and #171

| Pig no. (♀) | Body WT/KG | Treat. | Anticoag. citrate extrose sol. form. (ml) | Bl. Coll. (ml) | Plasma coll. (ml) | T. of blee. (min) | Amou. of bleed. (gr./ml) | Si. of liv. cut gr. | Clin. Eve. |
|---|---|---|---|---|---|---|---|---|---|
| 38 | 42 | Fresh Plasma and 4000 units of Clexane | 295 | 2562 | 676 | 25 | 178 | 16 | Hi. bl. Pres. |
| 171 | 45 | Plasminogen depleted plasma and 4000 units of Clexane | 282 | 2811 | 690 | 36 | 144 | 16 | Nor. |

Abbreviations: trea. (treatment), amou. (amount), bleed. (bleeding), Bl. (blood), Hi (high), Nor. (normal), eve. (events), liv. (liver), gr. (gram), We. (weight), anticoag. (anticoagulant), sol. (solution), form (formula), coll. (collect), si. (size), T (time), clin. (clinical).

TABLE 15

Results from the safety assessment in pigs #202, #204, #203 and #208

| Pig num. (♀) | Body WT/KG | Treat. | anticoag. citrate extrose solution form. (ml) | Bl. colle. (ml) | Plas. coll. (ml) | T. of blee. (min) | Amou. of blee. (gr./ml) | Si. of liv. cut gr. | Clin. eve. |
|---|---|---|---|---|---|---|---|---|---|
| 202 | 41 | Control (untreated) | 0 | 0 | 0 | 26 | 138 | 22 | Nor. |
| 204 | 42 | 4000 Units of Clexane | 0 | 0 | 0 | 30 | 300 | 18 | Hi. bl. press. |
| 203 | 40 | Fresh Plasma and 4000 units of Clexane | 307 | 2441 | 710 | 30 | 544 | 20 | Alm. dea. |
| 208 | 42 | Plasminogen depleted plasma and 4000 units of Clexane | 320 | 2534 | 729 | 26 | 148 | 20 | Nor. |

Abbreviations: trea. (treatment), anticoag. (anticoagulant), num. (number), form. (formula), coll. (collected), T. (time), bleed. (bleeding), Bl. (blood), Hi (high), Nor. (normal), clin. (clinical), press. (pressure), gr. (gram), sol. (solution), si. (size), plas. (plasma), liv. (liver), eve. (event), dia. (Dead), alm. (almost).

TABLE 16

Results from the safety assessment in pigs #223, #222, #224 and #220

| Pig num. (♀) | Body WT/KG | Trea. | anticoag. citrate extrose sol. form. (ml) | Bl. coll. (ml) | Plasm. coll. (ml) | T. of blee. (min) | Amou. of blee. (gr./ml) | Si. of liv. cut (gr.) | Clin. eve. |
|---|---|---|---|---|---|---|---|---|---|
| 223 | 24 | Cont. (un-trea. | 0 | 0 | 0 | 25 | 80 | 18 | Nor. |
| 222 | 43 | 4000 Un. of Clex. | 0 | 0 | 0 | 28 | 194 | 18 | Nor. |
| 224 | 45 | Fre. Plasma and 4000 un. of Clex. | 160 | 1926 | 530 | 25 | 594 | 18 | Alm. dea. hi. pu. And Bl. press. |
| 220 | 44 | Pla. dep. plas. And 4000 un. of Clex. | 167 | 2106 | 550 | 21 | 94 | 22 | Nor. |

Abbreviations: trea. (treatment), anticoag. (anticoagulant), num. (number), form. (formula), coll. (collected), T. (time), bleed. (bleeding), Bl. (blood), Hi (high), Nor. (normal), clin. (clinical), eve. (event), press. (pressure), gr. (gram), plasm (plasma), plas (plasminogen), dep. (depleted), clex. (Clexane), un-treat (untreated), sol. (solution), si. (size), plas. (plasma), liv. (liver), eve. (event), dea. (Dead), alm. (almost).

As expected, treating the animals with Clexane significantly increased the amount of extraverted blood from 187 cc to 274 cc. The data also show that giving the animal's one unit of fresh plasma (FP) increased the bleeding from 274 cc to 596 cc. Furthermore, depleting the FP from plasminogen decreased the bleeding size from 596 cc to 128.7 cc.

Postmortem data show that animals treated with PDP do not develop thrombotic or thromboembolic events. No clots were found in the lungs, heart or spleen of animals treated with PDP. The conclusion concerning the absence of thromboembolic events is further supported by the absence of D-Dimer in animals treated with PDP.

The data show that plasminogen depleted plasma is an effective anti-bleeding treatment even in animals treated with Clexane. The data also indicate that plasminogen PDP is effective even in animals treated with Clexane. Therefore, PDP could be good solution in patients treated with anticoagulants that have to be operated emergently. The data also suggest, that patient treated with PDP can be treated with Clexane with no risk to increase bleeding; such conclusion is relevant to patients need to be treated with anticoagulant in the post-operative period in order to prevent or treat DVT. The data also show that it is possible to co-treat patient with Clexane and PDP and by that to prevent bleeding and thrombotic events at the same time.

Example 9

Plasminogen Depleted Plasma (PDP) In Vitro Properties Compared with FFP

The coagulation parameters of Plasminogen Depleted Plasma (PDP) and Fresh-frozen plasma (FFP) were calculated according to the Experimental procedure and compared as detailed in Table 17. A volume of 215 ml of Fresh frozen plasma (FFP) was flow through ClearPlasma (denoted by PDP in Table 17; in contrast with FFP relating to untreated plasma). It appears that up to 80% of PLG was depleted in PPD.

TABLE 17

Coagulation parameters of PDP compared to FFP.

| Parameters | Units | FFP | PDP | P-value |
|---|---|---|---|---|
| Plasminogen | µg/mL | 155.41 | 33.06 | P < 0.01 |
| PTT | Seconds | 34.82 | 32.56 | N/S |
| Fibrinogen | mg/dl | 360.2 | 317.8 | N/S |

All experiments were done in triplicates. Statistics were computed using student t-test (Two tailed distribution equal variance)

In addition, multiple tests for specific blood components were performed to determine coagulation and biochemical states of treated and untreated plasma (examination of nutrition and protein contact). The tests were performed in Bnay-zion Hematological and biochemical laboratories. The results are presented in Table 18. It appears that there are no significant differences in biochemical parameters between FFP and PDP and therefore that ClearPlasma did not affect nutrition and/or levels protein contact.

TABLE 18

Biochemical parameters of PDP compared to FFP.

| Parameters | Units | FFP | PDP | P-value |
|---|---|---|---|---|
| Glucose | mg/dL | 384.00 | 341.80 | N/S |
| Alkaline phosphatase | U/L | 51.20 | 46.4 | N/S |
| Alanine transaminase | U/L | 10.80 | 10.40 | N/S |
| Amylase | U/L | 54.00 | 48.60 | N/S |
| Aspartate transaminase | U/L | 16.60 | 15.40 | N/S |
| Gamma glytamyl transferase | U/L | 9.40 | 9.60 | N/S |
| Lactic dehydrogenase | U/L | 290.20 | 254.00 | N/S |
| Sodium | mmol/L | 168.6 | 162.8 | N/S |
| Chloride | mmol/L | 73.06 | 74.68 | N/S |
| Total protein | g/dL | 6.37 | 5.89 | N/S |
| Globulin | g/dL | 2.33 | 2.30 | N/S |
| Urea | mg/del | 22.80 | 19.80 | N/S |

All experiments were done in triplicates. Statistics were computed using student t-test (Two tailed distribution equal variance)

In addition clot lysis was monitored by thromboelastography (TEG) in both PPD and FFD as detailed in the Experimental procedure section. The results are illustrated in FIG. 7. It appears that PDP abolished fibrinolytic activity in human plasma.

Example 10

Mice Safety Experiment—Evaluation of Anti-Fibrinolytic Technology in Tail Bleeding Assay The study was performed at Biocell Ltd. (Israel).

Objective

The purpose of this experiment is to examine the safety of intravenous injection of plasma without plasminogen in mice.

Study Endpoints

The safety of plasminogen-depleted plasma was evaluated through blood markers (blood count, biochemistry) and clinical observations (skin, coat, eye/mucous check, nervous system, somatic activity and general behavior). The parameters were measured prior to injection, 48 hours post-injection and 7 days post-injection.

Animals 12 animals

Species/Strain: Mice: C57black

Gender/Number/Age: Male 10-12 weeks

Source: Harlan Laboratories, Israel

Ethical Committee

This study was performed after approval by "The Israel Board for Animal Experiments" and in compliance with "The Israel Animal Welfare Act".

Study Design

In this experiment each mouse was injected with 200 µl of one of the treatments.

1. Healthy 12 weeks old C57black mice were anesthetized with a mixture of Ketamine and Xylazine (at 100 and 10 mg/kg, respectively) and their body weight was measured.
2. The mice were randomly divided to three different groups (four mice in each group) and injected with 200 µl of:
   1. Saline—group 1
   2. Regular plasma—group 2
   3. Plasma without plasminogen—group 3 originated from C57black mice and filtrated by ClearPlasma™).
3. Forty eight hours post injection, two mice from each group were sacrificed to evaluate the safety of the injection; blood was collected into EDTA K3 tubes for blood collection and was sent to blood tests (at 4° C.).
4. Seven days later two mice from each group were sacrificed to evaluate the safety of the injection; blood was collected into EDTA K3 tubes for blood collection and was sent to blood tests (at 4° C.).
5. Mice blood was tested for: blood count (CBC), LDH, AGT, ALT and full biochemistry analysis.

Physiological markers have demonstrated that intravenous injection of plasminogen-depleted plasma did not affect mouse physiology. Complete blood count (CBC), blood biochemistry, body weight, morphological appearance and animal behavior were examined and found normal in all groups. Thus, according to the results of this experiment, it appears that plasminogen-depleted plasma is safe to use.

Bleeding Test in Mice

Plasminogen depletion was also performed in mice: plasma originated form C57black mice was subjected to ClearPlasma (control plasma was not treated). The levels of plasminogen was then evaluated by Eliza [KIT: ab198511— Plasminogen Total (PLG) Mouse ELISA KIT] and show 97% depletion of plasminogen (As shown in the table below).

TABLE 19

PLG concentration in the samples:

| | Dilution factor | O.D | Ave | Without blank | * Concentration (µg/ml) |
|---|---|---|---|---|---|
| Treated plasma | $10^4$ | 0.249 | 0.238 | 0.0365 | 4.1 |
| | $10^4$ | 0.227 | | | |
| Untreated plasma | $10^4$ | 1.044 | 0.937 | 0.7355 | 118 |
| | $10^4$ | 0.83 | | | |

Bleeding test after tail snipping in mice was performed according to the procedures described in the Experimental procedure section. This non-GLP study aimed to investigate the use of ClearPlasma™ device and the benefit of plasma with reduced plasminogen as compared to normal plasma. The study was performed at Biocell Ltd. (Israel).

Objective

To test the effect of PDP on the bleeding rate of mice.

Study Endpoints

The amount of blood lost was graded using the following standard grading scheme:

TABLE 20

Bleeding grading scheme in tail bleeding assay model

| Category | Minimal bleeding | Moderated bleeding | Massive bleeding |
| --- | --- | --- | --- |
| Amount of blood loss | 0-1 ml | 1-3 ml | X > 3 ml |

Briefly, mice were injected with Saline or untreated plasma (FFP) or plasma devoid plasminogen, (treated plasma or PDP). Animals were placed in prone position. A distal 10-mm segment of the tail was amputated with a scalpel. The tail was immediately immersed in a 50-mL tube containing isotonic saline pre-warmed in a water bath to 37° C. The position of the tail was vertical with the tip and positioned about 2 cm below the body horizon. Each animal was monitored for 20 min (even if bleeding ceased, in order to detect potential re-bleeding event).

Bleeding Time

The tails of the participating mice were snipped at 7 mm and the time until bleeding stopped was measured. The test was conducted in groups of 3, with one mouse from each treatment group in each iteration. The results show that in all iterations of the test except for number 2, the PDP mice had the shortest bleeding time.

Amount of Bleeding

The tails of the mice were snipped at 7 mm and the time until bleeding stopped was measured. The test was conducted in groups of 3, with one mouse from each treatment group in each iteration. Blood was collected, centrifuged and the size was measured using ruler. The results show that in all iterations of the test except for number 2, the PDP mice had the smallest amount of bleeding (see FIG. 8).

Blood Cells Pellet Size at 24 Hours After the Bleeding Test

The blood cell pellet from the bleeding test was centrifuged and the supernatant was aspirated. Pellet size was then measured using a ruler. Statistics was calculated using One-way ANOVA followed by post hoc LSD/SCHELF ($p<0.05$ considered significant). FIG. 9 shows the pellet size results from each mouse. FIG. 10 summarizes the statistical analysis of pellet size measurement. It appears that PDP reduces bleeding by >40% in mice. These results demonstrate that PDP (ClearPlasma™) shortened bleeding times and amount of lost blood in mice treated with it, as compared to control groups.

Example 11

ClearPlasma Reduces Both Plasminogen and tPA Protein Levels in Pigs

Females pig underwent plasmapheresis using Haemonetics mcs+ system under anesthesia. Two groups of pigs were examined: a control group and a test group. In the test group, plasma of pigs was filtered with ClearPlasma. Similar procedures were conducted for both groups i.e. amount of filtrated blood: 700 ml, treatment with anticoagulant [anticoagulant citrate dextrose solution formula a], time: about 100 min and amount of 2500 of blood was proceeded ml: about 700 of plasma was collected. Following these procedures, plasma was returned to the animal.

Plasma samples of each group were analyzed for plasminogen depletion (Elisa KIT: ab108893 Human plasminogen as detailed in the Experimental procedure section) and for tPA depletion (Wild type-tPA Sandwich ELISA# Technozym T-PA AG EDTA Elisa Kit 96 TC12007). As illustrated in FIG. 11A-11B, it appears that samples of plasma that were filtered with ClearPlasma were depleted both of plasminogen and tPA.

Example 12

Plasma pH and Conductivity Objective

To compare pH and conductivity of the PDP and donor plasma.

Materials

Plasma: plasma from healthy donors

Final sterilized ClearPlasma™ device

Instruments: pH meter, electrical conductivity meter

A bag with human plasma was connected to the ClearPlasma™ device and the entire volume (200 ml) was flowed through the device into the receiving bag for 1 hour. The pH and conductivity of PDP and plasma were measured. Minor changes in pH and conductivity values were observed after treating plasma with the ClearPlasma™ device as detailed in Table 21.

TABLE 21

Comparison of pH and conductivity of treated and untreated plasma

| Plasma | Process | pH | Conductivity ($\mu$S/cm) |
| --- | --- | --- | --- |
| Plasma | Before filtration | 7.86 | 13.14 |
|  | After filtration | 7.88 | 12.44 |

Example 13

Safety Related Analysis

Hemocompatibility

The final sterilized ClearPlasma™ device (particles of polysaccharidic polymer encased in polycarbonate, housing) has been tested in an in vitro hemolysis test: total blood hemoglobin concentration measurements (cyanmethemoglobin method). The test was performed by Envigo (Israel). The study was conducted in compliance with OECD Principles of Good Laboratory Practice (GLP) (as revised in 1997), ENV/MC/CHEM(98)17.

The in vitro hemolysis test measures total blood hemoglobin concentration using the cyanmethemoglobin method. Pooled blood from 3 rabbits was incubated with Negative (Glass Vial, Batch: 16491) and Positive (Nitril examination Gloves, Batch: 41010104) Controls as well as with the Test item (ClearPlasma™). Following 3 hours of incubation at 37±1° C., hemoglobin content in the plasma was measured and hemolysis was determined.

The % Hemolysis of the Negative Control (Glass Vial, Batch: 16491) was −0.5%, thus graded as Non-haemolytic.

The % Hemolysis of the Positive Control (Nitril examination Gloves, Batch: 41010104) was 91.1%, thus graded as hemolytic.

The Negative and Positive Controls met the acceptance criteria, therefore confirming the validity of the test.

The % Hemolysis Index of the test item ClearPlasma™ (Batch No.: 18-0001) was −0.3% and −0.1% and is considered Non-Hemolytic.

Under the conditions of this study, and according to calculated hemoglobin content, Part A and Part B of the Test Item ClearPlasma™ (Batch No.: 18-0001) is considered Non-Hemolytic.

Material Mediated Pyrogenicity Test

The purpose of this study was to provide general information on the detection of material mediated pyrogenicity of the plasminogen depleted plasma.

The test was conducted by American Preclinical Services, LLC (MN, USA).

The study was conducted in compliance with:
United States Pharmacopeia (USP) <151> Pyrogen Test Regulatory Standards,
ISO 10993-11:2017 Biological Evaluation of Medical Devices, Part 11: Tests for Systemic Toxicity.

A total of 3 animals were used. A baseline control temperature was established for each animal not more than 30 minutes prior to injection. The test article (plasminogen depleted plasma, Lot No. 001) was warmed to 37±2° C., and intravenously injected within 10 minutes at 10 ml/kg into the lateral ear vein of each animal. Each animal's temperature was recorded at 30-minute intervals between 1 and 3 hours subsequent to the injection. Based on the results of this study, the test article showed no evidence of material mediated pyrogenicity in the rabbit.

Bacterial Endotoxin Test

The purpose of this study was to estimate the concentration of bacterial endotoxins (pyrogens) in the water extract prepared on the final sterile ClearPlasma™ device and beads.

The test was conducted by Milouda & Migal Laboratories (Israel).

The device and the beads were tested separately.

The device without beads was incubated with 50 ml LAL reagent water per sample for 1 hour. The LAL reagent water has been heated to 37° C. before the test. Then the extracts from the samples were tested for bacterial endotoxins using the Kinetic-Turbidimetric LAL test method.

The results of two tested samples were 0.00860 EU/ml and 0.0138 EU/ml.

Then, 3 vials of beads in 30% ethanol were tested as follows: each sample was diluted 1:10 with LAL reagent water and was incubated at 15-30° C. for 1 hour. The sample was centrifuged for 10 minutes at 5,000 RPM. The supernatant (dilution 1:10) was tested for bacterial endotoxins using the Kinetic-Turbidimetric LAL test method. The results were <0.05 EU/ml for each test.

The maximum summary result for [device+beads] was not greater that the limits established by USP <161> (20 EU/device):

[0.01380 EU/ml×50 ml]+[<0.05EU/ml×27 ml (to fill in the device)]=0.69 EU/device+[<1.35] EU/device=<2.04 EU/device.

LAL tests are conducted for each product batch as part of the release testing.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed examples in accordance with the presently disclosed subject matter, it will be appreciated that many changes may be made therein without departing from the spirit of the presently disclosed subject matter.

Example 14

Clinical Study to will be Evaluate the Efficacy and Safety of ClearPlasma™ in Patients with Acute Upper Gastrointestinal Bleeding A randomized, double blind, controlled trial is conducted to evaluate the safety and efficacy of PDP filtered by ClearPlasma™ device in patients presenting with acute upper gastrointestinal bleeding. This is a non-inferiority study. The main outcome is safety: thromboembolic events (venous or arterial). The study aimed to evaluated the following parameters:

1) the total blood loss after plasma transfusion [Time Frame: The first postoperative 48 h]. The blood loss is evaluated by: RBC's blood units transfused [Time Frame: 2 weeks], plasma units transfused [Time Frame: 2 weeks], hemoglobin drop—compare to baseline, platelets units transfused [Time Frame: 2 weeks] and re-bleeding episodes during the two weeks of follow-up;
2) the length of hospital stay [Time Frame during two weeks of follow-up];
3) the mortality related to plasma transfusion.

The study is conducted in several centers (multi-center) at phase 1/2, for a total duration of 12 months (study duration for each patient is of two weeks). The study comprises two arms:
a) transfusion of 250-500 ml of PDP, plus regular plasma if needed;
b) transfusion of regular plasma.

The patient population relates to patients with acute upper gastrointestinal bleeding (UGIB), diagnosed by melena/presence of blood in gastric lavage/hematemesis. The sample size is of 30 patients (15 of each group). The sample size calculation is based on review of medical articles in similar indications and clinical projects and involves descriptive analysis.

Patients are screened for study eligibility by assessment of inclusion and exclusion criteria. Screening procedures include collection of demographic data, medical history, physical examination and vital signs.

For inclusion in the study, patients should be at age ≥18 years, have acute upper gastro-intestinal bleeding (<24 h) diagnosed by a physician and provide a written informed consent. The informed consent process complies with the recommendations of ISO 14155:2011.

The following parameters excludes patients from the study: pregnancy, plasma infusion given in the previous month, known renal failure creatinine clearance <30 ml/min, arterial or venous thrombosis in the previous 3 months, previous allergic reaction to plasma, participation in another clinical study and anticoagulant treatment such as warfarin, apixaban, rivaroxaban, dabigatran, low molecular weight heparin.

The schedule of visits/assessments is baseline, after 8-12 hours (including blood sample), following morning (day 2), 72 hour and 14 days after the transfusion. The baseline evaluation comprises Blood pressure, pulse, blood testes including full CBC, PT, INR, PTT, biochemistry. The treatment schedule is a one-time transfusion and the follow-up schedule is 12 h, 24 h, 72 h and 2 weeks after transfusion.

Administration of ClearPlasma™ must be based on ABO-blood group compatibility. In emergency cases, Clear- Plasma™ blood group AB can be regarded as universal plasma. ClearPlasma™ must be administered by intravenous infusion after thawing using an infusion set with a filter. Aseptic technique must be used throughout the infusion.

Expected adverse effects are allergic reactions and fever. Patient can be withdrawn upon the occurrence of a serious adverse event that necessitates a change in treatment, withdrawal of consent, or Investigator's decision.

Data for this study is recorded in a case report form (CRF) in accordance with US Code of Federal Regulations, to enable clinical investigation data to be systematically captured, reviewed, managed, stored, analyzed and reported.

The study site is monitored:
a) prior to the start of the study (i.e., study initiation visit);
b) early in the study after the first patients have been enrolled and the crfs have been completed;
c) after 10-15 patients are enrolled during the course of the study;
d) after the last patient has been enrolled (i.e., study termination visit).

Additional on-site monitoring visits may be triggered by poor CRF returns, poor data quality or excessive numbers of patient withdrawals or deviations.

The study may be subject to audit by the Sponsor or its designees, as well as inspection by appropriate regulatory authorities. The Investigator must agree to the audit or inspection of study—related records and must allow direct access to source documents with due consideration to data protection and medical confidentiality.

Study data is captured in the CRF including all variables as per the final approved protocol. Data is collected, entered, cleaned and reported in accordance with the ICH-GCP (Good Clinical Practices), ISO 14155:2011 Clinical investigation of medical devices for human subjects—Good Clinical Practice, and FDA standards such as US 21 CFR Part 11 requirements.

The invention claimed is:

1. A plurality of conjugates or a composition comprising said plurality of conjugates, wherein each conjugate comprises a particle, at least one linker and at least one amino acid, derivative thereof or analog thereof, wherein the plurality of conjugates comprises at least two different conjugates, and wherein said amino acid, derivative thereof or analog thereof is 4-(aminomethyl)-cyclo-hexane-carboxylic acid (tranexamic acid), and wherein at least one conjugate in said plurality of conjugates is at least one of:

(a)

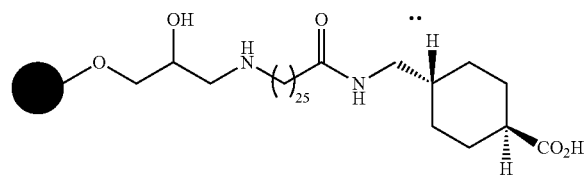

wherein

● represents a particle;

(b)

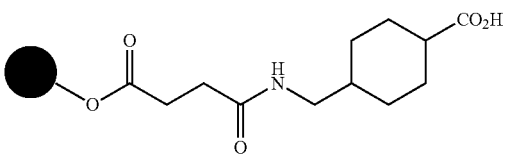 [SMILES: COC(=O)CCC(=O)NCC1CCC(C(=O)O)CC1]

wherein

● represents a particle;
(c)

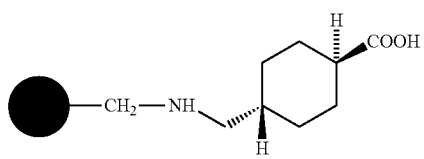

wherein

represents a particle;
(d)

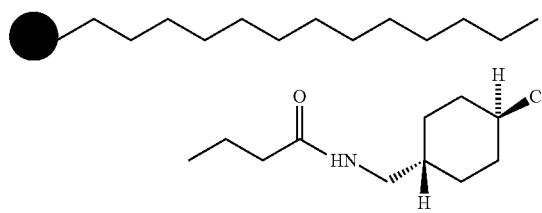

wherein

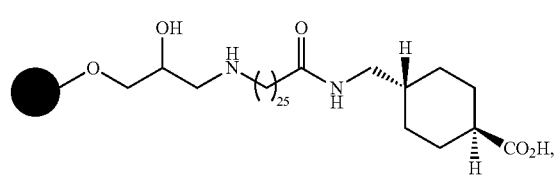

-continued

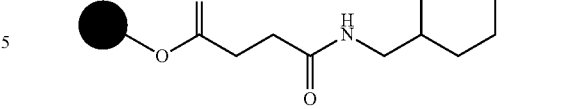

represents a particle,
wherein each said particle has an average particle size of 10 µm to 500 µm.

2. The plurality of conjugates or composition according to claim 1, wherein the particles and/or the linkers of the at least two different conjugates are different.

3. The plurality of conjugates or composition according to claim 1, wherein at least one of said conjugates is:

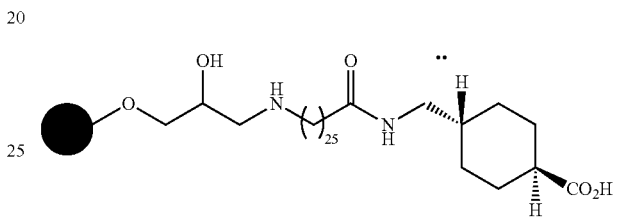

wherein

represents a particle.

4. A conjugate comprising a particle, at least one linker and at least one amino acid, derivative thereof or analog thereof, said conjugate being any one of:

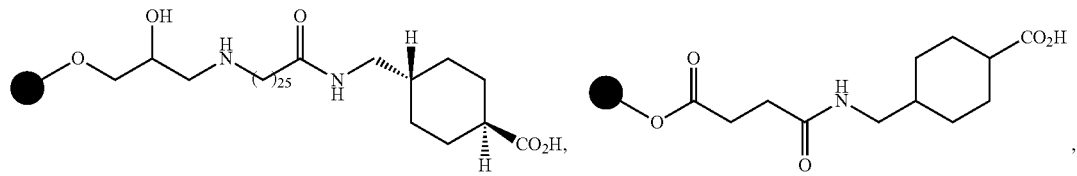

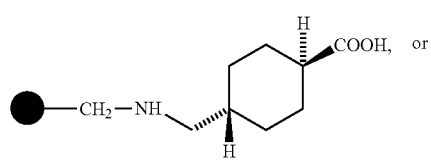

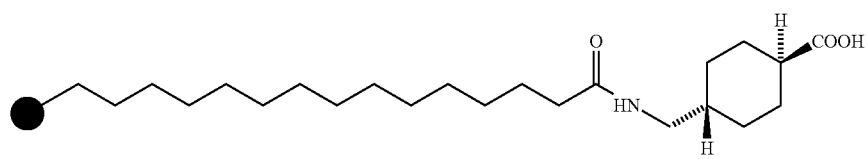

wherein

● represents a particle having an average particle size of 10 μm to 500 μm.

5. A device for depleting at least one fibrinolytic protein from mammalian body fluid/s, comprising:
a housing having at least one fluid inlet port, and at least one fluid outlet port;
the housing including at least one chamber, said at least one chamber defining a control volume in fluid communication with the at least one fluid inlet port and the at least one fluid outlet port;
said control volume accommodating a plurality of groups of particles, including at least a first group of first particles and a second group of second particles;
wherein said first particles are dimensionally different from said second particles; and
wherein at least one of said first particles and said second particles are conjugated particles that comprise the plurality of conjugates in accordance with claim 1.

6. The device according to claim 5, wherein said housing comprises a longitudinal axis, and comprises a main body portion, and a pair of end caps, including an inlet end cap having said at least one fluid inlet port, and an outlet end cap having said at least one fluid outlet port.

7. The device according to claim 6, wherein said control volume is defined by corresponding barrier members provided at opposite longitudinal ends of the main body portion, optionally said barrier members are configured for preventing said particles from exiting said control volume.

8. A battery comprising a plurality of devices according to claim 5 for use in depleting at least one fibrinolytic protein from mammalian body fluid/s, wherein said devices of the plurality of devices are interconnected in a manner to provide fluid communication between the respective said control volumes of said plurality of devices.

9. A kit comprising at least one device according to claim 5 for depleting at least one fibrinolytic protein from mammalian body fluid/s, comprising:
said at least one device,
a saline reservoir in selective fluid communication with said at least one inlet port;
an acceptor plasma reservoir and a wash waste reservoir, wherein said acceptor plasma reservoir and said wash waste reservoir are in selective and non-concurrent fluid communication with said at least one fluid outlet port.

10. A system comprising at least one device according to claim 5 for depleting at least one fibrinolytic protein from mammalian body fluid/s, comprising:
said at least one device,
a saline reservoir and a donor reservoir, wherein said saline reservoir and said donor reservoir are in selective and non-concurrent fluid communication with said at least one fluid inlet port;
an acceptor plasma reservoir and a wash waste reservoir, wherein said acceptor plasma reservoir and said wash waste reservoir are in selective and non-concurrent fluid communication with said at least one fluid outlet port.

11. A method for depleting at least one fibrinolytic protein from mammalian body fluid/s or any products thereof, the method comprising the steps of:
(i) subjecting said body fluid/s to affinity-depletion procedure specific for said at least one fibrinolytic protein/s; and
(ii) recovering the at least one fibrinolytic protein-depleted body fluid obtained in step (i);
wherein said affinity-depletion procedure comprises contacting said body fluid with an effective amount of a plurality of conjugates as defined in claim 1 or with a composition comprising said plurality of conjugates.

12. The method according to claim 11, wherein at least one of
(a) said body fluid is at least one of whole blood, plasma or blood-derived product comprising at least one coagulation factor, optionally said blood-derived product is at least one of whole blood, plasma, fresh frozen plasma (FFP), platelet rich plasma (PRP) and cryoprecipitate;
(b) said fibrinolytic protein is at least one of plasminogen and tissue plasminogen activator (tPA) or
(c) said method further comprises the step of measuring the amount of plasminogen in the fibrinolytic protein-depleted body fluid recovered in step (ii), by determining at least one of clotting time and time for total clot lysis in said fibrinolytic protein-depleted body fluid.

13. The method according to claim 11, for depleting at least one fibrinolytic protein from body fluid/s of a subject in need thereof by an extracorporeal procedure, the method comprising the steps of:
(i) transferring body fluids of said subject into an extracorporeal apparatus;
(ii) subjecting said body fluid to affinity depletion procedure specific for at least one fibrinolytic protein/s, wherein said depletion is performed before, during or after blood is being transferred into and out-off said apparatus, thereby obtaining an extracorporeal body fluid of said subject depleted in at least one fibrinolytic protein; and
(iii) reintroducing or returning said body fluid obtained in step (ii) to said subject;
wherein said affinity-depletion procedure comprises contacting said body fluid with an effective amount of said plurality of conjugates or said composition thereof comprised within said extracorporeal apparatus or within a device connected to said extracorporeal apparatus.

14. The method according to claim 13, wherein at least one of:
(a) said body fluid is at least one of whole blood and plasma,
(b) said at least one fibrinolytic protein is at least one of plasminogen and tPA or
(c) said method further comprises the step of recovering at least one of plasminogen and tPA from said plurality of conjugates or composition or conjugates.

15. The conjugate according to claim 4, being:

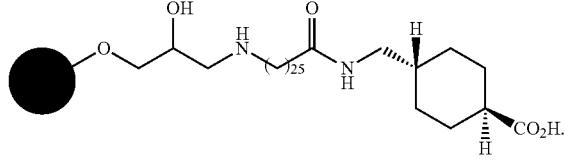

16. The plurality of conjugates or composition according to claim 1, wherein at least one of:
   (a) the particles have an average particle size of between about 90 µm to about 150 µm;
   (b) the linker comprises a linear chain of 1 atom to 40 atoms;
   (c) the ratio between the particle and the linker coverage of the particle's surface is about 9 to 23 µmol beads/ml drained medium;
   (d) the linker comprises at least one atom having a lone electron pair;
   the particle is at least one of polysaccharide bead, glass beads, cotton bead, plastic bead, nylon bead, latex bead, magnetic bead, paramagnetic bead, super paramagnetic bead, starch bead and the like, silicon bead, PTFE bead, polystyrene bead, gallium arsenide bead, gold bead, or silver bead; and
   (e) the particle is agarose bead or sepharose bead.

17. A conjugate according to claim 4, wherein the particle is an agarose bead or sepharose bead and has an average particle size of between about 90 µm to about 150 µm.

18. A device according to claim 7, wherein one of
   (i) said barrier members are configured for concurrently permitting the through-flow of the mammalian body fluid/s through the control volume or
   (ii) said barrier members are configured for concurrently permitting the through-flow of the mammalian body fluid/s through the control volume, wherein in use of the device, the mammalian body fluid/s enter the control volume via the inlet end cap and the fluid inlet port, and subsequent to exiting the control volume, flow via the outlet end cap and the fluid outlet port.

19. A device according to claim 18, wherein said barrier members each comprise a plurality of openings for allowing through-flow of the mammalian body fluid/s through the openings, the openings being of a size smaller than said particles.

20. A battery according to claim 8, wherein one of
   (a) at least a portion of said plurality of devices are interconnected serially, wherein for each pair of said serially interconnected said devices, the respective said fluid inlet port of one said device of said pair is connected to and in fluid communication with the respective said fluid outlet port of another said device of said pair,
   (b) at least a portion of said plurality of devices are interconnected in parallel, wherein for said parallel interconnected said devices, the respective said fluid inlet ports are interconnected and in fluid communication with one another, and wherein the respective said fluid outlet ports are interconnected and in fluid communication with one another, or
   (c) at least a portion of said plurality of devices are interconnected in parallel, wherein for said parallel interconnected said devices, the respective said fluid inlet ports are connected and in fluid communication with at least one donor plasma reservoir, and wherein the respective said fluid outlet ports are connected and in fluid communication with at least one acceptor plasma reservoir.

21. A method according to claim 11, wherein said plurality of conjugates, or composition comprising said plurality of conjugates, are within a device, battery or system.

22. A method for the preparation of at least one blood and/or blood-derived product that has a reduced fibrinolytic activity, comprising the steps of:
   (i) subjecting said body fluid/s to affinity-depletion procedure specific for said at least one fibrinolytic protein/s; and
   (ii) recovering the at least one fibrinolytic protein-depleted body fluid obtained in step (i);
   wherein said affinity-depletion procedure comprises contacting said body fluid with an effective amount of a plurality of conjugates as defined in claim 1, or with a composition comprising said plurality of conjugates, and
   wherein said at least one fibrinolytic protein-depleted body fluid is a blood and/or blood derived product that has a reduced fibrinolytic activity.

\* \* \* \* \*

SEQUENCE LISTING

```
<160> NUMBER OF SEQ ID NOS: 4

<210> SEQ ID NO 1
<211> LENGTH: 55266
<212> TYPE: DNA
<213> ORGANISM: Homo sapiens
<220> FEATURE:
<221> NAME/KEY: misc_feature
<223> OTHER INFORMATION: plasminogen AY192161.1

<400> SEQUENCE: 1
cactagtgat gctggaagtg ctcccaagaa gcagagaaaa gtcatgacat ttgacattac      60
aagaaaaact ggatttgctt gatatgtaac agagactgag gtctgtagct ggggttgctt     120
ccatttcaga cagatgattc atcttgtaaa caggtggtgt aaacttactg tatggaaaaa     180
tacataacag taccacagat gtattttctc cttacgaaca tttccttttc tctagcttac     240
tttattgtaa gaatacagta tatcatacat ataacataca aaatacatgt tattaactgt     300
tgctggtcaa cagcaggctg ttagtagtta agtttttgag agtcagagtt atacctggat     360
tttctactgt gtatggtcag tgtgccaacc cctgaaattg atcaagggtc aactgtaatc     420
ctaaaagaat ctaatacaat attgtaaaca gtaagtggtc aataaataag gaattgaact     480
aataagaata cataaatccc agaatatgtg caacctgatc atagtacaca gagatctctc     540
tatatatctc ttttcttagt tcatgctgtt ctttcaggta gaaagcgcct tattttgaat     600
tagttgtctt tagagcaaaa atccctccaa gagtgctgtg tggtttccta tgcacaacct     660
ggaatagtcc attgcttcat gcctaccctg gacatgaagg gccatgccgc agcggaagtc     720
tctatgcacc cacccccgtc tatacctgag caacacattc ctctttgctg ctctcttaca     780
ggctacagag tgcggtggcg ccagcacaga gctctgctca acgtccctct gtgctttcac     840
gatgctgatg gattatgaag gtagggaaga atgtacagcc aggaggccat taggagggca     900
actaatttat aaaatcacat ttgtagaatt taatgcatcc aacaactacc aggggaaagg     960
tgggcaaaag ctataccaac accacccaag tcaaaaccaa aacaacagga aaagaaaatt    1020
atgtggatgt agaatttctg ataacatcat tcccaaggtg ccttatccaa gaggaactgc    1080
tacaataata ttttaagtgg aaataaatac atgctggaag cattatatat tagtagagta    1140
tttttttttc ccaaagtact ttctcaagca catcaacatg agcccctaa gagacatttc     1200 acattaaaaa taaaatgtct gcccactgct ggtttctcaa tctgcctcca ccttctgtcc    1260
```

-continued

```
cctttaatga actgggccac gaggtgagtc agagaggata aagggagtgg taagaatttg    1320
aggagagaag agagtgaggc taaaatagga aatcaggaaa agcgattcgg tccccctgtc    1380
cctcacatgg ggccaccctc ttgttgccca gtgtggcttc ttcttgaggg ttctgcatgg    1440
ttcctcaatc ccagggaatt ccgcaggaca ttccacccaa gaccattggg ctcccacctc    1500
tactcttttg ccagttaatg aataggcagg aatttcactg cctggaaaga ggaacaatgc    1560
tttctggtcc ttatttcaca tctaaaatag agaggtcaat tgatttattc ctaaatatct    1620
ttgaacacta aaatagaagt tttacagcat atatactacc tggttgctct agacttaagc    1680
cagggaaaag tacagattca acatttaaaa ttgagataga cgctttccac ttaatgctac    1740
cagtcttgct ttatttcatg agaatgagaa tataataata tggcatacgt tcatttgggg    1800
gaaagattga tgtcttataa cataatttat aattacagaa acatgtgag ttcactggga     1860 ataaataaat tttgaagata ataagatact ttcacttatg tcgtaatttc tatgtcattt    1920
ggtgtaggat gtagagatat taacgtttac acctaactta agtttgtcat ctaagacctg    1980
aaagggtttt gtctatcagc tgcacccctg ggtagagaca caaccttggg gaaggcctca    2040
gccccatccc tcgtacagca ggaatgagaa cagccctgcc tgttgggaag cttgagggag    2100
gctatggacg tgcagcgctt ggcagagggt ctcgtcatgg aaggttccag caaatgtgag    2160 atactttat gatttcattt tctccaaaag aaagggaata agagaagagg ggaggaaata     2220
agactaattg cgagagataa agtacaaggg tgagggaagg aataaggaga catgacggca    2280
gcgtggagca gccgaggggg gagattgctt tcaccacttc ccagcatcta ttgcagattc    2340
caccctcaaa catgttgtaa ggactcttta ttcaaggtaa tgtttgaacc ctgctgagcc    2400
agtggcatgg gtctctgaga gaatcattaa cttaatttga ctatctggtt tgtggatgcg    2460
tttactctca tgtaagtcaa caacatcctg ggattgggac ccactttctg ggcactgctg    2520
gccagtccca aaatggaaca taaggaagtg gttcttctac ttcttttatt tctgaaatca    2580
ggtaagacat agttttttta aattataaga attatttttt ctcccacaat gtagtaaaaa    2640
tacatatgcc atggctttat gtgcaattca tttaattttt gattcatgaa acttccagtt    2700
gaaaatcttg tataagattg aggaattctt caagaaataa gtttaagttt cctgtgaaga    2760
ttgtcagggt gctggaatga atgggcagag aaaataatgg gtgatttttc aaatctaaat    2820
gagtgcaccc acataatggc cagtctaatt gaaaaagagc caatgtagct aattatgcaa    2880
aggacggcta agctctttgc ctggttctca gtttgactaa tttatatcat ctctgttacg    2940
gtgtcatgct cccctcactt gcaagttaaa acagtgaaat atctctttga atatattccg    3000
ttctctcacc agttcatggt ggcggcaggg tcggggactc agcatttctc cctttgttat    3060
ggcctgagga aggcttttcca tcagtatacg tttgcctctt atccccggaa aaatcacacg    3120
catccatttg ccagatgctg tgtgcagata tgatcaaca aatactcagt tgcttgggtt     3180
aggtccctac attttttacac atacatacat acctgtgtgt gaatgtgagt gtgagtgtgt   3240
atcctttaca aatactagct tatttagctc gtggtatagg tagggtagca tattcatcct    3300
cattttataa acaaagaaat cagacttagg aatatcatgt tatttgctca gtgaccaaat    3360
tctcagatct gggaaataaa gaaaactgga tttaagccag gtttcccaga aggaatctag    3420
ggctcttctc acttttcagc tttgtttaag cctttgaaag aatattctaa acatgtccta    3480
gtacttcttt ttcttaaaa aaaaaaaagc tttattgaga tataattaac atatagaatt     3540
cacccattta ggcatacaat ccaatggatt tcaagatatt gagagttgtg cagccaccat    3600
cagaataaat tttaaaacta ttcatacccc caaaaacgca ctccactctc cttagctgtt    3660
```

```
acccccaatc tgcagcttct ggcaaccact aatctacttt ctgtatttat atctttgcca    3720 tttttgaacat ttcatacaaa cggaatcata cgatttgcta gtagttcttc atgtaaataa   3780
tgtacgcttg aaattcaatc tataaattac cagataaaat tttacaagtt gcactttaga    3840
gtcaaataca tttgaattta gtggaagcca ttcaaggagc tatcaaagaa aatacagagc    3900
aggagaaaat taaagaaatt tttgtaagaa attggtgtat gttgggggt atgaatatta    3960 tatttcaatg catggaaact aggacataga tcactatgaa cttattcagt gggctacacc    4020
caaaggctag atcaaacttc tctgccacag gattaacata tgttttaacc cacctggtgg    4080
gcacattctc tcataagctc ttttggaaag ccaggttttc tgtggatgta tcatctttcc    4140
agtgtgctgc aatgcccggg gagagggaaa agtttctttt acagccatgc ttagtgggaa    4200
gtggagaaac atcttccatt tcacaaatta agtcttttac acatgcaaat atgcatacac    4260
attcacacac cacagtgagg aagaaattct cacaccatta ataaaataca tttgcatcag    4320
tagcaatata catctgcatt ttgcctataa tataaatgta ttttccact aaaagatttg     4380 tttgatgttt ccttgccagc aaataagccc tatcaaatcc tattgccata tgagtcctag    4440
aggtgaataa gagaagaaaa aatgggggaa aattatttca aactgaaaag agaaaagttt    4500
gattctgttt tgggatattt cctagggaca tgagctgggg aggggatctc agcagcgatg    4560
cgctatgaag catagtaaca taacacagag aacttaattg aagggggaaa taatgggaag    4620
ttttcttttt ttgaatatca gttgtagcct gctctgctat acttcaaaaa aactcttcag    4680
aaagtttaac tgaactcact gtaggacaca ctttgtggat ttattgtgtg ttttgaagtc    4740
acactgtgag ctatatagaa ttaaccaaaa cacaactctt cttgaaaatg agagttcaag    4800
ttggcagaaa gtgcggggta aagacatgga tatgggccta aagcatctat ttctttgtga    4860
tcttttgata tatctctcaa gtgcttttta gtggattagc tttagaatgc atcagccaac    4920
tcctgctcaa taatccattt ttccagcccg gaatgtctta aattgaggaa ggacaaagtc    4980
ccagaggtgg ggagcagggg gactttggcc gaggactttg catgaatcga tgagcatgca    5040
tccacctccc tgtcctgccc cttgtgctct gtgtaccctc aggaggtcag gacaggcctt    5100
tctgagaatg aaaatctgtt catttgcttt cctactggat acttgtcatc agcatacaaa    5160
ccaatgcgct ctgcagtgtg tcatctttca gaacctcccc tgaccgcatg ttccctggag    5220
ggctcgctgt cttcagagcc aggcttgtct cctgctgcag cctccactgc tctcctagtc    5280
actctgtaac ccacccctc tgcctgcggc ccccaccacg cccctcaaag tggtcaaggt    5340
tgtcctgttg tctaattcca tggagcttgc ctgtcttcat tttattagcc tcttttggcc    5400 tctcacccctt gtgcaaatca ctagcattct gtgccaagga cggagctggc atctccaggc   5460
ttggaataga gctaccaaag ctcagccaga tgtctggaag agcctcagga caaggggaca    5520
ccctgtagcc ttgtggtggg agcacagctg aggcccccctt ggccacccctc tgccacgacc   5580 aggcagaaag cagctttcgg acagattcgt tgtctcagat ttgatctcaa agaaaaacca    5640
agaccagtat ttgtcccagg tcctgctttt ttacaatttc ctccgaaatc cagataccctg   5700 tcaacacctt ggaaaaactg acttctcccc aattagtagt gttgtgtgac tgtcataagc    5760
ccagtacaaa aatggccttc tttgttgggg agcttcttac cctccagtgt tttgcccaat    5820
ttttgtccaa ggtggcaaca taatttagtt cagttcttgt ttatttccac catcatctat    5880
gcaccaaaat ttatgtttct caaggaggga ccattcagag gatgcttccc accggttcaa    5940
gtgacagtgc cagaaccaaa gcgcatattg taggaaatca aacaatggcc tccaagttcc    6000
```

```
atttctaccc agggatgaac aaatcaacat caatcttggt aacacaactg ccactgatgg    6060
tgccttactc ttctctcatg acatggcaca atcaatagca aacataaaat ttgttcttgt    6120
ttaaggattt atatccacta atatggtaac atagtagtgg ttccatagtt ctaacctgtt    6180
tgtcaatcca gttaatcttt tactatcttg caatctgcta atgaaactgt ttttctttgt    6240
tttataattt caacttttag agtcaggggt acatgtgcag gtgtgttaca taactaaatt    6300
gcgtgacact gagctttggg gtacaaatga tcccatcacc caggtagtga gctaaatacc    6360
tactaaatag gtagttttc agcccttgcc ttgctccctc tctcccttct ctggtagtcc     6420
ccagtgtctt tagttgccat ctttatttat gtccaaatgc ccgactgtgt gttcttaact    6480
aaacattttg attcatagct acccattcta cttccagtaa acagaaagtt ttatttggtt    6540
aatgctaacc aaatagatta aaggaagtc atgacaatta gacattgaca ttgatttact     6600
gaccatttat tccacttgga tctcccacct ctaggtcaag gagagcctct ggatgactat    6660
gtgaataccc aggggcttc actgttcagt gtcactaaga agcagctggg agcaggaagt     6720
atagaagaat gtgcagcaaa atgtgaggag gacgaagaat tcacctgcag gtatttccat    6780
tgtcgttgca cctacgcagg aatctgtaat tcagatggca agtaatttac tcacaaattt    6840
attaatgatt taagaggaaa gagaaattta tggagccaga gtttggaact atatttgctc    6900
acagtatgtg aagccatact aacagcttct tgttaaggtt tattggagtc tttgttagaa    6960 aaatacccctc aaaggaagtt atttgttttt acaccggaca caaacattag cagttattgt   7020
tctgagctcc agttttcaac atcatcatca gtaaatgttt gttgaggatc aggtgaatga    7080
aagtgtccta gatagatctg agcaatgact tatagctaca agatccagtg cctgcccttt    7140
agtatttaag gtgtagtcaa agaaactgga tataatgtta aaaaaaaaa aaagacagcc      7200 caagtgaggt acaggcataa tcaatgcatg ctctacccag atccagaaga agaacagtg     7260 cctaaggttg aggcagctag agaaggctca gggaggaggt gggaactgag ctgggtttgg    7320
agttgagaga gctcttgaca agcaccagga aggcagggga agatgcggcc ctgcaccttc    7380 tgaggggac cattaagaga tgaagttgac taaagcagag actttgtgta ggtgacgggc     7440
ttgggaaggt agctatggaa tccagactga gcacccatag caggaccacg ggatggagat    7500
gggaggggtc aggggccagg gtggggtgga atgtggagca gaggttcagg ggaactgatc    7560
agagttggga ggtcatggag acggactatc ttggcgaatg ggttcaaagc aaccagagtt    7620
gcttctttcc aacccaaaaa caaaaattaa gaagatgagt gaagaagaag taaagcagtt    7680
gaaacaggaa gaaagggaaa attatgaggg agggaaggta agggcagata agatttgctg    7740
ccacgttggt gtattttgtt cagtacttca tcgatgccat gcccaaataa ctgaaagagg    7800
cagcaattct gagctctctg gtccctcaag atattcaatg atctttagca tgtctcactt    7860
attaataaac atttgttttc tttaaataaa gaaaaatact tattggattt cctgcttcgt    7920
tctgcagggc attccaatat cacagtaaag agcaacaatg tgtgataatg ctgaaaaca     7980 ggaagtcctc cataatcatt aggatgagag atgtagtttt atttgaaaag aaaggtgagt    8040 acatttctctt cctcctcctc ctactgtcct ccccatcctc ccactcttcc tctttctcta   8100
ttctatcttt aatttataag accagaggag gaaggcacta tcgtgttata aaactgaatt    8160
ctgagttagg acaggatttg attactaact aaccatgtca gcttgagtgt attacttcac    8220
ctcttagatt taatttttt tgttcaaaag atgaaaggat tagatttaca aaatcacttc     8280
tacctctatg accctgaaaa taagattttt aaaatattat tttatattta acaaggagat    8340
gggaagtcta agcattcctt ttggtcttgg cttcttattc tgcagggtga ccatggtcct    8400
```

```
tgggccctaa catctggatg aagccttgta aaacagaaat actgaggtgt tttaatcctc    8460
agaaacattt agattgggac acaaatctta tttttactct taaattttc acattttggg    8520 ggacatggtc tatattttc tcagatttct gaaatgttgt cttttaaaaa tgtgtaaaag    8580
ttacagttcc ttttctatag tttattttaa aatgtgggtc aatagtccca ctgcttagaa    8640
taagaggcag acaggattc aatagaaatt gcatgccttt ttagatgtgc aaatgtttca    8700
ttaagcattt cccatcaagt atatcccatc aagtatgctc ccattaagca tatcccatca    8760
agtataaata tttgaaggga tgcatgacac tttaaaaact gtttcctcta ctgtgttggt    8820
agccaggtat taagactgtt aatagtaaca atttagctct ccaaacattc tgcatcccag    8880
gtgttaaaga ggactggaaa caccttagtt cttgtattct tgaggatgat ttgccatatt    8940
gtgtctagta ttacggcaaa actcaagta gcatttaaa tagtatttat ttgggttgga     9000
attatttcta tgcattgact catcttcctg ggtttcatta gctgtacgca ttgtacttcc    9060
ttccttacca ctatttatct cgaattcttg agattaaagt gcagattaaa tctaaacttt    9120
atctggtgaa gttattagtt cttacaagta gcaagcaaac ggtaaactaa ataggatcac    9180
ctaattgtac cagattttaa aaaaaaaaaa ccctgattct cctgattctc tctacaaaat    9240
gctaacattt aaatatgtca tttgtaaatt gttaaccaga aggaacatgg gaatgactgt    9300
aggttgagtt tgaagtctga agtttgaagg cttagtttgc ttgttttcaa agtgacagaa    9360
gggagcaaaa ggttatataa actctgatgg gtacatacaa aaaaaaaga agtgaaaagt    9420 caaaagtcag tcattttttg gtccttgttt cttttgctgtg ggatattgac ctgctactaa    9480
cttacctgcc agggttttgc caggaacagt cagtgttaga tcacatttac ttctgccact    9540
tgccaccagc cacactgcct tcaccaagtc caagaccta tcaccactgg ttggggctac     9600
ttgtagctgt acacatgatc tctaagaaat gtaacttccc tgtttaaagc ccttcctagt    9660
gcccttaaaa taagacccaa agacttccca aatgtgctag ggcccagcat tatttaagta    9720
acccccagct gctgtttgct tggcttgcta aacttttcta cactggcctt acttctgttc    9780
cttcaccacc ccaagcacac acctcctgc ctgggaccct cttcaccttt gtcctgctgt     9840
gccagctcct tcttatctcc taggtgtcag ctcaatcatc atgtcctttg caaatcttcc    9900 ttgacccta gacctccctt tcacaaagta ccttgagttt acactttgga tgagtgtctt     9960
atgtctactg taatactatg tcccaatgaa gatgtacttg caatcataat acgcagtatt   10020
gggttaaaag cattagtttg ctgtaggtat gttaggagca ctttccccat gtgattgatc   10080
aattaattaa aaaatggcta aagtgggtaa ccttaaatga tggtgtaaat ataccttaaa   10140
cattttatat tttcattgaa aacacaagtg tacttgacac cttttgacgt agagcagagg   10200
cttttcttct tcgaatatgg ggtcaccagt agaaggtctc tggtgtattt cctgcataaa   10260
ctatgctcca gtgcaacatc tacaataatt actttcctta tttttgaagt ggaccatatc   10320
tcgacattta ttaatcaatc tgaatgtgta aaacctttag attttatga ttcctcctc     10380 aagctttata gtcaactata tgagtggatt gccctctgtg gatttgatag caattttta    10440 aatgattcat gtttcaactt gttaaaaaca tttaatttag ttaaaaacca aacaaaaaag   10500
agctttgttt ctttttcacat tcatttctca gtttagatca tctttaatta aatataaatg  10560
taagaaagtt ggaaaatgca aagaaatgac tcgttgtaag cacataactc acgtgggggg   10620
aacagacatg ggtgggcaca ctagcaaaca cctgccagct gcatgtggac ccaggtgggc   10680
accggactgt tttaaacaca ggagagggcc cgttgtctaa ctggtgagtt ggttgagtgg   10740
```

```
aagctggttg agaactttta ctgcaaacca tttacagtag accacaattt tatagccctg   10800
tttggcactt tttcatatca ctgggagcct gaagaaatag aagtgggttg gatctctttc   10860
agcctctgaa aagcctgcca ttcccccatc taaaaagccc tttccccatt ctctcactct   10920
gtctcatcat gtatgtaata tgtatcatca ttaagtgatc tcattttata ttgtttcctt   10980
gaatatttcc tgtaaccccc ctgcctgatt ccactagaat gtaagctcca tgacggccaa   11040
gcctctggct gcactgtgcc ccgtgtgtcc ccagcatcct ggtggggctc gatacacaga   11100
gagctcataa gtagcatttg aatacatgaa tcaaagaatg gctcagttta ctgcagcctt   11160
tttgcagatg caaagatgaa tcttttagaa agcagaaaca gggggtctgg tgcatgagat   11220 cttttctca acgtgactat gctgtgcaga ccttcatgtg gtgtcttgtg aaagactttg   11280
accactgtgt ggacttccct tcagtgtatc tctcagagtg caagactggg aatggaaaga   11340
actacagagg gacgatgtcc aaaacaaaaa atggcatcac ctgtcaaaaa tggagttcca   11400
cttctcccca cagacctagg taagacattc cctttcatct ttgtgttcat ctactgtaaa   11460
gttgtccctc tgtgtctgtg agggattggt tccaggaccc ctgtgctac caaaatccat   11520 gcttctcaag tcccttatat aaaatggtgc agtatttgca tataacctac ataccttctc   11580
ttgtataatc cctaatataa tgtaaatgct atttaatcgt tgttatactg tattgttttt   11640
atttgtatta tgttttattg tcatattgtt attttctgtc atcttttttca agtcttttcc   11700 atccacagtt ggttgaattt gtggatctgg aacccatgga tacagagggc caactgtatt   11760
taggataatt tcatcacttt taattcaaac cacaatatgt gaataagcag atagaaagaa   11820 tcttttttgat gtcgatgttc aactattttt ggcaccatag tagaacatgg ttgctttcta   11880 tttttttcttg gatatggagg tttcttgaag acctagaaca tagaagaatg cctagtttaa   11940
aaaaaatcaa tgaaactatg agttttaggc caaatctgag aaaagatcaa agatgactat   12000
gtttgggact gaagtaagca tatcaggtta gaactctcat cacatgttcg actcaaattg   12060
tggagcaaaa gagtaaataa gatataaaaa tgaaaatgaa gatacgtgaa attcaaatgt   12120
tgcaacttgc ctattatttta tttttagtgca ttttttttgta cttttcccag tttggtgtta   12180
ggtggcatta agttctcagt aatgacgctt atcaaatagg aacttagtgc ttgttactca   12240
cctttatcca ttcccccaac actcaacaaa ttgcctttgc tatatcccta tgagatgagc   12300
agatcaaata ttccccgtga gttaatgaaa actgattcaa ccaaatggca aagtcagaga   12360
ctatcggggg ccatggagac actctgggcc atttttatga ggtagtctag gctcatcttt   12420
atgagggaac tgaggtctcg gggggtgggg gttatcccaa ataggttcac agaagaacca   12480
gaaataaaac ctgcctttct agactgtaag tcttgtgatt ttcatctaaa tggttgtctc   12540
tatacagcaa ctcatctcta gaactgaaaa taagcttaaa tccctcctcc atccccaata   12600
attcaagctg catttcagag aaaaccagga ctttggaatc agacagatca actttgaatt   12660
cttgatctgc ttcttcatag ctatttacac ttaggcaagt tttgtttttgt tttgttttac   12720 gttgccactc agttttctca tctgtaaaat agggataata acaccttcct caaatggttt   12780
tattaggact aaaagagaga atgtgtggaa agatgttagt ggaattcctg gcagatagtt   12840
cacatggaca aaatggtatt aactacaaaa attttttacag agaaaacggt aactgacaaa   12900
agcaggtgtt tggaatgaat taagaccatg gcagccttt gaggccttta tatttctcct   12960
gactgtgcaa taaaaatatt ttggctctct aagacttggc tgtcacagta gcaatggtaa   13020
tattagctac tgtgccagaa gcagcctatc aatagagaaa ttgaaaatct gaccacacaa   13080
atgctgcagc acccagctga aatgcatttg gatgacaatc tcagatggga atcgagagca   13140
```

```
tctccttctg ccttgctaat agcaagctga tttttagaat atagtctaag tgcttctttt    13200
ccatcctccc cagattctca cctgctacac acccctcaga gggactggag gagaactact    13260
gcaggaatcc agacaacgat ccgcaggggc cctggtgcta tactactgat ccagaaaaga    13320
gatatgacta ctgcgacatt cttgagtgtg aaggtcagga gtggttctag aaaatgtttt    13380
catttctgcc cttcacctgt aaaataattt gttgtaaagc cccttcccac agggatgtta    13440
ttaataattg agtaacgtat tcacctctcg gaaagaagca aaaccccaga attaacctga    13500 atttttttt tttctgagac agagttttgc tctcgttgcc caggctagag tgcaaccgtg    13560
caatctcggc tcaccacaac ctccgcctcc gggttcaaga gattctgcta cctcagcctc    13620
ccaagtagct gggattacag gcatgtgcca ccatgcctgg ctaattttat attttagta    13680 gagacagggt ttctccacgt aggtcaggct ggtcttgaac tctcgacctc aggtgatccg    13740
cctgcctcag cctctcaaag tgctgggatt acaggcatga gccaccatgc ccagcagacc    13800
tgaattattt ttattaaaat gttacatcaa catgtacaaa tataaaacta catctaaact    13860
ctaagtacaa acttcttatg cttacaactc ttacacagtg ttaaccccaa gacaggtttg    13920
caattaaata gttaaaataa aacaacaaaa tcaataaaaa tcaaataaac aatatatatt    13980
taatgtggta gactttgctg ttttgctgaa gctaagcaag gaaccagttt ttaaatcagc    14040
aatccattat ttgaatggac tgagcaattt aatagtgcac ctcaaaggtc aatgctaaaa    14100
aattttaaaa aaatcctact gaaaaaactg tcatcgtttc acatttctgg ctacattagt    14160
gcaaaaggga ataaataaag gtgagatttg tgtgacagtg tggatatggt actgtgtgac    14220
aactcagttc tcccatcact tccacctgtt cgaatcacgg ggatcctta tttgtacacc    14280 atgttatagg tatttgccct taagcaccac caatgcatca ctgttatatt aagtctgccc    14340
gttttcctta gtactccata aaatttaagt cacatattac tctgcctcac catgttactt    14400
caataattct gaatcaaagt ttaagtttgt gaataatttt gcaaaaaaga gccaatcatg    14460
cttctcaaca acataaaaag agaagcgctg tcacttcagg tgaatattgt tctccctgag    14520
gccatgagca taaacaaaaa ctccagacta aaaccctgag acggtgccag gtcattcagc    14580
agtcagcgga atgatcagaa taatttcata caaagtttta aagatcatta ttgaaatgaa    14640
gatgccaaat attgaaaact cctaatggag aacgtagact cctgggaata tatgcaccct    14700
tgagctcccc actggcctgt gcatcccggt ctaaggacat ggcatcatgg aaattctgaa    14760
cttggtcatg actacaatag ttgagggagt attgactaaa atatgtgaat gttacggttt    14820
aaaaggaaaa tgcatttggg attatgctag aaaatcctga gtccttattg ccaattttat    14880
tgccaagtgc ctgttgtgaa ttacatcgga atgagaggca agtcgcactt aagtgagtag    14940
gattctggtt tttactctct attttgcttc atccatttca gttttcttct tcctctctgt    15000
ccttccttcc cactctgtcc agaggaatgt atgcattgca gtggagaaaa ctatgacggc    15060
aaaatttcca agaccatgtc tggactggaa tgccaggcct gggactctca gagcccacac    15120
gctcatggat acattccttc caagtaagtc tcactgggaa aaacattcca tgtttaatta    15180
aggctctgca gctctatcag acatttgctg tcatttagat attttagcat tcctcaagaa    15240
gtgaacgcct gatgttttta atttcaaagc taacctcctc ccacaatatt gcaagtgaaa    15300
tacgcattct tgctgctcaa aatatggtcc acgggtcagc agcagggatg ttttctgaga    15360
gtttgttaga aatccagaat gtcacaccct ctgaatctga tttgaataat aaccagatcc    15420
tcagctgatg tgcacacaca ttcaaacact aatgtcagta atgaatacat taacatctgt    15480
```

```
cttcagaaat gcacacacac atgttgctgg tgtattttcc aaatattttc cttttctctt    15540
tactccttgt ctttcttttc cctttgtacc aatgagattc aagtctccta acctttgacc    15600
tatgagcaga cgtcatggat ttttgaatcc ctgatgtttt atgtatattt acatcaatgt    15660 gttttctgg aatgaggatt cgtaacttcc atcagattct ctaaggggac cacgaattta    15720
aaataagaat aagcttcttg ctctagaaag tcatgatggt tcctagaata aggtttcgtg    15780
agtattctat ttcacattaa ttgtgctgga aaacacctcc cattccacag tcgcttctgg    15840
tcttcctctt cattctatga tgactacagg gccataccag ggctttcaag aatgcagaag    15900
tgaggctgag ccacagattc cacggtggaa agcagctcta ttgaatttgt acacctccca    15960
ttccaaatag ctagcttaaa acacagcagc tgccattttc cttcaaagga gaaatacagg    16020
aaagacctaa gggtccaaaa ctgggtaaag gcacttccag gaaaccagaa ggagaagagg    16080
attgcttaag ccgctgctgg ctcctctttc catcctggta agcatttaca atcagagagg    16140
gaatgaataa acgcagaggg ccaccaggca tggagtgcat ccaacagccc tggccactgg    16200
gccccactga ggaaggatcc agccccatac tgcatggtga gacccttgca agagcacagc    16260
ttctcctctt ggttttttcta agcttcaagg ctggtgggag cagagcctgg tagaccagaa    16320
ggaccattcc tttaagctat gaagatgcac atttcttggc tctgttaggt actagatgag    16380
tatctttagg cagggagcac tttacatttt aaagactgct atcatttgtg gttgaataac    16440
tggaatttgc ttacatcaat tttccagatg gccaaaatga taaggtcact gattctgttg    16500
agtgattttt acacatgtaa actgttagaa aaacagtgct tggcagccgg gcatggtggc    16560
acatgcctgt agtcctagtt acctaaaggg ctgaagcggg aggattgctt gagtgagttc    16620
aaggagttca aggcaagcct gggcaataag tgggaccctg tctctaaaaa caaacaaaaa    16680
aaagaaagtc cttggaatac agggccaacc ttgtttccta gttgccatct ctgaacacag    16740
ccttcatctg attacctcct ccatgcccga ctgtgcctag cacacagcag gtgctcaatg    16800
tttgctcttg aaaagagtc ttatccatga atgtaaatgt tcagtgctac taaaatcttt    16860
cttgtccatt cagatttcca aacaagaacc tgaagaagaa ttactgtcgt aaccccgata    16920
gggagctgcg gccttggtgt ttcaccaccg accccaacaa gcgctgggaa ctttgcgaca    16980
tcccccgctg cagtgagtat gatgcacacc cagattccag gatttggacc tgccctgttc    17040
ttgaaatcaa aagaaaacat gtgtcagtgc ctgagtgcag cctctgaaaa gtgacctaca    17100
agtcctatgg gatgttattg gtctttattt tattgctggt ttaaaacagt tatggttatt    17160
ggttactgtg ggtgattgat cagagcgtcc atttatcatg ttttctttc tttgcaactg    17220 aaacttctgc ctcaggagtt cactgaaatg taggctttag gtgttgttca tcctattctc    17280
tctgtgctaa agggaaatca gacccatgct ctctgacaca tggatttcat tttcaaccag    17340
agttctaata gttgttttgt aaacaaagag tgtctttgtt tacaatgttc aggtctgtgg    17400
gtgtccagtt tttccacctt ggggagcaga gggtgagtgg tgggggtggg aagagttca    17460 agaggagaag atgaaatggc agacctagta gaaatgatgt ggagtaaaca attttatcat    17520
attttcctct ctgagaattt gaagcaaagg attacacact aagagaaata caggcatgaa    17580
aggttaaaaa ggattcagtg agggttggcc tcccctcctt tcctctgaca tgtgtccttt    17640
gaaagcggaa gttcctcagg cattctccct ttttatgaat attaatttct ctttttttt    17700 cagtttctct ttttgtcatc tttttcctc aagaatatct tgattctgg atgcacacac    17760 ttttccttgg aggtgttttt tgccttcttt ccatggactc tttccctgtt gtttggcttt    17820
tatggcatgt tgggtgccat tcagtcatgt ctactcagtg aataatttat tcttcaggaa    17880
```

```
agagagtgga cctttggtgt atgtgagaat tcggggtgtg aggtgacacg tgttgatact   17940
taccaggtag gaagaactga gcaaagagaa catagaaaga agcacctacc caagggtctt   18000
tctctgaagg agttccttgt gaaagggtct cacaggcata gatgctacta aattgatttc   18060
atctgaaaac atgaaacaat tctcaagtgc caaattccaa gagaggctga gcagaagcca   18120
agacaggcca gaacaccctg cagccatcct ccttaacatc catctgtgca ttctctattt   18180
taaaattatt cattgtaggg ctgggcacgg tggctcacgc ctgtaatccc agcacttccg   18240
gaggccgagg tgggtggatc acgaggtcag gagttcaaga ccaacctggc caatatgatg   18300 aaacccacc tctactaaaa atacaaaaaa attagccagt tgtggtgaca cgcacctgta   18360
gtctgagcta ctcgggaggc tgaggcagga gaatgacttg aacccaggag gcagaggttg   18420
cagtgagctg agatcgtgcc actgactcca gcctgggcga cagagcgaga ctccgtctca   18480
aaaaatatat atatattcat tgtaacttat tttgcccatt caagcaacac ctccaccatc   18540
ttctggtccc acctaccagt gtctgaaggg aacaggtgaa aactatcgcg ggaatgtggc   18600
tgttaccgtg tccgggcaca cctgtcagca ctggagtgca cagacccctc acacacataa   18660
caggacacca gaaaacttcc cctgcaagta agtcccctcc ggtctcattc tgctgctatg   18720
gaatgtgaaa tcccattgac tttgccttag ttttagttac tgtaggaacg caggataaag   18780
tattctggaa gaaaaactga tctagtcata agtaaaggaa atgaacttta gcacgttttt   18840
tcccgtaacg gttgttctca aagcgtggtt ccctagactt ttttcttttt ggaaagctaa   18900
actcacaatc acttctttt cagaaatttg gatgaaaact actgccgcaa tcctgacgga   18960
aaaagggccc catggtgcca tacaaccaac agccaagtgc ggtgggagta ctgtaagata   19020
ccgtcctgtg actcctcccc agtatccacg gaacaattgg ctcccacagg taagcaaggg   19080
tatgggagct tactgagggc ccaagttttc tccttatttt tgtataccag tggcatcatc   19140
acaatataca gtagctttgt aagtttaatg ctattgtggt cagaaagcct gcccttatga   19200
tttcagtttt tttagatttg ttgaggtttg ttttatggtt cagaatatag ccatcttggt   19260
gaatgtttca tgtgctcttg aaaagaatgt gtcttctgcg gttgttgggt ggggtgttcc   19320
ctcaaggtca tttaggtgaa gttggttgct ggtgttcttc tgtatcctta ctgattgtct   19380
gtctcctcct tcattgacta ctgtggatga atggtgatgt gtccaacttt aactgtaaat   19440
tagtctattt ctcttttaga tcgtaactct tttgtatatt ttgaagctct tttgttaggc   19500
acatatgtat ttaggatggt tatgtcttct agatgaaagg acccctttat ctttatgtaa   19560
tgtttcttct tatctctggg aatatttctt cttctgaagt tctgaactct ctttatggtg   19620
atataaatac agtctcacag ctctattttc actagtattt gtgtgatata tcttttaaat   19680
ttgtatgata tatcttttaa atttatctga gcttttaaat tgagatgttc aaaccatttg   19740
cattcatgca attgttaata gagttgaatt tacatctacc atcaagttag ttatttctct   19800
ttgtcccatt taaactttgt tcctttttc atctttttct gccttcattt agattgagtt   19860
tatctccact actcacttag taaattaatt tttaatggtt ttagtatttt ccacaatgtt   19920
tataatatac atttttgact tttcacattc caccttcaaa tgatatcatt ctacttgaca   19980
tatgaatcct tacatcattg cagttctact tcctccctcc caaaatgcta tactattact   20040
ctttgtaata gaagcttact tctactatgt cacagatctc acaatacatt gacactattt   20100
ttgccctaat agttgtgttt taaagtgatc aagaataaaa ctattttaaa tatttcttt   20160 atttatttat tttaccattt ctggtgcttc tcatctactg gggtagatct caatttccat   20220
```

```
ctggtgtcag tttctttctg tgaaaaacaa cttttagcat tttttgtagc acaggtctgc    20280
tactgctgaa gtctttcaga ttttgagtgt ctgaaaaagt attttgcctt cagttttta a    20340 aagtaatttt gctgaatgta gatactgggt tgagagtttc atcacttgca acactttaat    20400
gatgatgttc cattatcttc tgttttaaat agtttgacta gtaatctgat ctttgttcct    20460
atgttttcaa taggtcattt ttctctgact acctttaaga ttttctcatc tttgttttc    20520 aacagttcga ctatgatgtg tttattatta atttctttgt gtttaatctg cttgaggtat    20580
tctgagttcc tagatttgta gattgttgat ttttttcttt tctctttttt cttttcttt    20640 cttttttttt ttttttttt tttttttga gatggagcct cactctgtca cccaggctgg    20700
agtgcagtgg cgcaatctcg gctcactgca aactccacct cccaggttca gtgattctc    20760 ctgcttcagc ctcctgagga gctgggacta caagcatgtg ccaccaggcc cagctaattt    20820
ttgtattttt ggtagagaca gagtttcgcc atgttggcca gactggtctc aaacttctga    20880
cctcagacgg tccatcacct tggccttcca aagtgctgac agtacaggtg tgagcaaccg    20940
tgcccagcct agattgttga ttttcattgt ccttgtaaaa ttcatagcca ttatctgttc    21000
aaacgtttct ttttgcactt ttctctctct gtattttcct tttgggactc taagtaccac    21060
gtgtttggga ttctaagtac ccacaacatt catgttgttt cataaatctt gtaagcttgt    21120
tctctttttt tttcagtaac tctttttcat tctttgtgtt ggtttggata agttctggta    21180
acctatttcc aagtttatgg attatttttt cagttgtttc tagtcatctc ctcagcccat    21240
tgagagaatt cttcatctct gatattatga ctttttttct agcattttca tgttactctt    21300
ttctatagtt tccatctttg ctgaaattct ctacctatct atgcatactg tccaccgtta    21360
caacaagatc ctttaacata ctaatgtagg tatcacacaa tcccaatctg atagtttcca    21420
gatggcgtct tctctaagtc tggctctctg gattgcttta ttattcaaca gtggcttttt    21480
gttccccctt gggttttttg gtgtgtctta taattcttta atcaaacact agacattata    21540
aatagaagaa cagtagaggt tacagtaaat attatttata ctttgaaatg gacacccttg    21600
tcttgcaaat atatatcgtg gataattgag tcaatgtagt cactagttta actgaattgg    21660
gatttgtgat tgctagttttt accttaagtg caccacagat ataaattcct ccagtgatgt    21720
gctgctgcta tcttttactt agagtggggc ctggggtgct aaagagtttt tccgtgttc    21780 ctatccattc ccagatttca gcagtcactg catgcctgca ctacagagga gatatcttca    21840
tacacataat ctaaccccat tgacactcgg ctgtttcttg ttactgaatg ctcacttttt    21900
ggtggacgta ggagaatact tatctccctg gtctacctcc ctcttaggcc agttgagcac    21960
agctcggctt tgaaagtagt gatttttcag tgttcttgtg cctccttctg atggaacttg    22020
tacctgtggt gggtttggaa agaaagagta gtaggcttct gcttcattgc aatgcaggat    22080
gttgggcaca agaggattcc ctgtaacttc tccaagggaa taagattttt gcctccacca    22140
ctctctgaga agctgtggat ctttgcctgc agtcctagat gcaggaccat ctcctgccct    22200
atcacccaga agctttggtc tttggctttg tttgaggaag gagctagaga aatgtgcaaa    22260
gctttcatgt ctgcccccca ctgacagcca ctcaccaccc acagcctgca ctgccgaatg    22320
catcctcctc tcatctgccc tcgtgttctc atgaacactc agtagggacc cataaaaaag    22380
agcttgcatg taagtgcaat ttccaattat aagtactcta tctgttcttt cacacccagg    22440
ttttaaatga aatattacta ggaacttatt aatgttctaa aatgctataa atctattttt    22500
atgttaatct gtctgctaat acagaaaaga gaacagtcat aattctcaga ggctaccgta    22560 ctgttttgt cataaattgc ttcatgcttc tttttttca gtaattgtta agcttgattt    22620
```

```
cttttatttt aatttcagca ccacctgagc taacccctgt ggtccaggac tgctaccatg   22680
gtgatggaca gagctaccga ggcacatcct ccaccaccac cacaggaaag aagtgtcagt   22740
cttggtcatc tatgacacca caccggcacc agaagacccc agaaaactac ccaaatgcgt   22800
atgtctttga ttttactgt aagaggggca tcagccaact gaaatttctg ttaaaagagc    22860
catgcttcat gcttcaagcc aacttcctag gaccaaattt ctcttagacc cagaatgtgt   22920
agaaaaatgt ctcaagaatc ttgcttttga agaaagggcc tgcgagaaga gaaattttag   22980
gctggctatt tttcctgagt agttttatgg atgcaggagg acatctggag gtgatgaggt   23040
cacattaatt gaaagctcag gagtacatat gagcaaatgc ttagaaacag taccattcca   23100
caatgcccac taaatatcag tgcaatattt ctaccataga aatctatcat tttaacctcc   23160 aaccccctgaa atgaaggttg aatttgctat ttttgtcttg ggtcacaagt aaatatactt   23220
tatatatata agtatgaata tatatacaca catatatatg tatacatatg tgtgcatata   23280
taaatacaca catatatgag atatacaagt atacatatat agtgtgtata tatatgtaca   23340
catatatgtg tgtatatata tgtacacata tatgtgtgta tattagaata tatataacat   23400
aaatatgtat atatatatat tctgacctgt ataaacacag tggatcctga gcaccagtgg   23460
cctgaaagga tatgggttgc tgggacatga agaacaaaag caggatacgc agatgctgaa   23520
cagcgaaaga ggccattaga tgaacagaaa accaggtcta acaaggacag ctttcttcc    23580 ataaatgagt acacaatata tggaaaaaac tatttttaca tattggagaa cagataaact   23640
gagataattt agaaagggaa tcaaatgaga tcaacccaat aactaccttg gctttgttcc   23700
tggagacttc ctgggctgaa gaacaaggag atggagccca gccgaccac agcagtcttg    23760 ctgaactgag gaaggagact ggagttggga ttactaaaac agctgagatt ttctaggcta   23820
ggtaataaca tgaaaggaaa cattgtggag gaaagcagct ccaggaatgt ccatagaaaa   23880
gtcctcaagt ctttggctaa atagaaagct gcatatgcac agggagaggt tccagagaga   23940
aaataggata aagaacagct actggggaaa gaaaaactgc aggggaacag tgagctcaat   24000
ggagatgcca gagctcacat agcactgggg gatatttgag ttctgaccag cctgaggaga   24060
gacctcgctg aacatcttgg gcattcagta gtcaccacat aaagccaaac tttgggagta   24120
ggattagtgt attcctataa taaaggccac tccagaaaca gcatagtaaa gctgaaaagc   24180
aagtctaaaa aaatcaacac gatctccaag taaattaact gattgccaga agaaaattca   24240
accctttaga ggcaaacaac aaaatcaagt tgctcagtta tgtggcatcc acaatgtgtg   24300
acctaaattt ataactttac cagacataca aaaagcattt actgtgatcc ataaccagga   24360 gaaaagcac tcaaaacaaa taaaccccaa aatgaagaaa ttggcaagaa gatttgaaat    24420
atatatatat cataattgtg ttcaaggatt taaataaaac atgaacatgg aagaaacaaa   24480
tggataatat caaaaaagaa aaattataaa ataaccaaat agaaattaaa taactaaaaa   24540
agtgcatgtt taatgaaaaa tgtactggct acccttacca tcaggttaga cattacagaa   24600 gaaaagtta actagaaaat aattcaatag aagtgataca aactgcagca cacacataca    24660
aagactgaaa agataaagaa acagagcctc aagaatatct atgaaaatat caaaagattt   24720
catatatgtg taaagcaagt cacaagagag gaaagagata ttgggacaga aaaaaatact   24780
tgaagcaaca agaaaaatct tattagaagc cagaagaaga aaatatatgt ttacacagaa   24840
gaatagtggt aaaaatgact gatgccttct cgtcagaaac tatgctggtc agaaacaatg   24900
aaataacacc tttaaagtga tagaaaaaaa taaaaaagat taacatagaa tgttatatcc   24960
```

```
agcaaaaata tcccttgaaa gtgaatgtta tataaataca tattctgcct cccccaaaat    25020
aaataaaaca ctaagagaat atttcattac taggcttata taataaaaga tgttctagaa    25080
atctattttg gtagaagaaa aatagtgcca gatgggaact ttatactaag taatgaagaa    25140
ccctggaaat ggcaaatgta aaagattcat atttaatgcc ttaatttctt taaaagataa    25200
ttgatgggag gctgagtcgg gcagatcatg gggtcaggag tttgagacca gcctgaccaa    25260
catggtgaaa ccccatctct actaaaaata caaaaattag ctgggcatgg tggcacgtgc    25320
ctgtaatccc agcaactcag gaggctgagg caggagaatc acttgaaccc aggaggtgga    25380
ggttgcagtg agctgagatc gtgccattac ggtccaacct gggtgacaga gcgagactca    25440
aaacaaacaa acaaacaaac aaacaaaaag ataataattt actacttgaa gcaaaatgat    25500
agcaatgtat tgctacttta acatatgtaa aagtaaaaat ttctaaataa taataatcac    25560
ataaataatg taggaaataa atggtagtat actgttctaa gtttcttgca ttatccatga    25620
agttatataa tacacatggt tgaaggtggt aagttaaaga gggttattgc aaatcctaga    25680
acaactgaaa aaatttaaac ttagaggaat agataataat aagaatgttc catttatcca    25740
aaagaaggaa agaaggaag aaaaaagaat gaagaagata tggcaaagag agaaaataca    25800
cagcattatg gtacacttaa actgaactga aaatatattt aatatactcc taagcatatt    25860
aaatataaag ggattaaaca ttgcacagaa aaggcagaga ttattaagct gaataaaaat    25920
caaagcccaa ttatgttctt tttactatac atgctcttta attgtaaaga gctagtccaa    25980
aaaccaagtg tggaaaatga catatcatga aaataagaat cagaagaaag ctggagtggt    26040
aatgttaatc ccaaagtaat ctacaagaaa taataccacg atgaaaaagt tatttcttaa    26100
gtaaaaaaag tttattcatc aagacttaac aatgctaaat gggttgcacc ctcataagag    26160
cccttctgat atatgaagca aacactgaca gaactgaaga gacaaacaga taagcccaca    26220
attagagtgg gagatatcct aatgtctctc tccgtatggt tatacatctt cccaaacaaa    26280
atataataga aaaaatacac aaaaaaatca gaaagaatat atatgttttta aaggaaattg    26340 tcaacctatt taacactatg ccaaactgca gaatacacat tcaagtatgc atggagcatt    26400
ccccaacata taccatatgt gtgggcctac agcaagtctt aatagattga aaagaattaa    26460
aatgatacag agtctgtttt tgagcaaaac agaattaaat gagatataaa taacaaaaaa    26520
attgggaaat tatcaaatat ctgaaaatga aacaacacat ttccaaatac ttcataagtc    26580
aaagaaggaa tttagaaaag ttttgaactg aataatagta aaaatacaac atatcaaagt    26640
tcgtatgatg cagcgaatgt ttttagggtt ttataacttt aaatgctttc agtagaaaat    26700
agaaacatgt aaaaatcaat gacttaagat ggcatttctc aaagtatgct ctggagaaac    26760
ctgaagtctc ttgagatccc ttcagagaca gtctatgagg ttaaaacacc tttaaattta    26820 aaaaaaaag atttatttg ctatttcact tttatttcct gataagtgta cagtggagtt    26880
ttccagaggc tacataatgt ttgatcacat tatctctctg atggctaata aaatgtgtga    26940
ttgtctatta tgtttaaaaa cattctcagt tttggatgca ataatattc atagtatata    27000 ttacaaaatg aaagctcttt agggtcccca atacttttta agagttaaag gggtcttaag    27060
accaaaaact ttgagaactg ttgatttaag ataacttaaa catctagaaa aggagaagca    27120
aataagatcc aaggtaagtg gaaggaagga aagaatgaaa atctgtgaaa tccagtgtat    27180
aagaatatag acaaacaatt gagtaaatct gtgaaacaga aagttggttc tttttgaaaga    27240 ttcatgtaat tgataaacct ctgcctaaac tgacgacaaa ggagggagca ccaccgtcaa    27300
catcaggagt aaaaaaaggg aagagtcatt gctataggat cttttttgata ttaaagctaa    27360
```

-continued

```
taaacaaata ttgagagcaa ctttacgtta acaaattcaa taacctagat aatatggact    27420
aattccttag aaaaaaacaa ataagcaaat tggacactga ataaactgaa tttctaacca    27480
atctgatatc tattaaagac aacatgtgta tataatcttt aatatgttaa tatatattaa    27540
taaatcaata aacttcccac agagaacact ctaagttcag atggcatcat tagaaatgtt    27600
attatttaaa aaaatccaa ttcttcacga tctgttacag aaaatagagg agaagggaaa    27660
tatttcttga ctcaatttgt gagaaaaaaa aaaaccta gttgtaaaaa agtagacaag      27720
gatattgtga gaaactatag cacattatgt attgtgaaca taaatataaa aagatgtaac    27780
aaaattttaa tcattaacat gatgaatatc ccaacaagt gaagcttctc ttcaagaatg     27840
caaggctggc ttaacattta caaaacaatc catgtaatcc aacatgttaa cagaataaaa    27900
gtgataaatc atatgattat gtcaatagat gcagaagaaa atgtgacaaa atttaacact   27960
tatccatgat aaaatgtctt agcaaactat gaatagactg gaacttcttt aacttgatca   28020
aaggcatcta caaagacct ccagataaca tcaacttaat ggtgaaagat taatgttttc    28080
tctctaagat tgggaataag aaaaatatgt ttgctctcag tacttctaat cagcatttta    28140
ctacattggt cacaaccatt gccataagac ctgaaaacaa aacaaaaaga gaggaaaaaa    28200
aggaaggaaa gaaagaaagg gcctaaagtt tggagaggaa gaattaaaac tgcctgtatt   28260
cacagaaagc ttaattaacg gatgcagaaa gtcctaaaga ttaataatta aattttgcaa   28320
gattggagaa cacataagta tatacatgat caatataata aaagtagttg tattttata    28380 cactgccaat gatcaactgg aaaataaaaa tgtcagagca ataccactga caatagtatc   28440
aaaaccacaa gatatttagt gatacattta acacaatatg cacaagaatt atgtactgca   28500
tactaaaaaa cattgttaag gaaggaatca aaagatctaa ataaagatat atcacgctta   28560
tatattaaga gtcaatatca cttctcacca aattgatctt tggattcagc ccatacccaa    28620
ccagaatctc agcagtcgtt ttttttaaaa aatgtgaaaa aatgtatatg ctagaatcac    28680
aaggacaata tttaaagaga agaaaaaagt tggaggactt acttacccaa aggtaaagac    28740
ctataaaggt acagtaaaca agatatgtgg tattgggaaa aaaaagtata cagatataga    28800
aatggatggt ccagaaacag atccacatat acatgatcaa tttagtttct aggtaggtga    28860
caaggaaatt caacagggaa aaacatcttt tccaaaatca ttgtgaaaca atcggatatc    28920
catctagaaa acaaaaataa aaacaaattt tgacttctac tttccatccc aaattaatgt   28980
gcaaaagctc ctagatctaa atgtaagagc taaaacttaa gctgaaataa aacaattcca   29040
ggaaaatata taatatttttc acaaacttga ggaaggcaaa attttttttca ggcaggaccc  29100 agaaaacact agctttaaaa gaaataaat tataatttgg gctttcataa aatgaaaatt    29160
atgttcatca aaagtcattg ttaagaaatc agtaggtaag taacagactg gaataaaaat    29220
tctctccatc catatatctg acaaatggtt tgtatctaga gtataaacgt ttctcccact    29280
cactaatcag aggacaaaca acctaattaa aatgggcaac agaattgaat aggaaatttc   29340
tcagggaacg atggacagat ggacaataag cacctgaaaa aatgctcaac attttagcca   29400
tcaaagatat aagaattata accatcacaa gatgtcacca acacttaatg ggcatgggta   29460
tcattaagaa gacacaacaa taagtgctgt cactgatgtg gagcgaggat gtgcagctct    29520
cgcatacgct ggttaaagta cagtatgctg gttttccata aagttaaata actatgagtc   29580
taccccaaaa aactgcaatt ctattcctga atatttaccc catggaaatg aaaacagaag   29640
tccacaaaga gatctacaag aatattcaca gcagctctag ttattataac cccaaactgt   29700
```

```
aaacaactac aaggtcaatc aatgagaaaa tgaatcgata atttgtgatc tattcatata    29760
atggaatatt attaagcaat taaaatgaag aagtgactga tcctctcaaa taggatggat    29820
ggaactcaaa aatatattaa ggaaaggagg cagatacata agtgtacatt ctgtatgagc    29880
ccatttatat caggtttgag gagaggtaaa actaatcttt agtgaaggaa accaatagta    29940
tttccctctg gcagtgggaa gagggtagca ggaattgaat gagcagtgac acagggtgtt    30000
tctagagtaa tggaagtgtt ctgtatcata tgggagtgtg gtttacacaa gtataggtga    30060
tcatcaaaac tcaccaaaca acatttaaga tctgtgcatt tcacactatg taaaagtata    30120
cctcaactga agagagtgga aatctgtttc aaatgctcag cctttttaaca catccagttg    30180
cttagactat gaacttcctc aaatgggtgt tctgggcttg agattagatc acatgtgtag    30240
agtcgctaga gagacaatgt tgcattccca tggtacataa tacatttccc gttttctcag    30300
acagccacag gtcatgaatg tgaggattct gagaggttgg agcaacattc ttgggaggca    30360
tgaggggag cacattctcc aagatccccc ccagcccggg gtcctcgcct gctttgacta    30420
ttactccgtt gttttcggac tcctccgtag ctgcccgacc tcttcagatc ccatagtctc    30480
cctttatatc ttgagtccca ctgttcttcc aactcatccc ccattccctc agacctggag    30540
tggcagtggc cagcagagga tggattgaga gcaggagagg atgtcctgcc caggaaccca    30600
tcctagagaa atggcatcct gcctgggagc tagtttccca gggtggcttt gatacgtctt    30660
gcagaaacaa acccacttga cacacctgat acggtattga cagtaacact attttttcgtg    30720
gttgttttttc atagtaaaag tagatccctt tagttacact gtgagtactt agagtaaggt    30780
gactggcctg ggaatgatac catcttggat gtcattttct ccttggagaa atgtattta    30840
gttccaatgc acatttcaca atacagtcct atagagagaa atacagagag ctagacagtt    30900
agagatatac ttttatgtgc ataaaaatat aaaatatgca ctttaaaaatc tgtacctgtt    30960
attcctgaga aatgtatttg gcagaaggtg ggagggggat attctgatcc ttttatttac    31020
atgtttatgt atgatctgag ttttttatatg gagcatatac tacttttgat ttttttaaaga    31080
aaaattaaaa tctgtctttg aaatgtacac agttgtttag aagttgagga ccattttgt    31140
ttgttacaac attattgtac ctataatggg aatatttcaa agccacttgt taacactttg    31200
ttagaacaaa atgtagaggg tgctgggtgc ccctgaatat tctcccacct cttgtgacct    31260
gtattgttttt ggaattttcca gtggcctgac aatgaactac tgcaggaatc cagatgccga    31320
taaaggcccc tggtgtttta ccacagaccc cagcgtcagg tgggagtact gcaacctgaa    31380
aaaatgctca ggaacagaag cgagtgttgt agcacctccg cctgttgtcc tgcttccaga    31440
tgtagagact ccttccgaag aaggtaagaa atctgtggct ggacatctac acacttggac    31500
gctgggatga aaagccatgg aaaatctcac tgatgcagaa accttccatg ctacacgaga    31560
aatcaagtgt ttttagaggg tctgccatgt ggaaggaagc ctcagtgcac tctctcaagg    31620
aggcagaggt gtgacttttg gcacaacatg agtgggctgt gccttagga caggtgcaaa    31680
ccctccaagg tgctcaactt aaccactcac cttgttctaa aatgggttat ctcagtatcc    31740
cagtccaaat tcgtattcta tcatgctgcc atatgtgtga ttctttccaa gccagtaagc    31800
atctccagta atttcttaag gtaggcagcg ttcattgcag tcttcagcat tgcagtttct    31860
gaggaatgtg gcccctgatt ctgtcatcct agagaaacct gacatgactg tattgattcc    31920
atatcatcct gggtctctgt ggctcttcat aatcatccat tttttccctg tacagactgt    31980
atgtttggga atgggaaagg ataccgaggc aagagggcga ccactgttac tgggacgcca    32040
tgccaggact gggctgccca ggagccccat agacacagca ttttcactcc agagacaaat    32100
```

```
ccacgggcgg gtctggaaaa aaatgtaagc cactttgatt tggactcttt ggccttttgc   32160
tcaccaatct ttgcaaacag aattggttct gtgttacaga aaatctgacc tggactgctc   32220 tttttttgtaa tgggggagag gggacagaag aaaatattgg aaaggcatca gggggctaag   32280
ctagaatata attggcctta gtatggaaag tacaagcagc acaggccagg aaacctccac   32340
acatgtgagg gttctcaggc ctcttccctt tagtgacatt tctttaaagt ttccattatt   32400
ggggactgtc tctagtttct agtgtttgta tgctaggttc cagtaatcaa agatgccctt   32460
tatgaaattt aagtcagatt tttcgagaaa aaatttggat gggccatcag gtcaccatgg   32520 gacttcccctt agcctcatgc attctctgcg atggtttact ttggggccta tgaataggga   32580
agactgagat ataggaaaaa ccaaagtgtc tgtgttcccc cactctcaca cccatgcagc   32640
ataacacttc tcacaccaga tgtgggggga tttctcctca cacccaagc gagtctccag    32700 cagataccag ctgggtgtcc tacaatgtaa ctcagtgctg acactctatc tggagacagt   32760
gtcagatccc ataagttaag gctcagtccc acaagaccgc cccactgcag atgccaatcc   32820
caagttccag gcggtgacct gtacttctgc ccaactggac aaaaatctgt ttttctactt   32880
gattactttg ctagagtggc tcacagaact caggggaaca cgttacttttt atttacccat   32940 ttgttataaa agatattaca aaggatcctg gtgaacagcc agacagaaga gatgcacggg   33000
gcaaggcatg tgagaagggg ctcagagttt ccatgccctc tccagtgcac cagccccgg    33060 taccccaagt gttcagcaac ccagaagctc tccaagtgca gtcttgctgg gttttatgg    33120 aggcttcatt acagaggcac agttgaatac atcgttggcc attggagacc agctcacctt   33180
cagctcctgt tccctccctg gaagttggac gtgggggct gaacagttcc aaccctgcaa    33240
tcacatggtt ggttcctttg gcaaccagcc ccatcctgag actatccaag aacccaccaa   33300
gagttgcttc attcaaacaa aagatgctcc cttcactcag gaaccccccaa gggatttagg   33360 agctccgtgt caggaactgg ggggcagaga ccaaatatac gtttcttatt ctaccacagt   33420
gtcatatgaa ggggaggaca acactgcctt tctgtgtctt gccccataga gggcgcacaa   33480
tgcatggaaa taaatgtttc tgaatcaaca gcaaacaggc ttcatcgggt aggagagcgc   33540
tgagccctcc agggacaatg cacatcaatg atgtcccact gtcctttggt gctgggctc    33600 taaggcctcc actgggtcag gctcctgaag ggagacccat tctccaaaga cccccgaggg   33660
tcaccactcc ctgtccaggg gtgtggcctc atagctcctt ttgaacaggg gcacaggaag   33720
gacggcttta gagcattcaa aaaataactt tgccaaaata ataataataa taatagaaag   33780
aaaggaagaa gaggctgagc atggtggctc acacctgtaa tccctacact ttgggaggct   33840
gagacaagca gatcacctga ggtcaggagt tcgagactag cctggccaaa atggtgaaac   33900
ctcatctcta ctgaaaatag aaaaaaaaat tagccaggtg tggtggcgtg cacctgcagt   33960
tgcagctact caggaggctg aagcaggaga atcgcttgaa cccaggagat ggaggttgca   34020
gtgagctgag atcatgccac tgcactccag cctgggcgac aagagcaaaa ctccacctca   34080
gaaaaaaaaa aaaaaaaaaa aaagaaggaa ggaaaaagaa acactccttt atgtcttcta   34140
aggatagaca tgaaatgcgt gagccttgga acaccttctc cctctcctgc cccacgtgag   34200
ctggagctta catgccttct tgttttcagt actgccgtaa ccctgatggt gatgtaggtg   34260
gtccctggtg ctacacgaca aatccaagaa aactttacga ctactgtgat gtccctcagt   34320
gtggtaggtt gccttctttt tggtaaggaa actgcttact taatatggat ttgcaacaaa   34380
aaaggaaaag ggcttctgag cagactgctt ctggggagga gatagctgcc ctctccatca   34440
```

```
gaccccactc ttcatcatgg gcatcttgaa tctgccctac tattggccac atttgttaga   34500
ggaacacctg cccatcgccc caggcacaca taaataaaat aaatgtaaaa ttcccaaaga   34560
gcaagcttag aggtaatcta gtcagcccca ggatggtccc actgaatgct gccatgtcta   34620
gcgtgggatg catgaaaaat ttagagtcat tcggatgaaa aactttccct ttccacagct   34680
gagaagtaag aaagaaaata caaacagcag gaaacaggta agcatgtaac gcacattgta   34740
aacctcagat ggccatccta ggaattcaat gaaaggtagt gcagctcttt agccccagat   34800
ggcctttctt ataagtttac tactcacaag tcacattagt gacatagctt agagactgct   34860
tgttgggttc catcctcatt gctctgagac tcttgttggg agtatgaggc ttggatcagg   34920
ggaaggggag ttgacattag ttcttaaaga attggaataa caaatccatg ggtatttctg   34980
aaaaaaaaaa aaaaaaaaag aaaggaagct acttggaatt gtcccatatt taacattctg   35040
ctgaccaatc aatttgtcct agttacagaa accaccctg gacttctcct atgcataatt    35100
tggttgcttg tggttgggtc tgccatgtgg agggaccttg agctggggga aggagcttgg   35160
cctccaagtc cactgaagac cagcatcctg agattgcctg gaaggtggt acagggcagt    35220 gatgaagatc atgggagcca cactgcccag cttcgcattt gggcttctcc tagggacacc   35280
aagagggagg aaggagggt taggatggta tgaaagattc tacttggcca atattattgt    35340
aatgcggcat tgtgatctct ggatttagca tgagttgata gctgactttt tctgcagaag   35400
catcttggtg gcacctctaa ctcaaagtcc ctcgatggag tcagtccag ttctccactt    35460 ctggccccat ctggtacaca ccactgcctc tcactgcccg ggctctctat ccttgacagg   35520
ctgccttgaa gttgagccca gactgattt cttgcctcag accccactac cgtgcctggg    35580
actcatgcac ctttgactcc catggaaggg aagtgcagta gtttcccagg tgcaattctg   35640
gtgtcctcac ccacattgag gatgtacaag aatcaggttc ttagagattg gagaaagaag   35700
gaagaatggg aacaagattt ttcccaaagg actgtgaggt cccccaccta accttgatgt   35760
gagacaagtg aggttaaccc caagcctggt gagaagcgtt cccatcagac acttggaaat   35820
cctgaggact gtttcatgca gaaggatatg gtttattcag gtttgactcg tgcttgagaa   35880
agctagagcc tctggtggtg aatgatttta ataactattt cctttccacc aacatataca   35940
gtacaaataa taataagcaa aaataaatag aaacattcag ttttgttttg aatagtagga   36000
gcagggtacc atcatttctg tagttactct tttagtacaa cgatgcatgt ctactgtatg   36060
taaggcatac tagcagaaat tgagctcagc actagagaag atgattgcat tctatgcctt   36120
gcttcttttt ttaaaaaaag gcttccatag atagattctc agaacagccc atggcaaatg   36180
taaagttatt tggaaaaccc aggttccaga ttcactagag catagaatct ctggttggtt   36240
gggaaggaat ttcctcttac agttgttact aataattgta tgaacaatta tttaaaatat   36300
taacatttac atttgtgaag accttgaagg gctggagaca acagagaagc atttttgaat   36360
accctctgca gcccctgcac tgttgtaggc attggtggat ggtaccaaag atgggacact   36420
gtccctacct ccagagaccc tgtgggctgg ctacagagag aaggcaggga ggaggaaaag   36480
aagaataaag tcatatgttt aagtcacccc cacggccgtt ggttagtcat gggaggctcc   36540
ccagaggagc tgtcctgaag ctggctgaca gaaggcaaca tttcaactta ggacagtaat   36600
ccttgctaca tacaatcaca tacacacaca cacacacgtg cacacacaga gactcacatg   36660
gaaaaataaa cctttgtgcc tttcagcagt gatgacaatt atggttttca gtaaacttta   36720
catggtttag atggtgatgg tgatgatgat gattatggga aggatggcat catgttctaa   36780
acatactgca tggagtcaga ataacaatga caaataacca tttgtcccaa tcaaggtttt   36840
```

```
ctcagaaaat atctcattct gatgctaaac tataccagtc tgtttgatca cttctccaac    36900
aaaataatta caaagtgctt atattttctt gaaaagagag ggtcctgtgt tgtctactac    36960
cacttttgaa acttagagaa aatgttccaa aagatgatga ttttactatt tagttcggcc    37020
tttaagatgt caaaaactca gtgcttggaa tttgtctcga attacaccac aaaattgcta    37080
ccttgtctca aatgggattt cttttcccacc ttgtgccaca gcggccccctt catttgattg   37140 tgggaagcct caagtggagc cgaagaaatg tcctggaagg gttgtagggg ggtgtgtggc    37200
ccacccacat tcctggccct ggcaagtcag tcttagaaca aggtaagaac aggcccagaa    37260
acgatttata ctgtccctcc acgtaagccc tgcaaaaccc ttctacattt acataaaatc    37320
cacacagctg aggcatcagc acctgcctct aagttttctg aaggaggaaa aaagctacaa    37380
aaattaatat atgtatatat acatatatat ttttataggt tctctactgt gaaaatgaca    37440
aaaattgctg tcttttttctt gatctgggca gctccatcaa aatctgtagg cacagtgatt    37500
tgcaccaagt tccaatattg ctggaaaata ctgaagatgc tctgaggatt tctatggata    37560
tccattgtct cattgtcaga tgaaaagagg gggaagtttt tagaaatgtg cactttctg     37620 ggttgggaga gcaaggacaa aattatctcc agtctatcac aggcacagat tcttttttctt   37680 tggacactt cgtgaatcat tgaattcaat gcagaggcta ctcatccatt cgcaaacaaa    37740
aaaattctag gtcatgatcc ccataaatga agagtgatca gtccaatccc agggaacctg    37800
gacattttgg gtattgtttc agtggaacat gcctttcata agttccattt tcttgggtat    37860
ctcttaggaa gcaagcatag gaaacaggcc catccgtctg cctgttttgc ttcctcatct    37920
cacttctaca cgagggcgcc tgtgctcaat tgctgttttc ccctaaagag actcttttcc    37980
ataagtttgt gaaatgccat cgacaaacct gatcgcattg catttcactc tgctgttgag    38040 tcgattttc tttatttat catttagtaa ctccttgctc tacagagctt tcaccttcca     38100
catatttcag attcattctt tcctaaacta tgtggtggtc tacgtcctca ctgacttatc    38160
aacatgctac catcatgcac ttcctatctc tattcctctt ctttaaaatt tggttccaaa    38220
tggctcacac cattattctg agctattacc tgcctacgca gtcctagaaa gtaagtgatt    38280
caggaaacat tccccaaaag taaagtttct caggtaagat cagaagactc ccatgagtca    38340
ctgctgctca ggatcacatc tggctccttg aagagtgatt catcagacct tacatagatc    38400
ttgtcataaa aatgaaagag gcctcggggg aaggtcttgg gctggtggct tctgttggag    38460
tcctgggctg tggggtgaaa gccgtggctg tagagcttca tgcggagtta cttagctttg    38520
ctctcctgtg gacaggccat gcctgtgcct cccccaagca tcggaaaaat tggcatagat    38580 gggccccttct caaaaatccc actcctggag cactggccaa aattactacc atcctgatgc    38640
tgggcttgca gtccttttcct ttgggaatat gaacatggtc aaaattaagt gaacgtgtct    38700
ttctggcttt ctgtacaatg gagcagaaca aagtatcaat ttaactaaaa tttgaactaa    38760
atcctctttc caggtttgga atgcacttct gtggaggcac cttgatatcc ccagagtggg    38820
tgttgactgc tgcccactgc ttggagaagt atgtttaggg gacaattgac atgaagtctt    38880
gtcttaaata cttttttctgt ccttctttc ctcctttcct cctttccttt ctcactcttc    38940
ctcccttcct tctctggctg tgacactagg gaccaggcca gggcaattgg ataagagaga    39000
agggaagggt ttctagaaag aaactgcaga ggaaagacac agtacagatg attttgtggg    39060
cctgaataaa ctgcagaaca gagctgttca ctaccatagg ctgtatcagt ctctgcccaa    39120
acagcccaag aacattcctt aactgcctgt ttcaagcaaa tcatgaattt tgcttcttgc    39180
```

```
cactcagaag tcactaattc tgagtggcca agggtgtcag ggagacagca ccaatttcat   39240
ggcacagagg ttacctgaag gggctggacc atatttteet cttgacatce teatcttttc   39300 taggtcccca aggccttcat cctacaaggt catcctgggt gcacaccaag aagtgaatct   39360
cgaaccgcat gttcaggaaa tagaagtgtc taggctgttc ttggagccca cacgaaaaga   39420
tattgccttg ctaaagctaa gcaggtactc gttcacctgt ggtcttcacc ccacgctggt   39480
gaagatattt gctttatgtc tgggttttat gggccatggc cactgcatgg cagtggggag   39540
gaactgtcta tcacatgaaa ggctcaaggg ctttgggggac agcatcaatc ttcaacccta   39600
gccctgccac atgctagctg tgctcttgag aaaggcagca ggactccgtt ttctcatgtg   39660
gaaaaagagt tgaaatgagg tactctgtta ctcctagaac tcacttaatg ttcaccagtt   39720
catacacatt catgatcaga gaacgattca gttattccag gctgacaatt cccccttcat   39780
cataatatgt ttaagagaat catataagac tatatttgtt tcaaagcact ttaaaaacca   39840
caagatcgag ttgggtgtct ggtgtgggtg cctgtaatcc cagctacttg ggaggctgag   39900
gcaggagggt cacttgagtc ccggagtttg aggctgcagt gagttatgat cgtgtcactg   39960
cattccagcc tgggcgacag agtaagacac tgtaccaaaa aaaaaaacac caaaaaaaca   40020 aaaacaaac  aaaaaaaaaa caacttcaca atgtcaaaaa aatcacaaat acagtttata   40080
aatgtaaatt atattattat tattgtcttc tttgatttga ttttctcttt cctgttgaaa   40140
tgttgtttca ctaagcctga caaagtgaaa catttgctta tgtcactcat ttagtgctgt   40200
ttggagccag atactagttg agtcagctaa gaaacagcta tttgtaggag aagcaggttt   40260
gggacaggtg acaaggcacg cagggcgctc gctgtgctgg tggttctgga agacagggtg   40320
tcagtgtgga cagggatgag catggcctgg atgagaaggc acggggcagg agcctgagct   40380
gctctcctgg gcctggccac aagcccaggg cagcttctct gggtctgtga actgaggggt   40440
gatgtcctgg gatgctctga cactctagaa ggagagaaga gcctttccag ctcagccttt   40500
ataaacagta gctgatctcc ctcctgctcc ccagtgtcct ccccgccatc ccagcaaatg   40560
tgcaaataga aggtccccgt tcctcatgat cctcagagag ctggggtgtt ctgatggctt   40620
gaacaagtaa tttggaaatt tgggttttg gaggagttct ctgataggct gatacatttc   40680
gagtttagag ttcccacccc acatccccac accccgagtc tagggcattt agtgctccac   40740
cagggaacct gtagagtgag gacgtctgca tgacaggctg ggccttctga tgatgctcag   40800
aagcagaaag tgtgcctgct tcaaagttgg tgacgatgat gtttcttgat cagaataggg   40860
catttcttat ttccaatcct ttatcctctt gaacttacta aagtagaatc aggtctaaaa   40920
accggagttc taatgtttga gagtccctgg gactctaaag tatatgaatg ttcttttgaaa   40980 acaaatacca ttttgttcaa gcaaaaggct tatttccaat cctctttcat ttggtatcaa   41040
gtattttact ggattcttac aactatggcg tagtaacatt cactgaggag gaaatggagg   41100
atccaaggat ggagcaagtt gctctgggca cacaacacat ttgcaatttt acagcctctt   41160
ggtggcatct cagtcagaca ttccatgcac tgatcaatgc cctattcgat taatgtaaaa   41220
ggacacactc agcatgagat tccagttgtg cacagaatat acatgagaag tgcgcctttg   41280
tcatccctac tttcaaaggt gaaggccacc agcagtatct tgcatgcaac tgatgccttt   41340
caaatgaaac cttacatctg catagtccat agacaaccac aggcaaatgt gagggtgaaa   41400
ctctgtgttc tacgttgctc tgtgtcagtg aagcaaggca gtgccagttc agagggctct   41460
ggggcctcaa dacagggatg actggttgtg ggtactgcag ctgcgagcag agcagtcaaa   41520
cataactgct gatgcttttc tttcagtcct gccgtcatca ctgacaaagt aatcccagct   41580
```

```
tgtctgccat ccccaaatta tgtggtcgct gaccggaccg aatgtttcat cactggctgg    41640
ggagaaaccc aaggtgagat aaattccatt gcccacataa cgaattggtt ttgacctaca    41700
gtccatgtga caaaatgatc attttggaga aagctgtgca aattcctatc catgaatgtg    41760
gtccacccca ctcctgattt tgcctgggca cctgtctatg tcttaatcag tcttcaaggc    41820
acatgatcaa agggaggaaa actgtgtctt tgagtctctc tctctctctc tgttttcaga    41880
acatttttat ttcaattaat taatttttaa cttttatttt aggttcaggg gtacatgtgc    41940
aagtttcttg tatatgtaaa cagtggtttg tcatgcagat tattttgtca cctaggtact    42000
aaccctagta cccaattctt agtatttcct gctcctctcc ctcctcccac tcttctccct    42060
caagtaggcc ccagtgtctg ttgctctctt ctttgtgtcc atgagttctc atcacttagc    42120
tcccacttat aactgtgaac atgtggtatt tggttttctg ttcctgtgtt agttttctaa    42180
gaataacggc ctccagctcc attcatgttc ctgtaaaaga tattacctca ttctttctta    42240
tggctaaaca gtattccatg gtgtatatgt accacatatt cttcatccaa tgtgtcattg    42300
atggtcatat aggtgattcc atgtctttgc tactgtgaat agtgctgcaa tgaacattca    42360
tgtgcatgtg tctttagggt agaatgattt atattcctct aggtatatcg ccagtagtag    42420
gattgctggg ttgaaagtta gttctgcttt tagctctttg agaatcacca tactgctttc    42480
tacagtggat gaactaattt acagtcccac cagctgttag tgttctcttt tctctgcaac    42540
cttgccagca tctgttattt tttgactttt taggaagcca ttctggctgg tgtgagatga    42600 ttttcattg tggttttgat ttgcatttct ctaacgatca gtgatattga gcttttttc     42660 atatgtttgt tggccacagg catgtcttct ttagaaaagt gtgttagtgt cccctgtcca    42720
ttttttaatg gggttttttt tttcttgtaa atttgtttaa gttcctcata gatgctggat    42780
attagacctt tttcaggtgc atagtttgca aatattttct cctgttctct aggttttccc    42840
tttactccct tgagagtttc tttttctgtc cagaagctct taagtttaat tagatcccat    42900
ttgtcaattt ttgcctttgt tgagattgct tttggcatct tcatgaaatt tttgcccgtt    42960
cctatgtcca ggatggtgtt acctaggttg tcttccagga ttttttgtact tttggatttt   43020 acatttaagt ctttaatcca tcttgagttg atttctgtat atggtgtaag gaaagggtc    43080 cagtttccat cttctacata tggctagcca gttaccccag caccatttat tgaataggga    43140 gttatttcc cattgcttgt ttttgtcagc tttgttaaaa atcagatgtc tgtaggtgtg    43200
tggccttatt tctgggctct ctattctgtt ccactggtct acgtgtcttt tttttttttt    43260 tttttacca gtaccatgct gttttgtta ctgtagccct gaagtatagt ttgaagccag     43320
gtaatgtgat gtctccagct ttgttctttt tgtttaggat tgccttggct attctggctc    43380 cttttggtt atatataaat ttttgaagta gttttttaat agtgctgtga agaatatcat    43440
tggcagtttg ataggaatag caatgaatct gtaaattact ttgggcagta tggccatttt    43500
aatgatattg attcttccaa tccatgagca tgggatgttt ttccattcat ttgtgtcatc    43560
tctgatttct ttgagcagtg ttttgtaatt cttattgtag atctcttac ctctctggtt     43620 agctgtattc ttacatattt tattctttt gtggcatttg tgaatgggac tgtgttcctg    43680
atttgcctct gggcttggct gttgttggtg taaagggatg ctagtgattt ttgtacattg    43740
attttatatc ctgaaacttt gctggagttg attatcagct gaaggagctt tgggctgag    43800 actatggggt tttctagaca tagagtcatg tcatctgcca acagggatcg tttgatttcc    43860
tctcttccta tctggatgcc ctttatttct ttctcttgcc tgattgctct gaccagggct    43920
```

```
tccaatacta tgttgaatag gagtggtgaa agagggcatc cttatcttgt gccagttttc   43980
aaggggaatg cttccagctt ttgcccattt agtatgatgt tggctgtgga cttgtcatag   44040
ctgtctctta ttattttgag atatattcct tcagtaccta gtttattgag agttttcaat   44100
ataaaggatg gtaaatttta tcaaaatcct tttctgcatc tattgagata atcatgtggg   44160
ttttctcttt agttatattt atgtgatgaa tcacatttat tgatttatgt atgttgaacc   44220
aagcttacat tctggggata aagcctactt gatcacgatg gattggcttt tttatgtgct   44280
gctggatttg gtttgcaagt attttgtaaa ggattttttgc atcagtgttc atcaaggata   44340
ttggcctgaa gttttttgtt gttttttgtgt ctctgccagg ttttggtatc aggatgatgc   44400
tgacctcata gaatgaattg gagaggagac cctcctcctc agttttttttg aacggtttca   44460 gtaggaatgg tcatagctct tctttgtaca tctggtggaa ttcagctgtg aatctatctg   44520
gtcctgggct tttgttggtt agtaggctat ttattactga ttcaattttg gagctcatta   44580
ttgttctgtt cagggaatca atttcttcct ggttcagtct tgggagggtg tatgtgtcca   44640
ggaatttatc catctctttt aggttttcta gtttgtgtgc atggagctgt tgtagtagt   44700 ttctgatggt tatttttatt tttgtggcat cagtgctaac atccccttttg tcatttctaa   44760 ttgtgtttat tttggtctta tcttccttttt cttcattagc ctagctagca gcctaccat   44820 cttattactg ttttcaaaaa accaactact ggacttgttg atcttttgaa tgaattttca   44880
tgtcttgact ttcttcagtt cagctctgat tttggttatt tcttgccatc tgctagcttt   44940
ggggttgatt tgctcttgtt tctctaattt tttccattgt gatgttaggt cttaatttg    45000 agatctttct tcttgatgct agcatttggt gctatgaatt tctctcttaa cactaccta   45060 gctctgtcca agagattctg gtatgttgta tctttattct cattagttca aagaacttcc   45120
tgatttctgc cataatttca ttattcaccc aaaagtcatt caggagcatg ttgtttgatt   45180
tccatgtaat tgtacggttt tgagttattt tcttagtctt gactggtatt tcattgtgct   45240
gtggtctgag agtgtgtttg gtatgatttt ggttctttgg cacttgctga agattgtttt   45300
atgtccaatt atgtggttga tttttagagt atgtgccaca tggtgatgaa aatgtacatt   45360
cagttgtttt gggaaagaga gttgtgtaga ggtctatcag atccatttgg tccaatgctg   45420
agttcaggtc ctgaatatct ttgttaattt tgtgcctcga tgatctgtct aatactgtca   45480
gtggagtact gaagtctccc actattattt tgtgggcgtc taagtctctt tgtaggtctc   45540
taagaacttt atgaagctgg gtgctcttgt gttgggttca catgtattta ggatagtaga   45600
tcttcttttt gaattgaacc ctttaccatt atgtaatgcc cttctttgtc ttttttggtc   45660
tttgttggtt taaagtctgt tttgtctgaa attaggatgg caaccctttgc ttttttgtct   45720 gatttccatt tgcttggtag gttctcctcc atccctttat tctgagccta tgggtgtcat   45780
tacatgtgag atgggtctct tgaaggtagc ataccagtgg gtcttgcttt ttatccagct   45840
tgccactctg tgcctcttaa gttgggcatt tagcccattt acattcaagg ttagtattgc   45900
tatgtgtgaa tttgatgccc tcattgtgtt gttatgctgg cttgtttgtg tgatggtttt   45960
atagtgtcat tggtctgcgt atttaagtat attttttgtat tggctggtag ccatcttgct   46020
atagttagtg cttcttttcaa gatctcttgt aaggcagttc tggtggtaac caactccctc   46080
aacatttgct tagctgaaaa tgatcttatt tctctgttgc ttaggaagct tagtttggct   46140
ggatatgaaa ttcttgggtg gatatttttt aagaatattg aatataggcc ccaatatctt   46200
ctagcttgta cgggttcagt tgagaggtat gctgttagat tgatgggggtt cccttttgtag   46260 acgacctgtc ctttctctct agctgccttt aacattctgt ctttcatttt gaccttggaa   46320
```

```
aatctgatga ttatgtgtct tgaggatgat cttcttgtat agaatctcac aggggttctc    46380
tgtattttct aaatttgact attggcctct ctagcaaggt tgaagaagtt ttcatggaca    46440
atatcctgaa atgttttcta aattgtttac tttctcccca tccctttcag aaatgccagt    46500
gatttgtaga tttggccttt ttacataatc ccatgtttct tggaggcttt gttcattcct    46560
tttcattctt ttttcttaat ttttgtcaac tgtcttattt cagaaagcca gtcttccatt    46620
tctgagattc tttcctcagc ttggtttatt ttgctattaa tacttggatt gctttgtgaa    46680
attcttacag tttgtttctc agctctcagc tctgtcagat ccattaggtt cttttttaaa    46740
ccagtgattt tgtcttttcag cttctatatc attttattgt gatcctcaat ttccttggat    46800
tggattttgc catcctcctg gatcttgatg atcttcattc ctatccatag tctgaattcc    46860
agttctatca tttcagccag ctcagccttg ttaagaaccc ttgttagaga actagtgtgg    46920
ttgtttggag gacatatggc actccggcct ttatgttcct ttaactgcag tgtaggttga    46980
atacagccaa tagacttgtt ctttggatgt ttttacaggg ccaaagcctt gtgcagggtc    47040
tttatttgta gttgatttct tgtctttggt ttcatagtgt ggtatgttag caaggtattt    47100
ttggtgttga agctttgggg tgtgatccat ttttatttg tatatttccc tacacctaaa    47160
acaagcaaaa aaacagtaaa ggtctttgag tctcttaatc cataatttca gcattcctga    47220
gtatgcttcc ctgggtaagt ggggttttca cccagccctc aagttaagag tgttagatta    47280
tttttcatgt gaaattagcc agactggctt tcttaacaca atgtaaaaca ataacaacaa    47340
aagttataat tagactagtc ttcttcccaa atacccacat gtctaatgta agtgggatgg    47400
tgttaaacag gggacctaca actgggggag aggcggacag gtcccatggc cccaggtcta    47460
ggatggcatt tggtattggt tgatgggtgt ggatgagaac aagagaggga acacttgtgc    47520
aggatatggt atcagcacct gtaatacatt ttagggattc tttcttctct ttgcagtatg    47580
ccctgacaat aattatatcc atcagcctag tccccttggc cattgaaaca ctaagactgt    47640
cttaggatcc ctgctgcagt ttctcagagg tgctaggagg gcattaggag tctgaagccc    47700
tggaagtgtg ttctgacttt gccactagct agatagacct ggactaggca cgttacctct    47760
ttgtaccact cagctctaac ccctcattca aaaacccagc attttcaagt ggtgtttttc    47820
acatcagcct ttgcataagt tttcatttga agaaaggttt gttttttgttt tcttggttta    47880 atcaaacatt taaaaacgaa tggtctagat gatttcaaag tggctttcct tttcctgtgc    47940
ttttcctact atttaaaaac tttacctcct tgatttcttg atctcccttt ctgcactgct    48000
gggtctggga gcattgaggc caagtaaaag gaaccttggc aaaggaggaa cacctatggg    48060
tgtgccaggc tgctcccagt gttttgcatt tttaaaaatt taaatgctgc aaacctctat    48120
gaattacata ttattgttcc tagtttacaa atgaggagcc tgaggctcag agaatgtgtg    48180
ggatggtaca gactaacctg aattagaacc ctggctccca tttactggct gtcaggactt    48240
agaaaagtca taaactctct ggctgggtgc agtggctcac gcctgtaatc ccagcacttt    48300
gggaggccga ggcaggcaga ccacgaggtc aggagcttga gacgagcctg accaacacgg    48360
tgaaaccccg tctctactaa aaatacaaaa attagccggg tgtggtagca caccctgta    48420 atcccagcta ctcaggaggc tgaggcagga gaatcgcttc aacctgggag gtggaggttg    48480
cagtgagcca agattgtgcc actgcactcc agcctgggtg acagagtgag actctatgtg    48540
agaaagaaag aaagaaggaa agaaggaaag aaggaagaaa agaaagagaa agaaagaaag    48600
aaagaaagaa agaaagaaag aaagaaagaa agaaaggaag aaagaaagaa agggaaagaa    48660
```

```
agagaacgaa agaaagaagg gagggaggga gggagggagg gagggaggga ggaagggtgg   48720
gtgggttgtg aactcttgtt gattgtttcc tcagctgaaa tgtgggctgc agggctattg   48780
ggggagaaac aataagaaag tgcaccaagc accaagcaca tgctaagaag tccatcatgg   48840
cagctcctga taataatatg gaatagagtt gtatctaaca tgactctttc ttgcaagtga   48900
cagaaaatgc aacttaagtt ggattaagca aaaagagaa atcattagtg aactgaaaat   48960
tctgcaggct cacatcatgg ccccagaccc tgtccattat tcttgggcac aaatgtgaca   49020
ttctcgtggc tgcagatgct gtggtggctc tggctctgcc aggaaaagaa ataaggaagg   49080
ccactctccc cattacacaa acaatagtct tccagctctg agaggtcgaa cttgtgtcac   49140
cagcctgccc ctaaacccgt cactgattaa ctccaacctg catcagctgt tccatgctgg   49200
aggtggacgc aggaccacac tcataccaag atgggggcaa agtgtagttc cctcaacagg   49260
attataggat atagtgtgat aggctgctgg gcagccaaaa agcaaacaga tcctctacaa   49320
ttcctcaact gatgaaagca cgaagctaaa atcataaaga tctgtgtgtg agttctggct   49380
ctcccatctt ccttgtgaga ttgagcagtt agttaatctc ttttagcctc agcttttctca  49440 cctgtaccaa catataaggt cattgtgagg attaagatta tgcctcatga tcatcattat   49500
catcatcacc atccacattg caaccacaac taccatcatc atcccacca acatcatcac    49560 caccaccacc atcacaatta tcattaccac caccaccatt gtcaccctca acatcaccat   49620
catcactatc accaccacca tcatcatcac taccactacc aacaccatca ctctcatcat   49680
tccaccacca tcaccattaa cattaccatc actatcatca ccaccaccac caccaccacc   49740
cccatcatta ctgccatcaa catcaccatc accatcatca ccaccatcac catcattatc   49800
aaccatcatc accaccattc caccaccatc accattatca tcactaccat tatcaccacc   49860
accatcatca ccaccaccac taccaccacc atcaccacca tcatccaccat aaccatcatc   49920 accactatca acatgatagt aattatgatt accaccacca ttagcattat cattaccacc   49980
accagtacca tcaccatcac caccgccacc acctccatga tcattactac ccaccaccat   50040
caccgtcacc atcatttcac taccagcaca attatcatta ccaccaccat cactaccacc   50100
cttatcacaa ccctcatcat caccaccatt ccaccactgc caccaccacc accaccatca   50160
ctatcattaa caatagacat cacataacca gtttgtagct ggaccttgag cccagagccc   50220
actcactgtt tcttcagtcc caccgccaac caccaggatg agtcacaaaa cataactcag   50280
gcctgctcct caattttcta catgtcaata atgacattga agcaatgggt gttctctgct   50340
tctcagaggg aagttgaaat tctcctgctc ttcccttcat gtttccagat gttccctgac   50400
ttggatattc caaacgcaga gtttggaggt gttgaggcca aggggttttt ccaggtcagc   50460
catcatctgc aatcactgag ctgatcctgc tgctggactt tccctgttgc cctctcccca   50520 acgcccatc ggggagggct tcaatcctca ggtcacctgt ggcctttctg ccctcagagg    50580
tgccatctct acatctacca ctggaaggca gcacctactc acagattgca tcaatttccc   50640
agcaactcat ggtgggtttt cccccttatc agcgtgtttg ccttgctcag agagcagatc   50700
ccagagcagt gacacctaac ttaattttca gcaaaacatt ttgagaaggg tgctccctca   50760
cacaactaca cagtccaggt gatgcaccca ctgcccaatg cttggtagtc aagaggagct   50820
tcctccctgc agctctgccc agatagggct gagctgggct ctggagccag gcgctgggat   50880
gagcctcttc catgctgctc atgtaaactc cagattcagt gtcggttttc tgaacccgag   50940
acaatgatct aaatgcagtc gaaggctttg gggaaagaga gagtgcctcg gttcttacct   51000
gtgtcatgct cgcaaagcaa agagtttgc aaaatttaa tgaaacctgg gcttgcaaaa     51060
```

```
ttggaaaact agattatttg tgacgacact gagacatccc tgggcatgtc tatctggaaa   51120
aacggcattt tctctggcaa ttttgcagac attctatttc aatttggcaa agaaaataaa   51180 gcagttttc acaaaggcag aaatacaact agaatgttca ctctccctaa ttgtcaaaga   51240
agtgtaaatt agaaaatgaa tcaggacaat ttcaacctat tagattagct aatattttaa   51300
aaattgaaga ctcatacaag tgaggtgaag tgattgtttt ctagtggcac ggtacactgt   51360
cacacccttt tagaaaataa tttggcaacg ttattgggag acagaaatat gtctatgtaa   51420
tttatgggaa cttagactca gaaaatgtta aggaataaga atgaacttta tgaacaaaga   51480 tgtgaaagc tggaagcaag agtggggcca acacgcatgg ggaggaagca tttgggcagt   51540
gactccacag acccaggctc aggctgaact acacaacctc cttacgcctc agtttcctta   51600
acagtagaac agaaatgata aaagtgcctg tttcacagga ctattgcgag gattaagtga   51660
gatacatcgc attataagct tgtgtctgga aaggttaatt cttggtaaat gatgactatt   51720
cttttttatt gcaataaaat atacaaaaca taaggtttac tattttaacc attttggaag   51780
gtaccactga gtggcattta gtacattcac aatcatgtgc aaccatcatc atatttccag   51840
aacattttcc tcattcccaa aggaaacctc atgttcatta agcagtagct ccccttaaca   51900
tattagttat gaagatcata gcattataca aaactcatga cacaatgatg agtgaaaaaa   51960
tcaagatgtg aaattttgtg ttatgatgta attagtaaaa gaagcatatt aaaacatctg   52020
aaaaaagagt atataaaaat agcaattgca tttttcagac tctacatttt aaacattatt   52080
ctttatagtt ttaaaagcaa aaagtaaaga aacaacaacc aacccaaaac caacacgaca   52140
aagccgagat tgttaattcc agggctcagg aacacagaat catatatgat gtttacactc   52200
tgcagggtca gagactccag cggcattggg agctgcctcg tgttctgcag cctcacagac   52260
aggaggtcca gtgccgctgc tctgttctgg aatatcctcc tgaatgtgtt ttgggtgcag   52320
ttgccatttc tttcatcttt ttaaacacag gtacttttgg agctggcctt ctcaaggaag   52380
cccagctccc tgtgattgag aataaagtgt gcaatcgcta tgagtttctg aatggaagag   52440
tccaatccac cgaactctgt gctgggcatt tggccggagg cactgacagt tgccaggtaa   52500
gcaaagatca agagaccaaa gttagtcttg tgctctcttg tctcagtctc agcccctcag   52560
acttcattcc ccaggtggca aattcaagga ttttcaaccg aagacccag tctaagtgtt   52620 gtttagaaac ttcctagatc tgtccctgaa tgcgtattca gatcatctaa ggggatgtct   52680
tggggcttga gttccaaatc agtagcaagc gagttttaag tgccataact acctcaggcc   52740
actcaccctc ctggggtgtg ctggtggcca gggactaaag tggtgacttt tccggtaggg   52800
aaggaggtag agggtacagg acagagacca actgcacaca ctttacactg atgcccaggc   52860
tagcccagtc taaggaaac accaacatag gaagggatgt gtgcaggatt cacaaaagat   52920
cttttctacc ccccggaaaa actaagtggt gtggtttcgc taaacagatt tgctaagta   52980 cttaagcact gcagatgctt gagtaatatg ctcataagtt cctttctgat ttcaattact   53040
gggaaaatgt atatatggat agtagaagga tggcatccca taataaaagg caggcagcct   53100
aaccctcaca tgcattttc tctccctctg tatagggtga cagtggaggg cctctggttt   53160
gcttcgagaa ggacaaatac attttacaag gagtcacttc ttgggtctt ggctgtgcac   53220 gccccaataa gcctggtgtc tatgttcgtg tttcaaggtt tgttacttgg attgagggag   53280
tgatgagaaa taattaattg gacgggagac agagtgacgc actgactcac ctagaggctg   53340
ggacgtgggt agggatttag catgctggaa ataactggca gtaatcaaac gaagacactg   53400
```

-continued

```
tccccagcta ccagctacgc caaacctcgg catttttgt gttatttct gactgctgga      53460
ttctgtagta aggtgacata gctatgacat ttgttaaaaa taaactctgt acttaacttt      53520
gatttgagta aattttggtt ttggtcttca acattttcat gctctttgtt caccccacca      53580
atttttaaat gggcagatgg ggggatttag ctgcttttga taaggaacag ctgcacaaag      53640
gactgagcag gctgcaaggt cacagagggg agagccaaga agttgtccac gcatttacct      53700
catcagctaa cgagggcttg acatgcattt ttactgtctt tattcctgac actgagatga      53760
atgttttcaa agctgcaaca tgtatgggga gtcatgcgaa ccgattctgt tattgggaat      53820
gaaatctgtc accgactgct tgacttgagc ccaggggaca cagagcagag agctgtatat      53880
gatggagtga accggtccat ggatgtgtaa cacaagacca actgagagtc tgaatgttat      53940
tctggggcac acgtgagtct aggattggtg ccaagagcat gtaaatgaac aacaagcaaa      54000
tattgaaggt ggaccactta tttcccattg ctaattgcct gcccggtttt gaaacagtct      54060
gcagtacaca cggtcacagg agaatgacct gtgggagaga tacatgttta gaaggaagag      54120
aaaggacaaa ggcacacgtt ttaccattta aatattgtt accaaacaaa aatatccatt      54180
caaaatacaa tttaacaatg caacagtcat cttacagcag agaaatgcag agaaaagcaa      54240
aactgcaagt gactgtgaat aaagggtgaa tgtagtctca aatcctcaaa gagctgtgtt      54300
tatttcattg acaaatagat tatttgtatt caattctgat gtgctttaag gatgaagttt      54360
ctcatttac aattagcaca cacttcgtat atgttgtcac ctgttctcct tacacaaatg      54420
ttgttcccca ttttgaagga ttccctttgg taccagtttt gcctgtccac ataaagtatt      54480
tcatttaaaa agctcagcat aaaatataga ctgcatctga aaagatattg aatataatat      54540
acatagcaga acacacacgt tccacatttc aaaagcctcg ataacaaaaa agaaagatca      54600
aagcccttat tagtcgctgt aaagccattt ataaagctcc tgctgatcct gttaagcatg      54660
gatataattg acctttcttt taaattaaaa tgtaagcttt tccccaagac aactcaaagt      54720
gccaagactg aatgggaact gtccatgttt ctaactcttg gccacgggca ccatcagaac      54780
tgaacttaac aaatatatga aaaatatctc ttcatttta aaatcctaag acccagaaat      54840
cataatccat gggatttgtt tagtaaagaa gaaaatctgt ggctctaggt gtccactaaa      54900
ggagagccaa aaatgtcccg aataatctca ggaccacagc atcattttat gaataacaga      54960
accaagacct cagattgtac aacagattgg ttcttattgc tggaatgggg cataaaccat      55020
gcctggaacc ccagatgcta cagagaaggt agatgggaga gacttctgac ctgttcatgt      55080
tgcaaaggcg tgcggagacc aaggtgagca gaggacacga atgctcacat tctgtggccc      55140
aggaacctgt gattcaatct cctcattaac aggattccca aattttcatc ctccctgcaa      55200
tttttcaaat gctcggttat gggcttagtc ccttgactga tcagatttga tgaacatttc      55260
tgcaca                                                                55266
```

<210> SEQ ID NO 2
<211> LENGTH: 810
<212> TYPE: PRT
<213> ORGANISM: Homo sapiens
<220> FEATURE:
<221> NAME/KEY: MISC_FEATURE
<223> OTHER INFORMATION: plasminogen AAN85555.1

<400> SEQUENCE: 2

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser

```
                20                  25                  30
Leu Phe Ser Val Thr Lys Lys Gln Leu Gly Ala Gly Ser Ile Glu Glu
             35                  40                  45
Cys Ala Ala Lys Cys Glu Glu Asp Glu Glu Phe Thr Cys Arg Ala Phe
         50                  55                  60
Gln Tyr His Ser Lys Glu Gln Cys Val Ile Met Ala Glu Asn Arg
 65                  70                  75                  80
Lys Ser Ser Ile Ile Ile Arg Met Arg Asp Val Val Leu Phe Glu Lys
                     85                  90                  95
Lys Val Tyr Leu Ser Glu Cys Lys Thr Gly Asn Gly Lys Asn Tyr Arg
             100                 105                 110
Gly Thr Met Ser Lys Thr Lys Asn Gly Ile Thr Cys Gln Lys Trp Ser
             115                 120                 125
Ser Thr Ser Pro His Arg Pro Arg Phe Ser Pro Ala Thr His Pro Ser
             130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                 165                 170                 175
Asp Ile Leu Glu Cys Glu Glu Glu Cys Met His Cys Ser Gly Glu Asn
             180                 185                 190
Tyr Asp Gly Lys Ile Ser Lys Thr Met Ser Gly Leu Glu Cys Gln Ala
             195                 200                 205
Trp Asp Ser Gln Ser Pro His Ala His Gly Tyr Ile Pro Ser Lys Phe
         210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                 245                 250                 255
Cys Asp Ile Pro Arg Cys Thr Thr Pro Pro Pro Ser Ser Gly Pro Thr
             260                 265                 270
Tyr Gln Cys Leu Lys Gly Thr Gly Glu Asn Tyr Arg Gly Asn Val Ala
             275                 280                 285
Val Thr Val Ser Gly His Thr Cys Gln His Trp Ser Ala Gln Thr Pro
             290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                 325                 330                 335
Thr Thr Asn Ser Gln Val Arg Trp Glu Tyr Cys Lys Ile Pro Ser Cys
             340                 345                 350
Asp Ser Ser Pro Val Ser Thr Glu Gln Leu Ala Pro Thr Ala Pro Pro
             355                 360                 365
Glu Leu Thr Pro Val Val Gln Asp Cys Tyr His Gly Asp Gly Gln Ser
             370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                 405                 410                 415
Pro Asn Ala Gly Leu Thr Met Asn Tyr Cys Arg Asn Pro Asp Ala Asp
             420                 425                 430
Lys Gly Pro Trp Cys Phe Thr Thr Asp Pro Ser Val Arg Trp Glu Tyr
             435                 440                 445
```

```
Cys Asn Leu Lys Lys Cys Ser Gly Thr Glu Ala Ser Val Val Ala Pro
    450                 455                 460

Pro Pro Val Val Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 3
<211> LENGTH: 2954
<212> TYPE: DNA
<213> ORGANISM: Homo sapiens
<220> FEATURE:
<221> NAME/KEY: misc_feature
<223> OTHER INFORMATION: tissue plasminogen activator NM_001319189.1
```

<400> SEQUENCE: 3

```
gaacttcctc cccctgcttt ataaaaacag gcctgcctca gctccctcat ggccctgtcc    60
actgagcatc ctcccgccac acagaaaccc gcccagccgg ggccaccgac cccaccccct   120
gcctggaaac ttaaaggagg ccggagctgt ggggagctca gagctgagat cctacaggag   180
tccagggctg gagagaaaac ctctgcgagg aagggaagg agcaagccgt gaatttaagg    240
gacgctgtga agcaatcatg gatgcaatga agagagggct ctgctgtgtg ctgctgctgt   300
gtggagcagt cttcgtttcg cccagccagg aaatccatgc ccgattcaga agaggagcca   360
gatcttacca agtgatctgc agagatgaaa aaacgcagat gatataccag caacatcagt   420
catggctgcg ccctgtgctc agaagcaacc gggtggaata ttgctggtgc aacagtggca   480
gggcacagtg ccactcagtg cctgtcaaaa gttgcagcga gccaaggtgt ttcaacgggg   540
gcacctgcca gcaggccctg tacttctcag atttcgtgtg ccagtgcccc gaaggatttg   600
ctggaagtg ctgtgaaata ggaaacagtg actgctactt tgggaatggg tcagcctacc    660
gtggcacgca gcctcacc gagtcgggtg cctcctgcct ccgtggaat tccatgatcc      720
tgataggcaa ggtttacaca gcacagaacc ccagtgccca ggcactgggc ctgggcaaac   780
ataattactg ccggaatcct gatggggatg ccaagccctg gtgccacgtg ctgaagaacc   840
gcaggctgac gtgggagtac tgtgatgtgc cctcctgctc cacctgcggc ctgagacagt   900
acagccagcc tcagtttcgc atcaaaggag ggtcttcgc cgacatcgcc tcccacccct    960
ggcaggctgc catctttgcc aagcacagga ggtcgcccgg agagcggttc ctgtgcgggg  1020
gcatactcat cagctcctgc tggattctct ctgccgccca ctgcttccag gagaggtttc  1080
cgccccacca cctgacggtg atcttgggca gaacataccg ggtggtccct ggcgaggagg  1140
agcagaaatt tgaagtcgaa aaatacattg tccataagga attcgatgat gacacttacg  1200
acaatgacat tgcgctgctg cagctgaaat cggattcgtc ccgctgtgcc caggagagca  1260
gcgtggtccg cactgtgtgc cttccccgg cggacctgca gctgccggac tggacggagt  1320
gtgagctctc cggctacggc aagcatgagg ccttgtctcc tttctattcg gagcggctga  1380
aggaggctca tgtcagactg tacccatcca gccgctgcac atcacaacat ttacttaaca  1440
gaacagtcac cgacaacatg ctgtgtgctg gagacactcg gagcggcggg ccccaggcaa  1500
acttgcacga cgcctgccag ggcgattcgg gaggccccct ggtgtgtctg aacgatggcc  1560
gcatgacttt ggtgggcatc atcagctggg gcctgggctg tggacagaag gatgtcccgg  1620
gtgtgtacac caaggttacc aactacctag actggattcg tgacaacatg cgaccgtgac  1680
caggaacacc cgactcctca aaagcaaatg agatcccgcc tcttcttctt cagaagacac  1740
tgcaaaggcg cagtgcttct ctacagactt ctccagaccc accacaccgc agaagcggga  1800
cgagacccta caggagaggg aagagtgcat tttcccagat acttcccatt ttggaagttt  1860
tcaggacttg gtctgatttc aggatactct gtcagatggg aagacatgaa tgcacactag  1920
cctctccagg aatgcctcct ccctgggcag aaagtggcca tgccaccctg ttttcagcta  1980
aagcccaacc tcctgacctg tcaccgtgag cagctttgga acaggacca caaaaatgaa    2040
agcatgtctc aatagtaaaa gataacaaga tcttcagga aagacggatt gcattagaaa    2100
tagacagtat atttatagtc acaagagccc agcagggcct caaagttggg gcaggctggc  2160
tggcccgtca tgttcctcaa aagcacccttgacgtcaagt ctccttcccc tttcccact    2220
ccctggctct cagaaggtat tccttttgtg tacagtgtgt aaagtgtaaa tcctttttct   2280
ttataaactt tagagtagca tgagagaatt gtatcatttg aacaactagg cttcagcata  2340
```

-continued

```
tttatagcaa tccatgttag tttttacttt ctgttgccac aaccctgttt tatactgtac    2400
ttaataaatt cagatatatt tttcacagtt tttccaaaat cagagtggaa tggttttgtt    2460
atagatgctg tatcccactc tttattcatg ttcacatttt aaaatcattt ggaattctgc    2520
ttcactcgct taacatatac acaacacctg taacatacaa ggcaatgggc taggtgctcc    2580
agaccgggaa aaggagggac aggaatgctt ggtctgatgg gctaatatgg catttagaga    2640
agtaccaagg tacagtggag ccggtcacaa aagggcagac ttgtagtaga attcagttgc    2700
aagagggatt ggggaatctt aaggaaaaaa tagaatctta aggaaaaaat aactgggtga    2760
gacgtggact gtggacaggt gtggaaaagg cactctccat ggaggtatga atatgtagag    2820
ggccaagaga ggggagtaca gggagaaatg agttgagctt gtctgaagtg aacttcagga    2880
agaggaacat aggctggaat ttagattatg ggggctctga acaccaaact gagtttggac    2940
ttaattgact tctg                                                     2954
```

<210> SEQ ID NO 4
<211> LENGTH: 473
<212> TYPE: PRT
<213> ORGANISM: Homo sapiens
<220> FEATURE:
<221> NAME/KEY: MISC_FEATURE
<223> OTHER INFORMATION: tissue plasminogen activator NP_001306118.1

<400> SEQUENCE: 4

```
Met Asp Ala Met Lys Arg Gly Leu Cys Cys Val Leu Leu Cys Gly
 1               5                  10                  15

Ala Val Phe Val Ser Pro Ser Gln Glu Ile His Ala Arg Phe Arg Arg
                20                  25                  30

Gly Ala Arg Ser Tyr Gln Val Ile Cys Arg Asp Glu Lys Thr Gln Met
                35                  40                  45

Ile Tyr Gln Gln His Gln Ser Trp Leu Arg Pro Val Leu Arg Ser Asn
     50                  55                  60

Arg Val Glu Tyr Cys Trp Cys Asn Ser Gly Arg Ala Gln Cys His Ser
 65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
                100                 105                 110

Gly Phe Ala Gly Lys Cys Cys Glu Ile Gly Asn Ser Asp Cys Tyr Phe
                115                 120                 125

Gly Asn Gly Ser Ala Tyr Arg Gly Thr His Ser Leu Thr Glu Ser Gly
     130                 135                 140

Ala Ser Cys Leu Pro Trp Asn Ser Met Ile Leu Ile Gly Lys Val Tyr
145                 150                 155                 160

Thr Ala Gln Asn Pro Ser Ala Gln Ala Leu Gly Leu Gly Lys His Asn
                165                 170                 175

Tyr Cys Arg Asn Pro Asp Gly Asp Ala Lys Pro Trp Cys His Val Leu
                180                 185                 190

Lys Asn Arg Arg Leu Thr Trp Glu Tyr Cys Asp Val Pro Ser Cys Ser
                195                 200                 205

Thr Cys Gly Leu Arg Gln Tyr Ser Gln Pro Gln Phe Arg Ile Lys Gly
     210                 215                 220

Gly Leu Phe Ala Asp Ile Ala Ser His Pro Trp Gln Ala Ala Ile Phe
225                 230                 235                 240
```

```
Ala Lys His Arg Arg Ser Pro Gly Glu Arg Phe Leu Cys Gly Gly Ile
                245                 250                 255

Leu Ile Ser Ser Cys Trp Ile Leu Ser Ala Ala His Cys Phe Gln Glu
                260                 265                 270

Arg Phe Pro Pro His His Leu Thr Val Ile Leu Gly Arg Thr Tyr Arg
                275                 280                 285

Val Val Pro Gly Glu Glu Gln Lys Phe Glu Val Glu Lys Tyr Ile
    290                 295                 300

Val His Lys Glu Phe Asp Asp Thr Tyr Asp Asn Asp Ile Ala Leu
305                 310                 315                 320

Leu Gln Leu Lys Ser Asp Ser Ser Arg Cys Ala Gln Glu Ser Ser Val
                325                 330                 335

Val Arg Thr Val Cys Leu Pro Pro Ala Asp Leu Gln Leu Pro Asp Trp
                340                 345                 350

Thr Glu Cys Glu Leu Ser Gly Tyr Gly Lys His Glu Ala Leu Ser Pro
                355                 360                 365

Phe Tyr Ser Glu Arg Leu Lys Glu Ala His Val Arg Leu Tyr Pro Ser
    370                 375                 380

Ser Arg Cys Thr Ser Gln His Leu Leu Asn Arg Thr Val Thr Asp Asn
385                 390                 395                 400

Met Leu Cys Ala Gly Asp Thr Arg Ser Gly Gly Pro Gln Ala Asn Leu
                405                 410                 415

His Asp Ala Cys Gln Gly Asp Ser Gly Gly Pro Leu Val Cys Leu Asn
                420                 425                 430

Asp Gly Arg Met Thr Leu Val Gly Ile Ile Ser Trp Gly Leu Gly Cys
                435                 440                 445

Gly Gln Lys Asp Val Pro Gly Val Tyr Thr Lys Val Thr Asn Tyr Leu
    450                 455                 460

Asp Trp Ile Arg Asp Asn Met Arg Pro
465                 470
```